US012290567B2

(12) United States Patent
Rajappan et al.

(10) Patent No.: US 12,290,567 B2
(45) Date of Patent: May 6, 2025

(54) ASIALOGLYCOPROTEIN RECEPTOR MEDIATED DELIVERY OF THERAPEUTICALLY ACTIVE CONJUGATES

(71) Applicant: Arcturus Therapeutics, Inc., San Diego, CA (US)

(72) Inventors: Kumar Rajappan, San Diego, CA (US); Padmanabh Chivukula, San Diego, CA (US); Kiyoshi Tachikawa, San Diego, CA (US); Steven Tanis, Carlsbad, CA (US); Priya Karmali, San Diego, CA (US)

(73) Assignee: Arcturus Therapeutics, Inc., San Diego, CA (US)

(*) Notice: Subject to any disclaimer, the term of this patent is extended or adjusted under 35 U.S.C. 154(b) by 1054 days.

(21) Appl. No.: 17/011,880

(22) Filed: Sep. 3, 2020

(65) Prior Publication Data

US 2021/0060168 A1  Mar. 4, 2021

Related U.S. Application Data

(60) Provisional application No. 62/895,417, filed on Sep. 3, 2019.

(51) Int. Cl.
*A61K 47/54* (2017.01)
*C07H 15/04* (2006.01)
*C12N 15/113* (2010.01)

(52) U.S. Cl.
CPC .......... *A61K 47/549* (2017.08); *C07H 15/04* (2013.01); *C12N 15/113* (2013.01); *C12N 2310/3515* (2013.01)

(58) Field of Classification Search
CPC ............ C12N 2310/351; C12N 15/113; A61K 47/549
See application file for complete search history.

(56) References Cited

U.S. PATENT DOCUMENTS

| 9,895,448 | B2 | 2/2018 | Manoharan |
| 2015/0018540 | A1 | 1/2015 | Prakash et al. |
| 2016/0030585 | A1 | 2/2016 | Barnes et al. |
| 2017/0043025 | A1 | 2/2017 | Migawa et al. |
| 2017/0166899 | A1 | 6/2017 | Prakash et al. |
| 2017/0183686 | A1 | 6/2017 | Khvorova et al. |
| 2017/0190661 | A1 | 7/2017 | Payne |
| 2017/0253875 | A1 | 9/2017 | Rozema et al. |
| 2017/0305956 | A1 | 10/2017 | Brown et al. |
| 2017/0349896 | A1 | 12/2017 | Albaek |
| 2018/0169268 | A1 | 6/2018 | Payne et al. |
| 2019/0224326 | A1 | 7/2019 | Bhat et al. |
| 2023/0227826 | A1* | 7/2023 | Tachikawa ........... A61K 31/713 514/44 A |
| 2023/0323345 | A1* | 10/2023 | Tachikawa ......... C12N 15/1138 514/44 A |

FOREIGN PATENT DOCUMENTS

| JP | 2017518278 A | 7/2017 | |
| JP | 2017519024 A | 7/2017 | |
| WO | WO-2009/082607 A2 | 2/2009 | |
| WO | WO-2014025805 | 2/2014 | |
| WO | 2014179620 | † 11/2014 | |
| WO | 2014179626 | † 11/2014 | |
| WO | 2014179627 A2 | 11/2014 | |
| WO | 2014205451 | † 12/2014 | |
| WO | 2015042447 | † 3/2015 | |
| WO | 2015168635 A2 | 11/2015 | |
| WO | WO-2017/156012 A1 | 9/2017 | |
| WO | WO-2017/174657 A1 | 10/2017 | |
| WO | WO-2018013525 | 1/2018 | |
| WO | WO-2018044350 A1 * | 3/2018 | ......... A61K 31/7008 |
| WO | WO-2018/067900 A1 | 4/2018 | |
| WO | WO-2019161213 A1 * | 8/2019 | ........... A61K 47/545 |

OTHER PUBLICATIONS

U.S. Appl. No. 18/001,571, filed Dec. 2022, Tachikawa; Kiyoshi.*
Østergaard, et al., Efficient Synthesis and Biological Evaluation of 5'-GalNAc Conjugated Antisense Oligonucleotides, Bioconjugate Chemistry, 2015, pp. 1451-1455.
Yamamoto, et al., Serial incorporation of a monovalent GalNAc phosphoramidite unit into hepatocyte-targeting antisense oligonucleotides, Bioorganic & Medicinal Chemistry, 2016, pp. 26-32.
Khorev, et al., Trivalent, Gal/GalNAc-containing ligands designed for the asialoglycoprotein receptor, Bioorganic & Medicinal Chemistry, 2008, pp. 5216-5231.
Migawa, et al., A convenient synthesis of 50-triantennary N-acetylgalactosamine clusters based on nitromethanetrispropionic acid, Bioorganic & Medicinal Chemistry Letters, 2016, pp. 2194-2197.
Prakash, et al., Synergistic effect of phosphorothioate, 5'-vinylphosphonate and GalNAc modification for enhancing activity of synthetic siRNA, Bioorganic & Medicinal Chemistry Letters, 2016, pp. 2817-2820.
Prakash, et al., Comprehensive Structure-Activity Relationship of Triantennary N-Acetylgalactosamine Conjugated Antisense Oligonucleotides for Targeted Delivery to Hepatocytes, J. Med. Chem. 2016, pp. 2718-2733.
Cedillo, et al., Synthesis of 5'-GalNAc-Conjugated Oligonucleotides: A Comparison of Solid and Solution-Phase Conjugation Strategies, Molecules 2017, 12 pages.
Prakash, et al., Targeted delivery of antisense oligonucleotides to hepatocytes using triantennary N-acetyl galactosamine improves potency 10-fold in mice, Nucleic Acids Research, 2014, pp. 8796-8807.
Rico, L.; Østergaard, M.E.; Bell, M.; Seth, P.P. Hanessian, S. "Studies Directed Toward the Asiaglycoprotein Receptor Mediated Delivery of 5-fluoro-2'-deoxyuridine for Hepatocellular Carcinoma" Bioorganic Med. Chem. Lett. 2018, 28, 2652-2654.

(Continued)

Primary Examiner — Eric Olson
(74) Attorney, Agent, or Firm — Mintz Levin Cohn Ferris Glovsky and Popeo, P.C.

(57) ABSTRACT

ASGP-R binding molecular conjugates are provided. The conjugates are useful to deliver therapeutically effective amounts of biologically active molecules to target cells and tissues of a subject. Compositions are also provided comprising the molecular conjugates.

19 Claims, 2 Drawing Sheets

(56) References Cited

OTHER PUBLICATIONS

Petrov et al. (Feb. 1, 2018) "Synthesis and Biological Evaluation of Novel Mono-and Bivalent ASGP-R-Targeted Drug-Conjugates", Bioorganic & Medicinal Chemistry Letters, 28(3):382-387.
Posocco et al. (2010) "Less is More-Multiscale Modelling of Self-Assembling Multivalency and Its Impact On DNA Binding and Gene Delivery", Chemical Science, 1(3):393-404.

\* cited by examiner
† cited by third party

ASIALOGLYCOPROTEIN RECEPTOR MEDIATED DELIVERY OF THERAPEUTICALLY ACTIVE CONJUGATES

CROSS-REFERENCES TO RELATED APPLICATIONS

This application claims the benefit of priority under 35 U.S.C. § 119(e) to U.S. Provisional Patent Application No. 62/895,417, entitled "Asialoglycoprotein Receptor Mediated Delivery of Therapeutically Active Conjugates," filed Sep. 30, 2019, the disclosure of which is incorporated herein by reference in its entirety.

TECHNICAL FIELD

The disclosure herein relates to conjugates of therapeutically active molecules and an ASGP-R (Asialogglycoprotein Receptor) binding ligand that facilitates the hepatocyte selective delivery of a therapeutic molecule. More specifically, the disclosure relates to conjugates of therapeutically active molecules and an ASGP-R binding ligand that facilitates the hepatocyte selective delivery of the therapeutic molecule in conjunction with lipids as disclosed herein.

BACKGROUND

The delivery of therapeutic agents into the cells or tissues of human subjects is important for its therapeutic effects and is usually impeded by a limited ability of the compound to reach targeted cells and tissues. Many macromolecules and molecules with net ionic charges face multiple hurdles in entering cells, and the problem becomes even more complicated when these types of molecules need to be delivered to targeted cell types. Unlike small molecules, macromolecules and molecules with net ionic charges do not undergo passive diffusion across cell membranes.

The ASGP-R is highly and selectively expressed on the surface of hepatocytes. This receptor was identified and characterized based on its ability to bind P-linked galactose or GalNAc (N-acetylgalactosamine) residues on proteins. ASGP-R can import large molecules across the cellular plasma membrane by endocytosis. This receptor has three geometrically arranged carbohydrate binding domains on the surface, and many molecular constructs consisting of multiple GalNAc molecules can bind to these domains with each GalNAc unit contributing to the overall binding affinity. Typically, constructs with three GalNAc units spaced approximately 21 Å apart and having a triangular orientation have a binding affinity that is sufficient to affect efficient internalization of conjugated therapeutic molecules.

While several constructs for binding therapeutic agents to a GalNAc construct have been developed, the role of linking moieties and the core structure of the contsructs are still under exploration. Specifically, there is a need to understand the role of several components of these constructs including stereochemical considerations, linking groups, the degradability of the constructs, and flexibility or rigidity of the core to which the linkers are attached. Thus, there remains an unmet need for ASGP-R binding ligand constructs coupled to therapeutic molecules for improved delivery to specific cell types.

SUMMARY

The disclosure relates to conjugates of therapeutically active molecules and an ASGP-R binding ligand that facilitates the hepatocyte selective delivery of the therapeutic molecule. The ASGP-R ligand consists of a modified triantennary presentation of N-acetylgalactosamine sugar units through a series of amide bonds using a conformationally restricted spacer unit as the anchor point for both ligand and therapeutic molecule. The molecular agent is suited for optimized presentation of the ligands to targeted cells. A pharmaceutical composition that comprises the ASGP-R binding molecular conjugate is useful to deliver therapeutically effective amounts of biologically active molecules into the liver cells of patients.

In one embodiment, disclosed herein is a compound of Formula IA:

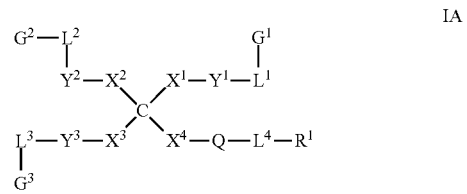

IA or a pharmaceutically acceptable salt or solvate thereof; $X^1$, $X^2$ and $X^3$ are each independently selected from the group consisting of $C_1$-$C_{10}$ alkyl, —$(CH_2)_m$—O—$(CH_2)_n$— and —$(CH_2)_m$—NR$^N$—$(CH_2)_n$—, wherein n is 1-36, m is 1-30 and R$^N$ is H, methyl, or $CH_2F$, $CHF_2$, or $CF_3$; $Y^1$, $Y^2$ and $Y^3$ are each independently selected from the group consisting of —NHC(O)—, —C(O)NH—, —OC(O)—, —C(O)O—, —SC(O)—, —C(O)S— and P(Z)(OH)$O_2$, wherein Z is O or S; $L^1$, $L^2$ and $L^3$ are each independently selected from the group consisting of a $C_1$-$C_{10}$ alkyl, —$(CH_2)_e$—O—$(CH_2)_f$—, —$(CH_2)_e$—S—$(CH_2)_f$—, —$(CH_2)_e$—S(O)$_2$—$(CH_2)_f$—, —$(CH_2)_e$—NR$^N$—$(CH_2)_f$— and —$(CH_2$—$CH_2$—O)$_k$($CH_2$)$_2$—, wherein e is 1-10, f is 1-16; k is 1-20, and R$^N$ is H, methyl, or $CH_2F$, $CHF_2$, or $CF_3$; $G^1$, $G^2$ and $G^3$ are each independently selected from the group consisting of a monosaccharide, a monosaccharide derivative, a vitamin, a polyol, a polysialic acid and a polysialic acid derivative; $X^4$ is selected from the group consisting of (a) —$(CH_2)_g$—O—$(CH_2)_h$— or —$(CH_2)_g$—NR$^N$—$(CH_2)_h$—, wherein g is 1-30, h is 1-36, and R$^N$ is H, methyl, or $CH_2F$, $CHF_2$, or $CF_3$, (b) an amino acid, and (c) —NHC(O)R$^2$, wherein R$^2$ is $C_1$-$C_{10}$ alkyl, a carbocycle, a heterocyclyl, a heteroaryl, a $C_1$-$C_{10}$ alkyl-carbocycle, a $C_1$-$C_{10}$ alkyl-heterocyclyl or a $C_1$-$C_{10}$ alkyl-heteroaryl, and wherein R$^2$ is optionally substituted; Q is absent, alkylamino, —C(O)—$(CH_2)_i$—, —$(CH_2)_i$—O—$(CH_2)_j$—, —$(CH_2)_i$—NR$^3$—$(CH_2)_j$—, —$(CH_2)_i$—S—S—$(CH_2)_j$—, —$(CH_2)_i$—S—$(CH_2)_j$—, —$(CH_2)_i$—S(O)$_2$—$(CH_2)_j$—, —$(CH_2)_i$—NHC(O)—$(CH_2)_j$—, —$(CH_2)_i$—C(O)NH—$(CH_2)_j$—, —$(CH_2)_i$—SC(O)—$(CH_2)_j$—, or —$(CH_2)_i$—C(O)S—$(CH_2)_j$—, wherein i is 1-30; j is 1-36; and R$^3$ is hydrogen or an alkyl; $L^4$ is absent, —C(O)O—, —C(O)NH—, a phosphate, $C_1$-$C_{10}$ alkyl-phosphate, $C_3$-$C_{10}$ alkenyl-phosphate, a phosphorothioate, alkyl-phosphorothioate, $C_3$-$C_{10}$ alkenyl-phosphorothioate, a boranophospate, a $C_1$-$C_{10}$ alkyl-boranophospate, a $C_3$-$C_{10}$ alkenyl-boranophospate, —C(O)NH—$C_3$-$C_{10}$ alkyl-phosphate, —C(O)NH—$C_3$-$C_{10}$ alkenyl-phosphate, —C(O)O—$C_1$-$C_{10}$ alkyl-phosphate, —C(O)O—$C_3$-$C_{10}$ alkenyl-phosphate, —C(O)NH—$C_1$-$C_{10}$ alkyl-phosphorothioate, —C(O)NH—$C_3$-$C_{10}$alkenyl-phosphorothioate, —C(O)O—$C_1$-$C_{10}$ alkyl-phosphorothioate, —C(O)O—$C_3$-$C_{10}$ alkenyl-phosphorothioate, —C(O)—NH—$C_1$-$C_{10}$ alkyl-boranophospate, —C(O)—NH—$C_3$-$C_{10}$ alkenyl-boranophospate, —C(O)O—C$_1$-C$_{10}$ alkyl-boranophospate or —C(O)O—C$_3$-C$_{10}$ alkenyl-boranophospate; and R$^1$ is a biologically active molecule.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments herein.

BRIEF DESCRIPTION OF THE DRAWINGS

Various features of illustrative embodiments of the disclosure are described below with reference to the drawings. The illustrated embodiments are intended to illustrate, but not to limit, the disclosure. The drawings contain the following figures.

DETAILED DESCRIPTION

Figure 1:
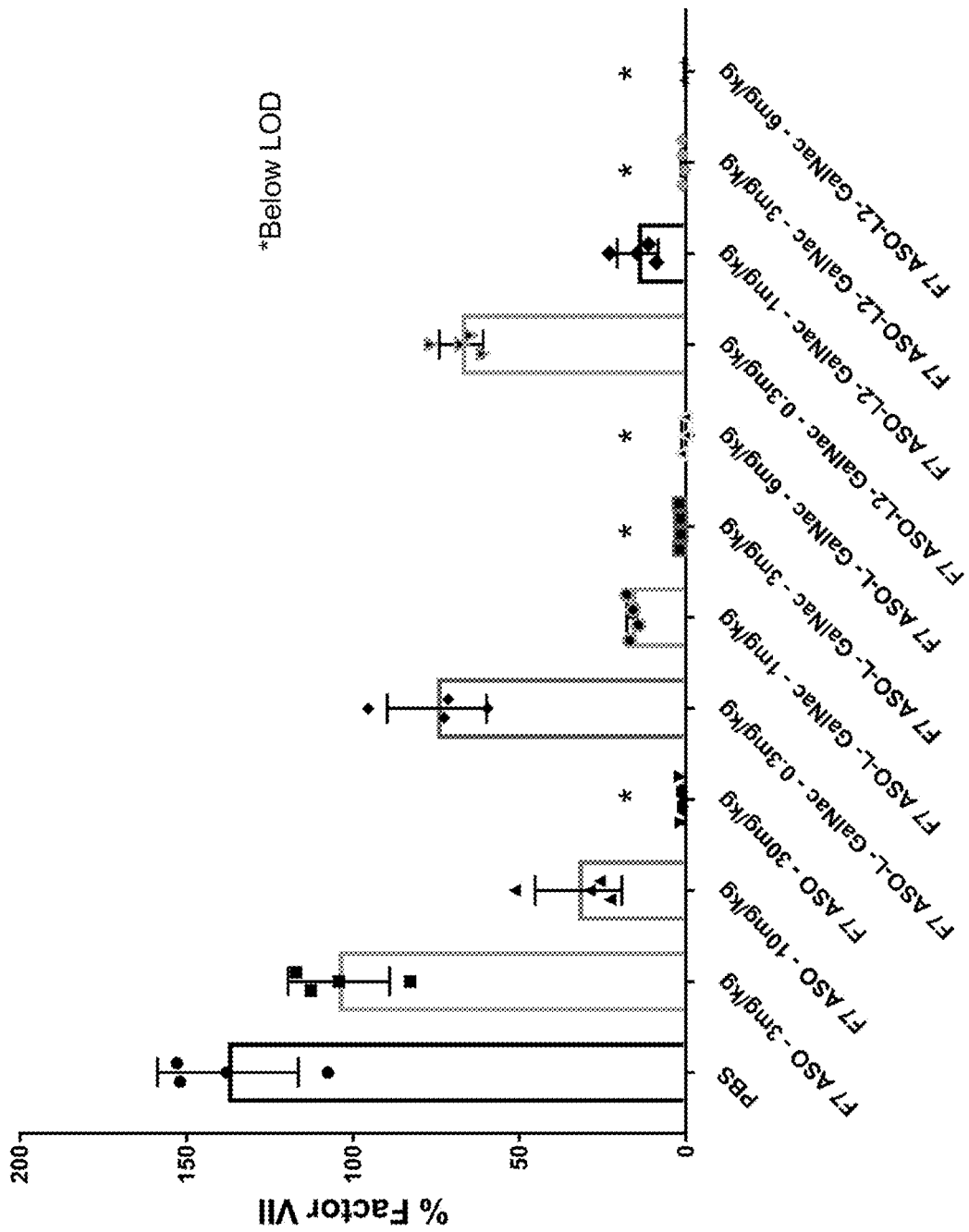
FIG. 1 shows FVII knockdown data for GalNAc constructs Conjugate 1 (F7 ASO-L-GalNAc) and Conjugate 27 (F7 ASO-L2-GalNAc).

Biologically active proteins, such as immunoglobulins and therapeutics of the polynucleotide class, such as genomic DNA, cDNA, mRNA, and siRNA, antisense oligonucleotides, and even certain low molecular weight peptides, peptide hormones and antibiotics represent classes of molecules where targeted delivery to a subject's tissues by diffusion across cell membranes faces significant hurdles.

Receptor mediated endocytosis (RME) is a well-known biological mechanism by which cells internalize extracellular molecules. This process requires binding of a given cell surface receptor to its cognate ligand, which may be expressed as an epitope on the surface of molecule to be internalized. This cognate ligand can be used as a targeting ligand for delivery of therapeutically relevant molecules to specific cells of interest. Therefore, if a receptor-ligand combination can be utilized with a therapeutically active molecule by conjugating the targeting ligand to the active molecule significant improvements in targeted delivery to specific cell types in a subject can be achieved. Some of the prominent examples of receptor-mediated endocytotic systems are those that recognize sugars such as galactose, mannose and mannose-6-phosphate, or peptides and proteins such as transferrin and asialoglycoprotein.

The ASGP-R is highly and selectively expressed on the surface of liver cells called hepatocytes. It was identified and characterized on the basis of its ability to bind P-linked galactose or GalNAc residues on proteins. In this aspect, ASGP-R can import large molecules and charged molecules across the cellular plasma membrane by endocytosis.

Disclosed herein are compounds and pharmaceutical compositions that comprise the ASGP-R binding molecular conjugates useful to deliver therapeutically effective amounts of biologically active molecules into the liver cells of a subject.

In one embodiment, disclosed herein is a compound of Formula IA:

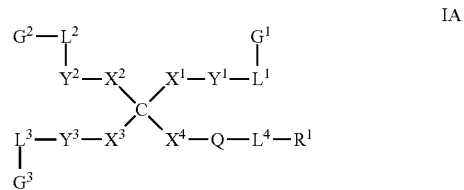

IA or a pharmaceutically acceptable salt or solvate thereof, wherein X$^1$, X$^2$ and X$^3$ are each independently selected from the group consisting of C$_1$-C$_{10}$ alkyl, —(CH$_2$)$_m$—O—(CH$_2$)$_n$— and —(CH$_2$)$_m$—NR$^N$—(CH$_2$)$_n$—, wherein n is 1-36, m is 1-30, and R$^N$ is H, methyl, or CH$_2$F, CHF$_2$, or CF$_3$; Y$^1$, Y$^2$ and Y$^3$ are each independently selected from the group consisting of —NHC(O)—, —C(O)NH—, —OC(O)—, —C(O)O—, —SC(O)—, —C(O)S— and P(Z)(OH)O$_2$, wherein Z is O or S; L$^1$, L$^2$ and L$^3$ are each independently selected from the group consisting of a C$_1$-C$_{10}$ alkyl, —(CH$_2$)$_e$—O—(CH$_2$)$_f$—, —(CH$_2$)$_e$—S—(CH$_2$)$_f$—, —(CH$_2$)$_e$—S(O)$_2$—(CH$_2$)$_f$—, —(CH$_2$)$_e$—NR$^N$—(CH$_2$)$_f$— and —(CH$_2$—CH$_2$—O)$_k$(CH$_2$)$_2$—, wherein e is 1-10, f is 1-16, k is 1-20, and R$^N$ is H, methyl, or CH$_2$F, CHF$_2$, or CF$_3$; G$^1$, G$^2$ and G$^3$ are each independently selected from the group consisting of a monosaccharide, a monosaccharide derivative, a vitamin, a polyol, a polysialic acid and a polysialic acid derivative; X$^4$ is selected from the group consisting of (a) —(CH$_2$)$_g$—O—(CH$_2$)$_h$— or —(CH$_2$)$_g$—NR$^N$—(CH$_2$)$_h$—, wherein g is 1-30, h is 1-36, and R$^N$ is H, methyl, or CH$_2$F, CHF$_2$, or CF$_3$, (b) an amino acid, and (c) —NHC(O)R$^2$, wherein R$^2$ is C$_1$-C$_{10}$ alkyl, a carbocycle, a heterocyclyl, a heteroaryl, a C$_1$-C$_{10}$ alkyl-carbocycle, a C$_1$-C$_{10}$ alkyl-heterocyclyl or a C$_1$-C$_{10}$ alkyl-heteroaryl, and wherein R$^2$ is optionally substituted; Q is absent, alkylamino, —C(O)—(CH$_2$)$_i$—, —(CH$_2$)$_i$—O—(CH$_2$)$_j$—, —(CH$_2$)$_i$—NR$^3$—(CH$_2$)$_j$—, —(CH$_2$)$_i$—S—S—(CH$_2$)$_j$—, —(CH$_2$)$_i$—S—(CH$_2$)$_j$—, —(CH$_2$)$_i$—S(O)$_2$—(CH$_2$)$_j$—, —(CH$_2$)$_i$—NHC(O)—(CH$_2$)$_j$—, —(CH$_2$)$_i$—C(O)NH—(CH$_2$)$_j$—, —(CH$_2$)$_i$—SC(O)—(CH$_2$)—, or —(CH$_2$)$_1$—C(O)S—(CH$_2$)—, wherein i is 1-30; j is 1-36; and R$^3$ is hydrogen or an alkyl; L$^4$ is absent, —C(O)O—, —C(O)NH—, a phosphate, C$_1$-C$_{10}$ alkyl-phosphate, C$_3$-C$_{10}$ alkenyl-phosphate, a phosphorothioate, alkyl-phosphorothioate, C$_3$-C$_{10}$ alkenyl-phosphorothioate, a boranophospate, a C$_1$-C$_{10}$ alkyl-boranophospate, a C$_3$-C$_{10}$ alkenyl-boranophospate, —C(O)NH—C$_1$-C$_{10}$ alkyl-phosphate, —C(O)NH—C$_3$-C$_{10}$ alkenyl-phosphate, —C(O)O—C$_1$-C$_{10}$ alkyl-phosphate, —C(O)O—C$_3$-C$_{10}$ alkenyl-phosphate, —C(O)NH—C$_1$-C$_{10}$ alkyl-phosphorothioate, —C(O)NH—C$_3$-C$_{10}$ alkenyl-phosphorothioate, —C(O)O—C$_1$-C$_{10}$ alkyl-phosphorothioate, —C(O)O—C$_3$-C$_{10}$ alkenyl-phosphorothioate, —C(O)—NH—C$_1$-C$_{10}$ alkyl-boranophospate, —C(O)—NH—C$_3$-C$_{10}$ alkenyl-boranophospate, —C(O)O—C$_1$-C$_{10}$ alkyl-boranophospate or —C(O)O—C$_3$-C$_{10}$ alkenyl-boranophospate; and R$^1$ is a biologically active molecule; and a lipid of Formula II, III or IV as disclosed herein.

In some embodiments, X$^1$, X$^2$ and X$^3$ are each independently selected from the group consisting of C$_1$-C$_{10}$ alkyl, —(CH$_2$)$_m$—O—(CH$_2$)$_n$— and —(CH$_2$)$_m$—NR$^N$—(CH$_2$)$_n$—, wherein m is 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 or 1, and R$^N$ is H, methyl, or CH$_2$F, CHF$_2$, or CF$_3$. In some embodiments, X$^1$, X$^2$ and X$^3$ are each independently selected from the group consisting of C$_1$-C$_{10}$ alkyl, —(CH$_2$)$_m$—O—(CH$_2$)$_n$—, and —(CH$_2$)$_m$—NR$^N$—(CH$_2$)$_n$—, wherein m is 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 and 1. In some embodiments, X$^1$, X$^2$ and X$^3$ are each independently (—CH$_2$)$_m$—O—CH$_2$—, wherein m is 1-4. In some embodiments, X$^1$, X$^2$ and X$^3$ are each independently (—CH$_2$)$_2$—O—CH$_2$—. In some embodiments, X$^1$, X$^2$ and X$^3$ are each independently are each C$_1$-C$_{10}$ alkyl, C$_1$-C$_9$ alkyl, C$_1$-C$_8$ alkyl, C$_1$-C$_7$ alkyl, C$_1$-C$_6$ alkyl, C$_1$-C$_4$ alkyl, C$_1$-C$_3$ alkyl, C$_1$-C$_2$ alkyl or —CH$_2$—.

In some embodiments, Y$^1$, Y$^2$ and Y$^3$ are each —NHC(O)— or —C(O)NH—. In some embodiments, Y$^1$, Y$^2$ and Y$^3$ are each —NHC(O)—.

In some embodiments, L$^1$, L$^2$ and L$^3$ are each C$_1$-C$_{10}$ alkyl, C$_1$-C$_9$ alkyl, C$_1$-C$_8$ alkyl, C$_1$-C$_7$ alkyl, C$_1$-C$_6$ alkyl, C$_1$-C$_5$ alkyl, C$_1$-C$_4$ alkyl, C$_1$-C$_3$ alkyl, C$_1$-C$_2$ alkyl or —CH$_2$—. In some embodiments, L$^1$, L$^2$ and L$^3$ are each independently C$_3$-C$_8$ alkyl or —(CH$_2$—CH$_2$—O)$_k$(CH$_2$)$_2$—, wherein k is 1-10. In some embodiments, L$^1$, L$^2$ and L$^3$ are each independently —(CH$_2$—CH$_2$—O)$_k$(CH$_2$)$_2$—, wherein k is 2-4. In some embodiments, L$^1$, L$^2$ and L$^3$ are each independently —(CH$_2$—CH$_2$—O)$_k$(CH$_2$)$_2$—, wherein k is 1-10, 1-9, 1-8, 1-7, 1-6, 1-5, 1-4, 1-3, 1-2 or 1. In some embodiments, L$^1$, L$^2$ and L$^3$ are each —(CH$_2$—CH$_2$—O)(CH$_2$)$_2$—.

In some embodiments, G$^1$, G$^2$ and G$^3$ are each independently selected from the group consisting of folic acid, ribose, retinol, niacin, riboflavin, biotin, glucose, mannose, fucose, sucrose, lactose, mannose-6-phosphate, N-acetyl galactosamine, N-acetylglucosamine, a sialic acid, a sialic acid derivative, allose, altrose, arabinose, cladinose, erythrose, erythrulose, fructose, fucitol, fucosamine, fucose, fuculose, galactosamine, galactosaminitol, galactose, glucosamine, glucosaminitol, glucose-6 phosphate, gulose glyceraldehyde, glycero-mannosheptose, glycerol, glycerone, gulose, idose, lyxose, mannosamine, psicose, quinovose, quinovosamine, rhamnitol, rhamnosamine, rhamnose, ribulose, sedoheptulose, sorbose, tagatose, talose, threose, xylose and xylulose. In some embodiments, G$^1$, G$^2$ and G$^3$ are each N-acetylgalactosamine.

In some embodiments, X$^4$ is selected from the group consisting of

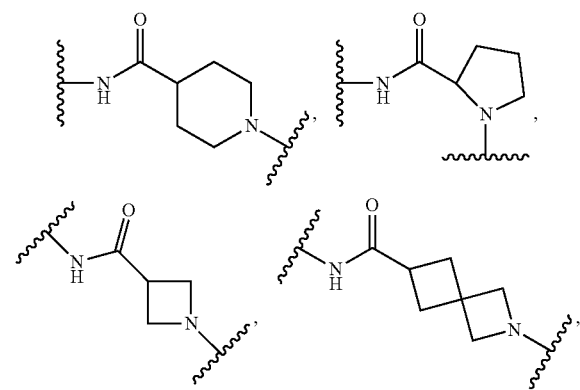

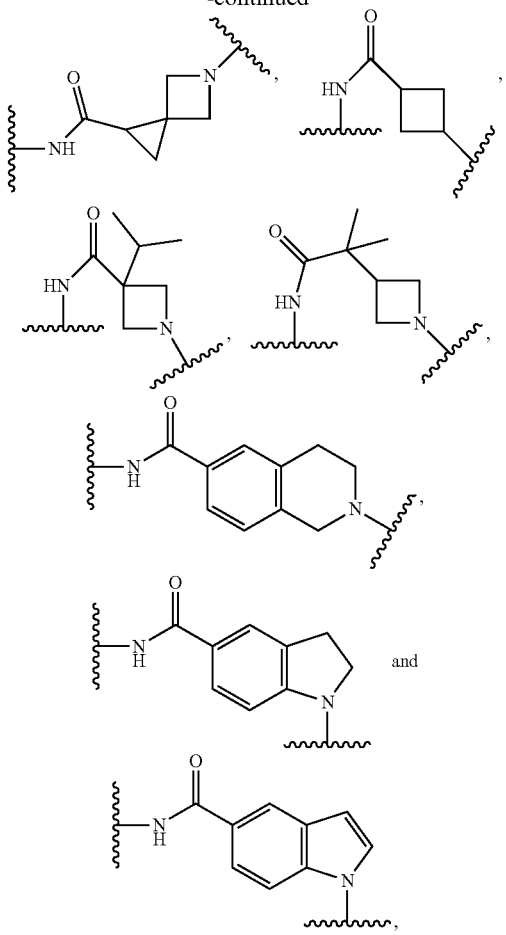

wherein X$^4$ is optionally substituted.

In some embodiments, X$^4$ is —NHC(O)R$^2$, wherein R$^2$ is a carbocycle, a heterocyclyl or a heteroaryl, wherein R$^2$ is optionally substituted. In some embodiments, X$^4$ is —NHC(O)R$^2$, wherein R$^2$ is a carbocycle, a heterocyclyl or a heteroaryl, wherein R$^2$ is optionally substituted with alkyl, alkoxy or amine. In some embodiments, X$^4$ is

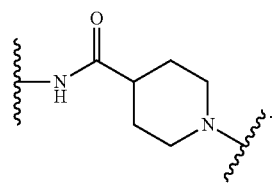 [SMILES: *NC(=O)C1CCN(*)CC1]

In some embodiments, Q is alkylamino, —C(O)—(CH$_2$)$_i$—, —(CH$_2$)$_i$—O—(CH$_2$)$_j$—, —(CH$_2$)$_i$—NR$^3$—(CH$_2$)$_j$—, —(CH$_2$)$_i$—S—S—(CH$_2$)$_j$—, —(CH$_2$)$_i$—S—(CH$_2$)$_j$—, —(CH$_2$)$_i$—S(O)$_2$—(CH$_2$)$_j$—, —(CH$_2$)$_i$—NHC(O)—(CH$_2$)$_j$—, —(CH$_2$)$_i$—C(O)NH—(CH$_2$)$_j$—, —(CH$_2$)$_i$—SC(O)—(CH$_2$)$_j$—, or —(CH$_2$)$_i$—C(O)S—(CH$_2$)$_j$—, wherein i is 1-10 and j is 1-10; and R$^3$ is hydrogen or an alkyl. In some embodiments, Q is alkylamino, —C(O)—(CH$_2$)$_i$—, —(CH$_2$)$_i$—O—(CH$_2$)$_j$—, —(CH$_2$)$_i$—NR$^3$—(CH$_2$)$_j$—, —(CH$_2$)$_i$—S—S—(CH$_2$)$_j$—, —(CH$_2$)$_i$—S—(CH$_2$)$_j$—, —(CH$_2$)$_i$—S(O)$_2$—(CH$_2$)$_j$—, —(CH$_2$)$_i$—NHC(O)—(CH$_2$)$_j$—, —(CH$_2$)$_i$—C(O)NH—(CH$_2$)$_j$—, —(CH$_2$)$_i$—SC(O)—

$(CH_2)_j$—, or —$(CH_2)_i$—C(O)S—$(CH_2)_j$—, wherein i is 1-10 and j is 1-10; i is 1-9 and j is 1-9; i is 1-8 and j is 1-8; i is 1-7 and j is 1-7; i is 1-6 and j is 1-6; i is 1-5 and j is 1-5; i is 1-5 and j is 1-4; i is 1-3 and j is 1-3; i is 1-2 and j is 1-2; or i is 1 and j is 1.

In some embodiments, Q is —C(O)—$(CH_2)_{1-10}$— and $L^4$ is a —C(O)NH—$(CH_2)_{1-10}$-phosphate. In some embodiments, Q is —C(O)—$(CH_2)_{1-9}$— and $L^4$ is a —C(O)NH—$(CH_2)_{1-9}$-phosphate; Q is —C(O)—$(CH_2)_{1-8}$— and $L^4$ is a —C(O)NH—$(CH_2)_{1-8}$-phosphate; Q is —C(O)—$(CH_2)_{1-7}$— and $L^4$ is a —C(O)NH—$(CH_2)_{1-7}$-phosphate; Q is —C(O)—$(CH_2)_{1-6}$— and $L^4$ is a —C(O)NH—$(CH_2)_{1-6}$-phosphate; Q is —C(O)—$(CH_2)_{1-5}$— and $L^4$ is a —C(O)NH—$(CH_2)_{1-5}$-phosphate; Q is —C(O)—$(CH_2)_{1-4}$— and $L^4$ is a —C(O)NH—$(CH_2)_{1-4}$-phosphate; Q is —C(O)—$(CH_2)_{1-3}$— and $L^4$ is a —C(O)NH—$(CH_2)_{1-3}$-phosphate; Q is —C(O)—$(CH_2)_{1-2}$— and $L^4$ is a —C(O)NH—$(CH_2)_{1-2}$-phosphate; or Q is —C(O)—$(CH_2)$— and $L^4$ is a —C(O)NH—$(CH_2)$-phosphate. In some embodiments, $L^4$ is a —C(O)NH—$(CH_2)_{1-10}$-phosphate. In some embodiments, $L^4$ is a —C(O)NH—$(CH_2)_{1-9}$-phosphate, —C(O)NH—$(CH_2)_{1-8}$-phosphate, —C(O)NH—$(CH_2)_{1-7}$-phosphate, —C(O)NH—$(CH_2)_{1-6}$-phosphate, —C(O)NH—$(CH_2)_{1-5}$-phosphate, —C(O)NH—$(CH_2)_{1-4}$-phosphate, —C(O)NH—$(CH_2)_{1-3}$-phosphate, —C(O)NH—$(CH_2)_{1-2}$-phosphate or —C(O)NH—$(CH_2)$-phosphate. In some embodiments, Q is —C(O)—$(CH_2)_3$— and $L^4$ is a —C(O)NH—$(CH_2)_6$-phosphate.

In some embodiments, $L^4$ is absent, —C(O)O—, —C(O)NH—, a phosphate, $C_1$-$C_{10}$ alkyl-phosphate, $C_3$-$C_{10}$ alkenyl-phosphate, a phosphorothioate, alkyl-phosphorothioate, $C_3$-$C_{10}$ alkenyl-phosphorothioate, a phosphorothioate, alkyl-phosphorothioate, $C_3$-$C_{10}$ alkenyl-phosphorothioate, a boranophospate, alkyl-boranophospate, $C_3$-$C_{10}$ alkenyl-boranophospate, —C(O)NH—$C_1$-$C_{10}$ alkyl-phosphate, —C(O)O—$C_1$-$C_{10}$ alkyl-phosphate, a phosphorothioate, —C(O)NH—$C_1$-$C_{10}$ alkyl-phosphorothioate, —C(O)O—$C_1$-$C_{10}$ alkyl-phosphorothioate, a boranophospate, —C(O)—NH—$C_1$-$C_{10}$ alkyl-boranophospate or —C(O)O—$C_1$-$C_{10}$ alkyl-boranophospate, —C(O)NH—$C_3$-$C_{10}$ alkenyl-phosphate, —C(O)O—$C_3$-$C_{10}$ alkenyl-phosphate, —C(O)NH—$C_3$-$C_{10}$ alkenyl-phosphorothioate, —C(O)O—$C_3$-$C_{10}$ alkenyl-phosphorothioate, —C(O)—NH—$C_3$-$C_{10}$ alkenyl-boranophospate or —C(O)O—$C_3$-$C_{10}$ alkenyl-boranophospate.

In some embodiments, $L^4$ is $C_1$-$C_{20}$ alkyl-phosphate, $C_1$-$C_{19}$ alkyl-phosphate, $C_1$-$C_{18}$ alkyl-phosphate, $C_1$-$C_{17}$ alkyl-phosphate, $C_1$-$C_{16}$ alkyl-phosphate, $C_1$-$C_{15}$ alkyl-phosphate, $C_1$-$C_{14}$ alkyl-phosphate, $C_1$-$C_{13}$ alkyl-phosphate, $C_1$-$C_{12}$ alkyl-phosphate, $C_1$-$C_{11}$ alkyl-phosphate, $C_1$-$C_{10}$ alkyl-phosphate, $C_1$-$C_9$ alkyl-phosphate, $C_1$-$C_8$ alkyl-phosphate, $C_1$-$C_7$ alkyl-phosphate, $C_1$-$C_6$ alkyl-phosphate, $C_1$-$C_5$ alkyl-phosphate, $C_1$-$C_4$ alkyl-phosphate, $C_1$-$C_3$ alkyl-phosphate, $C_1$-$C_2$ alkyl-phosphate or —$CH_2$-phosphate. In some embodiments, $L^4$ is $C_1$-$C_{20}$ alkyl-phosphorothioate, $C_1$-$C_{19}$ alkyl-phosphorothioate, $C_1$-$C_{18}$ alkyl-phosphorothioate, $C_1$-$C_{17}$ alkyl-phosphorothioate, $C_1$-$C_{16}$ alkyl-phosphorothioate, $C_1$-$C_{15}$ alkyl-phosphorothioate, $C_1$-$C_{14}$ alkyl-phosphorothioate, $C_1$-$C_{13}$ alkyl-phosphorothioate, $C_1$-$C_{12}$ alkyl-phosphorothioate, $C_1$-$C_{11}$ alkyl-phosphorothioate, $C_1$-$C_{10}$ alkyl-phosphorothioate, $C_1$-$C_9$ alkyl-phosphorothioate, $C_1$-$C_8$ alkyl-phosphorothioate, $C_1$-$C_7$ alkyl-phosphorothioate, $C_1$-$C_6$ alkyl-phosphorothioate, $C_1$-$C_5$ alkyl-phosphorothioate, $C_1$-$C_4$ alkyl-phosphorothioate, $C_1$-$C_3$ alkyl-phosphorothioate, $C_1$-$C_2$ alkyl-phosphorothioate or —$CH_2$-phosphorothioate. In some embodiments, $L^4$ is $C_1$-$C_{20}$ alkyl-boranophospate, $C_1$-$C_{19}$ alkyl-boranophospate, $C_1$-$C_{18}$ alkyl-boranophospate, $C_1$-$C_{17}$ alkyl-boranophospate, $C_1$-$C_{16}$ alkyl-boranophospate, $C_1$-$C_{15}$ alkyl-boranophospate, $C_1$-$C_{14}$ alkyl-boranophospate, $C_1$-$C_{13}$ alkyl-boranophospate, $C_1$-$C_{12}$ alkyl-boranophospate, $C_1$-$C_{11}$ alkyl-boranophospate, $C_1$-$C_{10}$ alkyl-boranophospate, $C_1$-$C_9$ alkyl-boranophospate, $C_1$-$C_8$ alkyl-boranophospate, $C_1$-$C_7$ alkyl-boranophospate, $C_1$-$C_6$ alkyl-boranophospate, $C_1$-$C_5$ alkyl-boranophospate, $C_1$-$C_4$ alkyl-boranophospate, $C_1$-$C_3$ alkyl-boranophospate, $C_1$-$C_2$ alkyl-boranopospate or —$CH_2$-boranophospate.

In some embodiments, $L^4$ is $C_3$-$C_{20}$ alkenyl-phosphate, $C_3$-$C_{19}$ alkenyl-phosphate, $C_3$-$C_{18}$ alkenyl-phosphate, $C_3$-$C_{17}$ alkenyl-phosphate, $C_3$-$C_{16}$ alkenyl-phosphate, $C_3$-$C_{15}$ alkenyl-phosphate, $C_3$-$C_{14}$ alkenyl-phosphate, $C_3$-$C_{13}$ alkenyl-phosphate, $C_3$-$C_{12}$ alkenyl-phosphate, $C_3$-$C_{11}$ alkenyl-phosphate, $C_3$-$C_{10}$ alkenyl-phosphate, $C_3$-$C_9$ alkenyl-phosphate, $C_3$-$C_8$ alkenyl-phosphate, $C_3$-$C_7$ alkenyl-phosphate, $C_3$-$C_6$ alkenyl-phosphate, $C_3$-$C_5$ alkenyl-phosphate, $C_3$-$C_4$ alkenyl-phosphate, or $C_3$ alkenyl-phosphate. In some embodiments, $L^4$ is $C_3$-$C_{20}$ alkenyl-phosphorothioate, $C_3$-$C_{19}$ alkenyl-phosphorothioate, $C_3$-$C_{18}$ alkenyl-phosphorothioate, $C_3$-$C_{17}$ alkenyl-phosphorothioate, $C_3$-$C_{16}$ alkenyl-phosphorothioate, $C_3$-$C_{15}$ alkenyl-phosphorothioate, $C_3$-$C_{14}$ alkenyl-phosphorothioate, $C_3$-$C_{13}$ alkenyl-phosphorothioate, $C_3$-$C_{12}$ alkenyl-phosphorothioate, $C_3$-$C_{11}$ alkenyl-phosphorothioate, $C_3$-$C_{10}$ alkenyl-phosphorothioate, $C_3$-$C_9$ alkenyl-phosphorothioate, $C_3$-$C_8$ alkenyl-phosphorothioate, $C_3$-$C_7$ alkenyl-phosphorothioate, $C_3$-$C_6$ alkenyl-phosphorothioate, $C_3$-$C_5$ alkenyl-phosphorothioate, $C_3$-$C_4$ alkenyl-phosphorothioate, or $C_3$ alkenyl-phosphorothioate. In some embodiments, $L^4$ is $C_3$-$C_{20}$ alkenyl-boranophospate, $C_3$-$C_{19}$ alkenyl-boranophospate, $C_3$-$C_{18}$ alkenyl-boranophospate, $C_3$-$C_{17}$ alkenyl-boranophospate, $C_3$-$C_{16}$ alkenyl-boranophospate, $C_3$-$C_{15}$ alkenyl-boranophospate, $C_3$-$C_{14}$ alkenyl-boranophospate, $C_3$-$C_{13}$ alkenyl-boranophospate, $C_3$-$C_{12}$ alkenyl-boranophospate, $C_3$-$C_{11}$ alkenyl-boranophospate, $C_3$-$C_{10}$ alkenyl-boranophospate, $C_3$-$C_9$ alkenyl-boranophospate, $C_3$-$C_8$ alkenyl-boranophospate, $C_3$-$C_7$ alkenyl-boranophospate, $C_3$-$C_6$ alkenyl-boranophospate, $C_3$-$C_5$ alkenyl-boranophospate, $C_3$-$C_4$ alkenyl-boranophospate, or $C_3$ alkenyl-boranophospate.

In some embodiments, $L^4$ is —C(O)NH—$C_1$-$C_{10}$ alkyl-phosphate, —C(O)NH—$C_1$-$C_9$alkyl-phosphate, —C(O)NH—$C_1$-$C_8$alkyl-phosphate, —C(O)NH—$C_1$-$C_7$alkyl-phosphate, —C(O)NH—$C_1$-$C_6$alkyl-phosphate, —C(O)NH—$C_1$-$C_5$alkyl-phosphate, —C(O)NH—$C_1$-$C_4$alkyl-phosphate, —C(O)NH—$C_1$-$C_3$alkyl-phosphate, —C(O)NH—$C_1$-$C_2$alkyl-phosphate, or —C(O)NH—$CH_2$-phosphate.

In some embodiments, $L^4$ is —C(O)NH—$C_3$-$C_{10}$alkenyl-phosphate, —C(O)NH—$C_3$-$C_9$alkenyl-phosphate, —C(O)NH—$C_3$-$C_8$alkenyl-phosphate, —C(O)NH—$C_3$-$C_7$alkenyl-phosphate, —C(O)NH—$C_3$-$C_6$alkenyl-phosphate, —C(O)NH—$C_3$-$C_5$alkenyl-phosphate, —C(O)NH—$C_3$-$C_4$alkenyl-phosphate, or —C(O)NH—$C_3$alkenyl-phosphate.

In some embodiments, $L^4$ is —C(O)O—$C_1$-$C_{10}$ alkyl-phosphate, —C(O)O—$C_1$-$C_9$alkyl-phosphate, —C(O)O—$C_1$-$C_8$alkyl-phosphate, —C(O)O—$C_1$-$C_7$alkyl-phosphate, —C(O)O—$C_1$-$C_6$alkyl-phosphate, —C(O)O—$C_1$-$C_5$ alkyl-phosphate, —C(O)O—$C_1$-$C_4$alkyl-phosphate, —C(O)O—$C_1$-$C_3$alkyl-phosphate, —C(O)O—$C_1$-$C_2$alkyl-phosphate, or —C(O)O—$CH_2$-phosphate.

In some embodiments, $L^4$ is —C(O)O—$C_3$-$C_{10}$alkenyl-phosphate, —C(O)O—$C_3$-$C_9$alkenyl-phosphate, —C(O)O—$C_3$-$C_8$alkenyl-phosphate, —C(O)O—$C_3$-$C_7$alkenyl-phosphate, —C(O)O—$C_3$-$C_6$alkenyl-phosphate, —C(O)

O—C$_3$-C$_5$alkenyl-phosphate, —C(O)O—C$_3$-C$_4$alkenyl-phosphate, or —C(O)O—C$_3$alkenyl-phosphate.

In some embodiments, L$^4$ is —C(O)NH—C$_1$-C$_{10}$ alkyl-phosphorothioate, —C(O)NH—C$_1$-C$_9$ alkyl-phosphorothioate, —C(O)NH—C$_1$-C$_8$ alkyl-phosphorothioate, —C(O)NH—C$_1$-C$_7$alkyl-phosphorothioate, —C(O)NH—C$_1$-C$_6$alkyl-phosphorothioate, —C(O)NH—C$_1$-C$_5$alkyl-phosphorothioate, —C(O)NH—C$_1$-C$_4$alkyl-phosphorothioate, —C(O)NH—C$_1$-C$_3$alkyl-phosphorothioate, —C(O)NH—C$_1$-C$_2$alkyl-phosphorothioate, or —C(O)NH—CH$_2$-phosphorothioate.

In some embodiments, L$^4$ is —C(O)NH—C$_3$-C$_{10}$alkenyl-phosphorothioate, —C(O)NH—C$_3$-C$_9$alkenyl-phosphorothioate, —C(O)NH—C$_3$-C$_8$alkenyl-phosphorothioate, —C(O)NH—C$_3$-C$_7$alkenyl-phosphorothioate, —C(O)NH—C$_3$-C$_6$alkenyl-phosphorothioate, —C(O)NH—C$_3$-C$_5$alkenyl-phosphorothioate, —C(O)NH—C$_3$-C$_4$alkenyl-phosphorothioate, or —C(O)NH—C$_3$alkenyl-phosphorothioate.

In some embodiments, L$^4$ is —C(O)O—C$_1$-C$_{10}$ alkyl-phosphorothioate, —C(O)O—C$_1$-C$_9$alkyl-phosphorothioate, —C(O)O—C$_1$-Cgalkyl-phosphorothioate, —C(O)O—C$_1$-C$_7$alkyl-phosphorothioate, —C(O)O—C$_1$-C$_6$alkyl-phosphorothioate, —C(O)O—C$_1$-C$_5$ alkyl-phosphorothioate, —C(O)O—C$_1$-C$_4$alkyl-phosphorothioate, —C(O)O—C$_1$-C$_3$alkyl-phosphorothioate, —C(O)O—C$_1$-C$_2$alkyl-phosphorothioate, or —C(O)O—CH$_2$-phosphorothioate.

In some embodiments, L$^4$ is —C(O)O—C$_3$-C$_{10}$alkenyl-phosphorothioate, —C(O)O—C$_3$-C$_9$alkenyl-phosphorothioate, —C(O)O—C$_3$-C$_8$alkenyl-phosphorothioate, —C(O)O—C$_3$-C$_7$alkenyl-phosphorothioate, —C(O)O—C$_3$-C$_6$alkenyl-phosphorothioate, —C(O)O—C$_3$-C$_5$alkenyl-phosphorothioate, —C(O)O—C$_3$-C$_4$alkenyl-phosphorothioate, or —C(O)O—C$_3$alkenyl-phosphorothioate.

In some embodiments, L$^4$ is —C(O)—NH—C$_1$-C$_{10}$alkyl-boranophospate, —C(O)—NH—C$_1$-C$_9$alkyl-boranophospate, —C(O)—NH—C$_1$-Cgalkyl-boranophospate, —C(O)—NH—C$_1$-C$_7$alkyl-boranophospate, —C(O)—NH—C$_1$-C$_6$alkyl-boranophospate, —C(O)—NH—C alkyl-boranophospate, —C(O)—NH—C$_1$-C$_4$alkyl-boranophospate, —C(O)—NH—C$_1$-C$_3$alkyl-boranophospate, —C(O)—NH—C$_1$-C$_2$alkyl-boranophospate, or —C(O)—NH—CH$_2$-boranophospate.

In some embodiments, L$^4$ is —C(O)—NH—C$_3$-C$_{10}$alkenyl-boranophospate, —C(O)—NH—C$_3$-C$_9$alkenyl-boranophospate, —C(O)—NH—C$_3$-C$_8$alkenyl-boranophospate, —C(O)—NH—C$_3$-C$_7$alkenyl-boranophospate, —C(O)—NH—C$_3$-C$_6$alkenyl-boranophospate, —C(O)—NH—C$_3$-C$_5$alkenyl-boranophospate, —C(O)—NH—C$_3$-C$_4$alkenyl-boranophospate, or —C(O)—NH—C$_3$alkenyl-boranophospate.

In some embodiments, L$^4$ is —C(O)O—C$_1$-C$_{10}$ alkyl-boranophospate, —C(O)O—C$_1$-C$_9$alkyl-boranophospate, —C(O)O—C$_1$-C$_8$alkyl-boranophospate, —C(O)O—C$_1$-C$_7$alkyl-boranophospate, —C(O)O—C$_1$-C$_6$alkyl-boranophospate, —C(O)O—C$_1$-C$_5$alkyl-boranophospate, —C(O)O—C$_1$-C$_4$alkyl-boranophospate, —C(O)O—C$_1$-C$_3$alkyl-boranophospate, —C(O)O—C$_1$-C$_2$alkyl-boranophospate, or —C(O)O—CH$_2$-boranophospate.

In some embodiments, L$^4$ is —C(O)O—C$_3$-C$_{10}$alkenyl-boranophospate, —C(O)O—C$_3$-C$_9$alkenyl-boranophospate, —C(O)O—C$_3$-C$_8$alkenyl-boranophospate, —C(O)O—C$_3$-C$_7$alkenyl-boranophospate, —C(O)O—C$_3$-C$_6$alkenyl-boranophospate, —C(O)O—C$_3$-C$_5$alkenyl-boranophospate, —C(O)O—C$_3$-C$_4$alkenyl-boranophospate, or —C(O)O—C$_3$alkenyl-boranophospate.

In some embodiments, R$^1$ is selected from the group consisting of pentafluorophenyl, tetrafluorophenyl, succinimide, maleimide, azide, pyridyldithiol, methyl phosphonate, a chiral-methyl phosphonate, a helper lipid, and a nucleic acid. In some embodiments, R$^1$ is an ASO (Antisense Oligonucleotide), a siRNA (Small Interfering RNA), a miRNA (MicroRNA), a microRNA mimic, an AMO (Anti-miRNA Oligonucleotide), a long non-coding RNA, a PNA (Peptide Nucleic Acid), a helper lipid, or a PMO (Phosphorodiamidate Morpholino Oligomer), wherein the nucleic acid is optionally modified. In some embodiments, le is an ASO (Antisense Oligonucleotide). In some embodiments, R$^1$ is a peg-lipid conjugate. In some embodiments, the peg-lipid conjugate is PEG-DMG. In some embodiments, the PEG-DMG is PEG2000-DMG.

In some embodiments, disclosed herein is a compound having the formula:

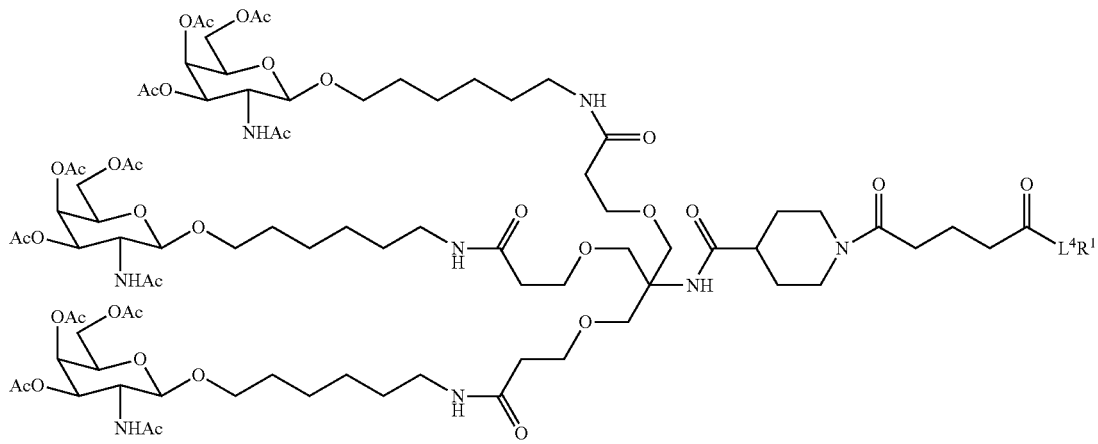

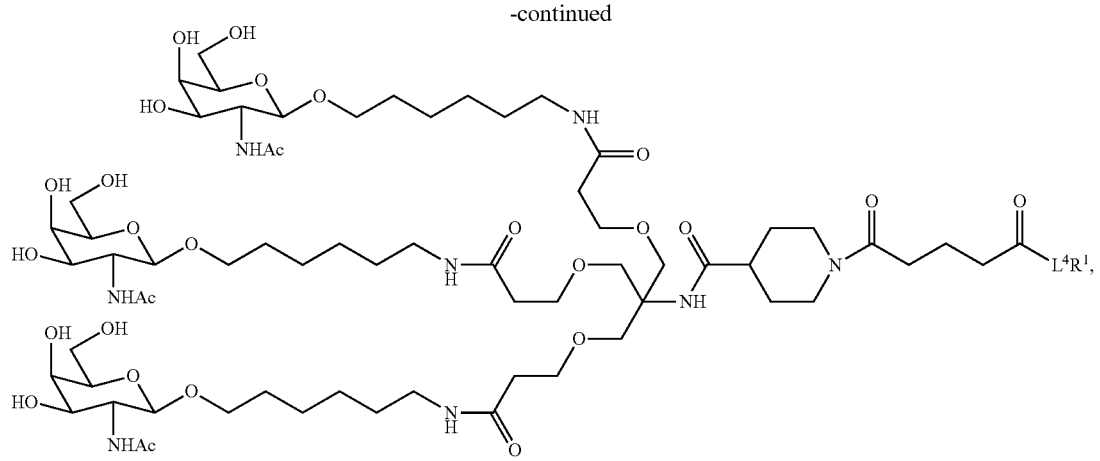

wherein R¹ is an ASO (Antisense Oligonucleotide), a siRNA (Small Interfering RNA), a miRNA (MicroRNA), a microRNA mimic, an AMO (Anti-miRNA Oligonucleotide), a long non-coding RNA, a PNA (Peptide Nucleic Acid), a helper lipid, or a PMO (Phosphorodiamidate Morpholino Oligomer), wherein the nucleic acid is optionally modified.

In some embodiments, the compound of Formula IA is selected from the group consisting of

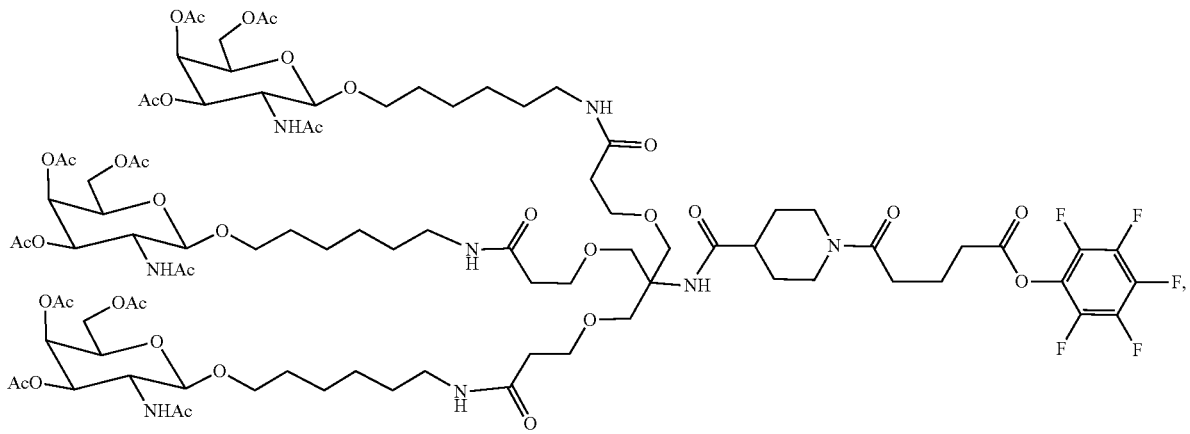

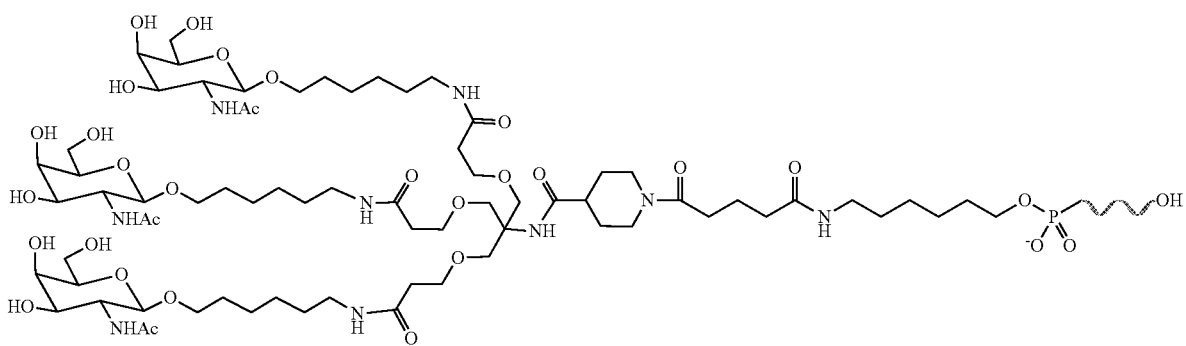

-continued
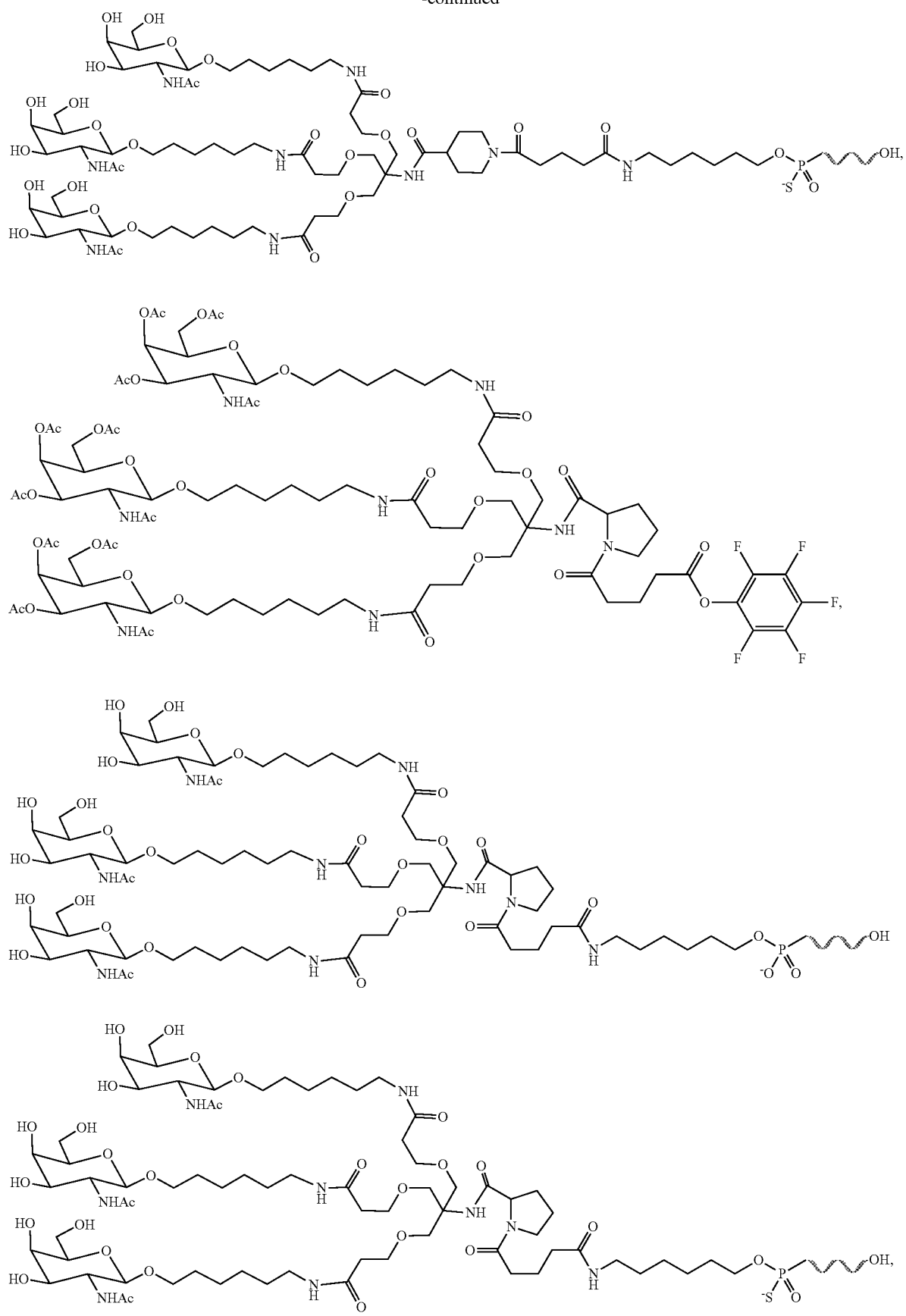

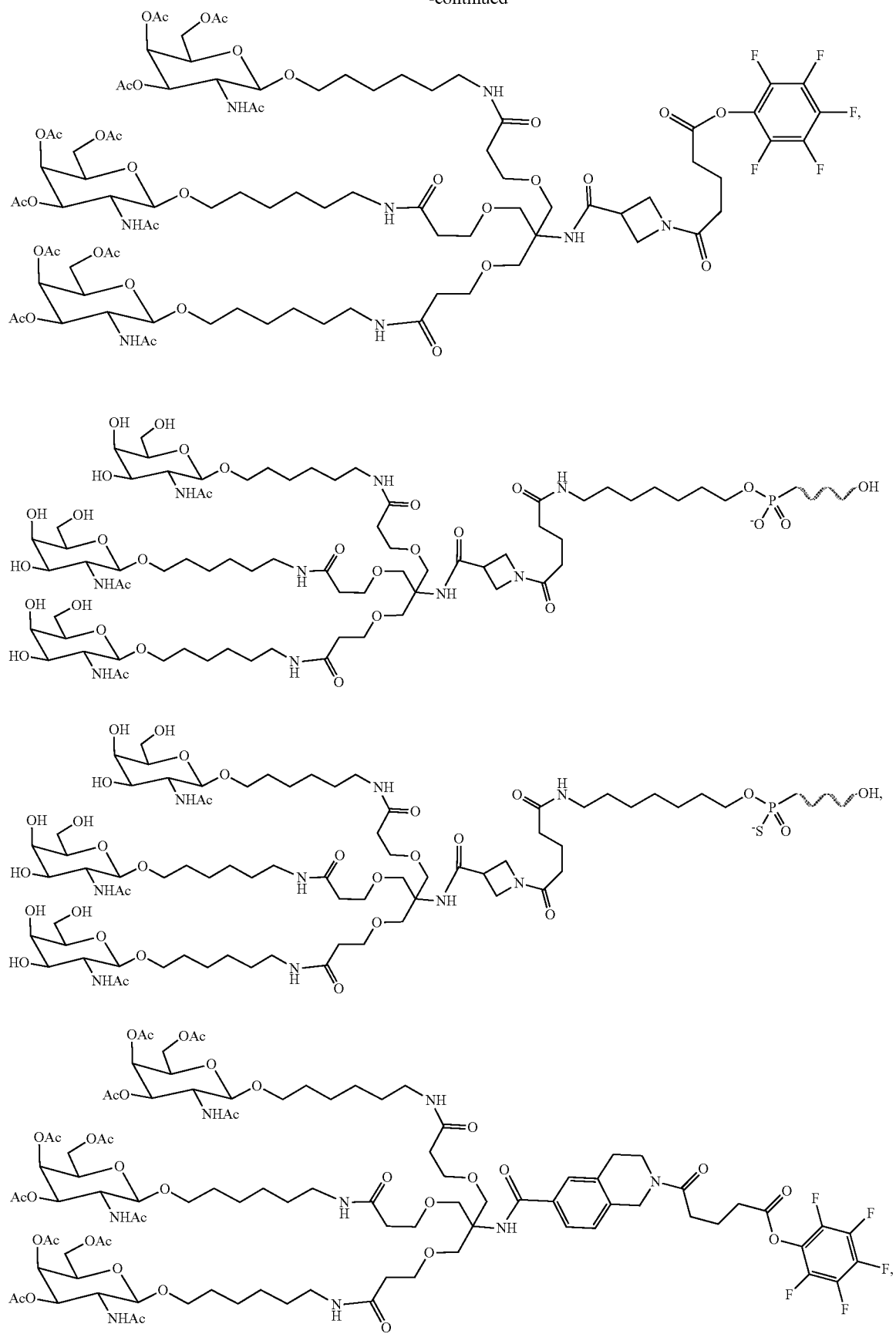

-continued
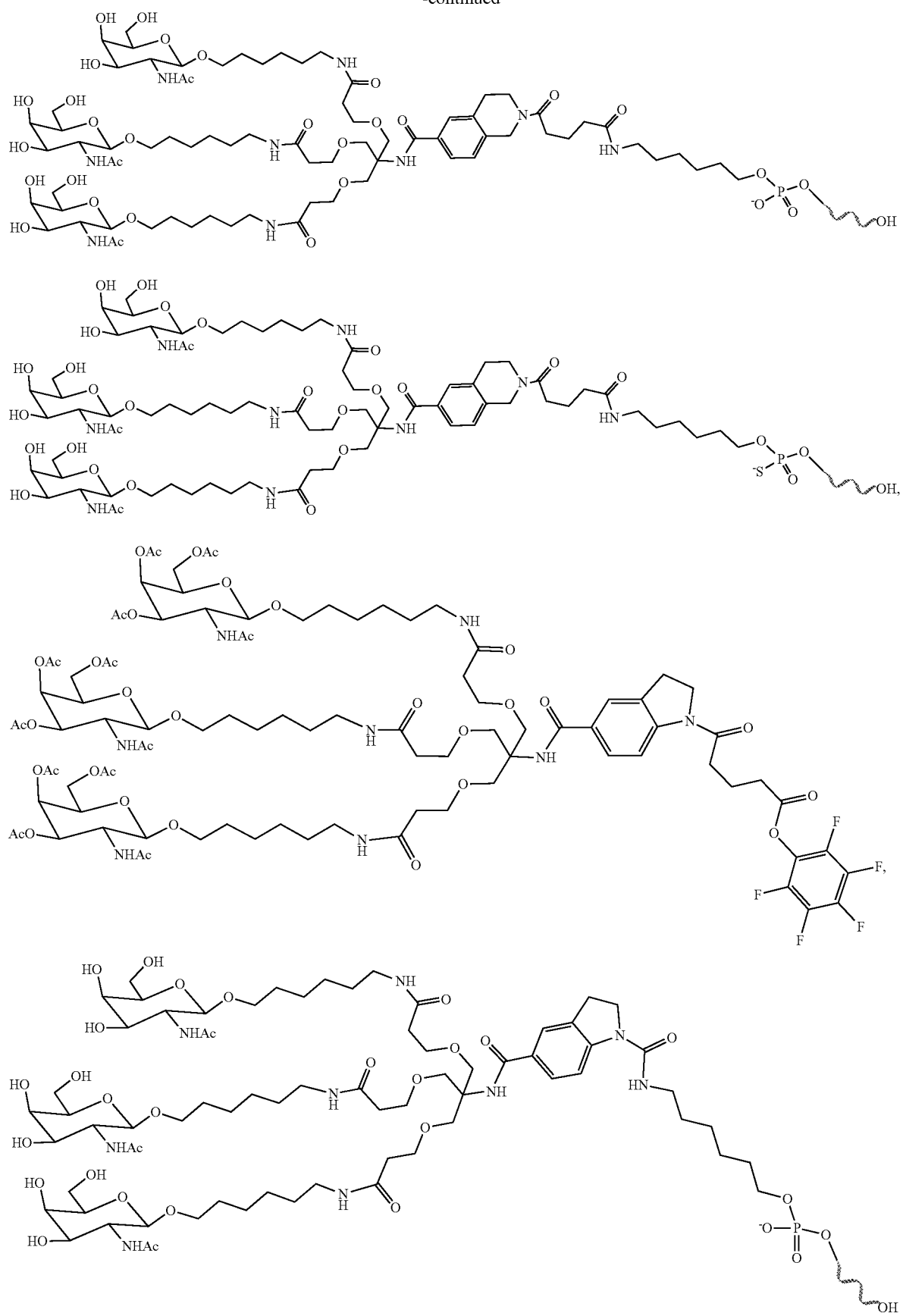

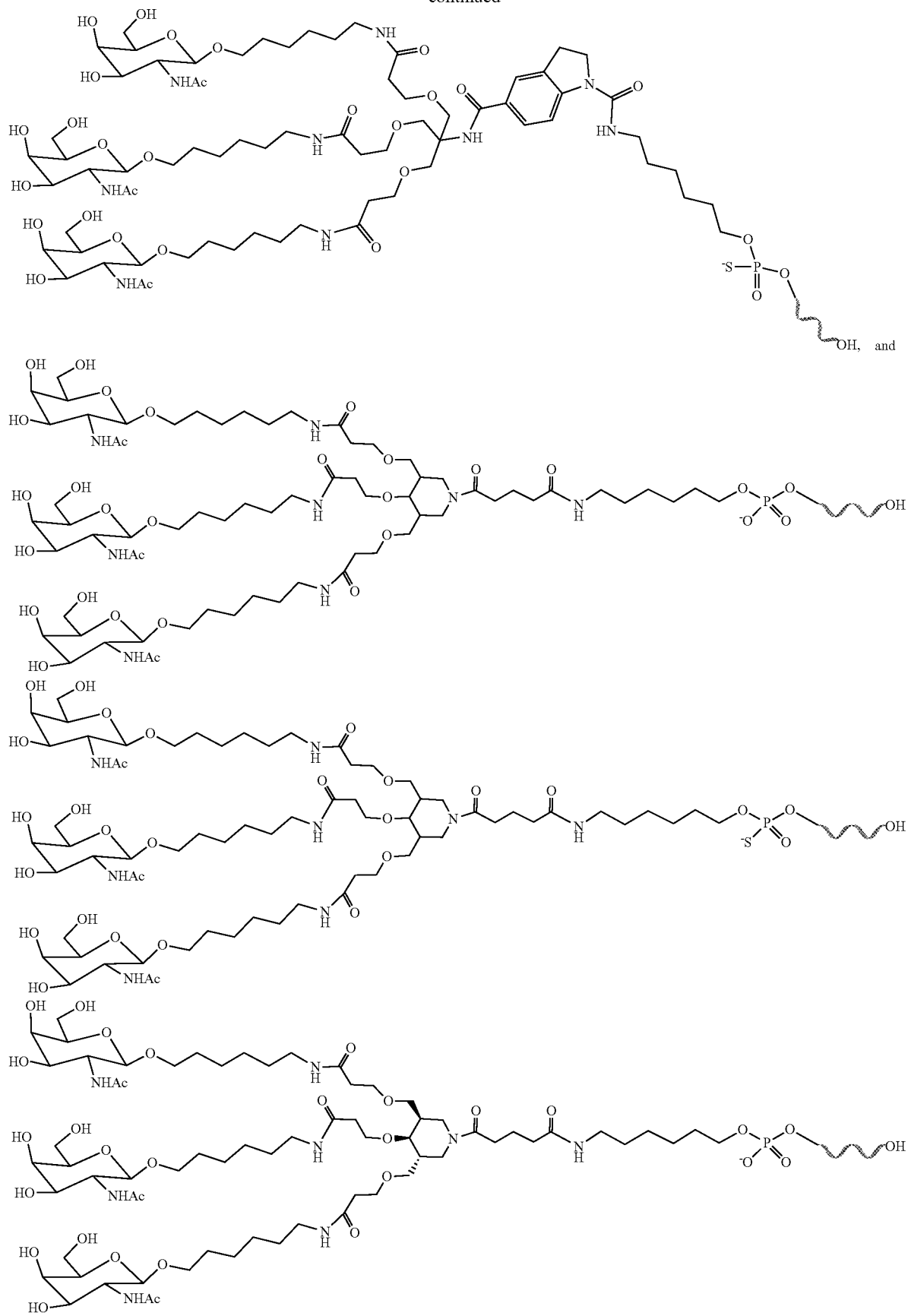

-continued

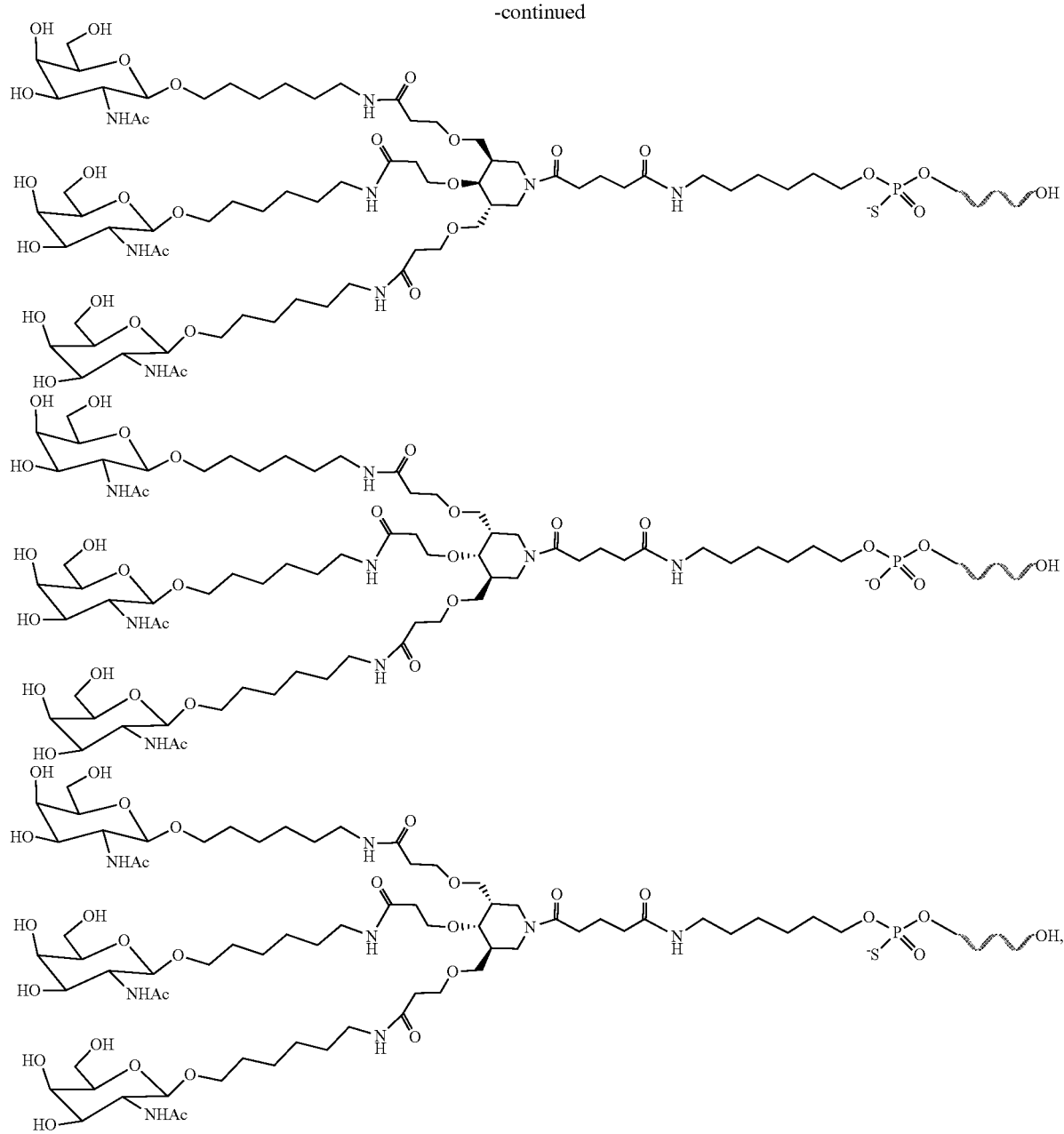

wherein 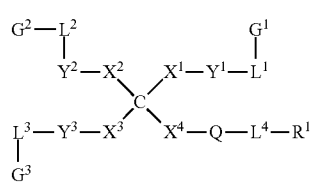 is an oligonucleotide.

In another embodiment, disclosed herein is a compound of Formula IB $$\begin{array}{c} G^2-L^2 \\ \quad | \\ Y^2-X^2 \quad X^1-Y^1-L^1-G^1 \\ \quad \diagdown \diagup \\ \quad C \\ \quad \diagup \diagdown \\ L^3-Y^3-X^3 \quad X^4-Q-L^4-R^1 \\ \quad | \\ G^3 \end{array}$$

IB or a pharmaceutically acceptable salt or solvate thereof, wherein $X^1$, $X^2$ and $X^3$ are each independently selected from the group consisting of $C_1$-$C_{10}$ alkyl, —$(CH_2)_m$—O—$(CH_2)_n$— and —$(CH_2)_m$—$NR^N$—$(CH_2)_n$—, wherein n is 1-36, m is 1-30, and $R^N$ is H, methyl, or $CH_2F$, $CHF_2$, or $CF_3$; $Y^1$, $Y^2$ and $Y^3$ are each independently selected from the group consisting of —NHC(O)—, —C(O)NH—, —OC(O)—, —C(O)O—, —SC(O)—, —C(O)S— and P(Z)(OH)$O_2$, wherein Z is O or S; $L^1$, $L^2$ and $L^3$ are each independently selected from the group consisting of a $C_1$-$C_{10}$ alkyl, —$(CH_2)_e$—O—$(CH_2)_f$—, —$(CH_2)_e$—S—$(CH_2)_f$—, —$(CH_2)_e$—$S(O)_2$—$(CH_2)_f$—, —$(CH_2)_e$—$NR^N$—$(CH_2)_f$— and —$(CH_2$—$CH_2$—$O)_k(CH_2)_2$—, wherein e is 1-10; f is 1-16, k is 1-20, and $R^N$ is H, methyl, or $CH_2F$, $CHF_2$, or $CF_3$; $G^1$, $G^2$ and $G^3$ are each independently selected from the group consisting of a monosaccharide, a monosaccharide derivative, a vitamin, a polyol, a polysialic acid and a polysialic acid derivative; $X^4$ is selected from the group consisting of (a) —$(CH_2)_g$—O—$(CH_2)_h$— or —$(CH_2)_g$—$NR^N$—$(CH_2)_h$—, wherein g is 1-30, h is 1-36, and $R^N$ is H, methyl, or $CH_2F$, $CHF_2$, or $CF_3$, (b) an amino acid, and (c) —NHC(O)$R^2$, wherein $R^2$ is $C_1$-$C_{10}$ alkyl, a carbocycle, a heterocyclyl, a heteroaryl, a $C_1$-$C_{10}$ alkyl-carbocycle, a $C_1$-$C_{10}$ alkyl-heterocyclyl or a $C_1$-$C_{10}$ alkyl-heteroaryl, and wherein $R^2$ is optionally substituted; Q is alkylamino, —C(O)—$(CH_2)_i$—, —$(CH_2)_i$—O—$(CH_2)_j$—, —$(CH_2)_i$—$NR^3$—$(CH_2)_j$—, —$(CH_2)_i$—S—S—$(CH_2)_j$—, —$(CH_2)_i$—S—$(CH_2)_j$—, —$(CH_2)_i$—S(O)$_2$—$(CH_2)_j$—, —$(CH_2)_i$—NHC(O)—$(CH_2)_j$—, —$(CH_2)_i$—C(O)NH—$(CH_2)_j$—, —$(CH_2)_i$—SC(O)—$(CH_2)_j$—, —$(CH_2)_i$—C(O)S—$(CH_2)_j$—, or

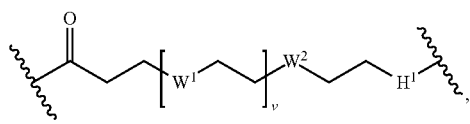

B wherein EV is a carbocycle, a heterocyclyl or a heteroaryl; EV is optionally substituted; i is 1-30 and j is 1-36; $R^3$ is hydrogen or an alkyl; $W^1$ and $W^2$ are each independently selected from —$CH_2$— and O; v is 1-6; Y is hydrogen or methyl; and T is $C_1$-$C_{10}$ alkyl or $C_2$-$C_{10}$ alkenyl; $L^4$ is —C(O)O—, —C(O)NH—, a phosphate, $C_1$-$C_{10}$ alkyl-phosphate, $C_3$-$C_{10}$ alkenyl-phosphate, a phosphorothioate, alkyl-phosphorothioate, $C_3$-$C_{10}$ alkenyl-phosphorothioate, a boranophospate, a $C_1$-$C_{10}$ alkyl-boranophospate, a $C_3$-$C_{10}$ alkenyl-boranophospate, —C(O)NH—$C_1$-$C_{10}$ alkyl-phosphate, —C(O)NH—$C_3$-$C_{10}$alkenyl-phosphate, —C(O)O—$C_1$-$C_{10}$ alkyl-phosphate, —C(O)O—$C_3$-$C_{10}$alkenyl-phosphate, —C(O)NH—$C_1$-$C_{10}$ alkyl-phosphorothioate, —C(O)NH—$C_3$-$C_{10}$alkenyl-phosphorothioate, —C(O)O—$C_1$-$C_{10}$alkyl-phosphorothioate, —C(O)O—$C_3$-$C_{10}$alkenyl-phosphorothioate, —C(O)—NH—$C_1$-$C_{10}$alkyl-boranophospate, —C(O)—NH—$C_3$-$C_{10}$alkenyl-boranophospate, —C(O)O—$C_1$-$C_{10}$alkyl-boranophospate or —C(O)O—$C_3$-$C_{10}$alkenyl-boranophospate; and $R^1$ is a biologically active molecule.

In some embodiments, $W^1$ and $W^2$ are each independently selected from —$CH_2$— and O, wherein v is 1-6, 1-5, 1-4, 1-3, 1-2 or —$CH_2$—.

In some embodiments, T is $C_1$-$C_{10}$ alkyl $C_1$-$C_9$ alkyl $C_1$-$C_6$ alkyl, $C_1$-$C_5$ alkyl, $C_1$-$C_4$ alkyl, $C_1$-$C_3$ alkyl, $C_1$-$C_2$ alkyl or —$CH_2$—. In some embodiments, T is $C_2$-$C_{10}$ alkenyl, $C_2$-$C_9$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl or —CH=CH—.

In some embodiments, $X^1$, $X^2$ and $X^3$ are each independently selected from the group consisting of $C_1$-$C_{10}$ alkyl, —$(CH_2)_m$—O—$(CH_2)_n$— and —$(CH_2)_m$—$NR^N$—$(CH_2)_n$—, wherein n is 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 and 1. In some embodiments, $X^1$, $X^2$ and $X^3$ are each independently selected from the group consisting of $C_1$-$C_{10}$alkyl, —$(CH_2)_m$—O—$(CH_2)_n$— and —$(CH_2)_m$—$NR^N$—$(CH_2)_n$—, wherein m is 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 and 1. In some embodiments, $X^1$, $X^2$ and $X^3$ are each independently —$(CH_2)_m$—O—$CH_2$—, wherein m is 1-4. In some embodiments, $X^1$, $X^2$ and $X^3$ are each independently —$(CH_2)_2$—O—$CH_2$—. In some embodiments, $X^1$, $X^2$ and $X^3$ are each independently are each $C_1$-$C_{10}$ alkyl, $C_1$-$C_9$ alkyl, $C_1$-$C_8$ alkyl, $C_1$-$C_7$alkyl, $C_1$-$C_6$ alkyl, $C_1$-$C_5$ alkyl, $C_1$-$C_4$ alkyl, $C_1$-$C_3$ alkyl, $C_1$-$C_2$ alkyl or —$CH_2$—.

In some embodiments, $Y^1$, $Y^2$ and $Y^3$ are each —NHC(O)— or —C(O)NH—. In some embodiments, $Y^1$, $Y^2$ and $Y^3$ are each —NHC(O)—.

In some embodiments, $L^1$, $L^2$ and $L^3$ are each $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl or —$CH_2$—. In some embodiments, $L^1$, $L^2$ and $L^3$ are each independently $C_3$-$C_8$ alkyl or —$(CH_2$—$CH_2$—O)_k(CH_2)_2$—, wherein k is 1-10. In some embodiments, $L^1$, $L^2$ and $L^3$ are each independently —$(CH_2$—$CH_2$—O)_k(CH_2)_2$—, wherein k is 2-4. In some embodiments, $L^1$, $L^2$ and $L^3$ are each independently —$(CH_2$—$CH_2$—O)_k(CH_2)_2$—, wherein k is 1-10, 1-9, 1-8, 1-7, 1-6, 1-5, 1-4, 1-3, 1-2 or 1. In some embodiments, $L^1$, $L^2$ and $L^3$ are each independently —$(CH_2$—$CH_2$—O)(CH_2)_2$—.

In some embodiments, $G^1$, $G^2$ and $G^3$ are each independently selected from the group consisting of folic acid, ribose, retinol, niacin, riboflavin, biotin, glucose, mannose, fucose, sucrose, lactose, mannose-6-phosphate, N-acetyl galactosamine, N-acetylglucosamine, a sialic acid, a sialic acid derivative, allose, altrose, arabinose, cladinose, erythrose, erythrulose, fructose, fucitol, fucosamine, fucose, fuculose, galactosamine, galactosaminitol, galactose, glucosamine, glucosaminitol, glucose-6 phosphate, gulose glyceraldehyde, glycero-mannoseptose, glycerol, glycerone, gulose, idose, lyxose, mannosamine, psicose, quinovose, quinovosamine, rhamnitol, rhamnosamine, rhamnose, ribulose, sedoheptulose, sorbose, tagatose, talose, threose, xylose and xylulose. In some embodiments, $G^2$ and $G^3$ are each N-acetylgalactosamine.

In some embodiments, $X^4$ is selected from the group consisting of

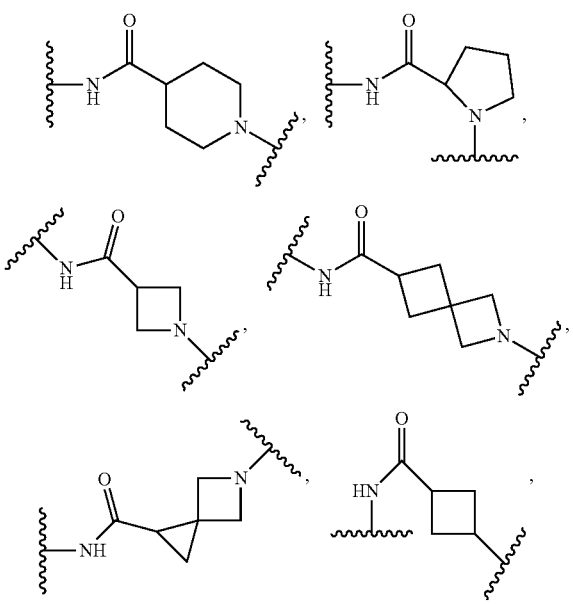

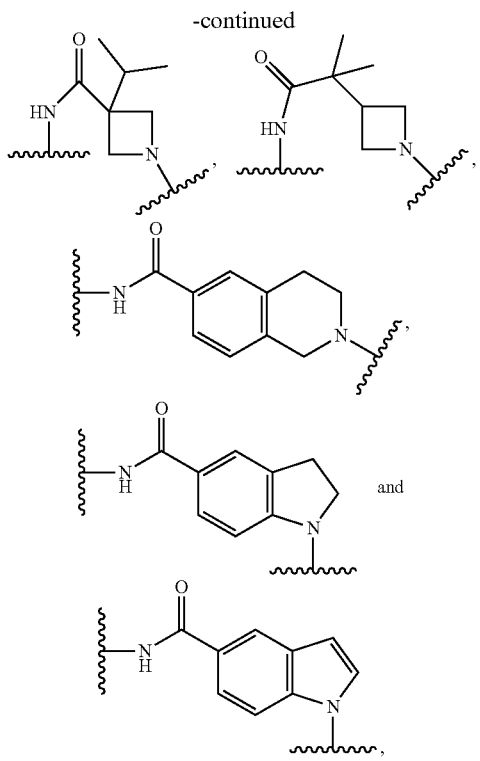

wherein X[4] is optionally substituted.

In some embodiments, X[4] is —NHC(O)R[2], wherein R[2] is a carbocycle, a heterocyclyl or a heteroaryl, wherein R[2] is optionally substituted. In some embodiments, X[4] is —NHC(O)R[2], wherein R[2] is a carbocycle, a heterocyclyl or a heteroaryl, wherein R[2] is optionally substituted with alkyl, alkoxy or amine.

In some embodiments, X[4] is

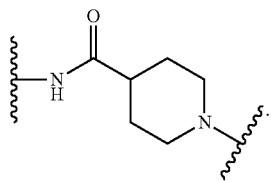

In some embodiments, Q is alkylamino, —C(O)—(CH$_2$)$_i$—, —(CH$_2$)$_i$—O—(CH$_2$)$_j$—, —(CH$_2$)$_i$—NR$^3$—(CH$_2$)$_j$—, —(CH$_2$)$_i$—S—S—(CH$_2$)$_j$—, —(CH$_2$)$_i$—S—(CH$_2$)$_j$—, —(CH$_2$)$_i$—S(O)$_2$—(CH$_2$)$_j$—, —(CH$_2$)$_i$—NHC(O)—(CH$_2$)$_j$—, —(CH$_2$)$_i$—C(O)NH—(CH$_2$)$_j$—, —(CH$_2$)$_i$—SC(O)—(CH$_2$)$_j$—, or —(CH$_2$)$_i$—C(O)S—(CH$_2$)$_j$—, wherein i is 1-10 and j is 1-10, and wherein R[3] is hydrogen or an alkyl. In some embodiments, Q is alkylamino, —C(O)—(CH$_2$)$_i$—, —(CH$_2$)$_i$—O—(CH$_2$)$_j$—, —(CH$_2$)$_i$—NR$^3$—(CH$_2$)$_j$—, —(CH$_2$)$_i$—S—S—(CH$_2$)$_j$—, —(CH$_2$)$_i$—S—(CH$_2$)$_j$—, —(CH$_2$)$_i$—S(O)$_2$—(CH$_2$)$_j$—, —(CH$_2$)$_i$—NHC(O)—(CH$_2$)$_j$—, —(CH$_2$)$_i$—C(O)NH—(CH$_2$)$_j$—, —(CH$_2$)$_i$—SC(O)—(CH$_2$)$_j$—, or —(CH$_2$)$_i$—C(O)S—(CH$_2$)$_j$—, wherein i is 1-10 and j is 1-10; i is 1-9 and j is 1-9; i is 1-8 and j is 1-8; i is 1-7 and j is 1-7; i is 1-6 and j is 1-6; i is 1-5 and j is 1-5; i is 1-5 and j is 1-4; i is 1-3 and j is 1-3; i is 1-2 and j is 1-2; or i is 1 and j is 1.

In some embodiments, L[4] is —C(O)O—, —C(O)NH—, a phosphate, $C_1$-$C_{10}$ alkyl-phosphate, $C_3$-$C_{10}$ alkenyl-phosphate, a phosphorothioate, $C_1$-$C_{10}$ alkyl-phosphorothioate, $C_3$-$C_{10}$ alkenyl-phosphorothioate, a boranophospate, a $C_1$-$C_{10}$ alkyl-boranophospate, a $C_3$-$C_{10}$ alkenyl-boranophospate, —C(O)NH—$C_1$-$C_{10}$ alkyl-phosphate, —C(O)NH—$C_3$-$C_{10}$alkenyl-phosphate, —C(O)O—$C_1$-$C_{10}$ alkyl-phosphate, —C(O)O—$C_3$-$C_{10}$ alkenyl-phosphate, —C(O)NH—$C_1$-$C_{10}$ alkyl-phosphorothioate, —C(O)NH—$C_3$-$C_{10}$alkenyl-phosphorothioate, —C(O)O—$C_1$-$C_{10}$ alkyl-phosphorothioate, —C(O)O—$C_3$-$C_{10}$alkenyl-phosphorothioate, —C(O)—NH—$C_1$-$C_{10}$ alkyl-boranophospate, —C(O)—NH—$C_3$-$C_{10}$alkenyl-boranophospate, —C(O)O—$C_1$-$C_{10}$ alkyl-boranophospate or —C(O)O—$C_3$-$C_{10}$alkenyl-boranophospate.

In some embodiments, L[4] is $C_1$-$C_{20}$ alkyl-phosphate, $C_1$-$C_{19}$ alkyl-phosphate, $C_{18}$ alkyl-phosphate, $C_1$-$C_{17}$ alkyl-phosphate, $C_1$-$C_{16}$ alkyl-phosphate, $C_1$-$C_{15}$ alkyl-phosphate, $C_1$-$C_{14}$ alkyl-phosphate, $C_1$-$C_{13}$ alkyl-phosphate, $C_1$-$C_{12}$ alkyl-phosphate, $C_1$-$C_{11}$ alkyl-phosphate, $C_1$-$C_{10}$ alkyl-phosphate, $C_1$-$C_9$ alkyl-phosphate, $C_1$-$C_8$ alkyl-phosphate, $C_1$-$C_7$ alkyl-phosphate, $C_1$-$C_6$ alkyl-phosphate, $C_1$-$C_5$ alkyl-phosphate, $C_1$-$C_4$ alkyl-phosphate, $C_1$-$C_3$ alkyl-phosphate, $C_1$-$C_2$ alkyl-phosphate or —CH$_2$-phosphate. In some embodiments, L[4] is $C_1$-$C_{20}$ alkyl-phosphorothioate, $C_1$-$C_{19}$ alkyl-phosphorothioate, $C_1$-$C_{18}$ alkyl-phosphorothioate, $C_1$-$C_{17}$ alkyl-phosphorothioate, $C_1$-$C_{16}$ alkyl-phosphorothioate, $C_1$-$C_{15}$ alkyl-phosphorothioate, $C_1$-$C_{14}$ alkyl-phosphorothioate, $C_1$-$C_{13}$ alkyl-phosphorothioate, $C_1$-$C_{12}$ alkyl-phosphorothioate, $C_1$-$C_{11}$ alkyl-phosphorothioate, $C_1$-$C_{10}$ alkyl-phosphorothioate, $C_1$-$C_9$ alkyl-phosphorothioate, $C_1$-$C_8$ alkyl-phosphorothioate, $C_1$-$C_7$ alkyl-phosphorothioate, $C_1$-$C_6$ alkyl-phosphorothioate, $C_1$-$C_5$ alkyl-phosphorothioate, $C_1$-$C_4$ alkyl-phosphorothioate, $C_1$-$C_3$ alkyl-phosphorothioate, $C_1$-$C_2$ alkyl-phosphorothioate or —CH$_2$-phosphorothioate. In some embodiments, L[4] is $C_1$-$C_{20}$ alkyl-boranophospate, $C_1$-$C_{19}$ alkyl-boranophospate, $C_1$-$C_{18}$ alkyl-boranophospate, $C_1$-$C_{17}$ alkyl-boranophospate, $C_1$-$C_{16}$ alkyl-boranophospate, $C_1$-$C_{15}$ alkyl-boranophospate, $C_1$-$C_{14}$ alkyl-boranophospate, $C_1$-$C_{13}$ alkyl-boranophospate, $C_1$-$C_{12}$ alkyl-boranophospate, $C_1$-$C_{11}$ alkyl-boranophospate, $C_1$-$C_{10}$ alkyl-boranophospate, $C_1$-$C_9$ alkyl-boranophospate, $C_1$-$C_8$ alkyl-boranophospate, $C_1$-$C_7$ alkyl-boranophospate, $C_1$-$C_6$ alkyl-boranophospate, $C_1$-$C_5$ alkyl-boranophospate, $C_1$-$C_4$ alkyl-boranophospate, $C_1$-$C_3$ alkyl-boranophospate, $C_1$-$C_2$ alkyl-boranophospate or —CH$_2$-boranophospate.

In some embodiments, L[4] is $C_3$-$C_{20}$ alkenyl-phosphate, $C_3$-$C_{19}$ alkenyl-phosphate, $C_3$-$C_{18}$ alkenyl-phosphate, $C_3$-$C_{17}$ alkenyl-phosphate, $C_3$-$C_{16}$ alkenyl-phosphate, $C_3$-$C_{15}$ alkenyl-phosphate, $C_3$-$C_{14}$ alkenyl-phosphate, $C_3$-$C_{13}$ alkenyl-phosphate, $C_3$-$C_{12}$ alkenyl-phosphate, $C_3$-$C_{11}$ alkenyl-phosphate, $C_3$-$C_{10}$ alkenyl-phosphate, $C_3$-$C_9$ alkenyl-phosphate, $C_3$-$C_8$ alkenyl-phosphate, $C_3$-$C_7$ alkenyl-phosphate, $C_3$-$C_6$ alkenyl-phosphate, $C_3$-$C_5$ alkenyl-phosphate, $C_3$-$C_4$ alkenyl-phosphate, or $C_3$ alkenyl-phosphate. In some embodiments, L[4] is $C_3$-$C_{20}$ alkenyl-phosphorothioate, $C_3$-$C_{19}$ alkenyl-phosphorothioate, $C_3$-$C_{18}$ alkenyl-phosphorothioate, $C_3$-$C_{17}$ alkenyl-phosphorothioate, $C_3$-$C_{16}$ alkenyl-phosphorothioate, $C_3$-$C_{15}$ alkenyl-phosphorothioate, $C_3$-$C_{14}$ alkenyl-phosphorothioate, $C_3$-$C_{13}$ alkenyl-phosphorothioate, $C_3$-$C_{12}$ alkenyl-phosphorothioate, $C_3$-$C_{11}$ alkenyl-phosphorothioate, $C_3$-$C_{10}$ alkenyl-phosphorothioate, $C_3$-$C_9$ alkenyl-phosphorothioate, $C_3$-$C_8$ alkenyl-phosphorothioate, $C_3$-$C_7$ alkenyl-phosphorothioate, $C_3$-$C_6$ alkenyl-phosphorothioate, $C_3$-$C_5$ alkenyl-phosphorothioate, $C_3$-$C_4$ alkenyl-phosphorothioate, or $C_3$ alkenyl-phosphorothioate. In some embodiments, L[4] is $C_3$-$C_{20}$ alkenyl-boranophospate, $C_3$-$C_{19}$ alkenyl-boranophospate, $C_3$-$C_{18}$ alkenyl-boranophospate, C₃-C₁₇ alkenyl-boranophospate, C₃-C₁₆ alkenyl-boranophospate, C₃-C₁₅ alkenyl-boranophospate, C₃-C₁₄ alkenyl-boranophospate, C₃-C₁₃ alkenyl-boranophospate, C₃-C₁₂ alkenyl-boranophospate, C₃-C₁₁ alkenyl-boranophospate, C₃-C₁₀ alkenyl-boranophospate, C₃-C₉ alkenyl-boranophospate, C₃-C₈ alkenyl-boranophospate, C₃-C₇ alkenyl-boranophospate, C₃-C₆ alkenyl-boranophospate, C₃-C₅ alkenyl-boranophospate, C₃-C₄ alkenyl-boranophospate, or C₃ alkenyl-boranophospate.

In some embodiments, L⁴ is —C(O)NH—C₁-C₁₀ alkyl-phosphate, —C(O)NH—C₁-C₉alkyl-phosphate, —C(O)NH—C₁-C₈alkyl-phosphate, —C(O)NH—C₁-C₇alkyl-phosphate, —C(O)NH—C₁-C₆alkyl-phosphate, —C(O)NH—C₁-C₅alkyl-phosphate, —C(O)NH—C₁-C₄alkyl-phosphate, —C(O)NH—C₁-C₃alkyl-phosphate, —C(O)NH—C₁-C₂alkyl-phosphate, or —C(O)NH—CH₂-phosphate.

In some embodiments, L⁴ is —C(O)NH—C₃-C₁₀alkenyl-phosphate, —C(O)NH—C₃-C₉alkenyl-phosphate, —C(O)NH—C₃-C₈alkenyl-phosphate, —C(O)NH—C₃-C₇alkenyl-phosphate, —C(O)NH—C₃-C₆alkenyl-phosphate, —C(O)NH—C₃-C₅alkenyl-phosphate, —C(O)NH—C₃-C₄alkenyl-phosphate, or —C(O)NH—C₃alkenyl-phosphate.

In some embodiments, L⁴ is —C(O)O—C₁-C₁₀ alkyl-phosphate, —C(O)O—C₁-C₉alkyl-phosphate, —C(O)O—C₁-C₈alkyl-phosphate, —C(O)O—C₁-C₇alkyl-phosphate, —C(O)O—C₁-C₆alkyl-phosphate, —C(O)O—C₁-C₅alkyl-phosphate, —C(O)O—C₁-C₄alkyl-phosphate, —C(O)O—C₁-C₃alkyl-phosphate, —C(O)O—C₁-C₂alkyl-phosphate, or —C(O)O—CH₂-phosphate.

In some embodiments, L⁴ is —C(O)O—C₃-C₁₀alkenyl-phosphate, —C(O)O—C₃-C₉alkenyl-phosphate, —C(O)O—C₃-C₈alkenyl-phosphate, —C(O)O—C₃-C₇alkenyl-phosphate, —C(O)O—C₃-C₆alkenyl-phosphate, —C(O)O—C₃-C₅alkenyl-phosphate, —C(O)O—C₃-C₄alkenyl-phosphate, or —C(O)O—C₃alkenyl-phosphate.

In some embodiments, L⁴ is —C(O)NH—C₁-C₁₀ alkyl-phosphorothioate, —C(O)NH—C₁-C₉alkyl-phosphorothioate, —C(O)NH—C₁-C₈alkyl-phosphorothioate, —C(O)NH—C₁-C₇alkyl-phosphorothioate, —C(O)NH—C₁-C₆alkyl-phosphorothioate, —C(O)NH—C₁-C₅alkyl-phosphorothioate, —C(O)NH—C₁-C₄alkyl-phosphorothioate, —C(O)NH—C₁-C₃alkyl-phosphorothioate, —C(O)NH—C₁-C₂alkyl-phosphorothioate, or —C(O)NH—CH₂-phosphorothioate.

In some embodiments, L⁴ is —C(O)NH—C₃-C₁₀alkenyl-phosphorothioate, —C(O)NH—C₃-C₉alkenyl-phosphorothioate, —C(O)NH—C₃-C₈alkenyl-phosphorothioate, —C(O)NH—C₃-C₇alkenyl-phosphorothioate, —C(O)NH—C₃-C₆alkenyl-phosphorothioate, —C(O)NH—C₃-C₅alkenyl-phosphorothioate, —C(O)NH—C₃-C₄alkenyl-phosphorothioate, or —C(O)NH—C₃alkenyl-phosphorothioate.

In some embodiments, L⁴ is —C(O)O—C₁-C₁₀ alkyl-phosphorothioate, —C(O)O—C₁-C₉alkyl-phosphorothioate, —C(O)O—C₁-C₈alkyl-phosphorothioate, —C(O)O—C₁-C₇alkyl-phosphorothioate, —C(O)O—C₁-C₆alkyl-phosphorothioate, —C(O)O—C₁-C₅alkyl-phosphorothioate, —C(O)O—C₁-C₄alkyl-phosphorothioate, —C(O)O—C₁-C₃alkyl-phosphorothioate, —C(O)O—C₁-C₂alkyl-phosphorothioate, or —C(O)O—CH₂-phosphorothioate.

In some embodiments, L⁴ is —C(O)O—C₃-C₁₀alkenyl-phosphorothioate, —C(O)O—C₃-C₉alkenyl-phosphorothioate, —C(O)O—C₃-C₈alkenyl-phosphorothioate, —C(O)O—C₃-C₇alkenyl-phosphorothioate, —C(O)O—C₃-C₆alkenyl-phosphorothioate, —C(O)O—C₃-C₅alkenyl-phosphorothioate, —C(O)O—C₃-C₄alkenyl-phosphorothioate, or —C(O)O—C₃alkenyl-phosphorothioate.

In some embodiments, L⁴ is —C(O)—NH—C₁-C₁₀ alkyl-boranophospate, —C(O)—NH—C₁-C₉alkyl-boranophospate, —C(O)—NH—C₁-Cgalkyl-boranophospate, —C(O)—NH—C₁-C₇alkyl-boranophospate, —C(O)—NH—C₁-C₆alkyl-boranophospate, —C(O)—NH—C oranophosp ate, —C(O)—NH—C₁-C₄alkyl-boranophospate, —C(O)—NH—C₁-C₃alkyl-boranophospate, —C(O)—NH—C₁-C₂alkyl-boranophospate, or —C(O)—NH—CH₂-boranophospate.

In some embodiments, L⁴ is —C(O)—NH—C₃-C₁₀alkenyl-boranophospate, —C(O)—NH—C₃-C₉alkenyl-boranophospate, —C(O)—NH—C₃-C₈alkenyl-boranophospate, —C(O)—NH—C₃-C₇alkenyl-boranophospate, —C(O)—NH—C₃-C₆alkenyl-boranophospate, —C(O)—NH—C₃-C₅alkenyl-boranophospate, —C(O)—NH—C₃-C₄alkenyl-boranophospate, or —C(O)—NH—C₃alkenyl-boranophospate.

In some embodiments, L⁴ is —C(O)O—C₁-C₁₀ alkyl-boranophospate, —C(O)O—C₁-C₉alkyl-boranophospate, —C(O)O—C₁-C₈alkyl-boranophospate, —C(O)O—C₁-C₇alkyl-boranophospate, —C(O)O—C₁-C₆alkyl-boranophospate, —C(O)O—C₅alkyl-boranophospate, —C(O)O—C₁-C₄alkyl-boranophospate, —C(O)O—C₁-C₃alkyl-boranophospate, —C(O)O—C₁-C₂alkyl-boranophospate, or —C(O)O—CH₂-boranophospate.

In some embodiments, L⁴ is —C(O)O—C₃-C₁₀alkenyl-boranophospate, —C(O)O—C₃-C₉alkenyl-boranophospate, —C(O)O—C₃-C₈alkenyl-boranophospate, —C(O)O—C₃-C₇alkenyl-boranophospate, —C(O)O—C₃-C₆alkenyl-boranophospate, —C(O)O—C₃-C₅alkenyl-boranophospate, —C(O)O—C₃-C₄alkenyl-boranophospate, or —C(O)O—C₃alkenyl-boranophospate.

In some embodiments, R¹ is selected from the group consisting of pentafluorophenyl, tetrafluorophenyl, succinimide, maleimide, azide, pyridyldithiol, methyl phosphonate, a chiral-methyl phosphonate, a helper lipid, and a nucleic acid. In some embodiments, R¹ is an ASO (Antisense Oligonucleotide), a siRNA (Small Interfering RNA), a miRNA (MicroRNA), a microRNA mimic, an AMO (Anti-miRNA Oligonucleotide), a long non-coding RNA, a PNA (Peptide Nucleic Acid), a helper lipid, or a PMO (Phosphorodiamidate Morpholino Oligomer), wherein the nucleic acid is optionally modified. In some embodiments, R¹ is an ASO (Antisense Oligonucleotide).

In another embodiment, disclosed herein is a compound of Formula IC

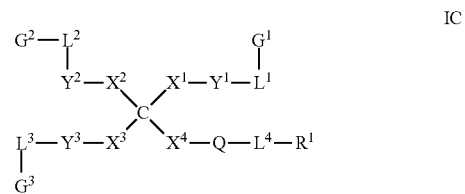

IC or a pharmaceutically acceptable salt or solvate thereof, wherein $X^1$, $X^2$ and $X^3$ are each independently selected from the group consisting of $C_1$-$C_{10}$ alkyl, —$(CH_2)_m$—O—$(CH_2)_n$— and —$(CH_2)_m$—$NR^N$—$(CH_2)_n$—, wherein n is 1-36, m is 1-30, and $R^N$ is H, methyl, or $CH_2F$, $CHF_2$, or $CF_3$; $Y^1$, $Y^2$ and $Y^3$ are each independently selected from the group consisting of —NHC(O)—, —C(O)NH—, —OC(O)—, —C(O)O—, —SC(O)—, —C(O)S— and P(Z)(OH)

$O_2$, wherein Z is O or S; $L^1$, $L^2$ and $L^3$ are each independently selected from the group consisting of a $C_1$-$C_{10}$ alkyl, —$(CH_2)_e$—O—$(CH_2)_f$—, —$(CH_2)_e$—S—$(CH_2)_f$—, —$(CH_2)_e$—S(O)$_2$—$(CH_2)_f$—, —$(CH_2)_e$—$NR^N$—$(CH_2)_f$— and —$(CH_2$—$CH_2$—O$)_k(CH_2)_2$—, wherein e is 1-10, f is 1-16, k is 1-20, and $R^N$ is H, methyl, or $CH_2F$, $CHF_2$, or $CF_3$; $G^1$, $G^2$ and $G^3$ are each independently selected from the group consisting of a monosaccharide, a monosaccharide derivative, a vitamin, a polyol, a polysialic acid and a polysialic acid derivative; $X^4$ is selected from the group consisting of (a) —$(CH_2)_g$—O—$(CH_2)_h$— or —$(CH_2)_g$—$NR^N$—$(CH_2)_h$—, wherein g is 1-30, h is 1-36, and $R^N$ is H, methyl, or $CH_2F$, $CHF_2$, or $CF_3$, (b) an amino acid, and (c) —NHC(O)$R^2$, wherein $R^2$ is $C_1$-$C_{10}$ alkyl, a carbocycle, a heterocyclyl, a heteroaryl, a $C_1$-$C_{10}$ alkyl-carbocycle, a $C_1$-$C_{10}$ alkyl-heterocyclyl or a $C_1$-$C_{10}$ alkyl-heteroaryl, and wherein $R^2$ is optionally substituted; Q is

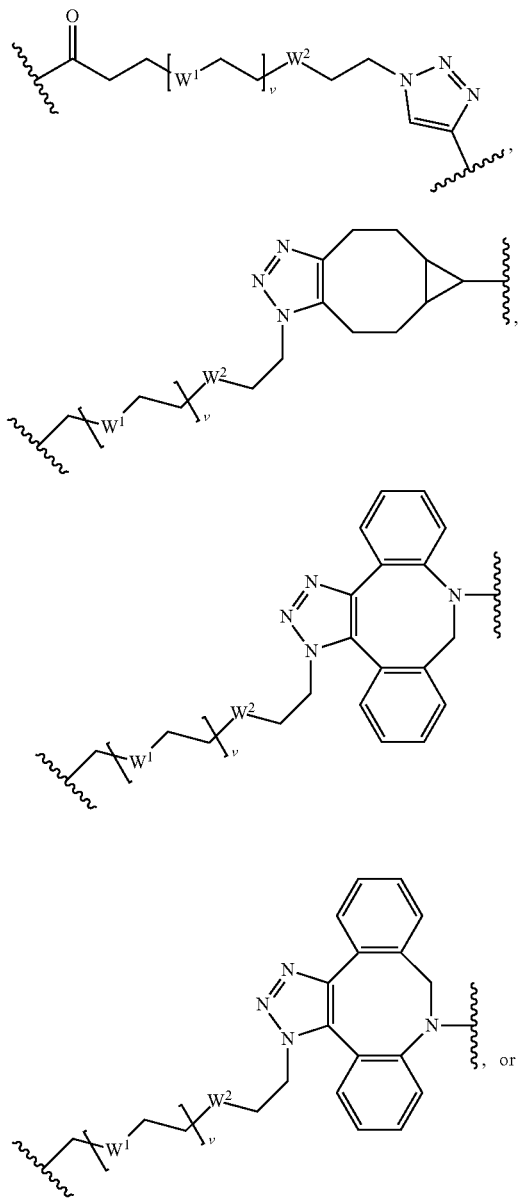

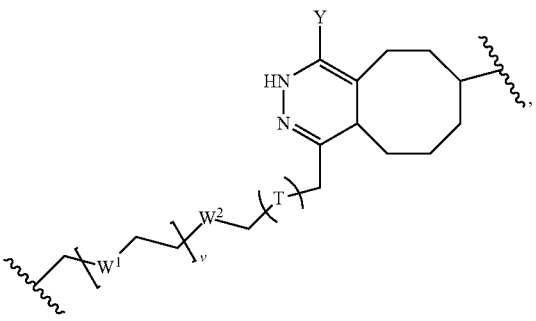

wherein $H^1$ is a carbocycle, a heterocyclyl or a heteroaryl; $H^1$ is optionally substituted; $W^1$ and $W^2$ are each independently selected from —$CH_2$— and O; v is 1-6; wherein Y is hydrogen or methyl; and T is $C_1$-$C_{10}$ alkyl or $C_1$-$C_{10}$ alkenyl; $L^4$ is —C(O)O—, —C(O)NH—, a phosphate, $C_1$-$C_{10}$ alkyl-phosphate, $C_3$-$C_{10}$ alkenyl-phosphate, a phosphorothioate, alkyl-phosphorothioate, $C_3$-$C_{10}$ alkenyl-phosphorothioate, a boranophospate, a $C_1$-$C_{10}$ alkyl-boranophospate, a $C_3$-$C_{10}$ alkenyl-boranophospate, —C(O)NH—$C_1$-$C_{10}$ alkyl-phosphate, —C(O)NH—$C_3$-$C_{10}$alkenyl-phosphate, —C(O)O—C malkyl-phosphate, —C(O)O—$C_3$-$C_{10}$ alkenyl-phosphate, —C(O)NH—$C_1$-$C_{10}$ alkyl-phosphorothioate, —C(O)NH—$C_3$-$C_{10}$alkenyl-phosphorothioate, —C(O)O—$C_1$-$C_{10}$ alkyl-phosphorothioate, —C(O)O—$C_3$-$C_{10}$alkenyl-phosphorothioate, —C(O)—NH—$C_1$-$C_{10}$alkyl-boranophospate, —C(O)—NH—$C_3$-$C_{10}$alkenyl-boranophospate, —C(O)O—$C_1$-$C_{10}$alkyl-boranophosphate or —C(O)O—$C_3$-$C_{10}$alkenyl-boranophospate; and $R^1$ is a biologically active molecule.

In some embodiments, $W^1$ and $W^2$ are each independently selected from —$CH_2$— and O, wherein v is 1-6, 1-5, 1-4, 1-3, 1-2 or —$CH_2$—.

In some embodiments, T is $C_1$-$C_{10}$ alkyl $C_1$-$C_9$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl or —$CH_2$—. In some embodiments, T is $C_2$-$C_{10}$ alkenyl, $C_2$-$C_9$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl or —CH=CH—.

In some embodiments, $X^1$, $X^2$ and $X^3$ are each independently selected from the group consisting of $C_1$-$C_{10}$ alkyl, —$(CH_2)_m$—O—$(CH_2)_n$— and —$(CH_2)_m$—$NR^N$—$(CH_2)_n$, wherein n is 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 and 1. In some embodiments, $X^1$, $X^2$ and $X^3$ are each independently selected from the group consisting of $C_1$-$C_{10}$ alkyl, —$(CH_2)_m$—O—$(CH_2)_n$— and —$(CH_2)_m$—$NR^N$—$(CH_2)_n$—, wherein m is 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 and 1. In some embodiments, $X^1$, $X^2$ and $X^3$ are each independently (—$CH_2)_m$—O—$CH_2$—, wherein m is 1-4. In some embodiments, $X^1$, $X^2$ and $X^3$ are each independently (—$CH_2)_2$—O—$CH_2$—. In some embodiments, $X^1$, $X^2$ and $X^3$ are each independently are each $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl or —$CH_2$—.

In some embodiments, $Y^1$, $Y^2$ and $Y^3$ are each —NHC(O)— or —C(O)NH—. In some embodiments, $Y^1$, $Y^2$ and $Y^3$ are each —NHC(O)—.

In some embodiments, $L^1$, $L^2$ and $L^3$ are each $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_2$ alkyl or —$CH_2$—. In some embodiments, $L^1$, $L^2$ and $L^3$ are each independently $C_3$-$C_8$ alkyl or —$(CH_2-CH_2-O)_k(CH_2)_2$—, wherein k is 1-10. In some embodiments, $L^1$, $L^2$ and $L^3$ are each independently —$(CH_2-CH_2-O)_k(CH_2)_2$—, wherein k is 2-4. In some embodiments, $L^1$, $L^2$ and $L^3$ are each independently —$(CH_2-CH_2-O)_k(CH_2)_2$—, wherein k is 1-10, 1-9, 1-8, 1-7, 1-6, 1-5, 1-4, 1-3, 1-2 or 1. In some embodiments, $L^1$, $L^2$ and $L^3$ are each independently —$(CH_2-CH_2-O)(CH_2)_2$—.

In some embodiments, $G^1$, $G^2$ and $G^3$ are each independently selected from the group consisting of folic acid, ribose, retinol, niacin, riboflavin, biotin, glucose, mannose, fucose, sucrose, lactose, mannose-6-phosphate, N-acetyl galactosamine, N-acetylglucosamine, a sialic acid, a sialic acid derivative, allose, altrose, arabinose, cladinose, erythrose, erythrulose, fructose, fucitol, fucosamine, fucose, fuculose, galactosamine, galactosaminitol, galactose, glucosamine, glucosaminitol, glucose-6 phosphate, gulose glyceraldehyde, glycero-mannosheptose, glycerol, glycerone, gulose, idose, lyxose, mannosamine, psicose, quinovose, quinovosamine, rhamnitol, rhamnosamine, rhamnose, ribulose, sedoheptulose, sorbose, tagatose, talose, threose, xylose and xylulose. In some embodiments, $G^1$, $G^2$ and $G^3$ are each N-acetylgalactosamine.

In some embodiments, $X^4$ is selected from the group consisting of

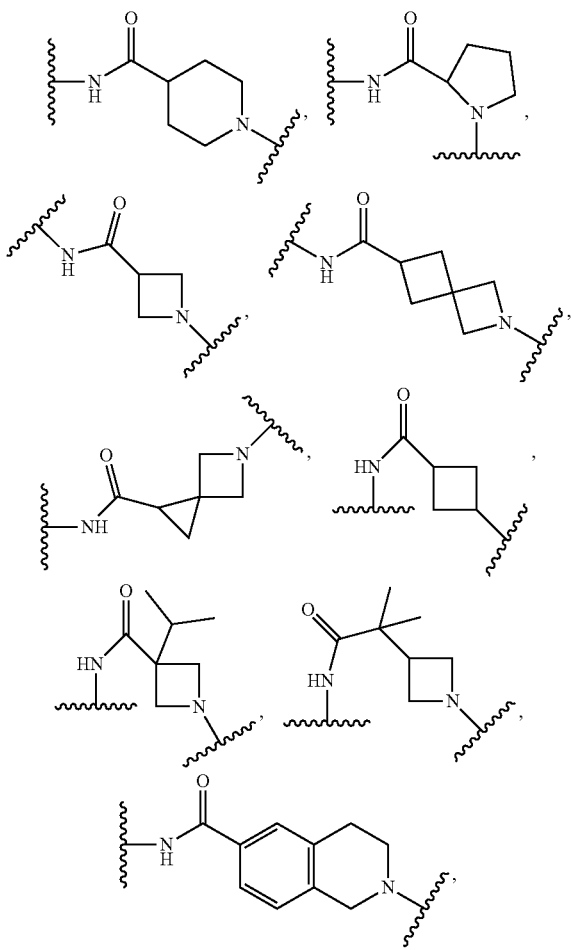

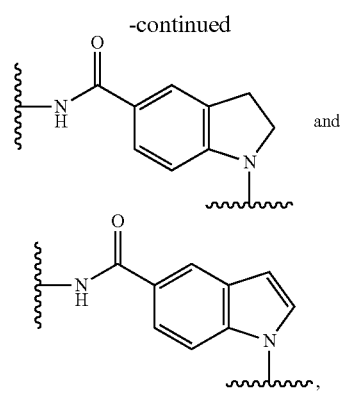

wherein $X^4$ is optionally substituted.

In some embodiments, $X^4$ is —$NHC(O)R^2$, wherein $R^2$ is a carbocycle, a heterocyclyl or a heteroaryl, wherein $R^2$ is optionally substituted. In some embodiments, $X^4$ is —$NHC(O)R^2$, wherein $R^2$ is a carbocycle, a heterocyclyl or a heteroaryl, wherein $R^2$ is optionally substituted with alkyl, alkoxy or amine. In some embodiments, $X^4$ is

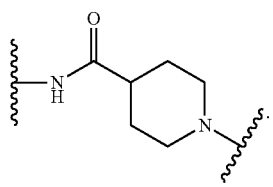 [SMILES: *NC(=O)C1CCN(*)CC1]

In some embodiments, $L^4$ is —C(O)O—, —C(O)NH—, a phosphate, $C_1$-$C_{10}$ alkyl-phosphate, $C_3$-$C_{10}$ alkenyl-phosphate, a phosphorothioate, $C_1$-$C_{10}$ alkyl-phosphorothioate, $C_3$-$C_{10}$ alkenyl-phosphorothioate, a boranophospate, a $C_1$-$C_{10}$ alkyl-boranophospate, a $C_3$-$C_{10}$ alkenyl-boranophospate, —C(O)NH—$C_1$-$C_{10}$ alkyl-phosphate, —C(O)NH—$C_3$-$C_{10}$alkenyl-phosphate, —C(O)O—$C_1$-$C_{10}$ alkyl-phosphate, —C(O)O—$C_3$-$C_{10}$alkenyl-phosphate, —C(O)NH—$C_1$-$C_{10}$ alkyl-phosphorothioate, —C(O)NH—$C_3$-$C_{10}$alkenyl-phosphorothioate, —C(O)O—$C_1$-$C_{10}$ alkyl-phosphorothioate, —C(O)O—$C_3$-$C_{10}$alkenyl-phosphorothioate, —C(O)—NH—$C_1$-$C_{10}$alkyl-boranophospate, —C(O)—NH—$C_3$-$C_{10}$alkenyl-boranophospate, —C(O)O—$C_1$-$C_{10}$alkyl-boranophospate or —C(O)O—$C_3$-$C_{10}$ alkenyl-boranophospate.

In some embodiments, $L^4$ is $C_1$-$C_{20}$ alkyl-phosphate, $C_1$-$C_{19}$ alkyl-phosphate, $C_1$-$C_{18}$ alkyl-phosphate, $C_1$-$C_{17}$ alkyl-phosphate, $C_1$-$C_{16}$ alkyl-phosphate, $C_1$-$C_{15}$ alkyl-phosphate, $C_1$-$C_{14}$ alkyl-phosphate, $C_1$-$C_{13}$ alkyl-phosphate, $C_1$-$C_{12}$ alkyl-phosphate, $C_1$-$C_{11}$ alkyl-phosphate, $C_1$-$C_{10}$ alkyl-phosphate, $C_1$-$C_9$ alkyl-phosphate, $C_1$-$C_8$ alkyl-phosphate, $C_1$-$C_7$ alkyl-phosphate, $C_1$-$C_6$ alkyl-phosphate, $C_1$-$C_5$ alkyl-phosphate, $C_1$-$C_4$ alkyl-phosphate, $C_1$-$C_3$ alkyl-phosphate, $C_1$-$C_2$ alkyl-phosphate or —$CH_2$-phosphate. In some embodiments, $L^4$ is $C_1$-$C_{20}$ alkyl-phosphorothioate, $C_1$-$C_{19}$ alkyl-phosphorothioate, $C_1$-$C_{18}$ alkyl-phosphorothioate, $C_1$-$C_{17}$ alkyl-phosphorothioate, $C_1$-$C_{16}$ alkyl-phosphorothioate, $C_1$-$C_{15}$ alkyl-phosphorothioate, $C_1$-$C_{14}$ alkyl-phosphorothioate, $C_1$-$C_{13}$ alkyl-phosphorothioate, $C_1$-$C_{12}$ alkyl-phosphorothioate, $C_1$-$C_{11}$ alkyl-phosphorothioate, $C_1$-$C_{10}$ alkyl-phosphorothioate, $C_1$-$C_9$ alkyl-phosphorothioate, $C_1$-$C_8$ alkyl-phosphorothioate, $C_1$-$C_7$ alkyl-phosphorothioate, $C_1$-$C_6$ alkyl-phosphorothioate, $C_1$-$C_5$ alkyl-phosphorothioate, $C_1$-$C_4$ alkyl-phosphorothioate, $C_1$-$C_3$ alkyl-phosphorothioate, $C_1$-$C_2$ alkyl-phosphorothioate or —$CH_2$-phosphorothioate. In some embodiments, $L^4$ is $C_1$-$C_{20}$ alkyl-boranophospate, $C_1$-$C_{19}$ alkyl-boranophospate, $C_1$-$C_{18}$ alkyl-boranophospate, $C_1$-$C_{17}$ alkyl-boranophospate, $C_1$-$C_{16}$ alkyl-boranophospate, $C_1$-$C_{15}$ alkyl-boranophospate, $C_1$-$C_{14}$ alkyl-boranophospate, $C_1$-$C_{13}$ alkyl-boranophospate, $C_1$-$C_{12}$ alkyl-boranophospate, $C_1$-$C_{11}$ alkyl-boranophospate, $C_1$-$C_{10}$ alkyl-boranophospate, $C_1$-$C_9$ alkyl-boranophospate, $C_1$-$C_8$ alkyl-boranophospate, $C_1$-$C_7$ alkyl-boranophospate, $C_1$-$C_6$ alkyl-boranophospate, $C_1$-$C_5$ alkyl-boranophospate, $C_1$-$C_4$ alkyl-boranophospate, $C_1$-$C_3$ alkyl-boranophospate, $C_1$-$C_2$ alkyl-boranophospate or —$CH_2$-boranophospate.

In some embodiments, $L^4$ is $C_3$-$C_{20}$ alkenyl-phosphate, $C_3$-$C_{19}$ alkenyl-phosphate, $C_3$-$C_{18}$ alkenyl-phosphate, $C_3$-$C_{17}$ alkenyl-phosphate, $C_3$-$C_{16}$ alkenyl-phosphate, $C_3$-$C_{15}$ alkenyl-phosphate, $C_3$-$C_{14}$ alkenyl-phosphate, $C_3$-$C_{13}$ alkenyl-phosphate, $C_3$-$C_{12}$ alkenyl-phosphate, $C_3$-$C_{11}$ alkenyl-phosphate, $C_3$-$C_{10}$ alkenyl-phosphate, $C_3$-$C_9$ alkenyl-phosphate, $C_3$-$C_8$ alkenyl-phosphate, $C_3$-$C_7$ alkenyl-phosphate, $C_3$-$C_6$ alkenyl-phosphate, $C_3$-$C_5$ alkenyl-phosphate, $C_3$-$C_4$ alkenyl-phosphate, or $C_3$ alkenyl-phosphate. In some embodiments, $L^4$ is $C_3$-$C_{20}$ alkenyl-phosphorothioate, $C_3$-$C_{19}$ alkenyl-phosphorothioate, $C_3$-$C_{18}$ alkenyl-phosphorothioate, $C_3$-$C_{17}$ alkenyl-phosphorothioate, $C_3$-$C_{16}$ alkenyl-phosphorothioate, $C_3$-$C_{15}$ alkenyl-phosphorothioate, $C_3$-$C_{14}$ alkenyl-phosphorothioate, $C_3$-$C_{13}$ alkenyl-phosphorothioate, $C_3$-$C_{12}$ alkenyl-phosphorothioate, $C_3$-$C_{11}$ alkenyl-phosphorothioate, $C_3$-$C_{10}$ alkenyl-phosphorothioate, $C_3$-$C_9$ alkenyl-phosphorothioate, $C_3$-$C_8$ alkenyl-phosphorothioate, $C_3$-$C_7$ alkenyl-phosphorothioate, $C_3$-$C_6$ alkenyl-phosphorothioate, $C_3$-$C_5$ alkenyl-phosphorothioate, $C_3$-$C_4$ alkenyl-phosphorothioate, or $C_3$ alkenyl-phosphorothioate. In some embodiments, $L^4$ is $C_3$-$C_{20}$ alkenyl-boranophospate, $C_3$-$C_{19}$ alkenyl-boranophospate, $C_3$-$C_{18}$ alkenyl-boranophospate, $C_3$-$C_{17}$ alkenyl-boranophospate, $C_3$-$C_{16}$ alkenyl-boranophospate, $C_3$-$C_{15}$ alkenyl-boranophospate, $C_3$-$C_{14}$ alkenyl-boranophospate, $C_3$-$C_{13}$ alkenyl-boranophospate, $C_3$-$C_{12}$ alkenyl-boranophospate, $C_3$-$C_{11}$ alkenyl-boranophospate, $C_3$-$C_{10}$ alkenyl-boranophospate, $C_3$-$C_9$ alkenyl-boranophospate, $C_3$-$C_8$ alkenyl-boranophospate, $C_3$-$C_7$ alkenyl-boranophospate, $C_3$-$C_6$ alkenyl-boranophospate, $C_3$-$C_5$ alkenyl-boranophospate, $C_3$-$C_4$ alkenyl-boranophospate, or $C_3$ alkenyl-boranophospate.

In some embodiments, $L^4$ is —C(O)NH—$C_1$-$C_{10}$ alkyl-phosphate, —C(O)NH—$C_1$-$C_9$alkyl-phosphate, —C(O)NH—$C_1$-$C_8$alkyl-phosphate, —C(O)NH—$C_1$-$C_7$alkyl-phosphate, —C(O)NH—$C_1$-$C_6$alkyl-phosphate, —C(O)NH—$C_1$-$C_5$alkyl-phosphate, —C(O)NH—$C_1$-$C_4$ alkyl-phosphate, —C(O)NH—$C_1$-$C_3$alkyl-phosphate, —C(O)NH—$C_1$-$C_2$alkyl-phosphate, or —C(O)NH—$CH_2$-phosphate.

In some embodiments, $L^4$ is —C(O)NH—$C_3$-$C_{10}$alkenyl-phosphate, —C(O)NH—$C_3$-$C_9$alkenyl-phosphate, —C(O)NH—$C_1$-$C_8$alkenyl-phosphate, —C(O)NH—$C_3$-$C_7$alkenyl-phosphate, —C(O)NH—$C_3$-$C_6$alkenyl-phosphate, —C(O)NH—$C_3$-$C_5$alkenyl-phosphate, —C(O)NH—$C_3$-$C_4$alkenyl-phosphate, or —C(O)NH—$C_3$alkenyl-phosphate.

In some embodiments, $L^4$ is —C(O)O—$C_1$-$C_{10}$ alkyl-phosphate, —C(O)O—$C_1$-$C_9$alkyl-phosphate, —C(O)O—$C_1$-$C_8$alkyl-phosphate, —C(O)O—$C_1$-$C_7$alkyl-phosphate, —C(O)O—$C_1$-$C_6$alkyl-phosphate, —C(O)O—$C_1$-$C_5$ alkyl-phosphate, —C(O)O—$C_1$-$C_4$alkyl-phosphate, —C(O)O—$C_1$-$C_3$alkyl-phosphate, —C(O)O—$C_1$-$C_2$alkyl-phosphate, or —C(O)O—$CH_2$-phosphate.

In some embodiments, $L^4$ is —C(O)O—$C_3$-$C_{10}$alkenyl-phosphate, —C(O)O—$C_3$-$C_9$alkenyl-phosphate, —C(O)O—$C_3$-$C_8$alkenyl-phosphate, —C(O)O—$C_3$-$C_7$alkenyl-phosphate, —C(O)O—$C_3$-$C_6$alkenyl-phosphate, —C(O)O—$C_3$-$C_5$alkenyl-phosphate, —C(O)O—$C_3$-$C_4$alkenyl-phosphate, or —C(O)O—$C_3$alkenyl-phosphate.

In some embodiments, $L^4$ is —C(O)NH—$C_1$-$C_{10}$ alkyl-phosphorothioate, —C(O)NH—$C_1$-$C_9$alkyl-phosphorothioate, —C(O)NH—$C_1$-$C_8$alkyl-phosphorothioate, —C(O)NH—$C_1$-$C_7$alkyl-phosphorothioate, —C(O)NH—$C_1$-$C_6$alkyl-phosphorothioate, —C(O)NH—$C_1$-$C_5$alkyl-phosphorothioate, —C(O)NH—$C_1$-$C_4$alkyl-phosphorothioate, —C(O)NH—$C_1$-$C_3$alkyl-phosphorothioate, —C(O)NH—$C_1$-$C_2$alkyl-phosphorothioate, or —C(O)NH—$CH_2$-phosphorothioate.

In some embodiments, $L^4$ is —C(O)NH—$C_3$-$C_{10}$alkenyl-phosphorothioate, —C(O)NH—$C_3$-$C_9$alkenyl-phosphorothioate, —C(O)NH—$C_3$-$C_8$alkenyl-phosphorothioate, —C(O)NH—$C_3$-$C_7$alkenyl-phosphorothioate, —C(O)NH—$C_3$-$C_6$alkenyl-phosphorothioate, —C(O)NH—$C_3$-$C_5$alkenyl-phosphorothioate, —C(O)NH—$C_3$-$C_4$alkenyl-phosphorothioate, or —C(O)NH—$C_3$alkenyl-phosphorothioate.

In some embodiments, $L^4$ is —C(O)O—$C_1$-$C_{10}$ alkyl-phosphorothioate, —C(O)O—$C_1$-$C_9$alkyl-phosphorothioate, —C(O)O—$C_1$-$C_8$alkyl-phosphorothioate, —C(O)O—$C_1$-$C_7$alkyl-phosphorothioate, —C(O)O—$C_1$-$C_6$alkyl-phosphorothioate, —C(O)O—$C_1$-$C_5$ alkyl-phosphorothioate, —C(O)O—$C_1$-$C_4$alkyl-phosphorothioate, —C(O)O—$C_1$-$C_3$alkyl-phosphorothioate, —C(O)O—$C_1$-$C_2$alkyl-phosphorothioate, or —C(O)O—$CH_2$-phosphorothioate.

In some embodiments, $L^4$ is —C(O)O—$C_3$-$C_{10}$alkenyl-phosphorothioate, —C(O)O—$C_3$-$C_9$alkenyl-phosphorothioate, —C(O)O—$C_3$-$C_8$alkenyl-phosphorothioate, —C(O)O—$C_3$-$C_7$alkenyl-phosphorothioate, —C(O)O—$C_3$-$C_6$alkenyl-phosphorothioate, —C(O)O—$C_3$-$C_5$alkenyl-phosphorothioate, —C(O)O—$C_3$-$C_4$alkenyl-phosphorothioate, or —C(O)O—$C_3$alkenyl-phosphorothioate.

In some embodiments, $L^4$ is —C(O)—NH—$C_1$-$C_{10}$ alkyl-boranophospate, —C(O)—NH—$C_1$-$C_9$alkyl-boranophospate, —C(O)—NH—$C_1$-$C_8$ alkyl-boranophospate, —C(O)—NH—$C_1$-$C_7$alkyl-boranophospate, —C(O)—NH—$C_1$-$C_6$alkyl-boranophospate, —C(O)—NH—$C_1$-$C_5$alkyl-boranophospate, —C(O)—NH—$C_1$-$C_4$alkyl-boranophospate, —C(O)—NH—$C_1$-$C_3$alkyl-boranophospate, —C(O)—NH—$C_2$alkyl-boranophospate, or —C(O)—NH—$CH_2$-boranophospate.

In some embodiments, $L^4$ is —C(O)—NH—$C_3$-$C_{10}$alkenyl-boranophospate, —C(O)—NH—$C_3$-$C_9$alkenyl-boranophospate, —C(O)—NH—$C_3$-$C_8$alkenyl-boranophospate, —C(O)—NH—$C_3$-$C_7$alkenyl-boranophospate, —C(O)—NH—$C_3$-$C_6$alkenyl-boranophospate, —C(O)—NH—$C_3$-$C_5$alkenyl-boranophospate, —C(O)—NH—$C_3$-$C_4$alkenyl-boranophospate, or —C(O)—NH—$C_3$alkenyl-boranophospate.

In some embodiments, $L^4$ is —C(O)O—$C_1$-$C_{10}$ alkyl-boranophospate, —C(O)O—$C_1$-$C_9$alkyl-boranophospate, —C(O)O—$C_1$-$C_8$alkyl-boranophospate, —C(O)O—$C_1$-$C_7$alkyl-boranophospate, —C(O)O—$C_1$-$C_6$alkyl-boranophospate, —C(O)O—$C_1$-$C_5$alkyl-boranophospate, —C(O)O—$C_1$-$C_4$alkyl-boranophospate, —C(O)O—$C_1$-$C_3$alkyl-boranophospate, —C(O)O—$C_1$-$C_2$alkyl-boranophospate, or —C(O)O—$CH_2$-boranophospate.

In some embodiments, $L^4$ is —C(O)O—$C_3$-$C_{10}$alkenyl-boranophospate, —C(O)O—$C_3$-$C_9$alkenyl-boranophospate, —C(O)O—$C_3$-$C_8$alkenyl-boranophospate, —C(O)O—$C_3$-$C_7$alkenyl-boranophospate, —C(O)O—$C_3$-$C_6$alkenyl-boranophospate, —C(O)O—$C_3$-$C_5$alkenyl-boranophospate, —C(O)O—$C_3$-$C_4$alkenyl-boranophospate, or —C(O)O—$C_3$alkenyl-boranophospate.

In some embodiments, $R^1$ is selected from the group consisting of pentafluorophenyl, tetrafluorophenyl, succinimide, maleimide, azide, pyridyldithiol, methyl phosphonate, a chiral-methyl phosphonate, a helper lipid, and a nucleic acid. In some embodiments, $R^1$ is an ASO (Antisense Oligonucleotide), a siRNA (Small Interfering RNA), a miRNA (MicroRNA), a microRNA mimic, an AMO (Anti-miRNA Oligonucleotide), a long non-coding RNA, a PNA (Peptide Nucleic Acid), a helper lipid, or a PMO (Phosphorodiamidate Morpholino Oligomer), wherein the nucleic acid is optionally modified. In some embodiments, le is an ASO (Antisense Oligonucleotide).

In some embodiments, the compound having the formula

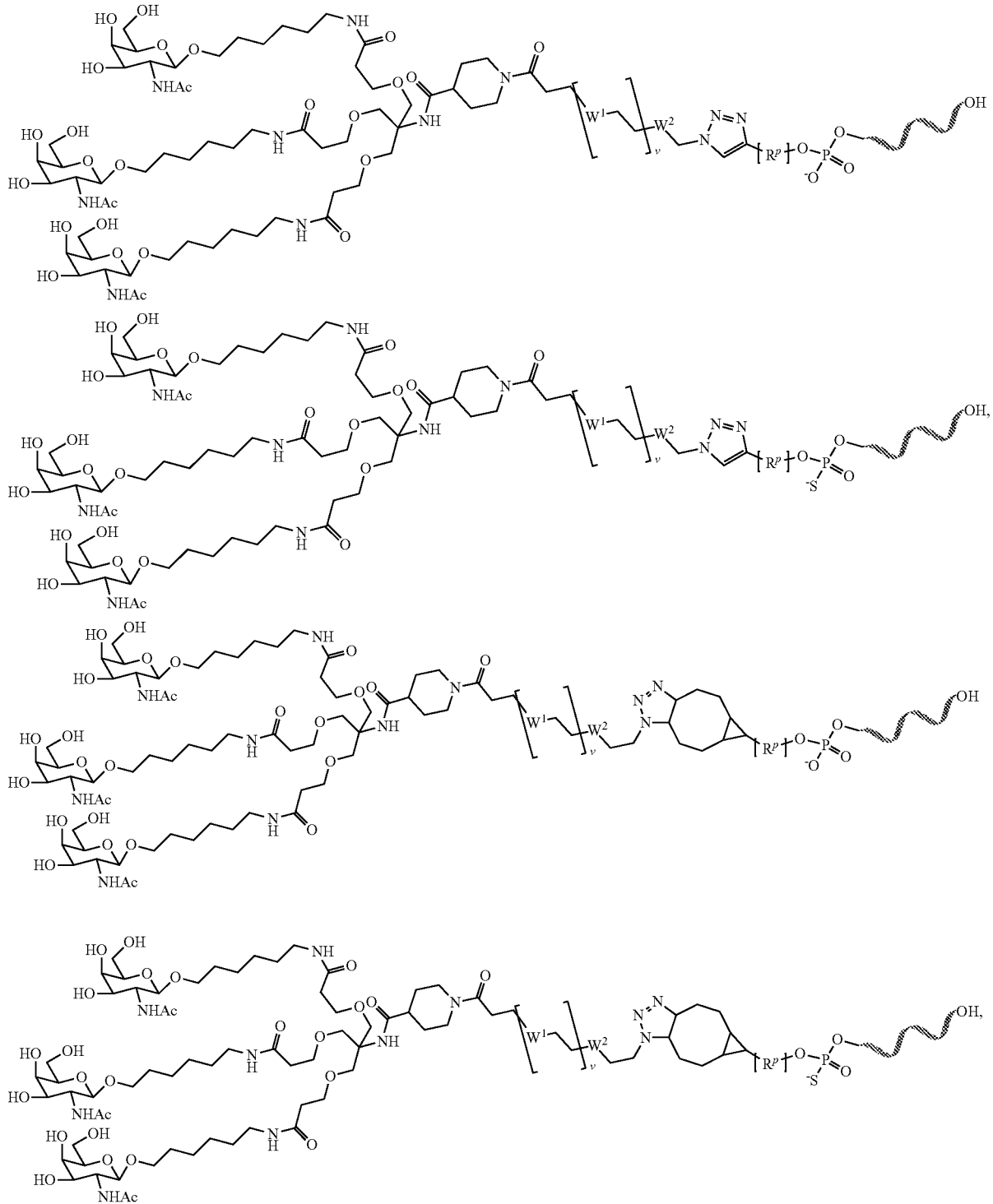

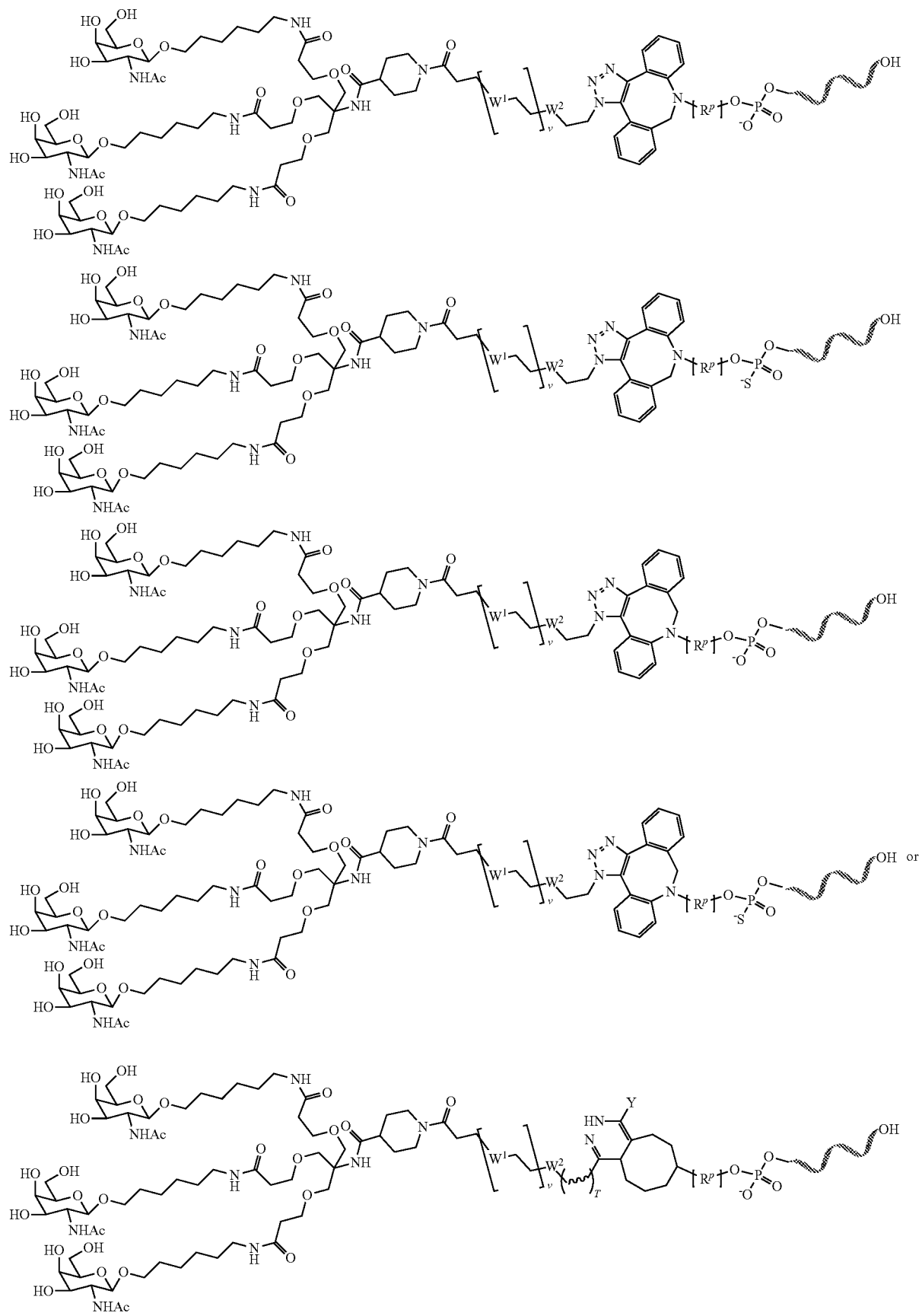

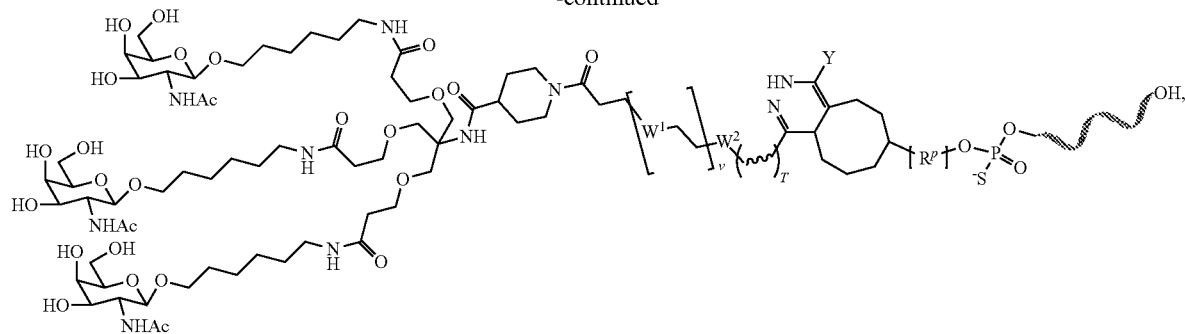

wherein ⟨⟨⟨OH is an oligonucleotide, and $R^p$ is $C_1$-$C_{10}$ alkyl or $C_2$-$C_{10}$ alkenyl. In some embodiments, $R^p$ is $C_1$-$C_{10}$ alkyl or $C_2$-$C_{10}$ alkenyl, $C_1$-$C_9$ alkyl or $C_2$-$C_9$ alkenyl, $C_1$-$C_8$ alkyl or $C_2$-$C_8$ alkenyl, $C_1$-$C_7$ alkyl or $C_2$-$C_7$ alkenyl, $C_1$-$C_6$ alkyl or $C_2$-$C_6$ alkenyl, $C_1$-$C_5$ alkyl or $C_2$-$C_5$ alkenyl, $C_1$-$C_4$ alkyl or $C_2$-$C_4$ alkenyl, $C_1$-$C_3$ alkyl or $C_2$-$C_3$ alkenyl, $C_1$-$C_2$ alkyl, —CH=CH— or —CH$_2$—.

In some embodiments, the compound is

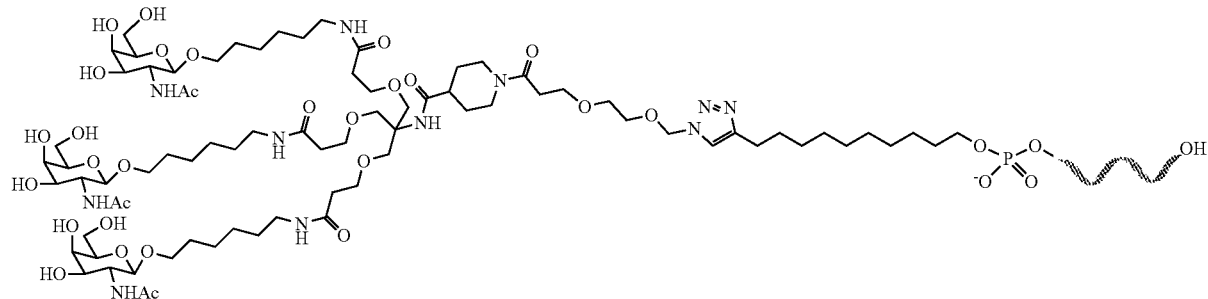

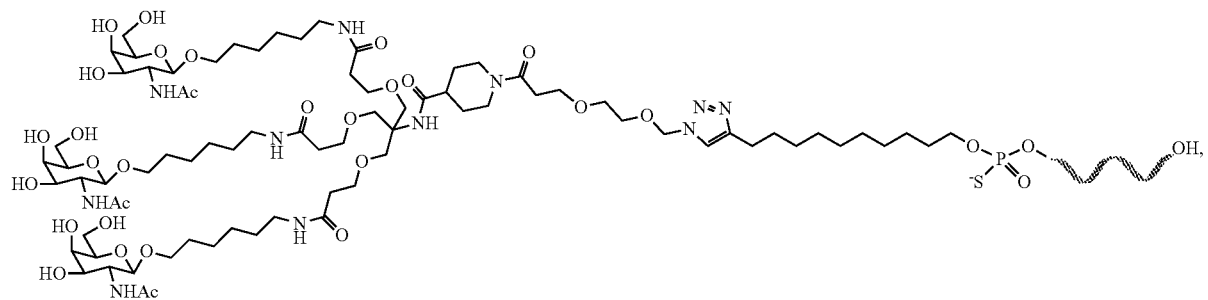

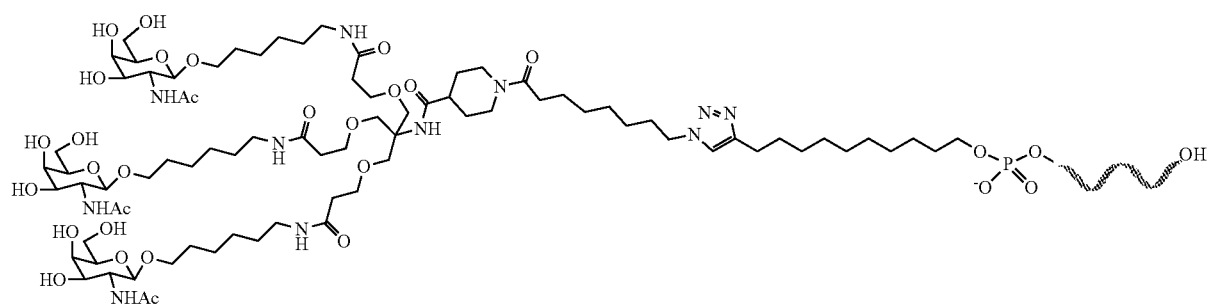

-continued
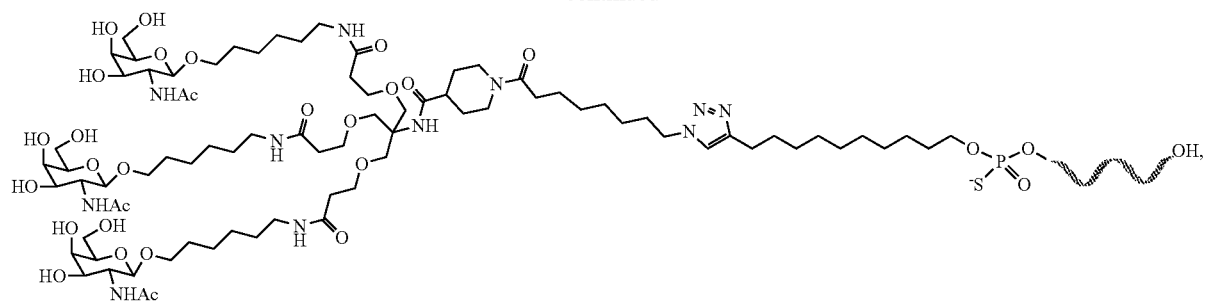
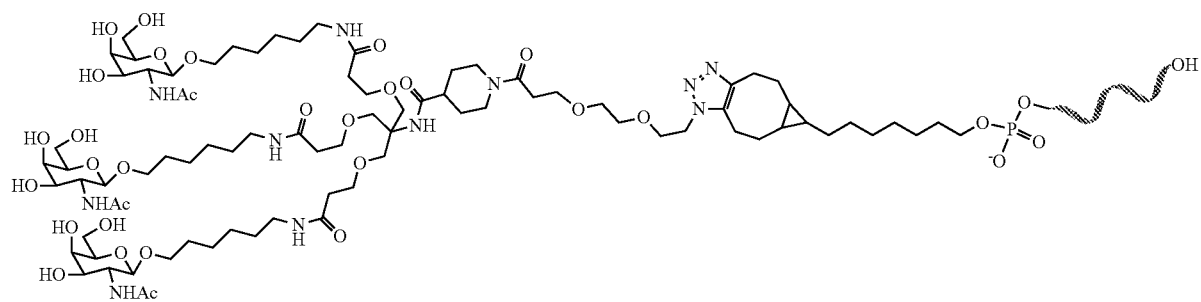
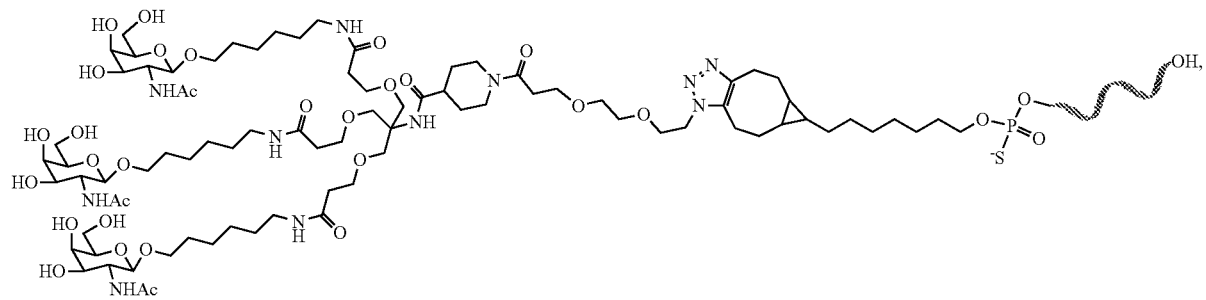
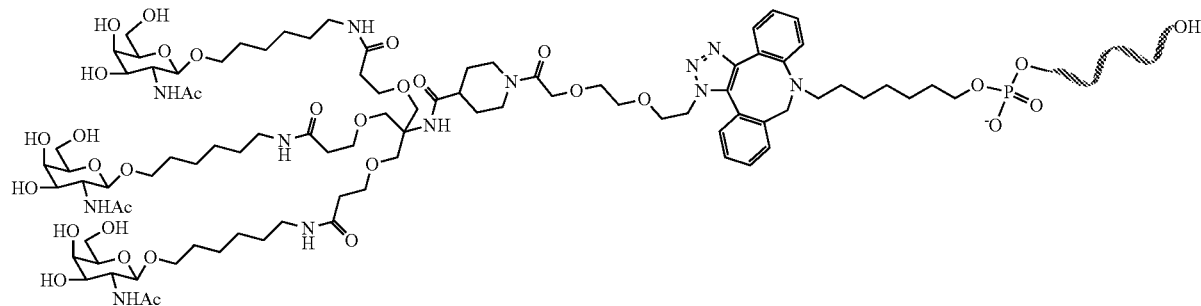
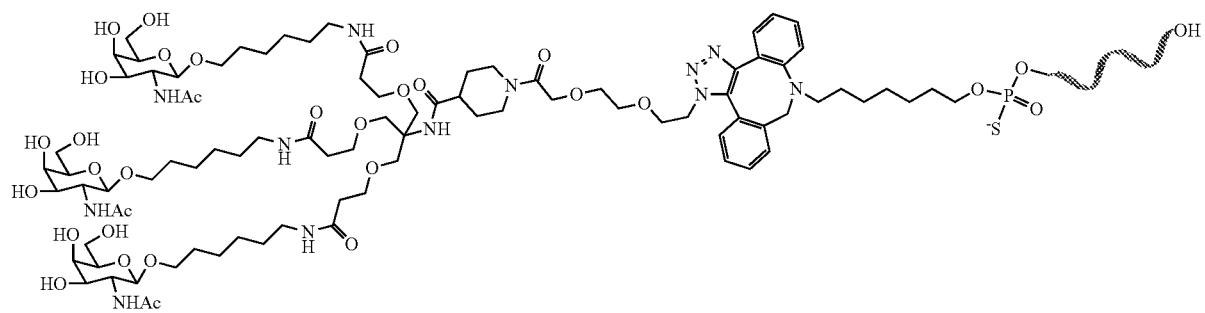

-continued

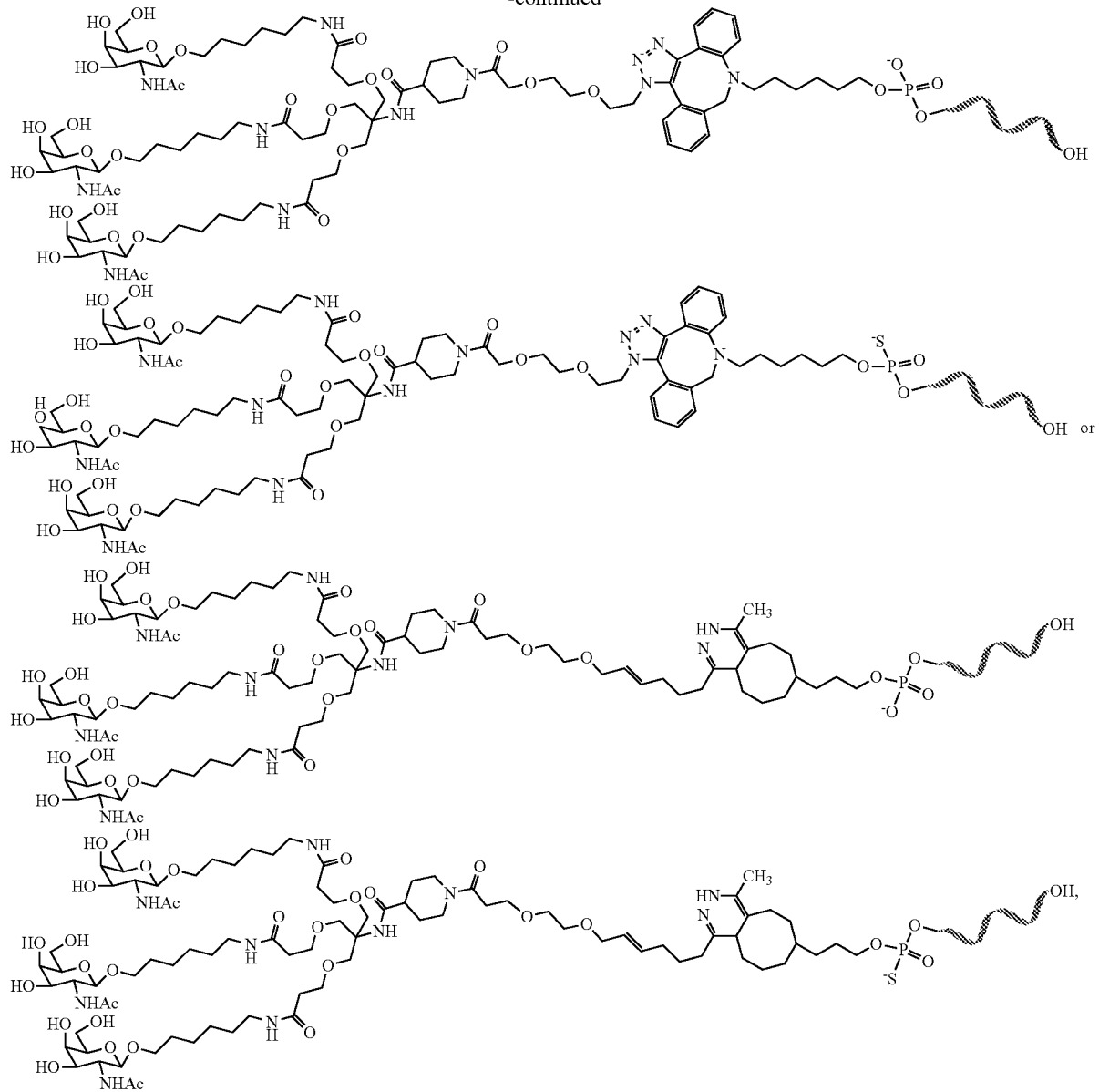

wherein 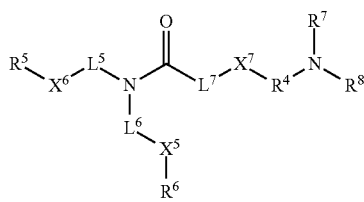 is an oligonucleotide.

In some embodiments, a compound comprising Formula B, Formula C, Formula D, Formula E and Formula F are each independently derived from a Click Chemistry process.

In another embodiment, disclosed herein is a pharmaceutical composition comprising a compound of Formula IA, Formula IB or Formula IC, and a lipid of Formula II $$II$$

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_1$-$C_{20}$ alkenyl; $X^5$ is —C(O)O— or —OC(O)—; $X^6$ is —C(O)O— and —OC(O)—; $X^7$ is S or O; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

In some embodiments, $X^7$ is S.

In some embodiments, $R^7$ and $R^8$ are each independently selected from the group consisting of methyl, ethyl and isopropyl. In some embodiments, $R^7$ and $R^8$ are each independently selected from the group consisting of propyl, butyl, isobutyl, t-butyl, pentyl and hexyl.

In some embodiments, $L^5$ and $L^6$ are each independently a $C_1$-$C_{10}$ alkyl. In some embodiments, $L^5$ and $L^6$ are each independently a $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl or —$CH_2$—. In some embodiments, $L^5$ is $C_1$-$C_3$ alkyl, and $L^6$ is $C_1$-$C_5$ alkyl. In some embodiments, $L^6$ is $C_1$-$C_2$ alkyl. In some embodiments, $L^5$ and $L^6$ are each a linear $C_7$ alkyl. In some embodiments, $L^5$ and $L^6$ are each a linear $C_9$ alkyl.

In some embodiments, $R^5$ and $R^6$ are each independently selected from the group consisting of a linear or branched $C_1$-$C_{31}$ alkyl, $C_1$-$C_{30}$ alkyl, $C_1$-$C_{29}$ alkyl, $C_1$-$C_{28}$ alkyl, $C_1$-$C_{27}$ alkyl, $C_1$-$C_{26}$ alkyl, $C_1$-$C_{25}$ alkyl, $C_1$-$C_{24}$ alkyl, $C_1$-$C_{23}$ alkyl, $C_1$-$C_{22}$ alkyl, $C_1$-$C_{21}$ alkyl, $C_1$-$C_{20}$ alkyl, $C_1$-$C_{19}$ alkyl, $C_1$-$C_{18}$ alkyl, $C_1$-$C_{17}$ alkyl, $C_1$-$C_{16}$ alkyl, $C_1$-$C_{is}$ alkyl, $C_1$-$C_{14}$ alkyl, $C_1$-$C_{13}$ alkyl, $C_1$-$C_{12}$ alkyl, $C_1$-$C_{11}$ alkyl, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl and —$CH_2$—.

In some embodiments, $R^5$ and $R^6$ are each independently selected from the group consisting of a linear or branched $C_2$-$C_{31}$ alkenyl, $C_2$-$C_{30}$ alkenyl, $C_2$-$C_{29}$ alkenyl, $C_2$-$C_{28}$ alkenyl, $C_2$-$C_{27}$ alkenyl, $C_2$-$C_{26}$ alkenyl, $C_2$-$C_{25}$ alkenyl, $C_2$-$C_{24}$ alkenyl, $C_2$-$C_{23}$ alkenyl, $C_2$-$C_{22}$ alkenyl, $C_2$-$C_{21}$ alkenyl, $C_2$-$C_{20}$ alkenyl, $C_2$-$C_{19}$ alkenyl, $C_2$-$C_{18}$ alkenyl, $C_2$-$C_{17}$ alkenyl, $C_2$-$C_{16}$ alkenyl, $C_2$-$C_{15}$ alkenyl, $C_2$-$C_{14}$ alkenyl, $C_2$-$C_{13}$ alkenyl, $C_2$-$C_{12}$ alkenyl, $C_2$-$C_{11}$ alkenyl, $C_2$-$C_{10}$ alkenyl, $C_2$-$C_9$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl and —CH=CH—. In some embodiments, $R^5$ and $R^6$ are each independently an alkenyl. In some embodiments, $R^6$ is alkenyl. In some embodiments, $R^6$ is $C_2$-$C_9$ alkenyl. In some embodiments, the alkenyl comprises a single double bond, two double bonds or three double bonds. In some embodiments, $R^5$ and $R^6$ are each alkyl. In some embodiments, $R^5$ is a branched alkane. In some embodiments, $R^5$ and $R^6$ are each independently selected from the group consisting of a $C_9$ alkyl, $C_9$ alkenyl and $C_9$ alkynyl. In some embodiments, $R^5$ and $R^6$ are each independently selected from the group consisting of a $C_{11}$ alkyl, $C_{11}$ alkenyl and $C_{11}$ alkynyl. In some embodiments, $R^5$ and $R^6$ are each independently selected from the group consisting of a $C_7$ alkyl, $C_7$ alkenyl and $C_7$ alkynyl. In some embodiments, $R^5$ is —$CH((CH_2)_pCH_3)_2$ or —$CH((CH_2)_pCH_3)((CH_2)_{p-1}CH_3)$, wherein p is 4-8. In some embodiments, p is 5 and $L^5$ is a $C_1$-$C_3$ alkyl. In some embodiments, p is 6 and $L^5$ is a $C_3$ alkyl. In some embodiments, p is 7. In some embodiments, p is 8 and $L^5$ is an $C_1$-$C_3$ alkyl. In some embodiments, $R^5$ consists of —$CH((CH_2)_pCH_3)((CH_2)_{p-1}CH_3)$, wherein p is 7 or 8.

In some embodiments, $R^4$ is ethylene or propylene. In some embodiments, $R^4$ is n-propylene or isobutylene.

In some embodiments, $L^7$ is absent, $R^4$ is ethylene, $X^7$ is S and $R^7$ and $R^8$ are each methyl. In some embodiments, $L^7$ is absent, $R^4$ is n-propylene, $X^7$ is S and $R^7$ and $R^8$ are each methyl. In some embodiments, $L^7$ is absent, $R^4$ is ethylene, $X^7$ is S and $R^7$ and $R^8$ are each ethyl.

In another embodiment, disclosed herein is a pharmaceutical composition comprising a compound of Formula IA, Formula IB or Formula IC, and a lipid selected from the group consisting of

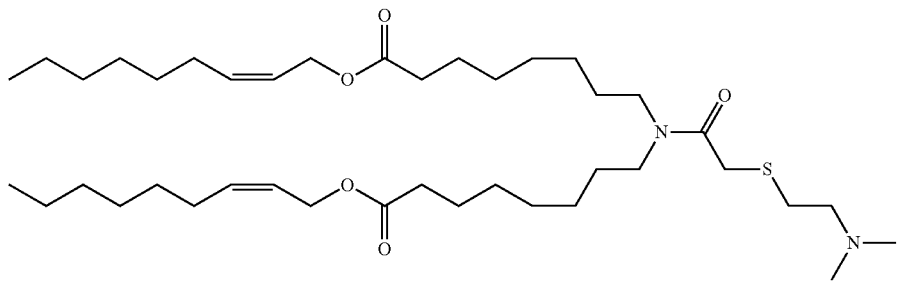

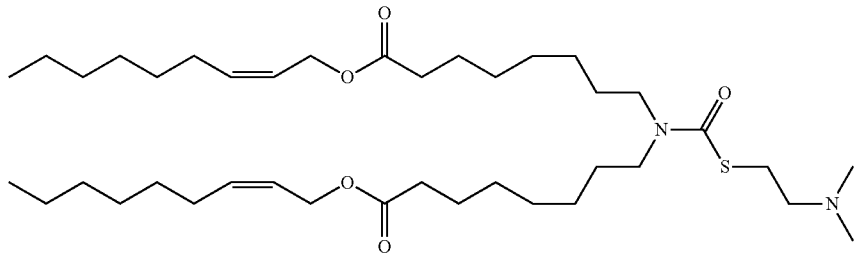

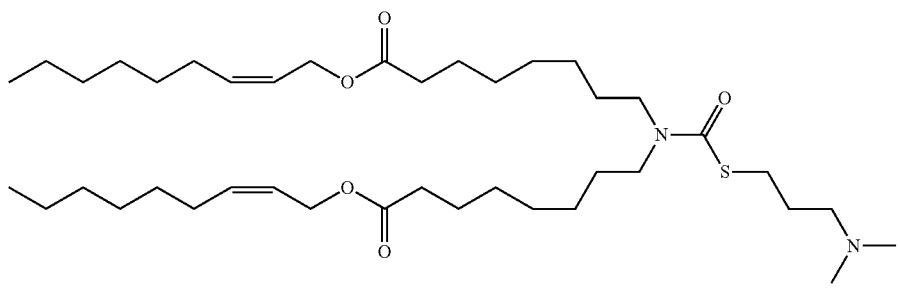

-continued
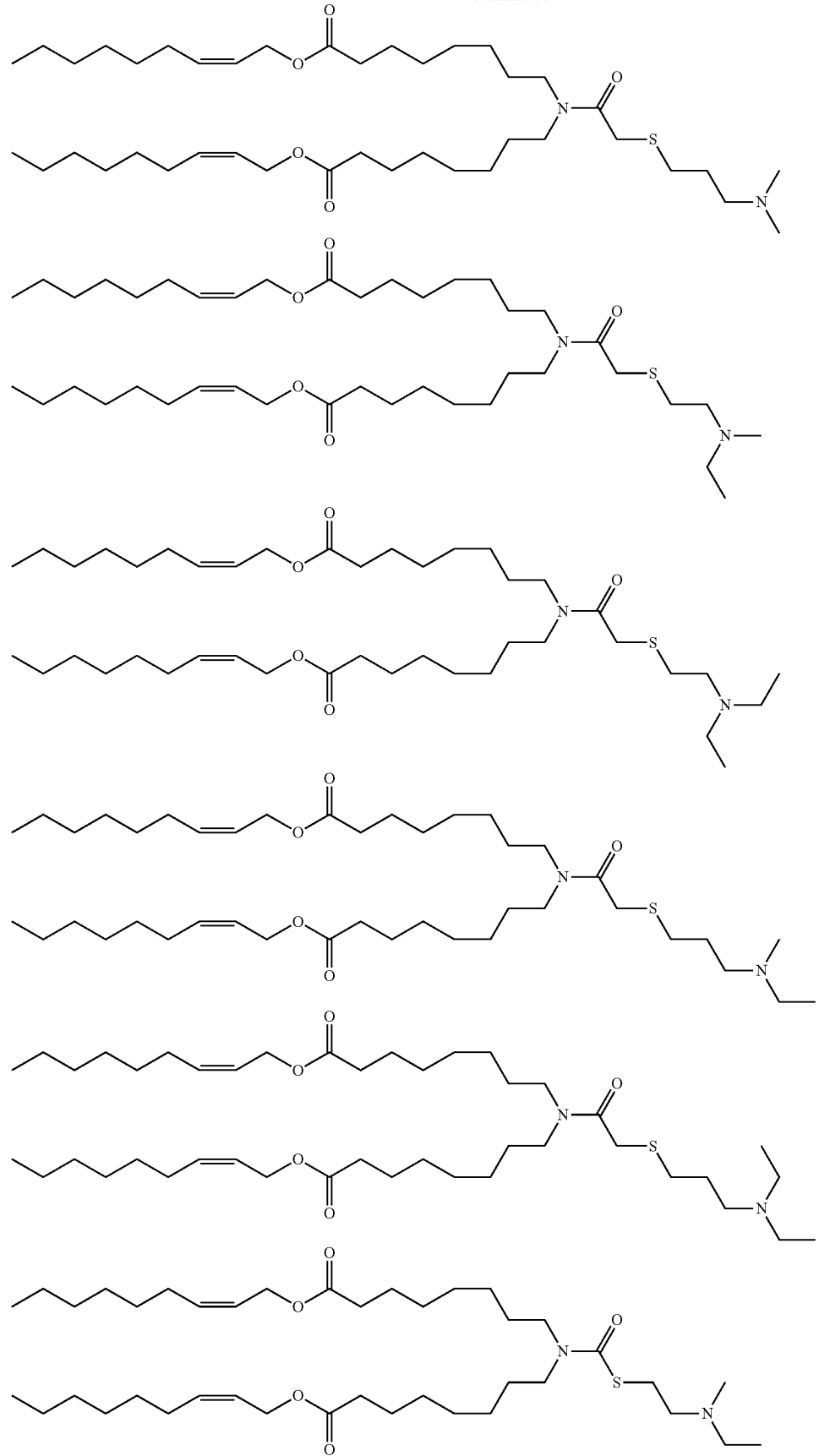

-continued
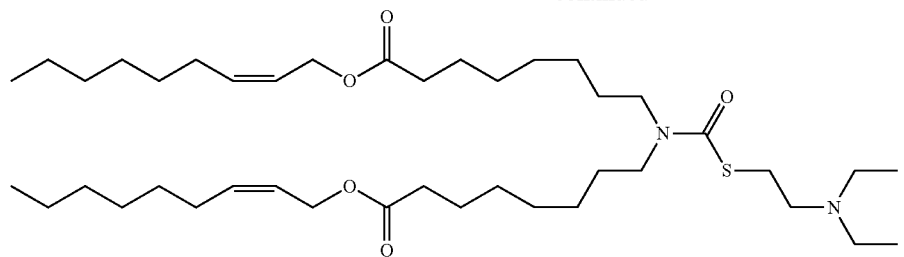
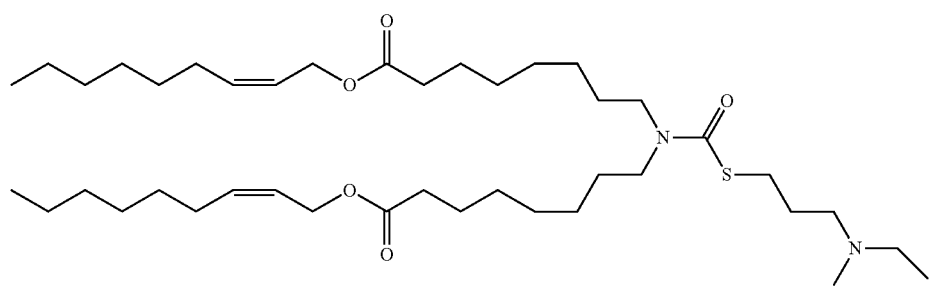
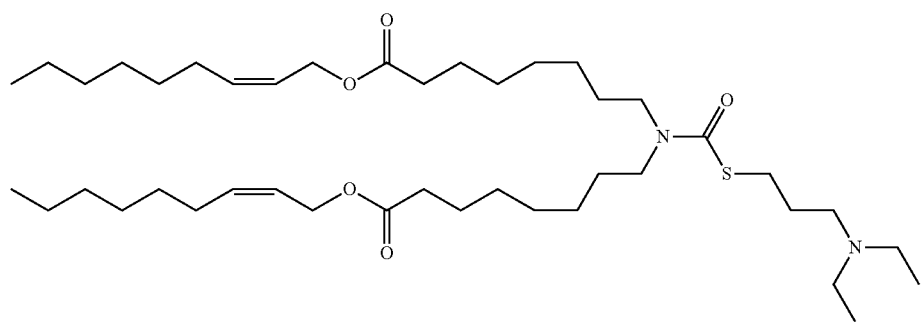
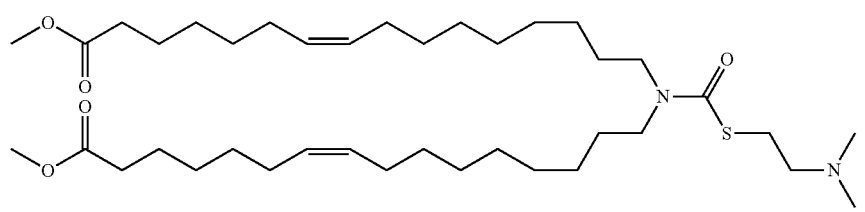
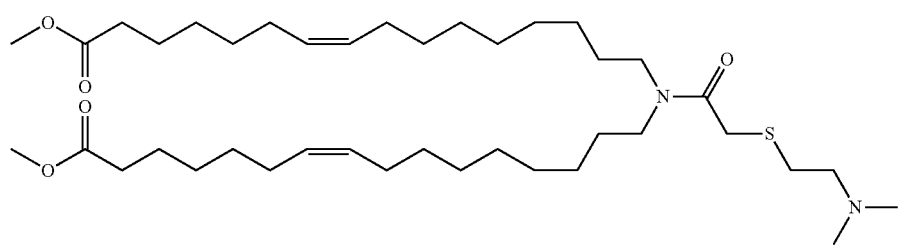
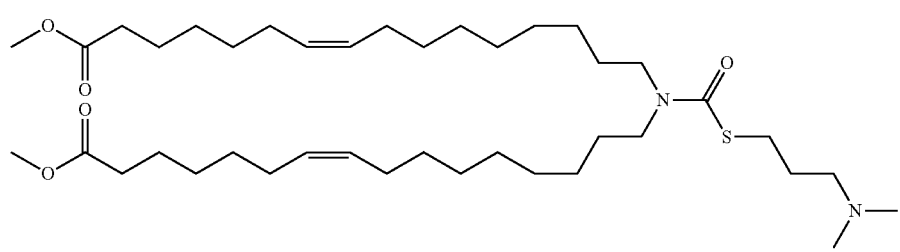

-continued
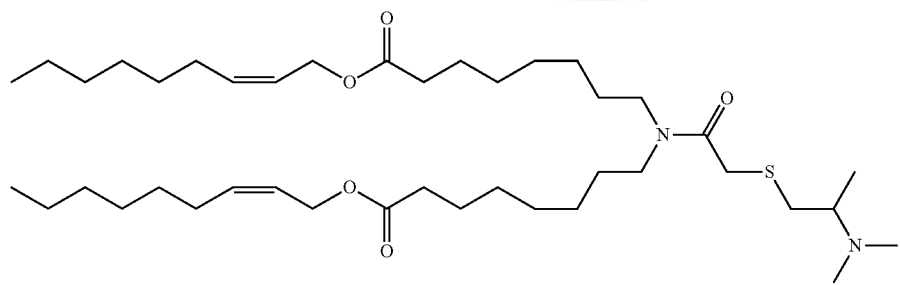
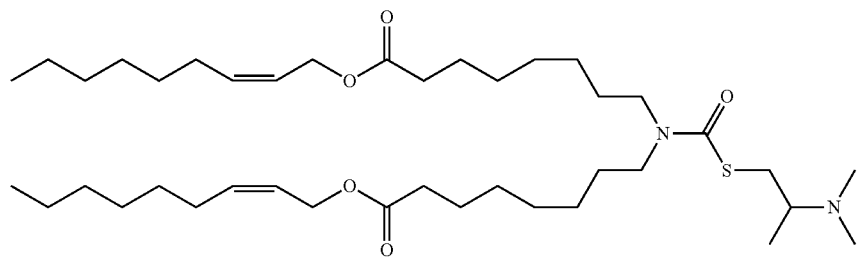
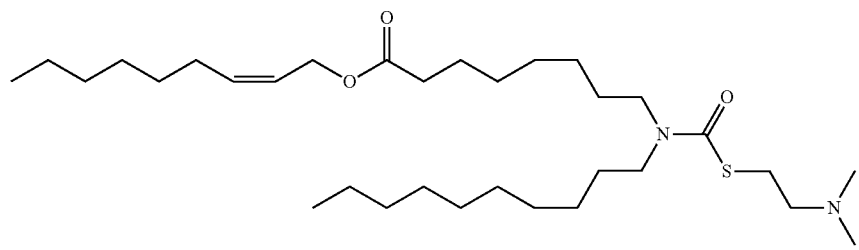
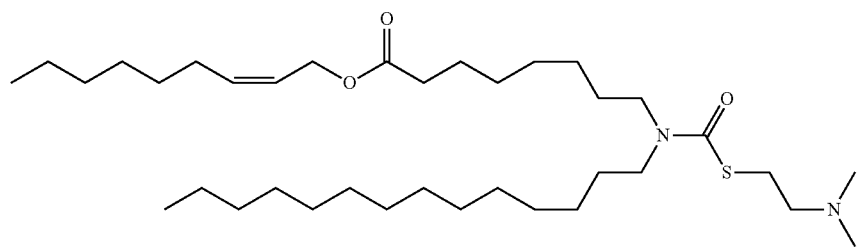
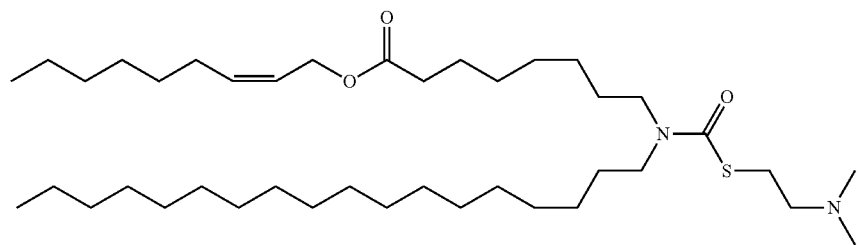
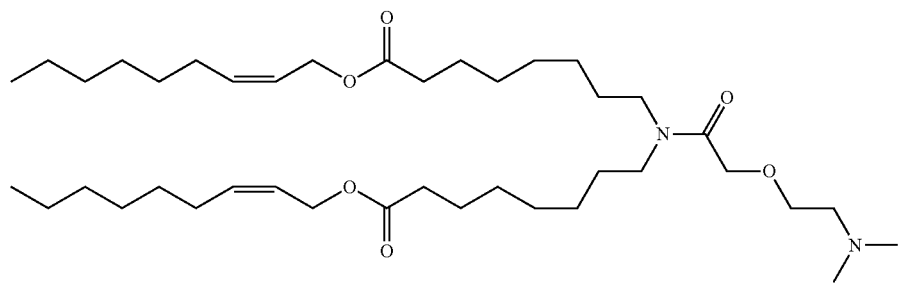

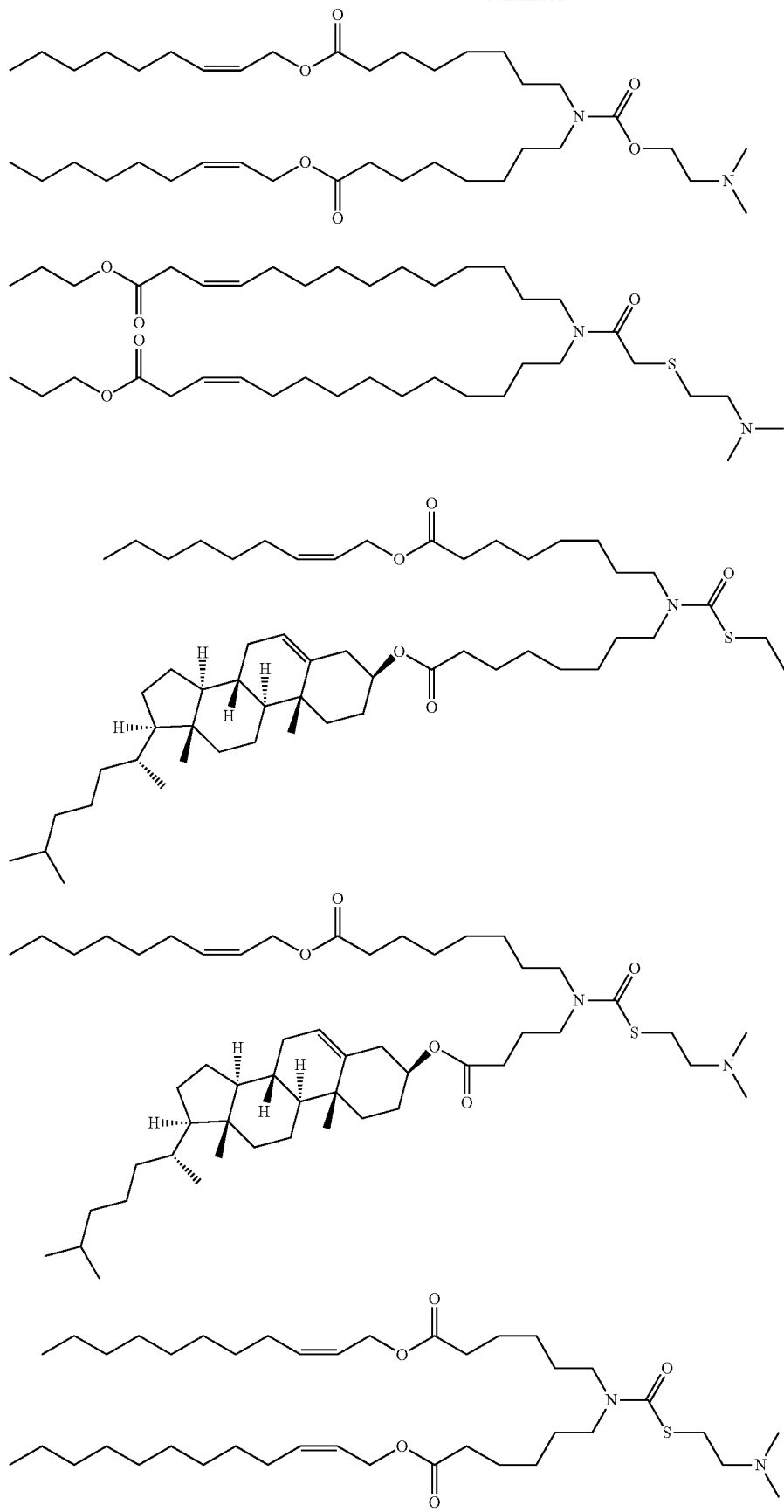

-continued
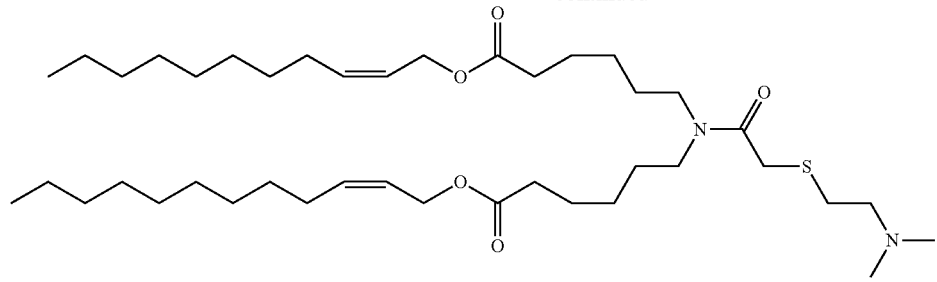
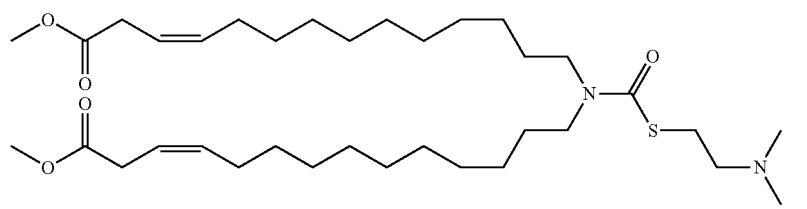
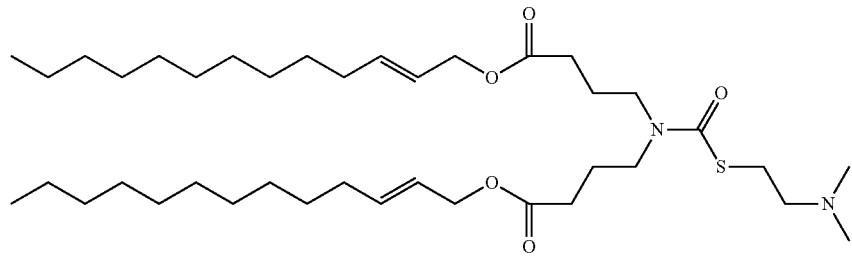
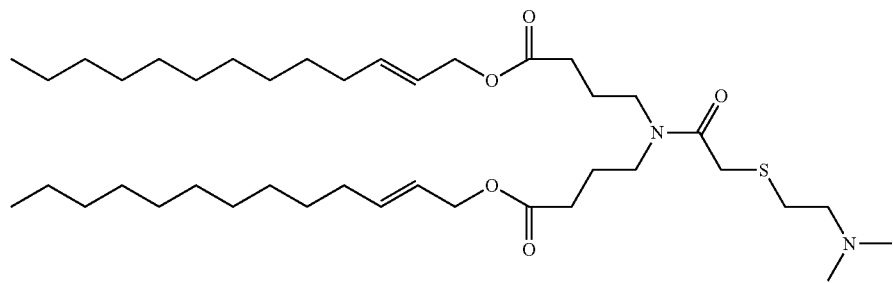
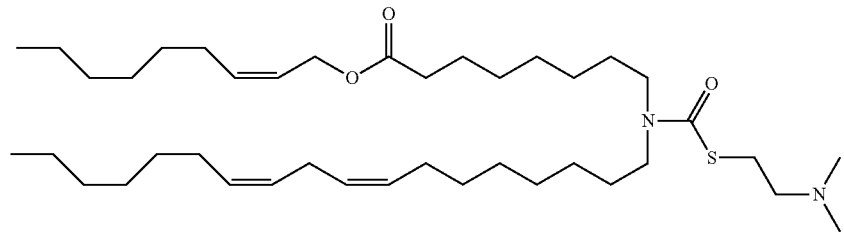
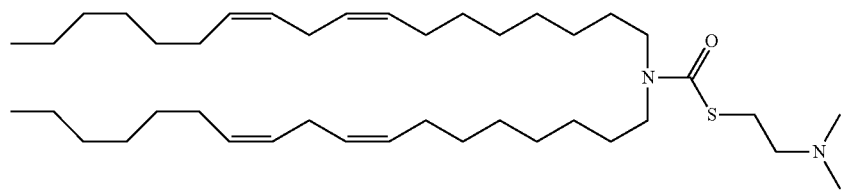

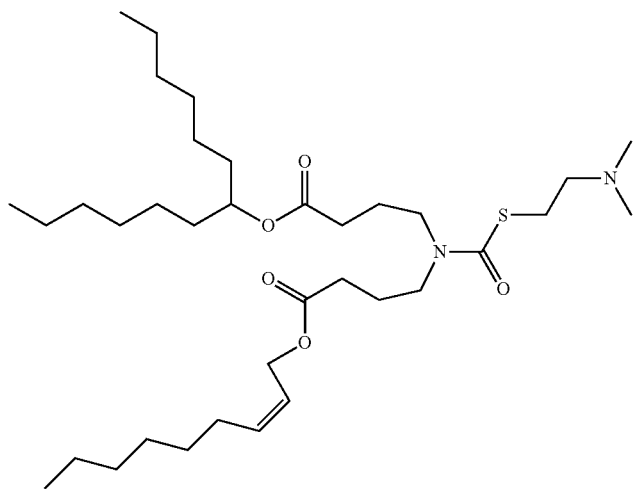
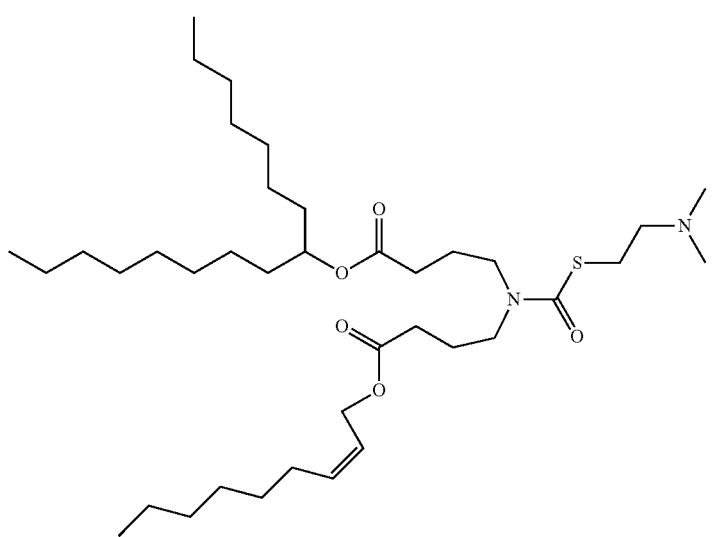
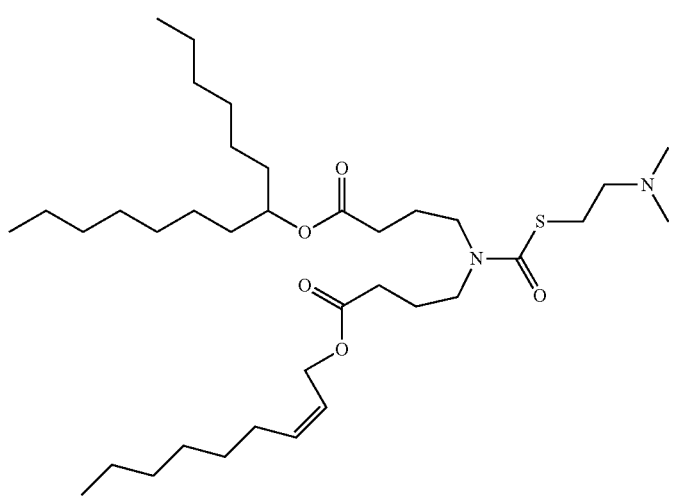

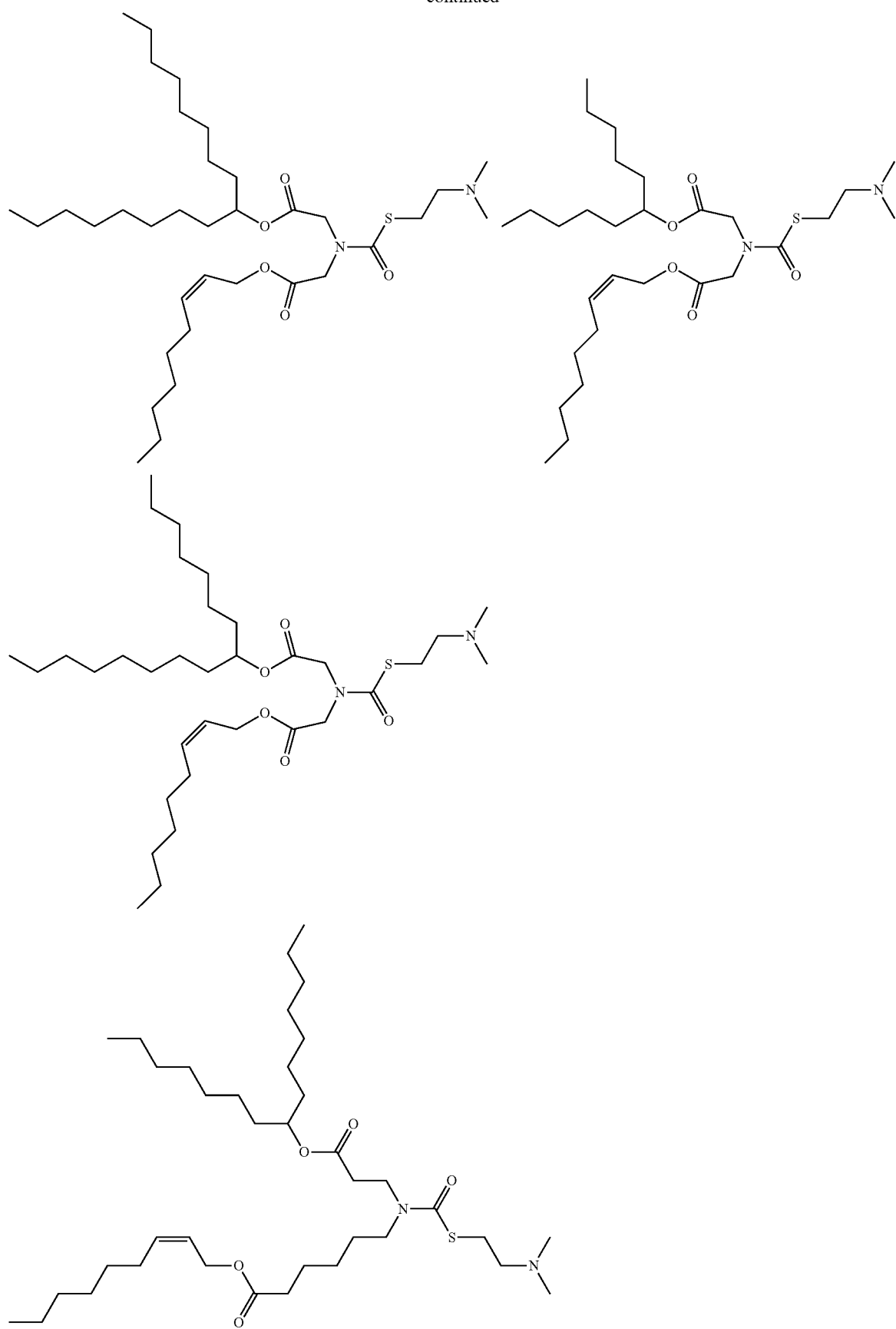

-continued
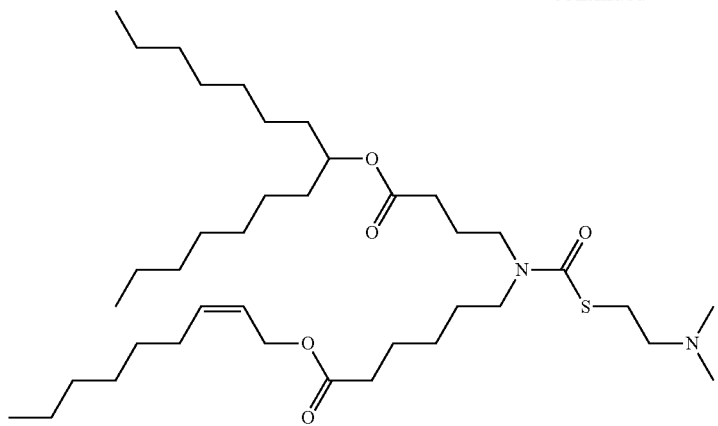
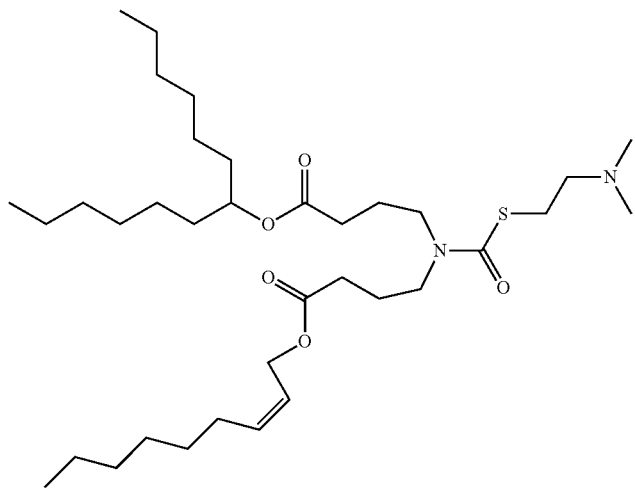
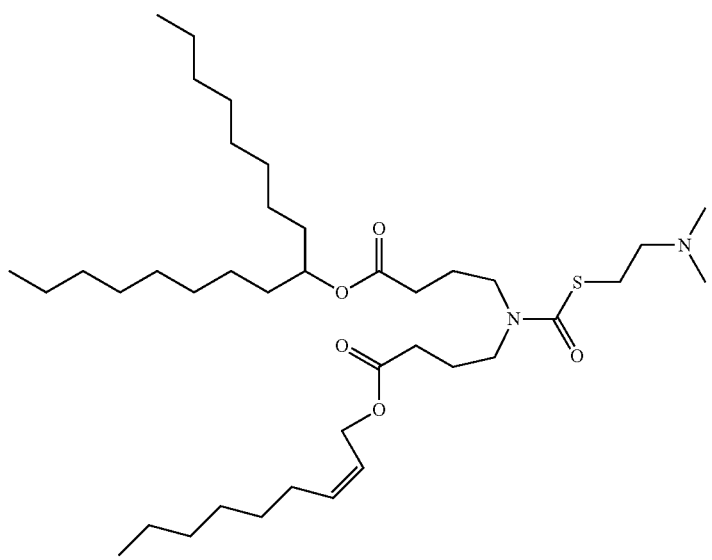

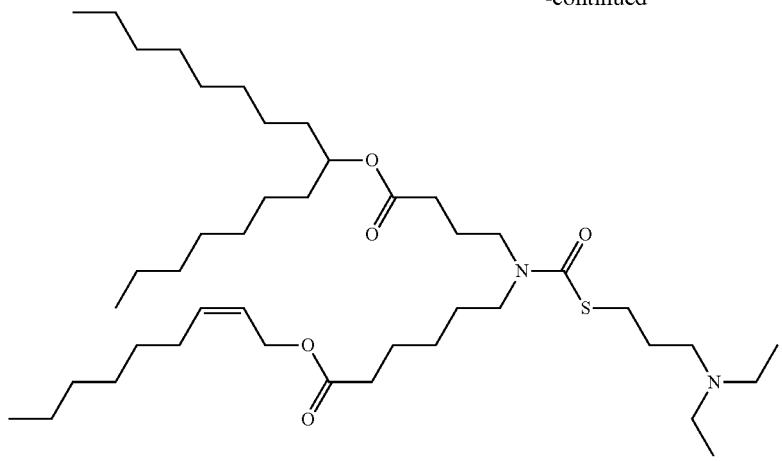
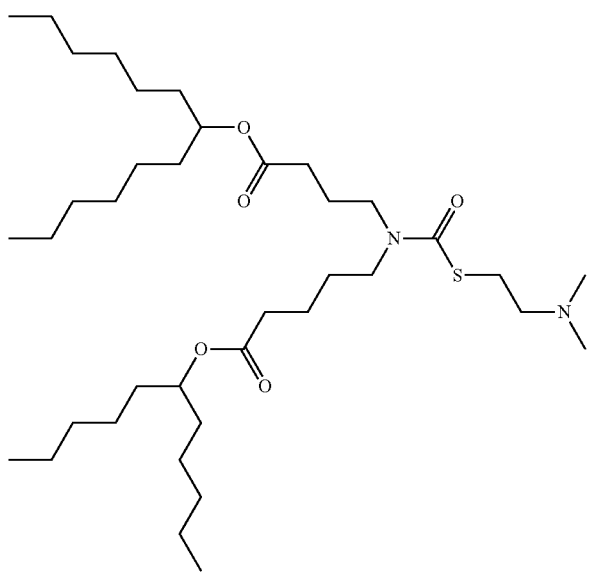
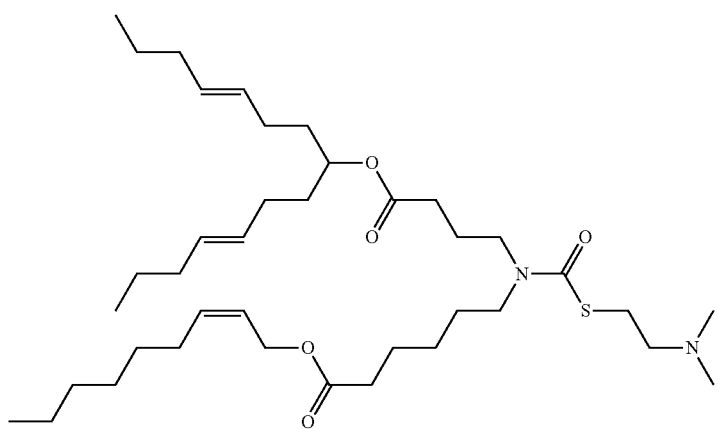

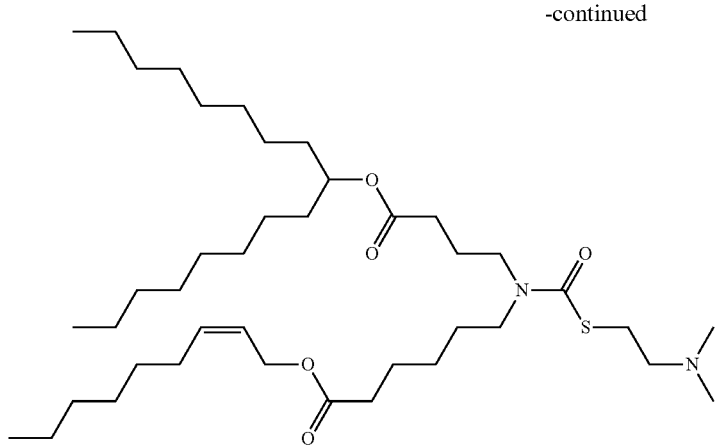
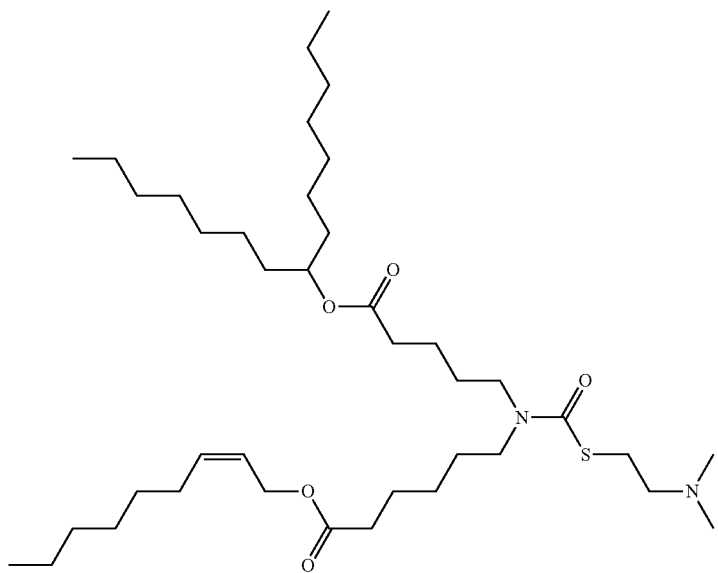
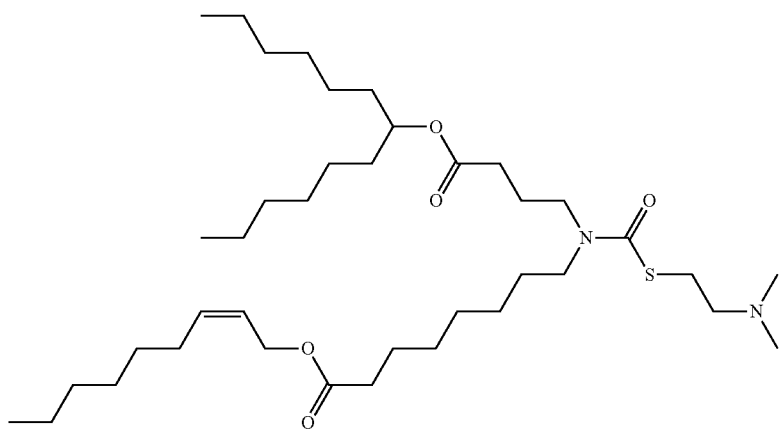

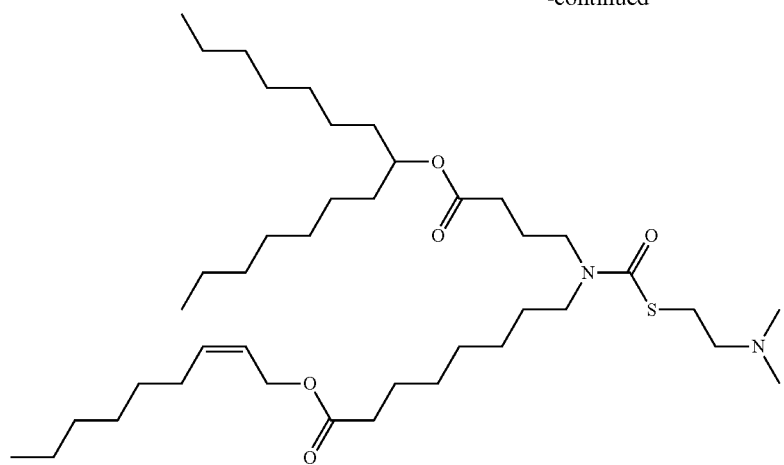
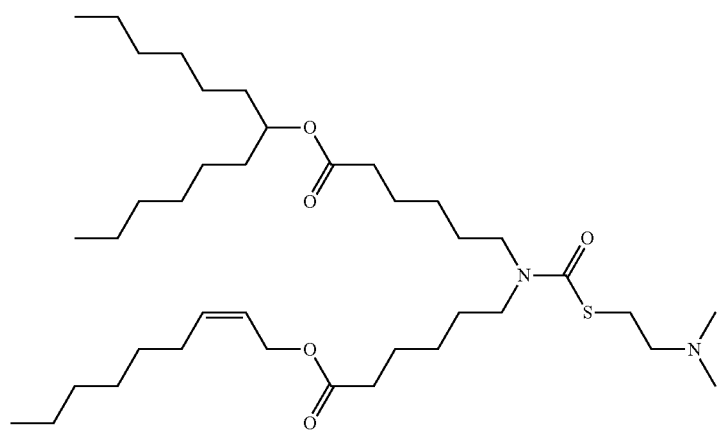
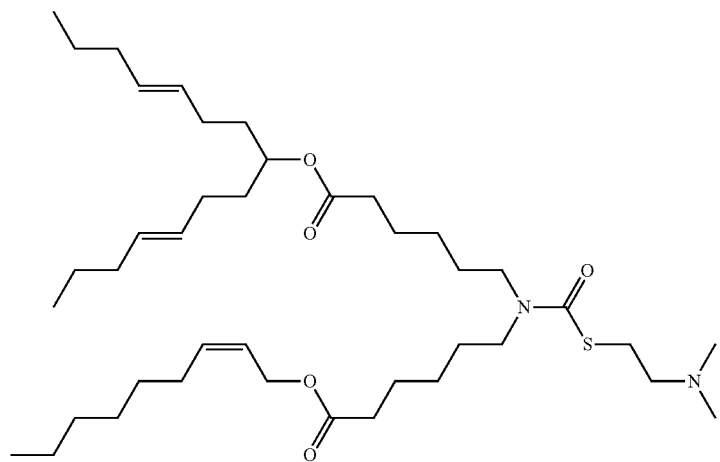

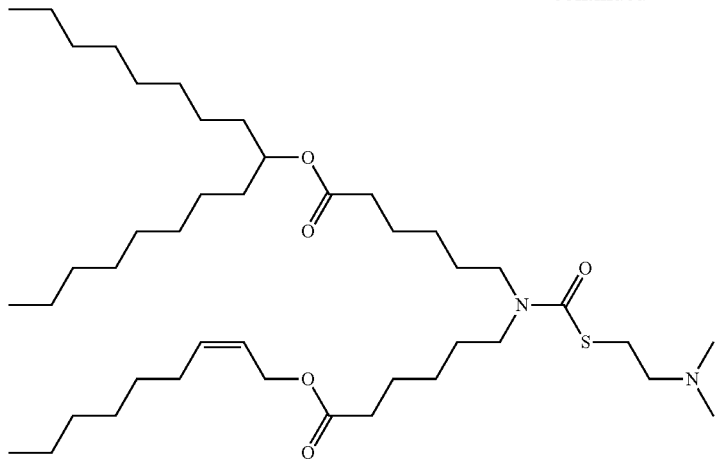
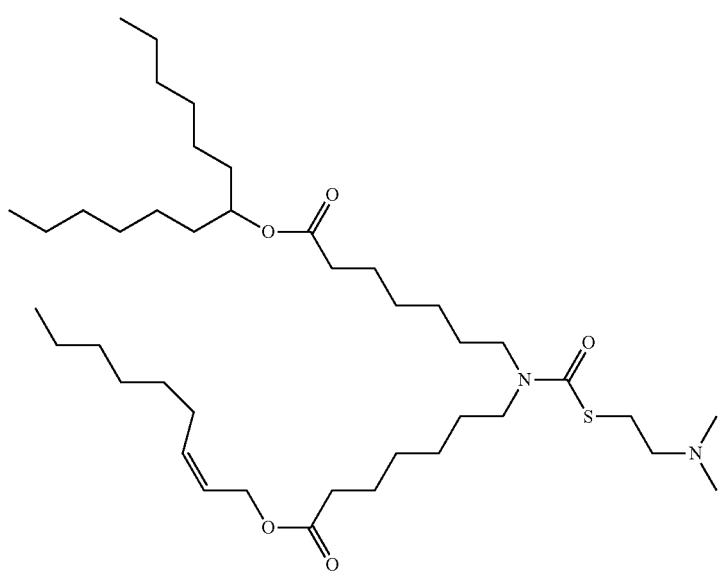
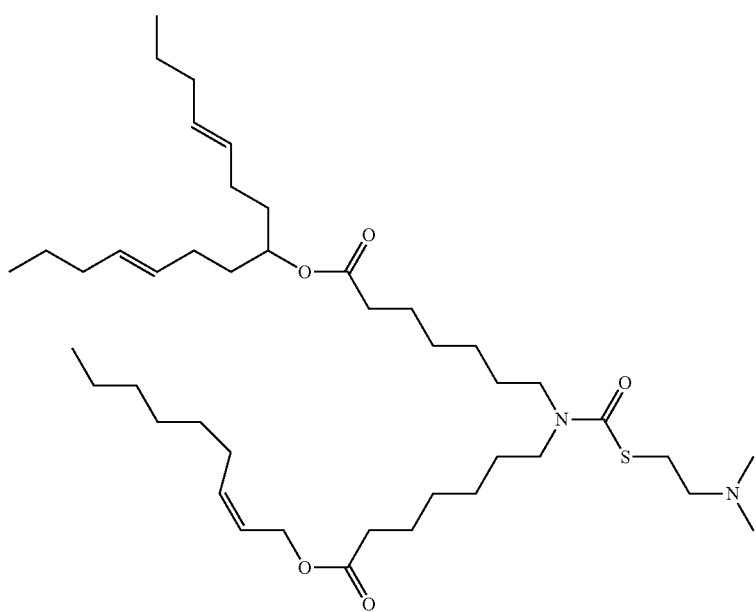

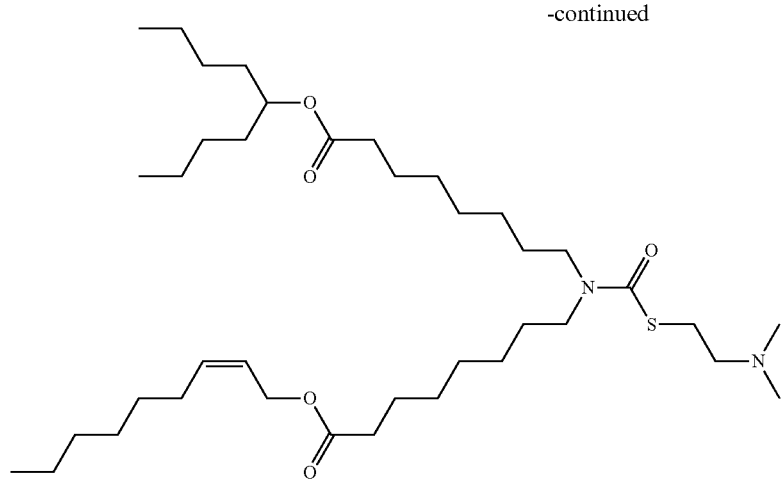
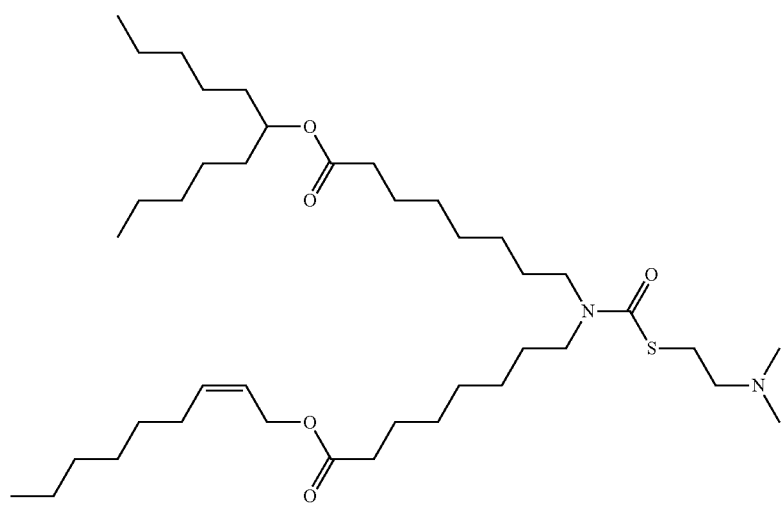
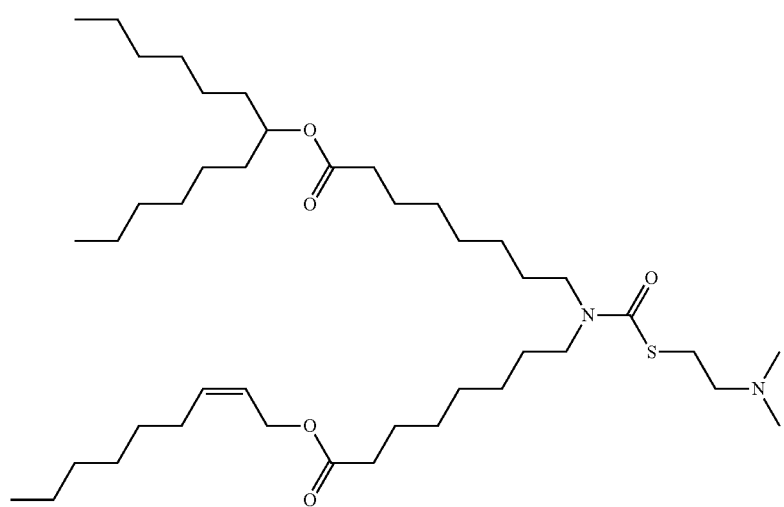

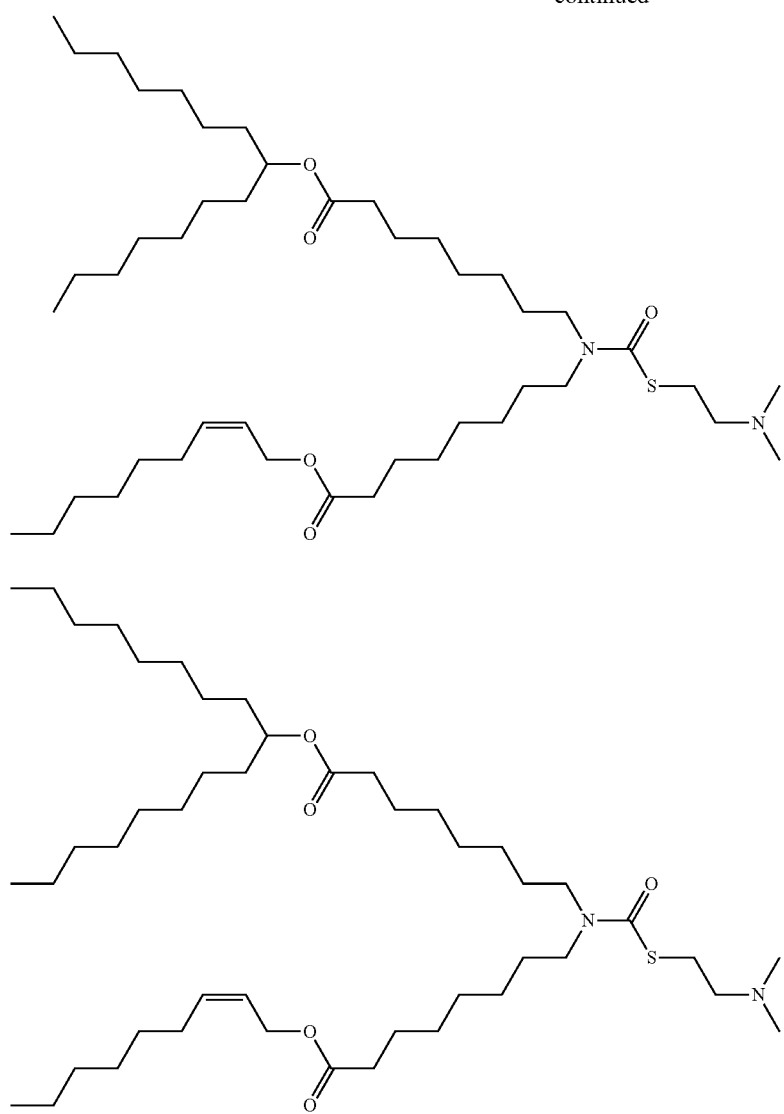
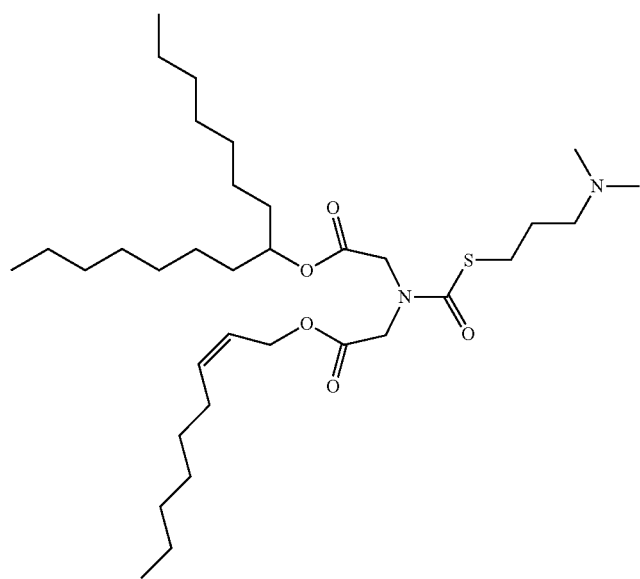

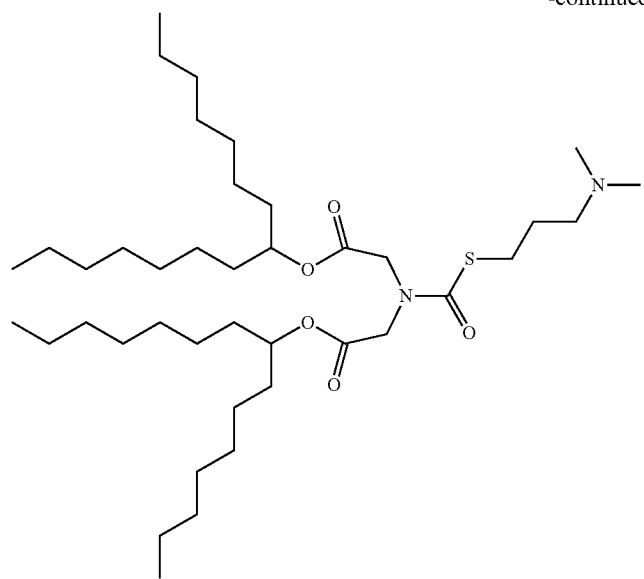
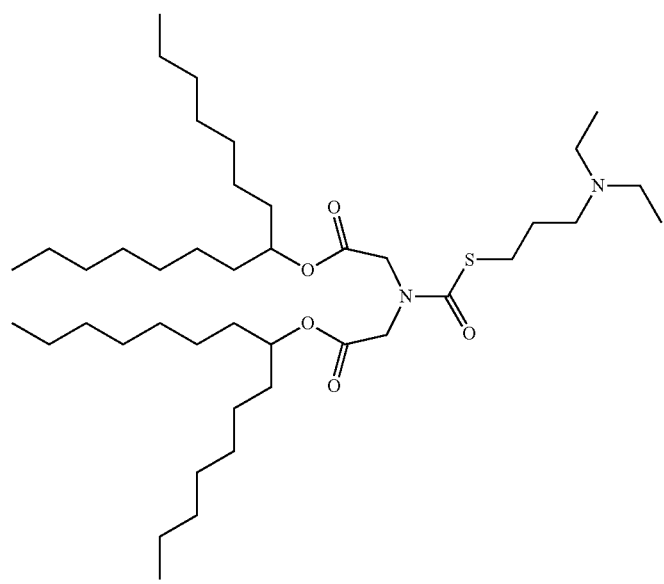

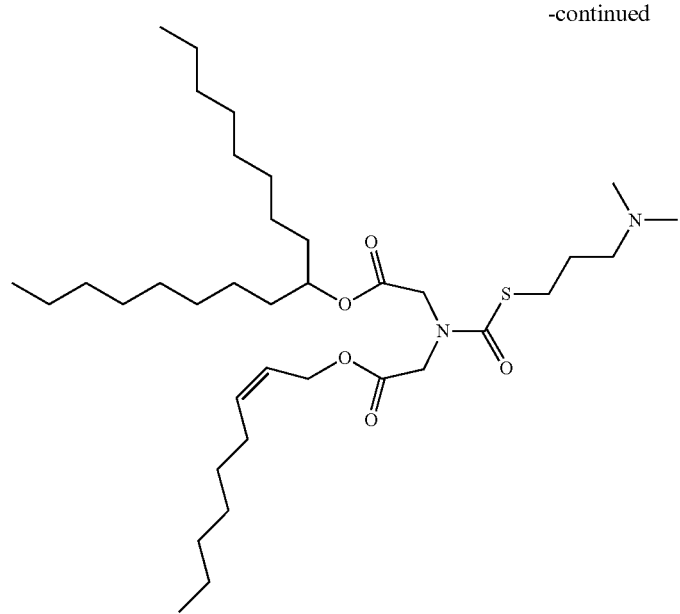
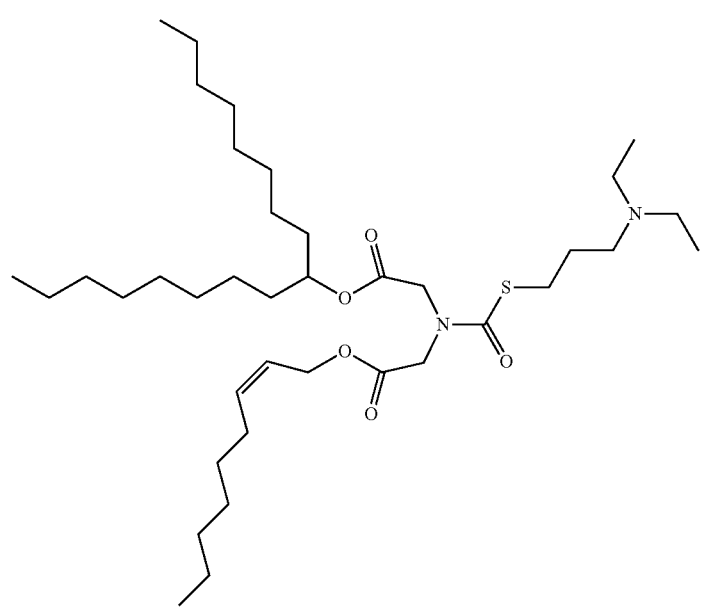

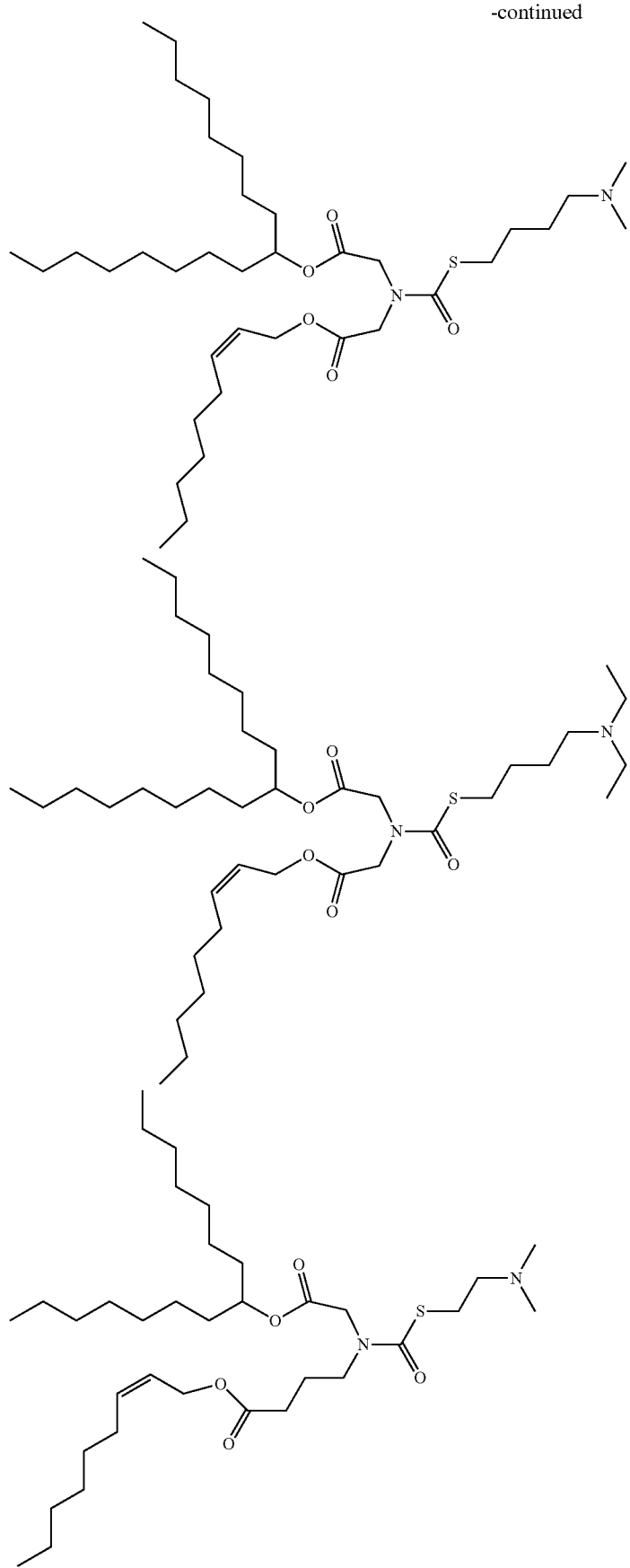

-continued
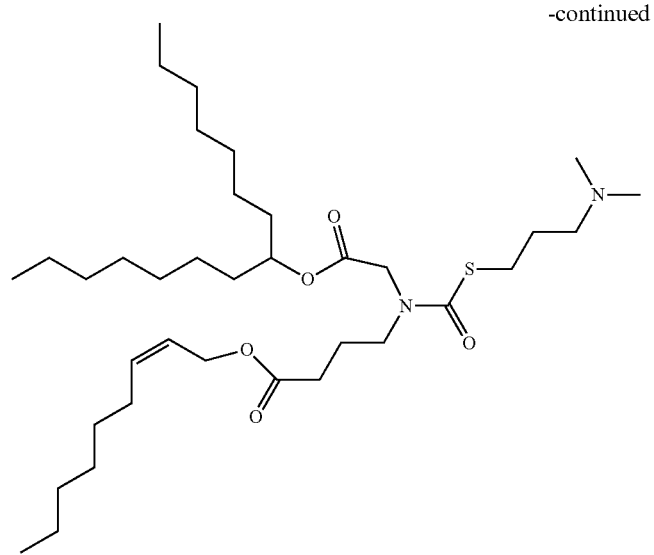
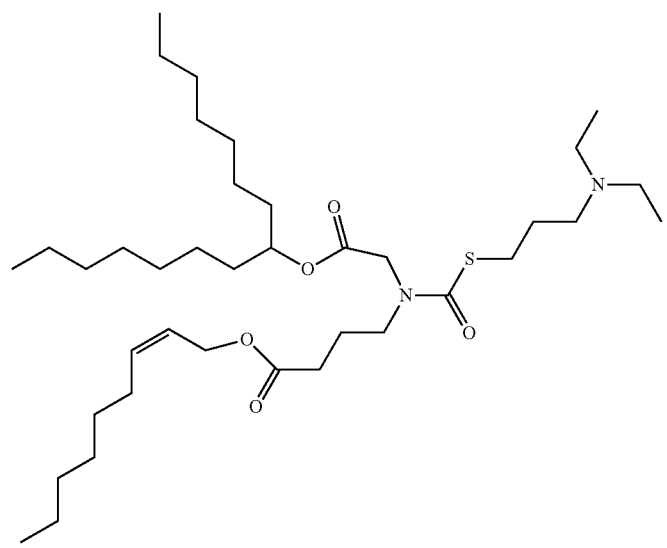
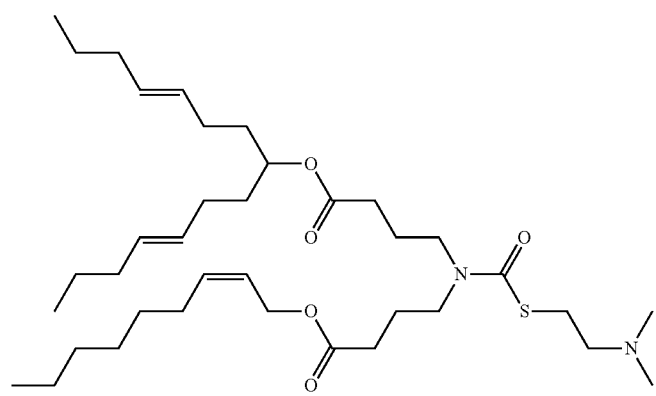

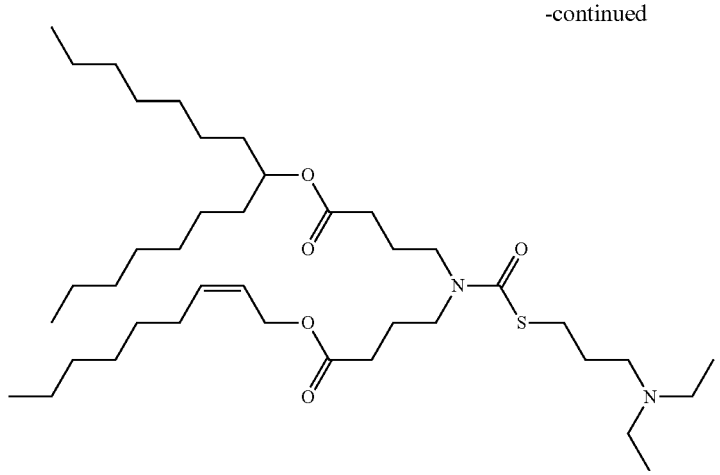
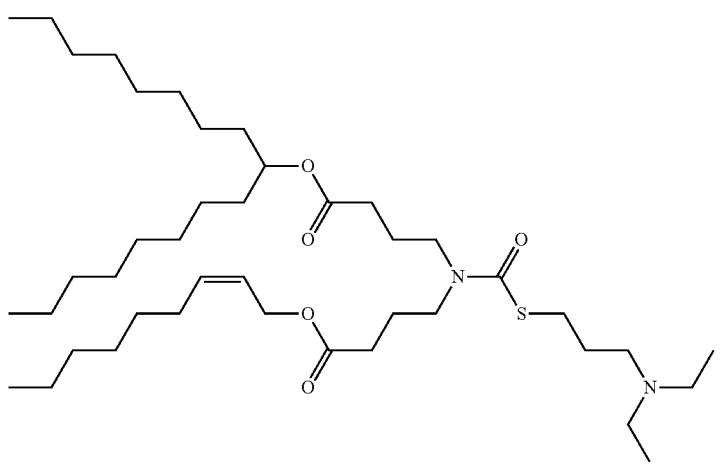
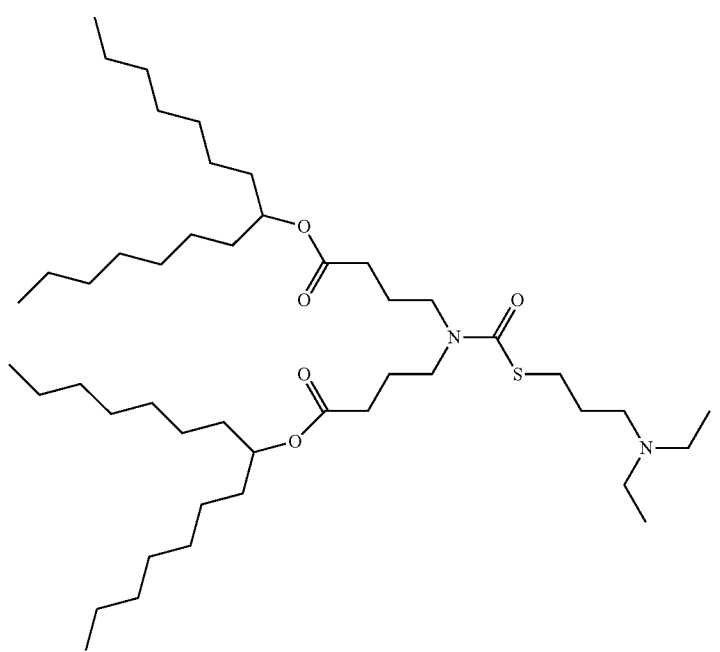

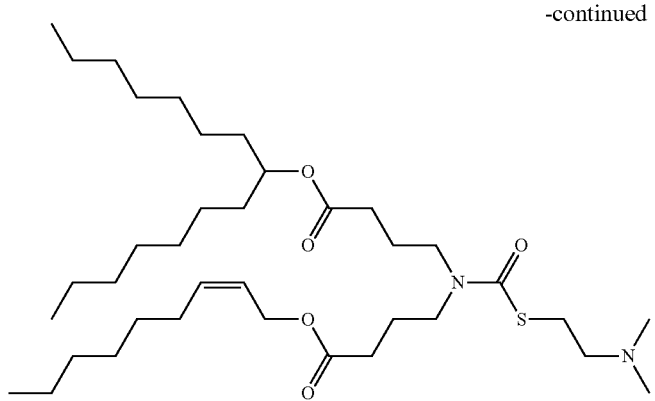
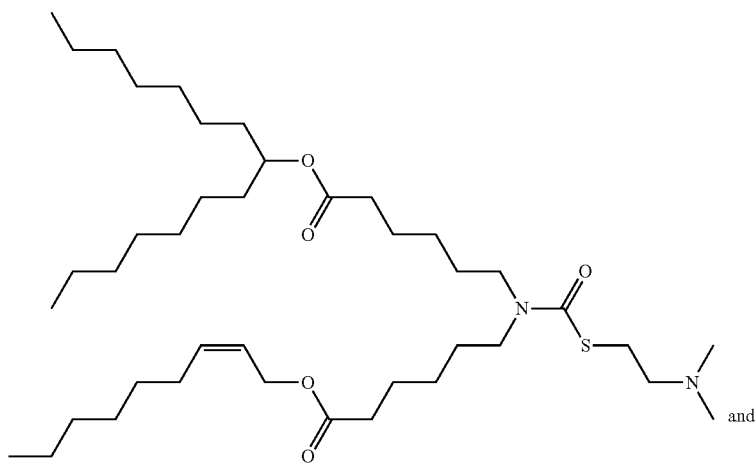
and
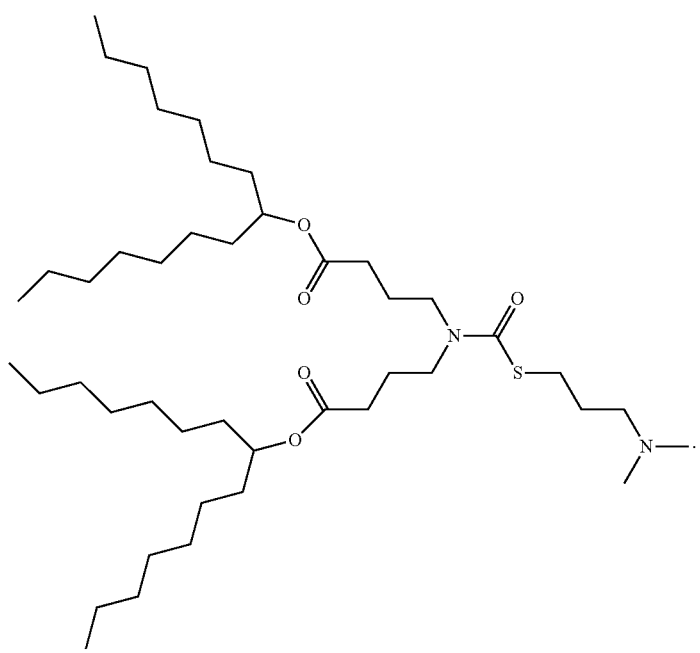
or a pharmaceutically acceptable salt or solvate thereof.

In another embodiment, disclosed herein is a pharmaceutical composition comprising a compound of Formula IA, Formula IB or Formula IC, and a lipid of Formula III

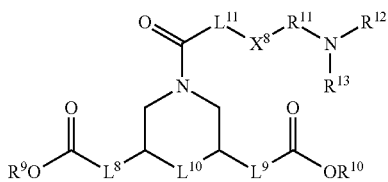

or a pharmaceutically acceptable salt or solvate thereof, wherein $R^9$ and $R^{10}$ are each independently selected from the group consisting of a linear or branched $C_{1-20}$ alkyl, a linear or branched $C_2$-$C_{20}$ alkenyl and $C_2$-$C_{20}$ alkynyl; $L^8$ and $L^9$ are each independently absent, a linear $C_1$-$C_{18}$ alkyl, or a linear $C_2$-$C_{18}$ alkenyl; $L^{11}$ is absent, a bond or a linear or branched $C_1$-$C_6$ alkyl; $L^{10}$ is absent or methyl; $X^8$ is S or O; $R^{11}$ is a linear or a branched $C_1$-$C_6$ alkyl; and $R^{12}$ and $R^{13}$ are each independently selected from the group consisting of a hydrogen, and a linear and branched $C_1$-$C_6$ alkyl.

In some embodiments, $R^9$ and $R^{10}$ are each independently a linear alkyl or alkenyl. In some embodiments, $R^9$ and $le°$ are each independently selected from the group consisting of a linear or branched $C_1$-$C_{20}$ alkyl, $C_1$-$C_{19}$ alkyl, $C_1$-$C_{18}$ alkyl, $C_1$-$C_{17}$ alkyl, $C_1$-$C_{16}$ alkyl, $C_1$-$C_{15}$ alkyl, $C_1$-$C_{14}$ alkyl, $C_1$-$C_{13}$ alkyl, $C_1$-$C_{12}$ alkyl, $C_1$-$C_{11}$ alkyl, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl and —$CH_2$—. In some embodiments, $R^9$ and $R^{10}$ are each independently selected from the group consisting of a linear or branched $C_2$-$C_{20}$ alkenyl, $C_2$-$C_{19}$ alkenyl, $C_2$-$C_{18}$ alkenyl, $C_2$-$C_{17}$ alkenyl, $C_2$-$C_{16}$ alkenyl, $C_2$-$C_{15}$ alkenyl, $C_2$-$C_{14}$ alkenyl, $C_2$-$C_{13}$ alkenyl, $C_2$-$C_{12}$ alkenyl, $C_2$-$C_{11}$ alkenyl, $C_2$-$C_{10}$ alkenyl, $C_2$-$C_9$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl and —CH=CH—. In some embodiments, $R^9$ and $R^{10}$ are each independently selected from the group consisting of a linear or branched $C_2$-$C_{20}$ alkynyl, $C_2$-$C_{19}$ alkynyl, $C_2$-$C_{18}$ alkynyl, $C_2$-$C_{17}$ alkynyl, $C_2$-$C_{16}$ alkynyl, $C_2$-$C_{15}$ alkynyl, $C_2$-$C_{14}$ alkynyl, $C_2$-$C_{13}$ alkynyl, $C_2$-$C_{12}$ alkynyl, $C_2$-$C_{11}$ alkynyl, $C_2$-$C_{10}$ alkynyl, $C_2$-$C_9$alkynyl, $C_2$-$C_8$ alkynyl, $C_2$-$C_7$alkynyl, $C_2$-$C_6$alkynyl, $C_2$-$C_5$alkynyl, $C_2$-$C_4$ alkynyl, $C_2$-$C_3$ alkynyl and $C_2$ alkynyl.

In some embodiments, $L^8$ and $L^9$ are each independently selected from the group consisting of a linear or branched $C_1$-$C_{18}$ alkyl, $C_1$-$C_{17}$ alkyl, $C_1$-$C_{16}$ alkyl, $C_1$-$C_{15}$ alkyl, $C_1$-$C_{14}$ alkyl, $C_1$-$C_{13}$ alkyl, $C_1$-$C_{12}$ alkyl, $C_1$-$C_{11}$ alkyl, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl and —$CH_2$—. In some embodiments, $L^8$ and $L^9$ are each independently selected from the group consisting of a linear or branched $C_2$-$C_{18}$ alkenyl, $C_2$-$C_{17}$ alkenyl, $C_2$-$C_{16}$ alkenyl, $C_2$-$C_{15}$ alkenyl, $C_2$-$C_{14}$ alkenyl, $C_2$-$C_{13}$ alkenyl, $C_2$-$C_{12}$ alkenyl, $C_2$-$C_{11}$ alkenyl, $C_2$-$C_{10}$ alkenyl, $C_2$-$C_9$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl and —CH=CH—. In some embodiments, $L^8$ and $L^9$ are each independently a linear alkyl. In some embodiments, $L^8$ and $L^9$ are each absent.

In some embodiments, $L^{11}$ is a branched $C_1$-$C_6$ alkyl, $C_1$-$C_5$ alkyl, $C_1$-$C_4$ alkyl, $C_1$-$C_3$ alkyl, $C_1$-$C_2$ alkyl or —$CH_2$—. In some embodiments, $L^{11}$ is a bond.

In some embodiments, $L^{10}$ is absent.

In some embodiments, $X^8$ is S.

In some embodiments, $R^{12}$ and $R^{13}$ are each independently a linear or branched $C_1$-$C_6$ alkyl, $C_1$-$C_5$ alkyl, $C_1$-$C_4$ alkyl, $C_1$-$C_3$ alkyl, $C_1$-$C_2$ alkyl or —$CH_2$—. In some embodiments, $R^{12}$ and $R^{13}$ are each independently a linear alkyl.

In another embodiment, disclosed herein is a pharmaceutical composition comprising a compound of Formula IA, Formula IB or Formula IC, and a lipid of Formula IV

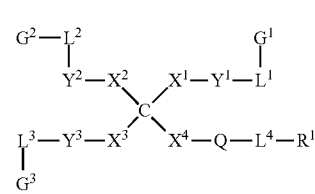

or a pharmaceutically acceptable salt or solvate thereof, wherein; $X^1$, $X^2$ and $X^3$ are each independently selected from the group consisting of $C_1$-$C_{10}$ alkyl, —$(CH_2)_m$—O—$(CH_2)_n$ and —$(CH_2)_m$—$NR^N$—$(CH_2)_n$—, wherein n is 1-36, m is 1-30, and $R^N$ is H, methyl, or $CH_2F$, $CHF_2$, or $CF_3$; $Y^1$, $Y^2$ and $Y^3$ are each independently selected from the group consisting of —NHC(O)—, —C(O)NH—, —OC(O)—, —C(O)O—, —SC(O)—, —C(O)S— and P(Z)(OH)$O_2$, wherein Z is O or S; $L^1$, $L^2$ and $L^3$ are each independently selected from the group consisting of a $C_1$-$C_{10}$ alkyl, —$(CH_2)_e$—O—$(CH_2)_f$—, —$(CH_2)_e$—S—$(CH_2)_f$—, —$(CH_2)_e$—S($O)_2$—$(CH_2)_f$— and —$(CH_2)_e$—$NR^N$—$(CH_2)_f$—, —$(CH_2$—$CH_2$—O$)_e(CH_2)_2$—, wherein e is 1-10, f is 1-16, k is 1-20, and $R^N$ is H, methyl, or $CH_2F$, $CHF_2$, or $CF_3$; $G^1$, $G^2$ and $G^3$ are each independently selected from the group consisting of a monosaccharide, a monosaccharide derivative, a vitamin, a polyol, a polysialic acid and a polysialic acid derivative; $X^4$ is selected from the group consisting of (a) —$(CH_2)_g$—O—$(CH_2)_h$— or —$(CH_2)_g$—$NR^N$—$(CH_2)_h$—, wherein g is 1-30, h is 1-36, and $R^N$ is H, methyl, or $CH_2F$, $CHF_2$, or $CF_3$, (b) an amino acid, and (c) —NHC(O)$R^2$, wherein $R^2$ is $C_1$-$C_{10}$ alkyl, a carbocycle, a heterocyclyl, a heteroaryl, a $C_1$-$C_{10}$ alkyl-carbocycle, a $C_1$-$C_{10}$ alkyl-heterocyclyl or a $C_1$-$C_{10}$ alkyl-heteroaryl, and wherein $R^2$ is optionally substituted; Q is alkylamino, —O(O)C—, —C(O)O—, —NHC(O)—, —C(O)NH—, —$(CH_2)$—NHC(O)—, —C(O)NH—$(CH_2)$—, —C(O)—$(CH_2)_i$—, —$(CH_2)_i$—O—$(CH_2)_j$—, —$(CH_2)_i$—$NR^3$—$(CH_2)$—, —$(CH_2)$—S—S—$(CH_2)$—, —$(CH_2)$—S—$(CH_2)$—, —$(CH_2)_i$—S($O)_2$—$(CH_2)_j$—, —$(CH_2)_i$NHC(O)—$(CH_2)_j$—, —$(CH_2)_i$—C(O)NH—$(CH_2)$—, —$(CH_2)_i$—SC(O)—$(CH_2)$—, or —$(CH_2)_i$—C(O)S—$(CH_2)_j$—, wherein i is 1-30 and j is 1-36, and wherein $R^3$ is hydrogen or an alkyl; $L^4$ is -PEG-C(O)O—, PEG-C(O)NH—, -PEG-NHC(O)—, -PEG-phosphate, -PEG-$C_1$-$C_{10}$ alkyl-phosphate, -PEG-$C_3$-$C_{10}$ alkenyl-phosphate, -PEG-phosphorothioate, -PEG-$C_1$-$C_{10}$ alkyl-phosphorothioate, -PEG-$C_3$-$C_{10}$ alkenyl-phosphorothioate, -PEG-boranophospate, alkyl-boranophospate, -PEG-$C_3$-$C_{10}$alkenyl-boranophospate, -PEG-C(O)NH—$C_1$-$C_{10}$alkyl-phosphate, -PEG-C(O)NH—$C_3$-$C_{10}$alkenyl-phosphate, -PEG-C(O)O—$C_1$-$C_{10}$alkyl-phosphate, -PEG-C(O)O—$C_3$-$C_{10}$alkenyl-phosphate, -PEG-C(O)NH—$C_1$-$C_{10}$ alkyl-phosphorothioate, -PEG-C(O)NH—$C_3$-$C_{10}$alkenyl-phosphorothioate, -PEG-C(O)O—$C_1$-$C_{10}$ alkyl-phosphorothioate, -PEG-C(O)O—$C_3$-$C_{10}$alkenyl-phosphorothioate, -PEG-C(O)—NH—$C_1$-$C_{10}$alkyl-boranophospate, -PEG-C(O)—NH—$C_3$-$C_{10}$alkenyl-boranophospate, -PEG-C(O)O—$C_1$-$C_{10}$alkyl-boranophospate or -PEG-C(O)O—$C_3$-$C_{10}$alkenyl-boranophospate; and $R^1$ is a helper lipid.

In some embodiments, PEG of $L^4$ is —$(CH_2—CH_2—O)_k$ $(CH_2)_2$—, wherein k is 10-100, 15-100, 10-90, 15-90, 10-80, 15-80, 10-70, 15-70, 10-60, 15-60, 10-50, 15-50, 10-40, 15-40, 10-30, 15-30, 10-20, 15-20, 20-90, 25-90, 20-80, 25-80, 20-70, 25-70, 20-60, 25-60, 20-50, 25-50, 20-40, 25-40, 20-30, 25-30, 30-80, 35-80, 30-70, 35-70, 30-60, 35-60, 30-50, 35-50, 30-40, 35-40, 40-90, 45-90, 40-80, 45-80, 40-70, 45-70, 40-60, 45-60, 40-50, 45-50, 50-90, 55-90, 50-80, 55-80, 50-70, 55-70, 50-60, or 55-60. In some embodiments, PEG of $L^4$ is —$(CH_2—CH_2—O)_k(CH_2)_2$—, wherein k is 10-100, 20-60, 30-60, 40-60, 40-50 or 45-50. In some embodiments, PEG of $L^4$ is —$(CH_2—CH_2—O)_k$ $(CH_2)_2$—, wherein k is 20-60.

In some embodiments, $X^1$, $X^2$ and $X^3$ are each independently selected from the group consisting of $C_1$-$C_{10}$ alkyl, —$(CH_2)_m$—O—$(CH_2)_n$— and —$(CH_2)_m$—$NR^N$—$(CH_2)_n$—, wherein n is 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 and 1. In some embodiments, $X^1$, $X^2$ and $X^3$ are each independently selected from the group consisting of $C_1$-$C_{10}$ alkyl, —$(CH_2)_m$ —O—$(CH_2)_n$— and —$(CH_2)_m$—$NR^N$—$(CH_2)_n$—, wherein m is 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 and 1. In some embodiments, $X^1$, $X^2$ and $X^3$ are each independently (—$CH_2)_m$—O—$CH_2$—, wherein m is 1-4. In some embodiments, $X^1$, $X^2$ and $X^3$ are each independently (—$CH_2)_2$—O—$CH_2$—. In some embodiments, $X^1$, $X^2$ and $X^3$ are each independently are each $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl or —$CH_2$—. In some embodiments, $X^1$, $X^2$ and $X^3$ are each independently (—$CH_2)_m$—O—$CH_2$—, wherein m is 1-4. In some embodiments, $X^1$, $X^2$ and $X^3$ are each independently (—$CH_2)_2$—O—$CH_2$—.

In some embodiments, $Y^1$, $Y^2$ and $Y^3$ are each —NHC(O)— or —C(O)NH—. In some embodiments, $Y^1$, $Y^2$ and $Y^3$ are each —NHC(O)—.

In some embodiments, $L^1$, $L^2$ and $L^3$ are each $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl or —$CH_2$—. In some embodiments, $L^1$, $L^2$ and $L^3$ are each independently $C_3$-$C_8$ alkyl or —$(CH_2—CH_2—O)_k(CH_2)_2$—, wherein k is 1-10. In some embodiments, $L^1$, $L^2$ and $L^3$ are each independently —$(CH_2—CH_2—O)_k(CH_2)_2$—, wherein k is 2-4. In some embodiments, $L^1$, $L^2$ and $L^3$ are each independently —$(CH_2—CH_2—O)_k(CH_2)_2$—, wherein k is 1-10, 1-9, 1-8, 1-7, 1-6, 1-5, 1-4, 1-3, 1-2 or 1. In some embodiments, $L^1$, $L^2$ and $L^3$ are each independently —$(CH_2—CH_2—O)(CH_2)_2$—.

In some embodiments, $G^1$, $G^2$ and $G^3$ are each independently selected from the group consisting of folic acid, ribose, retinol, niacin, riboflavin, biotin, glucose, mannose, fucose, sucrose, lactose, mannose-6-phosphate, N-acetyl galactosamine, N-acetylglucosamine, a sialic acid, a sialic acid derivative, allose, altrose, arabinose, cladinose, erythrose, erythrulose, fructose, fucitol, fucosamine, fucose, fuculose, galactosamine, galactosaminitol, galactose, glucosamine, glucosaminitol, glucose-6 phosphate, gulose glyceraldehyde, glycero-mannoheptose, glycerol, glycerone, gulose, idose, lyxose, mannosamine, psicose, quinovose, quinovosamine, rhamnitol, rhamnosamine, rhamnose, ribulose, sedoheptulose, sorbose, tagatose, talose, threose, xylose and xylulose.

In some embodiments, $G^1$, $G^2$ and $G^3$ are each N-acetyl-galactosamine.

In some embodiments, $X^4$ is selected from the group consisting of

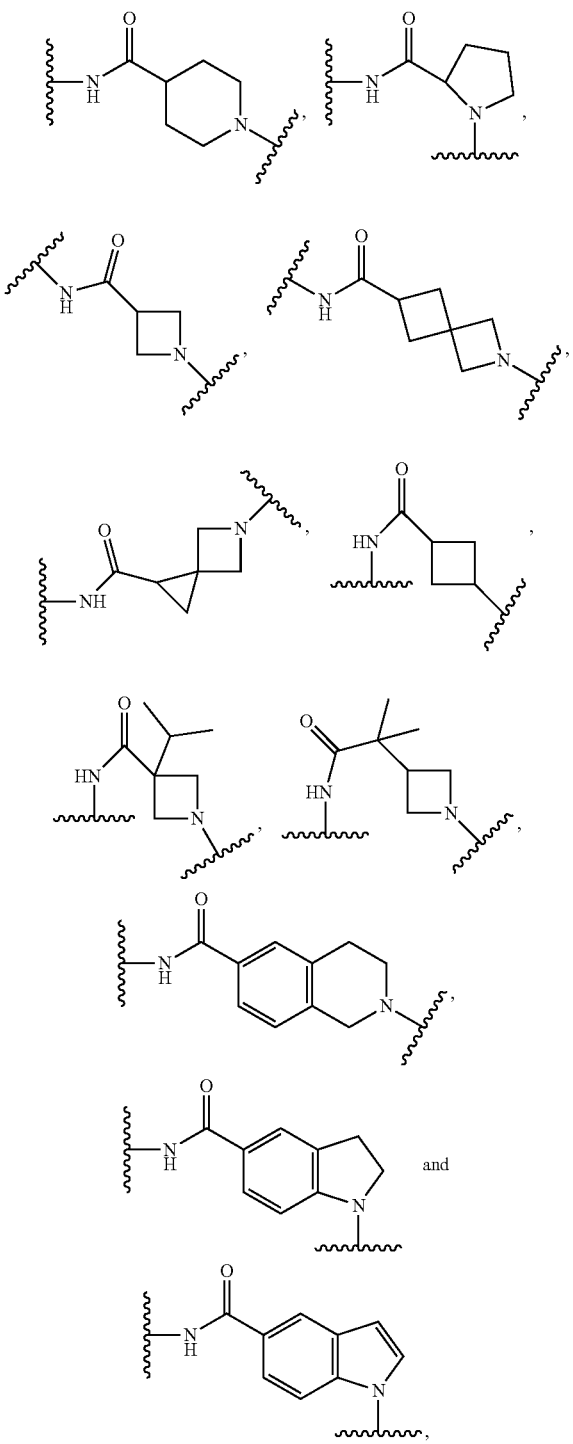

wherein $X^4$ is optionally substituted.

In some embodiments, $X^4$ is

In some embodiments, Q is alkylamino, —C(O)—$(CH_2)_i$—, —$(CH_2)_i$—O—$(CH_2)_j$—, —$(CH_2)_i$—$NR^3$—$(CH_2)_j$—, —$(CH_2)_i$—S—S—$(CH_2)_j$—, —$(CH_2)_i$—S—$(CH_2)_j$—, —$(CH_2)_i$—$S(O)_2$—$(CH_2)_j$—, —$(CH_2)_i$—NHC(O)—$(CH_2)_j$—, —$(CH_2)_i$—C(O)NH—$(CH_2)_j$—, —$(CH_2)_i$—SC(O)—$(CH_2)_j$—, or —$(CH_2)_i$—C(O)S—$(CH_2)_j$—, wherein i is 1-10 and j is 1-10, and wherein $R^3$ is hydrogen or an alkyl. In some embodiments, Q is alkylamino, —C(O)—$(CH_2)_i$—, —$(CH_2)_i$—O—$(CH_2)_j$—, —$(CH_2)_i$—$NR^3$—$(CH_2)_j$—, —$(CH_2)_i$—S—S—$(CH_2)_j$—, —$(CH_2)_i$—S—$(CH_2)_j$—, —$(CH_2)_i$—$S(O)_2$—$(CH_2)_j$—, —$(CH_2)_i$—NHC(O)—$(CH_2)_j$—, —$(CH_2)_i$—C(O)NH—$(CH_2)_j$—, —$(CH_2)_i$—SC(O)—$(CH_2)_j$—, or —$(CH_2)_i$—C(O)S—$(CH_2)_j$—, wherein i is 1-10 and j is 1-10; i is 1-9 and j is 1-9; i is 1-8 and j is 1-8; i is 1-7 and j is 1-7; i is 1-6 and j is 1-6; i is 1-5 and j is 1-5; i is 1-5 and j is 1-4; i is 1-3 and j is 1-3; i is 1-2 and j is 1-2; or i is 1 and j is 1. In some embodiments, Q is alkylamino, —C(O)—$(CH_2)_i$—, —$(CH_2)_i$—O—$(CH_2)_j$—, —$(CH_2)_i$—$NR^3$—$(CH_2)_j$—, —$(CH_2)_i$—S—S—$(CH_2)_j$—, —$(CH_2)_i$—S—$(CH_2)_j$—, —$(CH_2)_i$—$S(O)_2$—$(CH_2)_j$—, —$(CH_2)_i$—NHC(O)—$(CH_2)_j$—, —$(CH_2)_i$-C(O)NH—$(CH_2)_j$—, —$(CH_2)_i$—SC(O)—$(CH_2)_j$—, or —$(CH_2)_i$—C(O)S—$(CH_2)_j$—, wherein i is independently 1-10 and j is independently 1-10.

In some embodiments, $R^1$ is selected from the group consisting of lecithin, dialkyloxypropyl (DAA), diacylglycerol (DAG), dimyristoylglycerol (DMG), Dioleoylglycerol (DOG), Dipalmitoylglycerol (DPG), phosphatidylethanolamine (PE), Distearoylglycerol (DSG), lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, di stearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), phosphatidylethanolamine distearoyl-(DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, and dilinoleoylphosphatidylcholine.

In some embodiments, $R^1$ is selected from the group consisting of dimyristoylglycerol (DMG), Dioleoylglycerol (DOG), Dipalmitoylglycerol (DPG), and Distearoylglycerol (DSG).

In some embodiments, the pharmaceutical composition comprising a compound of Formula IA, Formula IB, or Formula IC, and a lipid of Formula II, Formula III, or Formula IV; and a lipid-NA (Nucleic Acid) nanoparticle comprising a cationic lipid, a non-cationic lipid, a PEG-lipid or a helper lipid.

In some embodiments, the lipid-NA nanoparticle encapsulates the compound of Formula IA, Formula IB or Formula IC.

In some embodiments, the lipid-NA nanoparticle has a size less than 100 nm.

In some embodiments, the cationic lipid is a phospholipid.

In some embodiments, the non-cationic lipid is cholesterol.

In some embodiments, the PEG-lipid is a PEG-diacylglycerol (PEG-DAG) or a PEG-dialkyloxyalkyl (PEG-DAA). In some preferred embodiments, the PEG-lipid is PEG550-PE.

In some preferred embodiments, the PEG-lipid is PEG750-PE. In some preferred embodiments, the PEG-lipid is PEG2000-DMG In some embodiments, the nucleic acid upregulates, suppresses, reduces, decreases, downregulates or silences the expression of a target gene.

In some embodiments, the nucleic acid modulates the expression of a target gene, wherein the target gene is selected from the group consisting of MUT (Methylmalonic acidemia), PCCA (Propionyl-CoA Carboxylase Subunit Alpha), PCCB (Propionyl-CoA Carboxylase Subunit Beta), ASL (Argininosuccinate Lyase), ASS1 (Argininosuccinate Synthase 1), FAH (Fumarylacetoacetate Hydrolase), HMBS (Hydroxymethylbilane Synthase), ATP7B (ATPase Copper Transporting Beta), LDLR (Low Density Lipoprotein Receptor), G6PC (Glucose-6-Phosphatase Catalytic Subunit) and AGXT (Alanine-Glyoxylate and Serine-Pyruvate Aminotransferase).

In some embodiments, the nucleic acid encodes an antibody.

In some embodiments, the antibody is capable of binding to a viral particle.

In some embodiments, the nucleic acid encodes a viral protein.

In some embodiments, the nucleic acid has ant (nucleotide) length of 200-1000 nt, 1000-5000 nt, 5000-10,000 nt or 10,000-25,000 nt.

In some embodiments, the nucleic acid is an mRNA and/or siRNA.

In some embodiments, the nucleic acid is a DNA.

In some embodiments, the nucleic acid is a pDNA (plasmid DNA).

In yet another embodiment, disclosed herein is a method of treating a disease in a subject, comprising administering the pharmaceutical composition comprising a compound of Formula IA, Formula IB, or Formula IC; and a lipid of Formula II, Formula III or Formula IV; and/or a lipid-NA (Nucleic Acid) nanoparticle comprising a cationic lipid, a non-cationic lipid, a PEG-lipid, and/or a helper lipid to the subject.

In some embodiments, administration is parenteral or by intravenous injection.

In some embodiments, administration is by subcutaneous injection, intradermal injection or intramuscular injection.

In some embodiments, the pharmaceutical composition is administered at least twice.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Where ranges are given it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any nucleic acid or protein encoded thereby; any method of production; any method of use; etc.) can be excluded from any one or more claims, for any reason, whether or not related to the existence of prior art.

At various places in the present specification, sub stituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The phrase "at least one" refers to one or more (e.g., 1-3, 1-2, or 1).

The term "composition" refers to a product comprising the specified ingredients in the specified amounts, as well as any product that results, directly or indirectly, from combination of the specified ingredients in the specified amounts.

The phrase "in combination with" refers to the administration of a compound of Formula I with other medicaments in the methods of treatment of this disclosure, means-that the compounds of Formula I and the other medicaments are administered sequentially or concurrently in separate dosage forms, or are administered concurrently in the same dosage form.

In the claims, "a," "an," and "the" refer to one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

The terms "administered in combination" or "combined administration" refer to two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

The term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

The terms "approximately" or "about" as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The terms "associated with", "conjugated", "linked", "attached" and "tethered" when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization-based connectivity sufficiently stable such that the "associated" entities remain physically associated.

The term "biodegradable" refers to being capable of being broken down into innocuous products by the action of living things.

The phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present disclosure may be considered biologically active if even a portion of the polynucleotide is biologically active or mimics an activity considered biologically relevant.

The term "acyl" refers to a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "acylamino" refers to an acyl group, as defined herein, attached to the parent molecular group though an amino group, as defined herein (i.e., —N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The term "acylaminoalkyl" refers to an acyl group, as defined herein, attached to an amino group that is in turn attached to the parent molecular group though an alkyl group, as defined herein (i.e., -alkyl-N($R^{N2}$)—C(O)—R, where R is H or an optionally substituted $C_{1-6}$, $C_{1-10}$, or $C_{1-20}$ alkyl group (e.g., haloalkyl) and $R^{N2}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —$NH_2$ or —$NHR^{N3}$, wherein $R^{N3}$ is, independently, OH, $NO_2$, $NH_2$, $NR^{N4}$, $SO_2OR^{N4}$, $SO_2R^{N4}$, $SOR^{N4}$, alkyl, aryl, acyl (e.g., acetyl, trifluoroacetyl, or others described herein), or alkoxycarbonylalkyl, and each R' can be H, alkyl, or aryl.

The term "acyloxy" refers to an acyl group, as defined herein, attached to the parent molecular group though an oxygen atom (i.e., —O—C(O)—R, where R is H or an optionally substituted $C_{1-6}$, $C_{1-10}$, or $C_{1-20}$ alkyl group). Exemplary unsubstituted acyloxy groups include from 1 to 21 carbons (e.g., from 1 to 7 or from 1 to 11 carbons). In some embodiments, the alkyl group is further substituted with 1, 2, 3, or 4 substituents as described herein.

The term "acyloxyalkyl" refers to an acyl group, as defined herein, attached to an oxygen atom that in turn is attached to the parent molecular group though an alkyl group (i.e., -alkyl-O—C(O)—R, where R is H or an optionally substituted $C_{1-6}$, $C_{1-10}$, or $C_{1-20}$ alkyl group). Exemplary unsubstituted acyloxyalkyl groups include from 1 to 21 carbons (e.g., from 1 to 7 or from 1 to 11 carbons). In some embodiments, the alkyl group is, independently, further substituted with 1, 2, 3, or 4 substituents as described herein.

The term "alkylaryl" refers to an aryl group, as defined herein, attached to the parent molecular group through an alkyl group, as defined herein. Exemplary unsubstituted alkylaryl groups are from 7 to 30 carbons (e.g., from 7 to 16 or from 7 to 20 carbons, such as $C_{1-6}$ alkyl-$C_{6-10}$ aryl, $C_{1-10}$ alkyl-$C_{6-10}$ aryl, or $C_{1-20}$ alkyl-$C_{6-10}$ aryl). In some embodiments, the alkyl and the aryl each can be further substituted with 1, 2, 3, or 4 substituent groups as defined herein for the respective groups. Other groups preceded by the prefix "alkyl" are defined in the same manner, where "alkyl" refers to a $C_{1-6}$ alkyl, unless otherwise noted, and the attached chemical structure is as defined herein.

The term "alkylcycloalkyl" refers to a cycloalkyl group, as defined herein, attached to the parent molecular group through an alkyl group, as defined herein (e.g., an alkyl group of from 1 to 4, from 1 to 6, from 1 to 10, or from 1 to 20 carbons). In some embodiments, the alkyl and the cycloalkyl each can be further substituted with 1, 2, 3, or 4 substituent groups as defined herein for the respective group.

The term "alkenyl" refers to a monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkenyloxy" refers to a chemical substituent of formula —OR, where R is a $C_{2-20}$ alkenyl group (e.g., $C_{2-6}$ or $C_{2-10}$ alkenyl), unless otherwise specified. Exemplary alkenyloxy groups include ethenyloxy, propenyloxy, and the like. In some embodiments, the alkenyl group can be further substituted with 1, 2, 3, or 4 substituent groups as defined herein (e.g., a hydroxy group).

An "alkenyl-phosphate" or "alkenyl-phosphorthioate" and the like describe an alkenyl group conjugated to a phosphate group. Those of skill in the art will recognize that such alkenyl groups will necessarily comprise at least 3 carbon atoms and that the alkenyl bond will not be proximate to the phosphate group (i.e, between the first and second carbon), as such would result in the formation of enol-phsophates.

The term "alkylheteroaryl" refers to a heteroaryl group, as defined herein, attached to the parent molecular group through an alkyl group, as defined herein. Exemplary unsubstituted alkylheteroaryl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alkyl-$C_{1-12}$ heteroaryl, $C_{1-10}$ alkyl-$C_{1-12}$ heteroaryl, or $C_{1-20}$ alkyl-$C_{1-12}$ heteroaryl). In some embodiments, the alkyl and the heteroaryl each can be further substituted with 1, 2, 3, or 4 substituent groups as defined herein for the respective group. alkylheteroaryl groups are a subset of alkylheterocyclyl groups.

The term "alkylheterocyclyl" refers to a heterocyclyl group, as defined herein, attached to the parent molecular group through an alkyl group, as defined herein. Exemplary unsubstituted alkylheterocyclyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alkyl-$C_{1-12}$ heterocyclyl, $C_{1-10}$ alkyl-$C_{1-12}$ heterocyclyl, or $C_{1-20}$ alkyl-$C_{1-12}$ heterocyclyl). In some embodiments, the alkyl and the heterocyclyl each can be further substituted with 1, 2, 3, or 4 substituent groups as defined herein for the respective group.

The term "alkoxy" refers to a chemical substituent of formula —OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), t-butoxy, and the like. In some embodiments, the alkyl group can be further substituted with 1, 2, 3, or 4 substituent groups as defined herein (e.g., hydroxy or alkoxy).

The term "alkoxyalkoxy" refers to an alkoxy group that is substituted with an alkoxy group. Exemplary unsubstituted alkoxyalkoxy groups include between 2 to 40 carbons (e.g., from 2 to 12 or from 2 to 20 carbons, such as $C_{1-6}$ alkoxy-$C_{1-6}$ alkoxy, $C_{1-10}$ alkoxy-$C_{1-10}$ alkoxy, or $C_{1-20}$ alkoxy-$C_{1-20}$ alkoxy). In some embodiments, the each alkoxy group can be further substituted with 1, 2, 3, or 4 substituent groups as defined herein.

The term "alkoxyalkyl" refers to an alkyl group that is substituted with an alkoxy group. Exemplary unsubstituted alkoxyalkyl groups include between 2 to 40 carbons (e.g., from 2 to 12 or from 2 to 20 carbons, such as $C_{1-6}$ alkoxy-$C_{1-6}$ alkyl, $C_{1-10}$ alkoxy-$C_{1-10}$ alkyl, or $C_{1-20}$ alkoxy-$C_{1-20}$ alkyl). In some embodiments, the alkyl and the alkoxy each can be further substituted with 1, 2, 3, or 4 substituent groups as defined herein for the respective group.

The term "alkoxycarbonyl" refers an alkoxy, as defined herein, attached to the parent molecular group through a carbonyl atom (e.g., —C(O)—OR, where R is H or an optionally substituted $C_{1-6}$, $C_{1-10}$, or $C_{1-20}$ alkyl group). Exemplary unsubstituted alkoxycarbonyl include from 1 to 21 carbons (e.g., from 1 to 11 or from 1 to 7 carbons). In some embodiments, the alkoxy group is further substituted with 1, 2, 3, or 4 substituents as described herein.

The term "alkoxycarbonylacyl" refers to an acyl group, as defined herein, that is substituted with an alkoxycarbonyl group, as defined herein (e.g., —C(O)-alkyl-C(O)—OR, where R is an optionally substituted $C_{1-6}$, $C_{1-10}$, or $C_{1-20}$ alkyl group). Exemplary unsubstituted alkoxycarbonylacyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ acyl, $C_{1-10}$ alkoxycarbonyl-$C_{1-10}$ acyl, or $C_{1-20}$ alkoxycarbonyl-$C_{1-20}$ acyl). In some embodiments, each alkoxy and alkyl group is further independently substituted with 1, 2, 3, or 4 substituents, as described herein (e.g., a hydroxy group) for each group.

The term "alkoxycarbonylalkoxy" refers to an alkoxy group, as defined herein, that is substituted with an alkoxycarbonyl group, as defined herein (e.g., —O-alkyl-C(O)—OR, where R is an optionally substituted $C_{1-6}$, $C_{1-10}$, or $C_{1-20}$ alkyl group). Exemplary unsubstituted alkoxycarbonylalkoxy include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkoxy, $C_{1-10}$ alkoxycarbonyl-$C_{1-10}$ alkoxy, or $C_{1-20}$ alkoxycarbonyl-$C_{1-20}$ alkoxy). In some embodiments, each alkoxy group is further independently substituted with 1, 2, 3, or 4 substituents, as described herein (e.g., a hydroxy group).

The term "alkoxycarbonylalkyl" refers to an alkyl group, as defined herein, that is substituted with an alkoxycarbonyl group, as defined herein (e.g., -alkyl-C(O)—OR, where R is an optionally substituted $C_{1-20}$, $C_{1-10}$, or $C_{1-6}$ alkyl group). Exemplary unsubstituted alkoxycarbonylalkyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkyl, $C_{1-10}$ alkoxycarbonyl-$C_{1-10}$ alkyl, or $C_{1-20}$ alkoxycarbonyl-$C_{1-20}$ alkyl). In some embodiments, each alkyl and alkoxy group is further independently substituted with 1, 2, 3, or 4 substituents as described herein (e.g., a hydroxy group).

The term "alkoxycarbonylalkenyl" refers to an alkenyl group, as defined herein, that is substituted with an alkoxycarbonyl group, as defined herein (e.g., -alkenyl-C(O)—OR, where R is an optionally substituted $C_{1-20}$, $C_{1-10}$, or $C_{1-6}$ alkyl group). Exemplary unsubstituted alkoxycarbonylalkenyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkenyl, $C_{1-10}$ alkoxycarbonyl-$C_{2-10}$ alkenyl, or $C_{1-20}$ alkoxycarbonyl-$C_{2-20}$ alkenyl). In some embodiments, each alkyl, alkenyl, and alkoxy group is further independently substituted with 1, 2, 3, or 4 substituents as described herein (e.g., a hydroxy group).

The term "alkoxycarbonylalkynyl" refers to an alkynyl group, as defined herein, that is substituted with an alkoxycarbonyl group, as defined herein (e.g., -alkynyl-C(O)—OR, where R is an optionally substituted $C_{1-20}$, $C_{1-10}$, or $C_{1-6}$ alkyl group). Exemplary unsubstituted alkoxycarbonylalkynyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkynyl, $C_{1-10}$ alkoxycarbonyl-$C_{2-10}$ alkynyl, or $C_{1-20}$ alkoxycarbonyl-$C_{2-20}$ alkynyl). In some embodiments, each alkyl, alkynyl, and alkoxy group is further independently substituted with 1, 2, 3, or 4 substituents as described herein (e.g., a hydroxy group).

The term "alkyl" refers to both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —$NH_2$) or a substituted amino (i.e., —$N(R^{N5})_2$, where $R^{N6}$ is as defined for amino); (4) COO aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —$CO2R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ to aryl, (d) hydrogen, (e) $C_{1-6}$ alkyl-$C_{6-10}$ aryl, (f) amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N5}(CH_2)_{s2}(CH_2CH_2O)_{s1}(CH_2)_{s3}NR^{N5}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N5}$ is, independently, hydrogen or optionally substituted $C_{1-6}$ alkyl; (15) —$C(O)NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ to aryl, and (d) $C_{1-6}$ alkyl-$C_{6-10}$ aryl; (16) —$SO2R^{D'}$, where $R^{D'}$ is selected from the group consisting of (a) $C_{1-6}$ alkyl, (b) $C_{6-10}$ aryl, (c) $C_{1-6}$ alkyl-$C_{6-10}$ aryl, and (d) hydroxy; (17) —$SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —$C(O)R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alkyl-$C_{6-10}$ aryl, (f) amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N5}(CH_2)_{s2}(CH_2CH_2O)_{s1}(CH_2)_{s3}NR^{N5}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N5}$ is, independently, hydrogen or optionally substituted $C_{1-6}$ alkyl; (19) —$NR^{H'}C(O)R^{I'}$, wherein $R^{H'}$ is selected from the group consisting of (a1) hydrogen and (b1) $C_{1-6}$ alkyl, and $R^{J'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alkyl-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N5}(CH_2)_{s2}(CH_2CH_2O)_{s1}(CH_2)_{s3}NR^{N5}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N5}$ is, independently, hydrogen or optionally substituted $C_{1-6}$ alkyl; (20) —$NR^{J'}C(O)OR^{K'}$, wherein $R^{J'}$ is selected from the group consisting of (a1) hydrogen and (1)1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alkyl-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N5}(CH_2)_{s2}(CH_2CH_2O)_{s1}(CH_2)_{s3}NR^{N5}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N5}$ is, independently, hydrogen or optionally substituted $C_{1-6}$ alkyl; and (21) amidine. In some embodiments, each of these groups can be further substituted as described herein. For example, the alkyl group of a $C_1$-alkaryl can be further substituted with an oxo group to afford the respective aryloyl sub stituent.

The term "alkylsulfinyl" refers to an alkyl group attached to the parent molecular group through an —S(O)— group. Exemplary unsubstituted alkylsulfinyl groups are from 1 to 6, from 1 to 10, or from 1 to 20 carbons. In some embodiments, the alkyl group can be further substituted with 1, 2, 3, or 4 substituent groups as defined herein.

The term "alkylsulfinylalkyl" refers to an alkyl group, as defined herein, substituted by an alkylsulfinyl group. Exemplary unsubstituted alkylsulfinylalkyl groups are from 2 to 12, from 2 to 20, or from 2 to 40 carbons. In some embodiments, each alkyl group can be further substituted with 1, 2, 3, or 4 substituent groups as defined herein.

The term "alkynyl" refers to a monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "alkynyloxy" refers to a chemical substituent of formula —OR, where R is a $C_{2-20}$ alkynyl group (e.g., $C_{2-6}$ or $C_{2-10}$ alkynyl), unless otherwise specified. Exemplary alkynyloxy groups include ethynyloxy, propynyloxy, and the like. In some embodiments, the alkynyl group can be further substituted with 1, 2, 3, or 4 substituent groups as defined herein (e.g., a hydroxy group).

The term "amidine" refers to a —$C(=NH)NH_2$ group.

The term "amino" refers to a —$N(R^{N6})_2$, wherein each $R^{N6}$ is, independently, H, OH, $NO_2$, $N(R^{N7})_2$, $SO_2OR^{N7}$, $SO_2R^{N7}$, $SOR^{N7}$, an N-protecting group, alkyl, alkenyl, alkynyl, alkoxy, aryl, alkaryl, cycloalkyl, alkylcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl or alkylheterocyclyl, wherein each of these recited $R^{N1}$ groups can be optionally substituted, as defined herein for each group; or two $R^{N1}$ combine to form a heterocyclyl or an N-protecting group, and wherein each $R^{N7}$ is, independently, H, alkyl, or aryl. The amino groups of the disclosure can be an unsubstituted amino (i.e., —$NH_2$) or a substituted amino (i.e., —$N(R')_2$). In a preferred embodiment, amino is —$NH_2$ or —$NHR^{N5}$, wherein $R^{N6}$ is, independently, OH, $NO_2$, $NH_2$, $NR^{N7}_2$, $SO_2OR^{N7}$, $SO_2R^{N7}$, $SOR^{N7}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N7}$ can be H, $C_{1-20}$ alkyl (e.g., $C_{1-6}$ alkyl), or $C_{1-10}$ aryl.

The term "amino acid" refers to a molecule having a side chain, an amino group, and an acid group (e.g., a carboxy group of —$CO_2H$ or a sulfo group of —$SO_3H$), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —$NH_2$) or a substituted amino (i.e., —$N(R^{N6})_2$, where $R^{N6}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —$CO_2R^{A'}$, where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}(OCH_2CH_2)_{s1}(CH_2)_{s3}NR^{N5}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N5}(CH_2)_{s2}(CH_2CH_2O)_{s1}(CH_2)_{s3}NR^{N5}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N5}$ is, independently, hydrogen or optionally substituted $C_{1-6}$ alkyl; (15) —$C(O)NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —$SO_2R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —$SO_2NR^{E'}R^{F'}$, where each of $R^{E'}$ and $R^{F'}$, is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —$C(O)R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}(OCH_2CH_2)_{s1}$ $(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N5}(CH_2)_{s2}$ $(CH_2CH_2O)_{s1}(CH_2)_{s3}NR^{N5}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N5}$ is, independently, hydrogen or optionally substituted $C_{1-6}$ alkyl; (19) —$NR^{H'}C(O)R^{I'}$, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N5}(CH_2)_{s2}(CH_2CH_2O)_{s1}$ $(CH_2)_{s3}NR^{N5}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N5}$ is, independently, hydrogen or optionally substituted $C_{1-6}$ alkyl; (20) —$NR^{J'}C(O)OR^{K'}$, wherein $R^{J'}$ is selected from the group consisting of (a1) hydrogen and (1)1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}$ $(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N5}(CH)_{s2}(CH_2CH_2O)_{s1}(CH_2)_{s3}NR^{N5}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N5}$ is, independently, hydrogen or optionally substituted $C_{1-6}$ alkyl; and (21) amidine. In some embodiments, each of these groups can be further substituted as described herein.

The term "aminoalkoxy" refers to an alkoxy group, as defined herein, substituted by an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy).

The term "aminoalkyl" refers to an alkyl group, as defined herein, substituted by an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The term "aminoalkenyl" refers to an alkenyl group, as defined herein, substituted by an amino group, as defined herein. The alkenyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The term "aminoalkynyl" refers to an alkynyl group, as defined herein, substituted by an amino group, as defined herein. The alkynyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The term "aryl" refers to a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{1-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) —$(CH_2)_q$ $SO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$heteroaryl); (26) $C_{2-20}$ alkenyl; and (27) $C_{1-20}$ alkynyl. In some embodiments, each of these groups can be further substituted as described herein. For example, the alkyl group of a $C_1$-alkaryl or a $C_1$-alkheterocyclyl can be further substituted with an oxo group to afford the respective aryloyl and (heterocyclyl)oyl substituent group.

The term "arylalkoxy" refers to an alkaryl group, as defined herein, attached to the parent molecular group through an oxygen atom. Exemplary unsubstituted arylalkoxy groups include from 7 to 30 carbons (e.g., from 7 to 16 or from 7 to 20 carbons, such as $C_{6-10}$ aryl-$C_{1-6}$ alkoxy, $C_{6-10}$ aryl-$C_{1-10}$ alkoxy, or $C_{6-10}$ aryl-$C_{1-20}$ alkoxy). In some embodiments, the arylalkoxy group can be substituted with 1, 2, 3, or 4 substituents as defined herein.

The term "arylalkoxycarbonyl" refers to an arylalkoxy group, as defined herein, attached to the parent molecular group through a carbonyl (e.g., —C(O)—O-alkyl-aryl). Exemplary unsubstituted arylalkoxy groups include from 8 to 31 carbons (e.g., from 8 to 17 or from 8 to 21 carbons, such as $C_{6-10}$ aryl-$C_{1-6}$ alkoxy-carbonyl, $C_{6-10}$ aryl-$C_{10}$ alkoxy-carbonyl, or $C_{6-10}$ aryl-$C_{1-20}$ alkoxy-carbonyl). In some embodiments, the arylalkoxycarbonyl group can be substituted with 1, 2, 3, or 4 substituents as defined herein.

The term "aryloxy" refers to a chemical substituent of formula —OR', where R' is an aryl group of 6 to 18 carbons, unless otherwise specified. In some embodiments, the aryl group can be substituted with 1, 2, 3, or 4 substituents as defined herein.

The term "aryloyl" refers to an aryl group, as defined herein, that is attached to the parent molecular group through a carbonyl group. Exemplary unsubstituted aryloyl groups are of 7 to 11 carbons. In some embodiments, the aryl group can be substituted with 1, 2, 3, or 4 substituents as defined herein.

The term "azido" refers to an —$N_3$ group, which can also be represented as —N=N=N.

The term "bicyclic" refers to a structure having two rings, which may be aromatic or non-aromatic. Bicyclic structures include spirocyclyl groups, as defined herein, and two rings that share one or more bridges, where such bridges can include one atom or a chain including two, three, or more atoms. Exemplary bicyclic groups include a bicyclic carbocyclyl group, where the first and second rings are carbocyclyl groups, as defined herein; a bicyclic aryl groups, where the first and second rings are aryl groups, as defined herein; bicyclic heterocyclyl groups, where the first ring is a heterocyclyl group and the second ring is a carbocyclyl (e.g., aryl) or heterocycyl (e.g., heteroaryl) group; and bicyclic heteroaryl groups, where the first ring is a heteroaryl group and the second ring is a carbocyclyl (e.g., aryl) or heterocyclyl (e.g., heteroaryl) group. In some embodiments, the bicyclic group can be substituted with 1, 2, 3, or 4 substituents as defined herein for cycloalkyl, heterocyclyl, and aryl groups.

The term "boranyl" refers to -B($R^{B1}$)$_3$, where each $R^{B1}$ is, independently, selected from the group consisting of H and optionally substituted alkyl. In some embodiments, the boranyl group can be substituted with 1, 2, 3, or 4 substituents as defined herein for alkyl.

The terms "carbocyclic" and "carbocyclyl" refers to an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbamoyl" refers to a —C(O)—N($R^{N1}$)$_2$, where the meaning of each $R^{N1}$ is found in the definition of "amino" provided herein.

The term "carbamoylalkyl," as used herein, represents an alkyl group, as defined herein, substituted by a carbamoyl group, as defined herein. The alkyl group can be further substituted with 1, 2, 3, or 4 substituent groups as described herein.

The term "carbamyl" refers to a carbamate group having the structure —$NR^{N8}$C(=O)Or —OC(=O)N($R^{N8}$)$_2$, where the meaning of each $R^{N8}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "carbonyl" refers to a C(O) group, which can also be represented as C=O.

The term "carboxyaldehyde" refers to an acyl group having the structure —CHO.

The term "carboxy," refers to a —$CO_2$H.

The term "carboxyalkoxy" refers to an alkoxy group, as defined herein, substituted by a carboxy group, as defined herein. The alkoxy group can be further substituted with 1, 2, 3, or 4 substituent groups as described herein for the alkyl group, and the carboxy group can be optionally substituted with one or more O-protecting groups.

The term "carboxyalkyl" refers to an alkyl group, as defined herein, substituted by a carboxy group, as defined herein. The alkyl group can be further substituted with 1, 2, 3, or 4 substituent groups as described herein, and the carboxy group can be optionally substituted with one or more O-protecting groups.

The term "carboxyaminoalkyl" refers to an aminoalkyl group, as defined herein, substituted by a carboxy, as defined herein. The carboxy, alkyl, and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group, and/or an O-protecting group).

The term "cyano" refers to an —CN group.

The term "cycloalkoxy" refers to a chemical substituent of formula —OR, where R is a $C_{3-8}$ cycloalkyl group, as defined herein, unless otherwise specified. The cycloalkyl group can be further substituted with 1, 2, 3, or 4 substituent groups as described herein. Exemplary unsubstituted cycloalkoxy groups are from 3 to 8 carbons. In some embodiment, the cycloalkyl group can be further substituted with 1, 2, 3, or 4 substituent groups as described herein.

The term "cycloalkyl" refers to a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this disclosure can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-12}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}R^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19)—(CH$_2$)$_q$ SO$_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) —(CH$_2$)$_q$SO$_2$NR$^{E'}R^{F'}$, where q is an integer from zero to four and where each of $R^{E'}$ and $R^{F'}$, is, independently, selected from the group consisting of (a) hydrogen, (b) $C_{6-10}$ alkyl, (c) $C_{6-10}$ aryl, and (d) $C_{1-6}$ alk-$C_{1-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$heteroaryl); (26) oxo; (27) $C_{2-20}$ alkenyl; and (28) $C_{2-20}$ alkynyl. In some embodiments, each of these groups can be further substituted as described herein. For example, the alkyl group of a $C_1$-alkaryl or a $C_1$-alkheterocyclyl can be further substituted with an oxo group to afford the respective aryloyl and (heterocyclyl)oyl substituent group.

The term "diastereomer" refers to stereoisomers that are not mirror images of one another and are non-superimposable on one another.

The term "effective amount" of an agent refers to an amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

The term "enantiomer" refers to each individual optically active form of a compound of the disclosure, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo" refers to a halogen selected from bromine, chlorine, iodine, or fluorine.

The term "haloalkoxy" refers to an alkoxy group, as defined herein, substituted by a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —OCF$_3$), —OCHF$_2$, —OCH$_2$F, —OCCl$_3$, —OCH$_2$CH$_2$Br, —OCH$_2$CH(CH$_2$CH$_2$Br)CH$_3$, and —OCHICH$_3$. In some embodiments, the haloalkoxy group can be further substituted with 1, 2, 3, or 4 substituent groups as described herein for alkyl groups.

The term "haloalkyl" refers to an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —CF$_3$), —CHF$_2$, —CH$_2$F, —CCl$_3$, —CH$_2$CH$_2$Br, —CH$_2$CH(CH$_2$CH$_2$Br)CH$_3$, and —CHICH$_3$. In some embodiments, the haloalkyl group can be further substituted with 1, 2, 3, or 4 substituent groups as described herein for alkyl groups.

The term "heteroalkyl" refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups.

The term "heteroaryl" refers to a subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heterocyclyl" refers to a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazineyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4, 5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1, 6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1, 6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2, 3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3 ethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydropyrrolo [3,4-b]pyrrol-(2H)-yl, and 2,5-diazabicyclo [2.2.1] heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

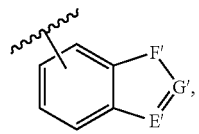

wherein, E' is selected from the group consisting of —N═ and —CH═; F' is selected from the group consisting of —N═CH—, —NH—C(O)—, —NH—, —CH═N═, —C(O)—NH—, —CH═CH—, —CH$_2$—, —CH$_2$CH$_2$—, —CH$_2$O—, —OCH$_2$—, —O—, and —S—; and G' is selected from the group consisting of ═CH— and ═N—.

Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH$_2$)$_q$(SO$_2$R$^{D'}$, where q is an integer from zero to four and where R$^{D'}$ is selected from the group consisting of (a) $C_{1-6}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl)imino; (28) $C_{2-20}$ alkenyl; and (29) $C_{2-20}$ alkynyl. In some embodiments, each of these groups can be further substituted as described herein. For example, the alkyl group of a $C_1$-alkaryl or a $C_1$-alkheterocyclyl can be further substituted with an oxo group to afford the respective aryloyl and (heterocyclyl)oyl substituent group.

The term "(heterocyclyl) imino" refers to a heterocyclyl group, as defined herein, attached to the parent molecular group through an imino group. In some embodiments, the heterocyclyl group can be substituted with 1, 2, 3, or 4 substituent groups as defined herein.

The term "(heterocyclyl)oxy" refers to a heterocyclyl group, as defined herein, attached to the parent molecular group through an oxygen atom. In some embodiments, the heterocyclyl group can be substituted with 1, 2, 3, or 4 substituent groups as defined herein.

The term "(heterocyclyl)oyl" refers to a heterocyclyl group, as defined herein, attached to the parent molecular group through a carbonyl group. In some embodiments, the heterocyclyl group can be substituted with 1, 2, 3, or 4 substituent groups as defined herein.

The term "hydrocarbon" refers to a group consisting only of carbon and hydrogen atoms.

The term "hydroxy" refers to an —OH group. In some embodiments, the hydroxy group can be substituted with 1, 2, 3, or 4 substituent groups (e.g., O-protecting groups) as defined herein for an alkyl.

The term "hydroxyalkenyl" refers to an alkenyl group, as defined herein, substituted by one to three hydroxy groups, with the proviso that no more than one hydroxy group may be attached to a single carbon atom of the alkyl group, and is exemplified by dihydroxypropenyl, hydroxyisopentenyl, and the like. In some embodiments, the hydroxyalkenyl group can be substituted with 1, 2, 3, or 4 substituent groups (e.g., O-protecting groups) as defined herein for an alkyl.

The term "hydroxyalkyl" refers to an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like. In some embodiments, the hydroxyalkyl group can be substituted with 1, 2, 3, or 4 substituent groups (e.g., O-protecting groups) as defined herein for an alkyl.

The term "hydroxyalkynyl" refers to an alkynyl group, as defined herein, substituted by one to three hydroxy groups, with the proviso that no more than one hydroxy group may be attached to a single carbon atom of the alkyl group. In some embodiments, the hydroxyalkynyl group can be substituted with 1, 2, 3, or 4 substituent groups (e.g., O-protecting groups) as defined herein for an alkyl.

The term "isomer" refers to any tautomer, stereoisomer, enantiomer, or diastereomer of any compound of the disclosure. It is recognized that the compounds of the disclosure can have one or more chiral centers and/or double bonds and, therefore, exist as stereoisomers, such as double-bond isomers (i.e., geometric E/Z isomers) or diastereomers (e.g., enantiomers (i.e., (+) or (-)) or cis/trans isomers). According to the disclosure, the chemical structures depicted herein, and therefore the compounds of the disclosure, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the disclosure can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "monosaccharide" refers to a monomeric sugar. Examples of monosaccharides, include but are not limited to allose, altrose, arabinose, cladinose, erythrose, erythrulose, fructose, D-fucitol, L-fucitol, fucosamine, fucose, fuculose, galactosamine, D-galactosaminitol, N-acetyl-galactosamine, galactose, glucosamine, N-acetyl-glucosamine, glucosaminitol, glucose, glucose-6-phosphate, gulose glyceraldehyde, L-glycero-D-mannos:-heptose, glycerol, glycerone, gulose, idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tartaric acid, threose, xylose and xylulose. The monosaccharide can be in D- or L-configuration. The term "monosaccharide derivative" refers to a deoxy sugar (alcoholic hydroxy group replaced by hydrogen), amino sugar (alcoholic hydroxy group replaced by amino group), a thio sugar (alcoholic hydroxy group replaced by thiol, or C=O replaced by C=S, or a ring oxygen of cyclic form replaced by sulfur), a seleno sugar, a telluro sugar, an aza sugar (ring carbon replaced by nitrogen), an amino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, preferably galactosamine, glucosamine, mannosamine, fucosamine, quinovosamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine and rhodosamine. It is understood that the monosaccharide and the like can be further substituted.

The term "disaccharide" refers to a dimer consisting of two monomeric sugars linked via a saccharide bond. Examples of disaccharides include but are not limited to sucrose, lactose, isomaltulose, maltose, trehalose and trehalulose.

The term "vitamin" refers to an organic molecule that is an essential micronutrient. Examples of vitamins, include but are not limited to retinol, retinal, retinyl esters and retinoic acid; vitamin $B_3$ and nicotinic acid; biotin; vitamin $B_2$; vitamin $B_3$ and nicotinic acid; vitamin $B_5$; vitamin $B_6$, pyridoxal and pyridoxine; vitamin $B_{12}$; vitamin C; choline; vitamin D; vitamin E; vitamin $B_9$, folate and folacin; and vitamin K and glutathione.

The term "polyol" refers to sugar alcohols such as but not limited to maltitol, sorbitol, mannitol, lactitol, xylitol, erythritol and isomalt; monomeric polyols such as but not limited to glycerin, pentaerythritol, ethylene glycol and sucrose.

The term "polysialic acid" refers to naturally occurring polymers of sialic acid produced in certain bacterial strains and in mammals in certain cells. The abbreviation "PSA" used herein refers to the term "polysialic acid". Similarly, the term "mPSA" used herein refers to the term "modified polysialic acid" or a derivative of polysialic acid. PSAs consist of polymers (generally homopolymers) of N-acetylneuraminic acid. The secondary amino group normally bears an acetyl group, but it may instead bear a glycolyl group as a mPSA. Possible substituents on the hydroxyl groups to form a mPSA include acetyl, lactyl, ethyl, sulfate, and phosphate groups.

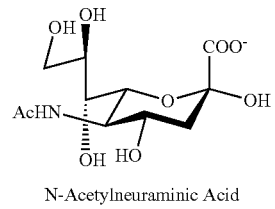

N-Acetylneuraminic Acid

PSAs and mPSAs generally comprise linear polymers consisting essentially of N-acetylneuraminic acid moieties linked by 2,8- or 2,9-glycosidic linkages or combinations of these (e.g. alternating 2,8- and 2,9-linkages). In particularly preferred PSAs and mPSAs, the glycosidic linkages are α-2,8. Such PSAs and mPSAs are conveniently derived from colominic acids and are referred to herein as "CAs" and "mCAs". Typical PSAs and mPSAs comprise at least 2, preferably at least 5, more preferably at least 10 and most preferably at least 20 N-acetylneuraminic acid moieties. Thus, they may comprise from 5 to 500 N-acetylneuraminic acid moieties, preferably from 10 to 300 N-acetylneuraminic acid moieties. PSAs and CAs can be polymers comprising different sugar moieties. They can be copolymers. PSAs and CAs preferably are essentially free of sugar moieties other than N-acetylneuraminic acid. PSAs and CAs preferably comprise at least 90%, more preferably at least 95% and most preferably at least 98% N-acetylneuraminic acid moieties.

Where PSAs and CAs comprise moieties other than N-acetylneuraminic acid (as, for example in mPSAs and mCAs) these are preferably located at one or both of the ends of the polymer chain. Such "other" moieties may, for example, be moieties derived from terminal N-acetylneuraminic acid moieties by oxidation or reduction.

For example, WO 2001/087922 describes such mPSAs and mCAs in which the non-reducing terminal N-acetylneuraminic acid unit is converted to an aldehyde group by reaction with sodium periodate. Additionally, WO 2005/016974 describes such mPSAs and mCAs in which the reducing terminal N-acetylneuraminic acid unit is subjected to reduction to reductively open the ring at the reducing terminal N-acetylneuraminic acid unit, whereby a vicinal diol group is formed, followed by oxidation to convert the vicinal diol group to an aldehyde group. [0009] Sialic acid rich glycoproteins bind selectin in humans and other organisms. They play an important role in human influenza infections. For example, sialic acid can hide mannose antigens on the surface of host cells or bacteria from mannose-binding lectin. This prevents activation of complement. Sialic acids also hide the penultimate galactose residue thus preventing rapid clearance of the glycoprotein by the galactose receptor on the hepatic parenchymal cells.

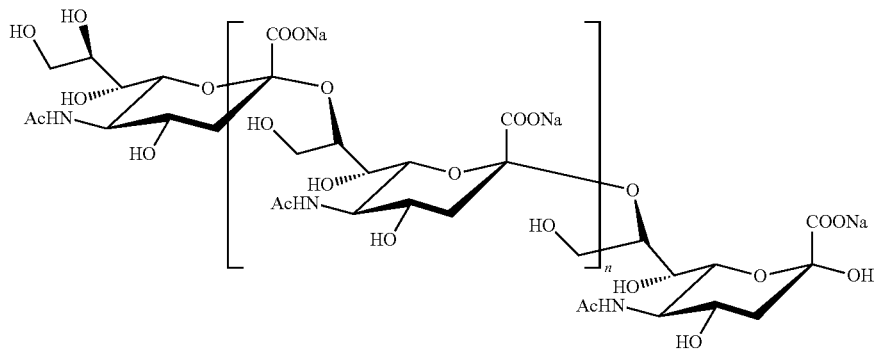

Structure of Colominic Acid (Homopolymer of N-Acetylneuraminic Acid)

The term "derivative" refers to without limitation any compound which has a structure derived from the structure of the compounds of the present disclosure and whose structure is sufficiently similar to those disclosed herein and based upon that similarity, would be expected, by one skilled in the art, to exhibit the same or similar activities and utilities as the claimed and/or referenced compounds.

The term "N-protected amino" refers to an amino group, as defined herein, to which is attached one or two N-protecting groups, as defined herein.

The term "N-protecting group" refers to groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyl oxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyl oxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenyithiocarbonyl, and the like, al karyl groups such as benzyl, triphenylmethyl, benzyloxymethyl, and the like and silyl groups, such as trimethylsilyl, and the like. Preferred N-protecting groups are formyl, acetyl, benzoyl, pivaloyl, t-butylacetyl, alanyl, phenyl sulfonyl, benzyl, t-butyl oxycarbonyl (Boc), and benzyloxycarbonyl (Cbz).

The term "nitro" refers to an —NO₂ group.

The term "O-protecting group" refers to groups intended to protect an oxygen containing group (e.g., alcohol or carbonyl) against undesirable reactions during synthetic procedures. Commonly used O-protecting groups are disclosed in Greene and Wuts, "The Role of Protective Groups in Organic Synthesis," 5th Edition (John Wiley & Sons, New York, 2014), which is incorporated herein by reference. Exemplary O-protecting groups include acyl, aryloyl, or carbamyl groups, such as formyl, acetyl, propionyl, pivaloyl, t-butyl acetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylphenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyl dim ethyl silyl (TBDMS), tri-i so-propyl silyloxymethyl (TOM), triisopropylsilyl (TIPS), and the like; ether-forming groups with the hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted aryl al koxycarb onyl groups, such as benzyloxycarbonyl, p-methylbenzyloxycarbonyl, p-methoxyb enzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, fluorenylmethyloxycarbonyl, and the like; and optionally substituted aryloxycarbonyl groups, such as phenoxycarbonyl, p-nitrophenoxycarbonyl, o-nitrophenoxy carb onyl, 2,4-dinitrophenoxycarb onyl, p-m ethyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethyl silyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethyl silyl; triethylsilyl; triisopropylsilyl; dimethylisopropylsilyl; t-butyldimethyl silyl; t-butyldiphenylsilyl; tribenzylsilyl; triphenylsilyl; and diphenylmethylsilyl); carbonates (e.g., methyl, methoxymethyl, 9-fluorenylm ethyl; ethyl; 2,2,2-tri chl oroethyl; 2(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dithiolane, and the like); carboxylic acid-protecting groups (e.g., ester groups, such as methyl ester, benzyl ester, t-butyl ester, orthoesters, and the like; and oxazoline groups.

The term "oxo" refers to =O.

The term "perfluoroalkyl" refers to an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy" refers to an alkoxy group, as defined herein, where each hydrogen radical bound to the alkoxy group has been replaced by a fluoride radical. Perfluoroalkoxy groups are exemplified by trifluoromethoxy, pentafluoroethoxy, and the like.

The term "spirocyclyl" refers to a $C_{2-7}$ alkyl diradical, both ends of which are bonded to the same carbon atom of the parent group to form a spirocyclic group, and also a $C_{1-6}$ heteroalkyl diradical, both ends of which are bonded to the same atom. The heteroalkyl radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the disclosure may be optionally substituted with 1, 2, 3, or 4 substituents provided herein as optional substituents for cycloalkyl and/or heterocyclyl groups.

The term "stereoisomer" refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present disclosure may exist in different tautomeric forms, all of the latter being included within the scope of the present disclosure.

The term "sulfoalkyl" refers to an alkyl group, as defined herein, substituted by a sulfo group of —SO$_3$H. In some embodiments, the alkyl group can be further substituted with 1, 2, 3, or 4 substituent groups as described herein, and the sulfo group can be further substituted with one or more O-protecting groups (e.g., as described herein).

The term "sulfonyl," refers to an —S(O)$_2$— group.

The term "thioalkaryl" as used herein, represents a chemical substituent of formula SR, where R is an alkaryl group. In some embodiments, the alkaryl group can be further substituted with 1, 2, 3, or 4 substituent groups as described herein.

The term "thioalkheterocyclyl" refers to a chemical substituent of formula —SR, where R is an alkheterocyclyl group. In some embodiments, the alkheterocyclyl group can be further substituted with 1, 2, 3, or 4 substituent groups as described herein.

The term "thioalkoxy" refers to a chemical substituent of formula —SR, where R is an alkyl group, as defined herein.

In some embodiments, the alkyl group can be further substituted with 1, 2, 3, or 4 substituent groups as described herein.

The term "compound" includes all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

The term "cyclic" refers to the presence of a continuous loop. Cyclic molecules need not be circular, only joined to form an unbroken chain of subunits. Cyclic molecules such as the mRNA of the present disclosure may be single units or multimers or comprise one or more components of a complex or higher order structure.

The term "delivery" refers to the act or manner of delivering a compound, substance, entity, moiety, cargo or payload.

The term "delivery agent" refers to any substance which facilitates, at least in part, the in vivo delivery of a polynucleotide to targeted cells.

The term "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides or proteins disclosed herein. They may be within the amino acids, the peptides, or proteins, or located at the N- or C-termini.

The term "engineered" refers to a molecule being designed to have a feature or property, whether structural or chemical, that varies from a starting point, wild type or native molecule.

The term "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

The term "feature" refers to a characteristic, a property, or a distinctive element.

The term "fragment" refers to a portion. For example, fragments of proteins may comprise polypeptides obtained by digesting full-length protein isolated from cultured cells.

The term "functional" biological molecule is a biological molecule in a form in which it exhibits a property and/or activity by which it is characterized.

The phrase "inhibit expression of a gene" refers to causing a reduction in the amount of an expression product of the gene. The expression product can be an RNA transcribed from the gene (e.g., an mRNA) or a polypeptide translated from an mRNA transcribed from the gene. Typically, a reduction in the level of an mRNA results in a reduction in the level of a polypeptide translated therefrom. The level of expression may be determined using standard techniques for measuring mRNA or protein.

The term "in vitro" refers to events that occur in an artificial environment, e.g., in a test tube or reaction vessel, in cell culture, in a Petri dish, etc., rather than within an organism (e.g., animal, plant, or microbe).

The term "in vivo" refers to events that occur within an organism (e.g., animal, plant, or microbe or cell or tissue thereof).

The term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

The term "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form multimers (e.g., through linkage of two or more polynucleotides) or conjugates, as well as to administer a payload, as described herein. Examples of chemical groups that can be incorporated into the linker include, but are not limited to, alkyl, alkenyl, alkynyl, amido, amino, ether, thioether, ester, alkyl, heteroalkyl, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

The term "modified" refers to a changed state or structure of a molecule of the disclosure. Molecules may be modified in many ways including chemically, structurally, and functionally. In one embodiment, the mRNA molecules of the present disclosure are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

The term "naturally occurring" means existing in nature without artificial aid.

The term "operably linked" refers to a functional connection between two or more molecules, constructs, transcripts, entities, moieties or the like.

The term "patient" refers to a subject who may seek or be in need of treatment, requires treatment, is receiving treatment, will receive treatment, or a subject who is under care by a trained professional for a particular disease or condition.

The phrase "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional. Whenever a group is described as being "optionally substituted" that group may be unsubstituted or substituted with one or more of the indicated substituents. Likewise, when a group is described as being "unsubstituted or substituted" if substituted, the substituent may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, heterocyclyl, cycloalkenyl, cycloalkynyl, aryl, heteroaryl, aralkyl, heteroaralkyl, hydroxy, protected hydroxyl, alkoxy, aryloxy, acyl, ester, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Each of these substituents can be further substituted.

The term "peptide" is less than or equal to 50 amino acids long, e.g., about 5, 10, 15, 20, 25, 30, 35, 40, 45, or 50 amino acids long.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroi odi de, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, salicylates, stearate, succinate, sulfonates, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine or lysine. Basic nitrogen-containing groups may be quarternized with agents such as lower alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), P. Gould, International J Pharmaceutics (1986) 33 201-217; Anderson et al., The Practice of Medicinal Chemistry (1996), Academic Press, New York; and in The Orange Book (Food & Drug Administration, Washington, D.C. on their website). These disclosures are incorporated by reference herein in their entirety.

All such acid and base salts are intended to be pharmaceutically acceptable salts within the scope of the disclosure and all acid and base salts are considered equivalent to the free forms of the corresponding compound of Formula I for purposes of the disclosure.

The term "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

The term "pharmaceutically acceptable solvate," refers to a compound of the disclosure wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "physicochemical" refers to a physical and/or chemical property.

The term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

The terms "proteins of interest" or "desired proteins" include those provided herein and fragments, mutants, variants, and alterations thereof.

The terms "purify", "purified", or "purification" relates to making substantially pure or clear from unwanted components, material defilement, admixture or imperfection.

The term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

The term "significant" or "significantly" are used synonymously with the term "substantially."

The phrase "single unit dose" refers to a dose of any therapeutic administered in one dose/at one time/single route/single point of contact, i.e., single administration event.

The term "split dose" refers to the division of single unit dose or total daily dose into two or more doses.

The term "stable" refers to a compound that is sufficiently robust to survive isolation to a useful degree of purity from a reaction mixture, and preferably capable of formulation into an efficacious therapeutic agent.

The terms "subject" or "patient" refer to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

The term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The term "substantially equal" refers to time differences between doses, the term means plus/minus 2%.

The term "substantially simultaneously" refers to a plurality of doses, the term means within 2 seconds.

An individual who is "suffering from" a disease, disorder, and/or condition has been diagnosed with or displays one or more symptoms of a disease, disorder, and/or condition.

An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

The term "synthetic" refers to a molecule being produced, prepared, and/or manufactured by the hand of man. Synthesis of polynucleotides or polypeptides or other molecules of the present disclosure may be chemical or enzymatic.

The term "targeted cells" refers to any one or more cells of interest. The cells may be found in vitro, in vivo, in situ or in the tissue or organ of an organism. The organism may be an animal, preferably a mammal, more preferably a human and most preferably a patient.

The term "therapeutic agent" refers to any agent that, when administered to a subject, has a therapeutic, diagnostic, and/or prophylactic effect and/or elicits a desired biological and/or pharmacological effect.

The term "therapeutically effective amount" relates to an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

The term "therapeutically effective outcome" relates to an outcome that is sufficient in a subject suffering from or susceptible to an infection, disease, disorder, and/or condition, to treat, improve symptoms of, diagnose, prevent, and/or delay the onset of the infection, disease, disorder, and/or condition.

The phrase "total daily dose" relates to an amount given or prescribed in 24 hr period. It may be administered as a single unit dose.

The term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

The term "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

The term "Antisense nucleic acid" refers to an non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector equivalent thereof "Antisense RNA" is an RNA strand having a sequence complementary to a target gene mRNA, that can induce RNAi by binding to the target gene mRNA. "Antisense RNA" is an RNA strand having a sequence complementary to a target gene mRNA and thought to induce RNAi by binding to the target gene mRNA. "Sense RNA" has a sequence complementary to the antisense RNA and annealed to its complementary antisense RNA to form iNA. These antisense and sense RNAs have been conventionally synthesized with an RNA synthesizer.

The term "Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-0-methyl ribonucleotides, peptide-nucleic acids (PNAs).

The term "RNA" refers to a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant disclosure can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue, including siRNA, antisense RNA, single stranded RNA, microRNA, mRNA, noncoding RNA, and multivalent RNA. A ribonucleotide is a nucleotide with a hydroxyl group at the 2' position of a β-D-ribo-furanose moiety. These terms include double-stranded RNA, single-stranded RNA, isolated RNA such as partially purified RNA, essentially pure RNA, synthetic RNA, recombinantly produced RNA, as well as modified and altered RNA that differs from naturally occurring RNA by the addition, deletion, substitution, modification, and/or alteration of one or more nucleotides. Alterations of an RNA can include addition of non-nucleotide material, such as to the end(s) of an interfering RNA or internally, for example at one or more nucleotides of an RNA nucleotides in an RNA molecule include non-standard nucleotides, such as non-naturally occurring nucleotides or chemically synthesized nucleotides or deoxynucleotides. These altered RNAs can be referred to as analogs.

The term "Nucleotides" refers to natural bases (standard) and modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al., International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include: inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkyl cytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine, and uracil at 1' position or their equivalents.

The phrase "Complementary nucleotide bases" refers to a pair of nucleotide bases that form hydrogen bonds with each other. Adenine (A) pairs with thymine (T) or with uracil (U) in RNA, and guanine (G) pairs with cytosine (C). Complementary segments or strands of nucleic acid that hybridize (i.e. join by hydrogen bonding) with each other. By "complementary" is meant that a nucleic acid can form hydrogen bond(s) with another nucleic acid sequence either by traditional Watson-Crick or by other non-traditional modes of binding.

The term "MicroRNAs" (miRNA) refers to single-stranded RNA molecules of 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

The phrases "Small interfering RNA (siRNA)", "short interfering RNA" and "silencing RNA" refer to a class of double-stranded RNA molecules, 16-40 nucleotides in length, that play a variety of roles in biology. Most notably, siRNA is involved in the RNA interference (RNAi) pathway, where it interferes with the expression of a specific gene. In addition to their role in the RNAi pathway, siRNAs also act in RNAi-related pathways, e.g., as an antiviral mechanism or in shaping the chromatin structure of a genome; the complexity of these pathways is only now being elucidated.

The term "RNAi" refers to an RNA-dependent gene silencing process that is controlled by the RNA-induced silencing complex (RISC) and is initiated by short double-stranded RNA molecules in a cell, where they interact with the catalytic RISC component argonaute. When the double-stranded RNA or RNA-like iNA or siRNA is exogenous (coming from infection by a virus with an RNA genome or from transfected iNA or siRNA), the RNA or iNA is imported directly into the cytoplasm and cleaved to short fragments by the enzyme dicer. The initiating dsRNA can also be endogenous (originating in the cell), as in pre-microRNAs expressed from RNA-coding genes in the genome. The primary transcripts from such genes are first processed to form the characteristic stem-loop structure of pre-miRNA in the nucleus, then exported to the cytoplasm to be cleaved by dicer. Thus, the two dsRNA pathways, exogenous and endogenous, converge at the RISC complex. The active components of an RNA-induced silencing complex (RISC) are endonucleases called argonaute proteins, which cleave the target mRNA strand complementary to their bound siRNA or iNA. As the fragments produced by dicer are double-stranded, they could each in theory produce a functional siRNA or iNA. However, only one of the two strands, which is known as the guide strand, binds the argonaute protein and directs gene silencing. The other anti-guide strand or passenger strand is degraded during RISC activation.

The term "miRNA mimic" refers to a chemically modified double-stranded RNAs that mimic endogenous miRNAs and enable miRNA functional analysis by up-regulation of miRNA activity.

The phrase "commercially available chemicals" relates to the chemicals used in the Examples as set forth herein may be obtained from standard commercial sources, where such sources include, for example, Acros Organics (Pittsburgh, Pa.), Sigma-Adrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

The phrase "compounds described in the chemical literature" relates to compounds that may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," 2nd Ed., Academic Press, New York, 1983; H. O. House, "Modern Synthetic Reactions," 2nd Ed., W. A. Benjamin, Inc. Menlo Park, Calif., 1972; T. L. Glichrist, "Heterocyclic Chemistry," 2nd Ed. John Wiley and Sons, New York, 1992; J. March, "Advanced Organic Chemistry: reactions, Mechanisms and Structure," 5th Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C. may be contacted for more details). Chemicals that are known but not commercially available in catalogs may be prepared by custom chemical synthesis houses, where many of the standard chemical supply houses (such as those listed above) provide custom synthesis services.

The term "lipid" refers to an organic compound that comprises an ester of fatty acid and is characterized by being insoluble in water, but soluble in many organic solvents. Lipids are usually divided into at least three classes: (1) "simple lipids," which include fats and oils as well as waxes; (2) "compound lipids," which include phospholipids and glycolipids; and (3) "derived lipids" such as steroids.

The term "lipid particle" refers to a lipid formulation that can be used to deliver a therapeutic nucleic acid (e.g., mRNA) to a target site of interest (e.g., cell, tissue, organ, and the like). In preferred embodiments, the lipid particle is a nucleic acid-lipid particle, which is typically formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., mRNA) may be encapsulated in the lipid portion of the particle, thereby protecting it from enzymatic degradation.

Lipid particles typically have a mean diameter of from 30 nm to 150 nm, from 40 nm to 150 nm, from 50 nm to 150 nm, from 60 nm to 130 nm, from 70 nm to 110 nm, from 70 nm to 100 nm, from 80 nm to 100 nm, from 90 nm to 100 nm, from 70 to 90 nm, from 80 nm to 90 nm, from 70 nm to 80 nm, or 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 1 15 nm, 120 nm, 125 nm, 130 nm, 135 nm, 140 nm, 145 nm, or 150 nm, and are substantially non-toxic. In addition, nucleic acids, when present in the lipid particles of the present disclosure, are resistant in aqueous solution to degradation with a nuclease.

The term "solvate" relates to a physical association of a compound of this disclosure with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

The term "lipid encapsulated" refers to a lipid particle that provides a therapeutic nucleic acid such as an mRNA with full encapsulation, partial encapsulation, or both. In a preferred embodiment, the nucleic acid (e.g., mRNA) is fully encapsulated in the lipid particle.

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers, and mixtures thereof. PEG or POZ can be conjugated directly to the lipid or may be linked to the lipid via a linker moiety. Any linker moiety suitable for coupling the PEG or the POZ to a lipid can be used including, e.g., non-ester-containing linker moieties and ester-containing linker moieties. In certain preferred embodiments, non-ester-containing linker moieties, such as amides or carbamates, are used.

The term "amphipathic lipid" refers to the material in which the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to a lipid species that exists either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosi des, and diacylglycerols.

The term "non-cationic lipid" refers to an amphipathic lipid or a neutral lipid or anionic lipid and is described in more detail below.

The term "anionic lipid" refers to a lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipids" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N-N-dialkylamino, 1,2-diacyloxy-3-aminopropane, and 1,2-dialkyl-3-aminopropane.

The terms "cationic lipid" and "amino lipid" are used interchangeably and mean those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the disclosure may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DMA, DLin-K-C4-DMA, DLen-C2K-DMA, y-DLen-C2K-DMA, DLin-M-C2-DMA (also known as MC2), DLin-M-C3-DMA (also known as MC3) and DLin-MP-DMA (also known as 1-Bl1).

"Substituted" means substitution with specified groups other than hydrogen, or with one or more groups, moieties, or radicals which can be the same or different, with each, for example, being independently selected.

Equivalents and Scope

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

It is also noted that the term "comprising" is intended to be open and permits but does not require the inclusion of additional elements or steps. When the term "comprising" is used herein, the term "consisting of" is thus also encompassed and disclosed.

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Pharmaceutical Compositions

Compounds disclosed herein are understood to optionally include reference to salts thereof, unless otherwise indicated. The term "salt(s)", as employed herein, denotes acidic salts formed with inorganic and/or organic acids, as well as basic salts formed with inorganic and/or organic bases. In addition, when compound of Formula I contain both a basic moiety, such as, but not limited to, a pyridine or imidazole, and an acidic moiety, such as, but not limited to, a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of a compound of Formula I may be formed, for example, by reacting a compound of Formula I with an amount of acid or base, such as an equivalent amount, in a medium such as one in which the salt precipitates or in an aqueous medium followed by lyophilization.

Compounds disclosed herein can exist in unsolvated and solvated forms, including hydrated forms. In general, the solvated forms, with pharmaceutically acceptable solvents such as water, ethanol, and the like, are equivalent to the unsolvated forms for the purposes of this disclosure.

Compounds disclosed herein and salts, solvates thereof, may exist in their tautomeric form (for example, as an amide or imino ether). All such tautomeric forms are contemplated herein as part of the present disclosure.

Also, within the scope of the present disclosure are polymorphs of the compound of this disclosure (i.e., polymorphs of the compound of Formula I are within the scope of this disclosure).

All stereoisomers (for example, geometric isomers, optical isomers, and the like) of the present compound (including those of the salts, solvates, and prodrugs of the compound as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compound of this disclosure may, for example, be substantially free of other isomers, or may be admixed, for example, as racemates or with all other, or other selected, stereoisomers. The chiral centers of the compound herein can have the S or R configuration as defined by the $IUPAC_{1974}$ Recommendations. The terms "salt", "solvate" and the like, are intended to equally apply to the salt and solvate of enantiomers, stereoisomers, rotamers, tautomers, racemates, or prodrugs of the disclosed compound.

Lipid Nanoparticles

A compound of Formula I or a pharmaceutically acceptable salt thereof can be included in a lipid composition, comprising a nanoparticle or a bilayer of lipid molecules. The lipid bilayer preferably further comprises a neutral lipid or a polymer. The lipid composition preferably comprises a liquid medium. The composition preferably further encapsulates a nucleic acid. The nucleic acid is preferably an mRNA that encodes a protein or polypeptide of interest and has an activity of translating to produce the target protein. Alternatively, the nucleic acid is preferably an siRNA that modulates gene expression and preferably induces gene expression knockdown (i.e., gene silencing). The lipid composition preferably further comprises an siRNA and/or mRNA and a neutral lipid or a polymer. The lipid composition preferably encapsulates the siRNA and/or mRNA.

In certain aspects, the lipid nanoparticles of the description herein include four lipid components: a phospholipid; cholesterol; a PEG-lipid; and an ionizable lipid. Preferably, the phospholipid is DSPC, the PEG-lipid is PEG-DMG and the cationic lipid is a lipid of Formula II, Formula III or Formula IV. In some embodiments, the molar composition is about 40-70:5-20:20-50:1-10 or 50-60:5-10:30-40:1-5 Lipid:DSPC:Cholesterol:PEG-DMG. Most preferably, the molar composition is about 58:7:33.5:1.5 or 50:7:40:3, Lipid:DSPC:Cholesterol:PEG-DMG. In certain embodiments, the organic solvent concentration wherein the lipids are solubilized is about 45% v/v to about 90% v/v. In certain preferred aspects, the organic solvent is a lower alkanol. Suitable lower alkanols include, e.g., methanol, ethanol, propanol, butanol, pentanol, their isomers and combinations thereof. The solvent is preferably ethanol with a volume of about 50-90% v/v. Preferably, the lipids occupy a volume of about 1 mL/g to about 5 mL/g.

In some embodiments, the siRNA and/or mRNA is fully encapsulated within the lipid portion of the lipid particle such that the siRNA and/or mRNA in the lipid particle is resistant in aqueous solution to nuclease degradation. In other embodiments, the lipid particles described herein are substantially non-toxic to mammals such as humans. The lipid particles typically have a mean diameter of from 30 nm to 150 nm, from 40 nm to 150 nm, from 50 nm to 150 nm, from 60 nm to 130 nm, from 70 nm to 110 nm, or from 70 to 90 nm. The lipid particles of the disclosure also typically have a lipid:RNA ratio (mass/mass ratio) of from 1:1 to 100:1, from 1:1 to 50:1, from 2:1 to 25:1, from 3:1 to 20:1, from 5:1 to 15:1, or from 5:1 to 10:1, or from 10:1 to 14:1, or from 9:1 to 20:1.

In preferred embodiments, the lipid particles comprise siRNA and/or mRNA, an ionizable lipid (e.g., one or more cationic lipids or salts thereof described herein), a phospholipid, and a conjugated lipid that inhibits aggregation of the particles (e.g., one or more PEG-lipid conjugates). The lipid particles can also include cholesterol. The lipid particles may comprise at least 1, 2, 3, 4, 5, 6, 7, 8, 9, 10, or more mRNA that express one or more polypeptides. The lipid particles may comprise at least 1, 2, 3, 4, 5, 6, 7, 8, 9, 10, or more siRNA that induce gene expression knockdown In the nucleic acid-lipid particles the siRNA and/or mRNA may be fully encapsulated within the lipid portion of the particle, thereby protecting the RNA from nuclease degradation. In preferred embodiments, a lipid particle comprising an siRNA and/or mRNA is fully encapsulated within the lipid portion of the particle, thereby protecting the nucleic acid from nuclease degradation. In certain instances, the siRNA and/or mRNA in the lipid particle is not substantially degraded after exposure of the particle to a nuclease at 37° C. for at least 20, 30, 45, or 60 minutes. In certain other instances, the siRNA and/or mRNA in the lipid particle is not substantially degraded after incubation of the particle in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the siRNA and/or mRNA is complexed with the lipid portion of the particle. One of the benefits of the formulations of the present disclosure is that the nucleic acid-lipid particle compositions are substantially non-toxic to mammals such as humans.

"Fully encapsulated" means that the nucleic acid (e.g., siRNA and/or mRNA) in the nucleic acid-lipid particle is not significantly degraded after exposure to serum or a nuclease assay that would significantly degrade free siRNA and/or mRNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

"Lipid-NA nanoparticle" is any lipid composition that can be used to deliver a compound including, but not limited to, liposomes, which comprise a lipid bilayer, either as unilamellar or multilamellar structure, in which the RNA is encapsulated at least in part by ionic pairing with ionizable lipids.

"Lamellar morphology" refers to a bilayer structure. The lamellar morphology, bilayer structure of the lipid particles disclosed herein can be determined using analytical techniques, e.g., by cryo-TEM images.

"Lipid-encapsulated" can refer to a lipid formulation which provides a compound with full encapsulation, partial encapsulation, or both, in which RNA is not accessible to RNase-mediated hydrolysis or to intercalation of dyes.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_0-I)/I_0$, where/and $I_0$ refers to the fluorescence intensities before and after the addition of detergent.

In other embodiments, the present disclosure provides a siRNA and/or mRNA-lipid particle composition comprising a plurality of siRNA and/or mRNA-lipid particles.

The lipid particle comprises siRNA and/or mRNA that is fully encapsulated within the lipid portion of the particles, such that from 30% to 100%, from 40% to 100%, from 50% to 100%, from 60% to 100%, from 70% to 100%, from 80% to 100%, from 90% to 100%, from 30° A to 95%, from 40° A to 95%, from 50° A to 95%, from 60° A to 95%, from 70° A to 95%, from 80° A to 95%, from 85° A to 95%, from 90° A to 95%, from 30° A to 90%, from 40° A to 90%, from 50° A to 90%, from 60° A to 90%, from 70° A to 90%, from 80° A to 90%, or at least 30%, 35%, 40%, 45%, 50%, 55%, 60%, 65%, 70%, 75%, 80%, 85%, 90%, 91%, 92%, 93%, 94%, 95%, 96%, 97%, 98%, or 99° A (or any fraction thereof or range therein) of the particles have the siRNA and/or mRNA encapsulated therein.

Depending on the intended use of the compositions as disclosed herein comprising therapeutic siRNA and/or mRNA molecules and lipid particles, the proportions of the components can be varied, and the delivery efficiency of a particular formulation can be measured using assays known in the art.

Cationic Lipids

The compositions can include a cationic lipid suitable for forming a cationic liposome or lipid nanoparticle. Cationic lipids are widely studied for nucleic acid delivery because they can bind to negatively charged membranes and induce uptake. Generally, cationic lipids are amphiphiles containing a positive hydrophilic head group, two (or more) lipophilic tails, or a steroid portion and a connector between these two domains. Preferably, the cationic lipid carries a net positive charge at about physiological pH. Cationic liposomes have been traditionally the most commonly used non-viral delivery systems for oligonucleotides, including plasmid DNA, antisense oligos, and siRNA/small hairpin RNA-shRNA. Cationic lipids, such as DOTAP, (1,2-dioleoyl-3-trimethyl-ammonium-propane) and DOTMA (N-[1-(2,3-dioleoyloxy)propyl]-N,N,N-trimethyl-ammonium methyl sulfate) can form complexes or lipoplexes with negatively charged nucleic acids by electrostatic interaction, providing high in vitro transfection efficiency.

In the presently disclosed compositions, the cationic lipid may be, for example, N,N-dioleyl-N,N-dimethylammonium chloride (DODAC), N,N-distearyl-N,N-dimethylammonium bromide (DDAB), 1,2-dioleoyltrimethylammonium-propane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethyl aminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinol eyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLin-DAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.C1), 1,2-Dilinoleoyl-3-trimethylaminopropane chloride salt (DLin-TAP.C1), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanediol (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3 aR,5s, 6a S)-N,N-dimethyl-2,2-di ((9Z,12Z)-octadeca-9,12-dienyl)tetrahydro-3aH-cyclopenta [d] [1,3]dioxol-5-amine, (6Z,9Z,28Z,31Z)-heptatriaconta-6,9,28,31-tetraen-19-yl4-(dim ethyl amino) butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6, 9,28 31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31 Z)-heptatriaconta-6, 9,28,31-tetraen-19-yloxy)-N,N-dimethylbutan-1-amine (MC4 Ether), or any combination thereof. Other cationic lipids include, but are not limited to, N,N-distearyl-N,N-dimethylammonium bromide (DDAB), 3P-(N-(N',N'-dimethylaminoethane)-carbamoyl)cholesterol (DC-Choi), N-(1-(2,3-dioleyloxy)propyl)-N-2-(sperminecarboxamido)ethyl)-N,N-dimethylammoniumtrifluoracetate (DOSPA), dioctadecylamidoglycyl carboxyspermine (DOGS), 1,2-dileoyl-sn-3-phosphoethanolamine (DOPE), 1,2-dioleoyl-3-dimethylammoniumpropane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl [1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010, the contents of which are herein incorporated by reference.

Other suitable cationic lipids include those having alternative fatty acid groups and other dialkylamino groups, including those, in which the alkyl substituents are different (e.g., N-ethyl-N-methylamino-, and N-propyl-N-ethylamino-). These lipids are part of a subcategory of cationic lipids referred to as amino lipids. In some embodiments of the lipid formulations described herein, the cationic lipid is an amino lipid. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ may be used. Other scaffolds can also be used to separate the amino group and the fatty acid or fatty alkyl portion of the amino lipid.

In some embodiments, the compositions described herein comprise the cationic lipid with Formula I according to the patent application PCT/EP2017/064066. In this context, the disclosure of PCT/EP2017/064066 is also incorporated herein by reference.

In some embodiments, amino or cationic lipids of the present disclosure are ionizable and have at least one protonatable or deprotonatable group, such that the lipid is positively charged at a pH at or below physiological pH (e.g., pH 7.4), and neutral at a second pH, preferably at or above physiological pH. Of course, it will be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11. In some embodiments, the ionizable cationic lipid has a pKa of about 5 to about 7. In some embodiments, the pKa of an ionizable cationic lipid is about 6 to about 7.

The cationic lipid compounds may be combined with an agent to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. These particles may then optionally be combined with a pharmaceutical excipient to form a pharmaceutical composition.

The present description provides novel cationic lipid compounds and drug delivery systems based on the use of such cationic lipid compounds. The system may be used in the pharmaceutical/drug delivery arts to deliver polynucleotides, proteins, small molecules, peptides, antigen, or drugs, to a patient, tissue, organ, or cell. These novel compounds may also be used as materials for coating, additives, excipients, materials, or bioengineering.

The cationic lipid compounds of the present description provide for several different uses in the drug delivery art. The amine-containing portion of the cationic lipid compounds may be used to complex polynucleotides, thereby enhancing the delivery of polynucleotide and preventing their degradation. The cationic lipid compounds may also be used in the formation of picoparticles, nanoparticles, microparticles, liposomes, and micelles containing the agent to be delivered. Preferably, the cationic lipid compounds are biocompatible and biodegradable, and the formed particles are also biodegradable and biocompatible and may be used to provide controlled, sustained release of the agent to be delivered. These and their corresponding particles may also be responsive to pH changes given that these are protonated at lower pH. They may also act as proton sponges in the delivery of an agent to a cell to cause endosome lysis.

In certain embodiments, the cationic lipid compounds are relatively non-cytotoxic. The cationic lipid compounds may be biocompatible and biodegradable. The cationic lipid may have a $pK_a$ in the range of approximately 5.5 to approximately 7.5, more preferably between approximately 6.0 and approximately 7.0. It may be designed to have a desired $pK_a$ between approximately 3.0 and approximately 9.0, or between approximately 5.0 and approximately 8.0. The cationic lipid compounds described herein are particularly attractive for drug delivery for several reasons: they contain amino groups for interacting with DNA, RNA, other polynucleotides, and other negatively charged agents, for buffering the pH, for causing endo-osmolysis, for protecting the agent to be delivered, they can be synthesized from commercially available starting materials; and/or they are pH responsive and can be engineered with a desired $pK_a$.

Neutral Helper Lipids

Non-limiting examples of non-cationic lipids include phospholipids such as lecithin, dialkyloxypropyl (DAA), diacylglycerol (DAG), dimyristoylglycerol (DMG), Dioleoylglycerol (DOG), Dipalmitoylglycerol (DPG), phosphatidylethanol amine (PE), Distearoylglycerol (DSG), lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoylol eoyl-phosphatidyl ethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5a-cholestanol, 5a-coprostanol, cholesteryl-(2'-hydroxy)-ethyl ether, cholesteryl-(4'-hydroxy)-butyl ether, and 6-ketocholestanol; non-polar analogues such as 5a-cholestane, cholestenone, 5a-cholestanone, 5a-cholestanone, and cholesteryl decanoate; and mixtures thereof. In preferred embodiments, the cholesterol derivative is a polar analogue such as cholesteryl-(4'-hydroxy)-butyl ether.

In some embodiments, the non-cationic lipid present in lipid particles comprises or consists of a mixture of one or more phospholipids and cholesterol or a derivative thereof. In other embodiments, the non-cationic lipid present in the lipid particles comprises or consists of one or more phospholipids, e.g., a cholesterol-free lipid particle formulation. In yet other embodiments, the non-cationic lipid present in the lipid particles comprises or consists of cholesterol or a derivative thereof, e.g., a phospholipid-free lipid particle formulation.

Other examples of non-cationic lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkylaryl sulfate polyethyloxylated fatty acid amides, dioctadecyldimethyl ammonium bromide, ceramide, and sphingomyelin.

In some embodiments, the non-cationic lipid comprises from 10 mol % to 60 mol %, from 20 mol % to 55 mol %, from 20 mol % to 45 mol %, 20 mol % to 40 mol %, from 25 mol % to 50 mol %, from 25 mol % to 45 mol %, from 30 mol % to 50 mol %, from 30 mol % to 45 mol %, from 30 mol % to 40 mol %, from 35 mol % to 45 mol %, from 37 mol % to 42 mol %, or 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to 40 mol %, 45 mol %, 50 mol %, 55 mol %, or 60 mol % of the total lipid present in the particle.

In some embodiments, the phospholipid component in the mixture may comprise from 2 mol % to 20 mol %, from 2 mol % to 15 mol %, from 2 mol % to 12 mol %, from 4 mol % to 15 mol %, or from 4 mol % to 10 mol % (or any fraction thereof or range therein) of the total lipid present in the particle. In certain preferred embodiments, the phospholipid component in the mixture comprises from 5 mol % to 10 mol %, from 5 mol % to 9 mol %, from 5 mol % to 8 mol %, from 6 mol % to 9 mol %, from 6 mol % to 8 mol %, or 5 mol %, 6 mol %, 7 mol %, 8 mol %, 9 mol %, or 10 mol % (or any fraction thereof or range therein) of the total lipid present in the particle.

In other embodiments, the cholesterol component in the mixture may comprise from 25 mol % to 45 mol %, from 25 mol % to 40 mol %, from 30 mol % to 45 mol %, from 30 mol % to 40 mol %, from 27 mol % to 37 mol %, from 25 mol % to 30 mol %, or from 35 mol % to 40 mol % (or any fraction thereof or range therein) of the total lipid present in the particle. In certain preferred embodiments, the cholesterol component in the mixture comprises from 25 mol % to 35 mol %, from 27 mol % to 35 mol %, from 29 mol % to 35 mol %, from 30 mol % to 35 mol %, from 30 mol % to 34 mol %, from 31 mol % to 33 mol %, or 30 mol %, 31 mol %, 32 mol %, 33 mol %, 34 mol %, or 35 mol % (or any fraction thereof or range therein) of the total lipid present in the particle.

In embodiments where the lipid particles are phospholipid-free, the cholesterol or derivative thereof may comprise up to 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from 25 mol % to 45 mol %, from 25 mol % to 40 mol %, from 30 mol % to 45 mol %, from 30 mol % to 40 mol %, from 31 mol % to 39 mol %, from 32 mol % to 38 mol %, from 33 mol % to 37 mol %, from 35 mol % to 45 mol %, from 30 mol % to 35 mol %, from 35 mol % to 40 mol %, or 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle.

In other embodiments, the non-cationic lipid comprises from 5 mol % to 90 mol %, from 10 mol % to 85 mol %, from 20 mol % to 80 mol %, 10 mol (e.g., phospholipid only), or 60 mol % (e.g., phospholipid and cholesterol or derivative thereof) (or any fraction thereof or range therein) of the total lipid present in the particle.

The percentage of non-cationic lipid present in the lipid particles is a target amount, and that the actual amount of non-cationic lipid present in the formulation may vary, for example, by ±5 mol %.

A composition containing a cationic lipid compound may be 30-70% cationic lipid compound, 0-60% cholesterol, 0-30% phospholipid and 1-10% polyethylene glycol (PEG). Preferably, the composition is 30-40% cationic lipid compound, 40-50% cholesterol, and 10-20% PEG. In other preferred embodiments, the composition is 50-75% cationic lipid compound, 20-40% cholesterol, and 5-10% phospholipid, and 1-10% PEG. The composition may contain 60-70% cationic lipid compound, 25-35% cholesterol, and 5-10% PEG. The composition may contain up to 90% cationic lipid compound and 2-15% helper lipid.

The formulation may be a lipid particle formulation, for example containing 8-30% compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Lipid Conjugates

In addition to cationic, the lipid particles described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof.

In a preferred embodiment, the lipid conjugate is a PEG-lipid. Examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), such as distearoyl-glycero-phosphoethanolamine (PEG-DSPE), such as Dimyristoyl-glycerol (PEG-DMG), such as Dioleoyl-glycerol (PEG-DOG), such as Dipalmitoyl-glycerol (PEG-DPG), such as Di stearoyl-glycerol (PEG-DSG), such as dimyri stoyl-glycero-3-phosphoethanolamine (PEG-DMPE), such as dipalmitoyl-glycero-3-phosphoethanolamine (PEG-DPPE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights; and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-$NH_2$).

The PEG moiety of the PEG-lipid conjugates described herein may comprise an average molecular weight ranging from 550 daltons to 10,000 daltons. In certain instances, the PEG moiety has an average molecular weight of from 750 daltons to 5,000 daltons (e.g., from 1,000 daltons to 5,000 daltons, from 1,500 daltons to 3,000 daltons, from 750 daltons to 3,000 daltons, from 750 daltons to 2,000 daltons). In preferred embodiments, the PEG moiety has an average molecular weight of 2,000 daltons or 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In a preferred embodiment, the linker moiety is a non-ester-containing linker moiety. Suitable non-ester-containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulfide, as well as combinations thereof (such as a linker containing both a carbamate linker moiety and an amido linker moiety). In a preferred embodiment, a carbamate linker is used to couple the PEG to the lipid.

In other embodiments, an ester-containing linker moiety is used to couple the PEG to the glycerol lipid. Suitable ester-containing linker moieties include, e.g., carbonate (—OC(O)O—), succinoyl, phosphate esters (—O—(O)POH—O—), sulfonate esters, —C(O)O—, —O(O)C—, —NH(O)C—, —C(O)NH—, a phosphate, $C_1$-$C_{10}$ alkyl-phosphate, $C_3$-$C_{10}$ alkenyl-phosphate, a phosphorothioate, $C_1$-$C_{10}$ alkyl-phosphorothioate, $C_3$-$C_{10}$ alkenyl-phosphorothioate, a boranophospate, a $C_1$-$C_{10}$ alkyl-boranophospate, a $C_3$-$C_{10}$ alkenyl-boranophospate, —C(O)NH—$C_1$-$C_{10}$alkyl-phosphate, —C(O)NH—$C_3$-$C_{10}$alkenyl-phosphate, —C(O)O—$C_1$-$C_{10}$alkyl-phosphate, —C(O)O—$C_3$-$C_{10}$alkenyl-phosphate, —C(O)NH—$C_1$-$C_{10}$ alkyl-phosphorothioate, —C(O)NH—$C_3$-$C_{10}$alkenyl-phosphorothioate, —C(O)O—$C_1$-$C_{10}$alkyl-phosphorothioate, —C(O)O—$C_3$-$C_{10}$alkenyl-phosphorothioate, —C(O)—NH—$C_1$-$C_{10}$ alkyl-boranophospate, —C(O)—NH—$C_3$-$C_{10}$alkenyl-boranophospate, —C(O)O—$C_1$-$C_{10}$alkyl-boranophospate or —C(O)O—$C_3$-$C_{10}$alkenyl-boranophospate, and combinations thereof.

Phosphatidylethanolamines having a variety of acyl chain groups of varying chain lengths and degrees of saturation can be conjugated to PEG to form the lipid conjugate. Such phosphatidylethanolamines are commercially available or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoyl-phosphatidylethanolamine (DOPE), and distearoyl-phosphatidylethanolamine (DSPE).

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., di stearoyl).

The term "dialkyloxypropyl" or "DAA" includes a compound having 2 alkyl chains, both of which have independently between 2 and 30 carbons. The alkyl groups can be saturated or have varying degrees of unsaturation.

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of 750 or 2,000 daltons. In particular embodiments, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In some embodiments, the lipid conjugate (e.g., PEG-lipid) comprises from 0.1 mol % to 2 mol %, from 0.5 mol % to 2 mol %, from 1 mol % to 2 mol %, from 0.6 mol % to 1.9 mol %, from 0.7 mol % to 1.8 mol %, from 0.8 mol % to 1.7 mol %, from 0.9 mol % to 1.6 mol %, from 0.9 mol % to 1.8 mol %, from 1 mol % to 1.8 mol %, from 1 mol % to 1.7 mol %, from 1.2 mol % to 1.8 mol %, from 1.2 mol % to 1.7 mol %, from 1.3 mol % to 1.6 mol %, or from 1.4 mol % to 1.5 mol % (or any fraction thereof or range therein) of the total lipid present in the particle. In other embodiments, the lipid conjugate (e.g., PEG-lipid) comprises from 0 mol % to 20 mol %, from 0.5 mol % to 20 mol %, from 2 mol % to 20 mol %, from 1.5 mol % to 18 mol %, from 2 mol % to 15 mol %, from 4 mol % to 15 mol %, from 2 mol % to 12 mol %, from 5 mol % to 12 mol %, or 2 mol % (or any fraction thereof or range therein) of the total lipid present in the particle.

In further embodiments, the lipid conjugate (e.g., PEG-lipid) comprises from 4 mol % to 10 mol %, from 5 mol % to 10 mol %, from 5 mol % to 9 mol %, from 5 mol % to 8 mol %, from 6 mol % to 9 mol %, from 6 mol % to 8 mol %, or 5 mol %, 6 mol %, 7 mol %, 8 mol %, 9 mol %, or 10 mol % (or any fraction thereof or range therein) of the total lipid present in the particle.

The percentage of lipid conjugate (e.g., PEG-lipid) present in the lipid particles of the disclosure is a target amount, and the actual amount of lipid conjugate present in the formulation may vary, for example, by ±2 mol %. One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. In addition, other variables including, e.g., pH, temperature, or ionic strength, can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle size.

Compositions and Formulations for Administration

The nucleic acid-lipid compositions of this disclosure may be administered by various routes, for example, to effect systemic delivery via intravenous, parenteral, intraperitoneal, or topical routes. In some embodiments, a siRNA may be delivered intracellularly, for example, in cells of a target tissue such as lung or liver, or in inflamed tissues. In some embodiments, this disclosure provides a method for delivery of siRNA in vivo. A nucleic acid-lipid composition may be administered intravenously, subcutaneously, or intraperitoneally to a subject. In some embodiments, the disclosure provides methods for in vivo delivery of interfering RNA to the lung of a mammalian subject.

In some embodiments, this disclosure provides a method of treating a disease or disorder in a mammalian subject. A therapeutically effective amount of a composition of this disclosure containing a nucleic acid, a cationic lipid, an amphiphile, a phospholipid, cholesterol, and a PEG-linked cholesterol may be administered to a subject having a disease or disorder associated with expression or overexpression of a gene that can be reduced, decreased, down-regulated, or silenced by the composition.

The compositions and methods of the disclosure may be administered to subjects by a variety of mucosal administration modes, including by oral, rectal, vaginal, intranasal, intrapulmonary, or transdermal or dermal delivery, or by topical delivery to the eyes, ears, skin, or other mucosal surfaces. In some aspects of this disclosure, the epithelial tissue layer includes an epithelial cell layer. The epithelial cell can be pulmonary, tracheal, bronchial, alveolar, nasal, buccal, epidermal, or gastrointestinal. Compositions of this disclosure can be administered using conventional actuators such as mechanical spray devices, as well as pressurized, electrically activated, or other types of actuators.

Compositions of this disclosure may be administered in an aqueous solution as a nasal or pulmonary spray and may be dispensed in spray form by a variety of methods known to those skilled in the art. Pulmonary delivery of a composition of this disclosure is achieved by administering the composition in the form of drops, particles, or spray, which can be, for example, aerosolized, atomized, or nebulized. Particles of the composition, spray, or aerosol can be in either a liquid or solid form. Preferred systems for dispensing liquids as a nasal spray are disclosed in U.S. Pat. No. 4,511,069. Such formulations may be conveniently prepared by dissolving compositions according to the present disclosure in water to produce an aqueous solution, and rendering said solution sterile. The formulations may be presented in multi-dose containers, for example in the sealed dispensing system disclosed in U.S. Pat. No. 4,511,069. Other suitable nasal spray delivery systems have been described in TRANSDERMAL SYSTEMIC MEDICATION, Y. W. Chien ed., Elsevier Publishers, New York, 1985; and in U.S. Pat. No. 4,778,810. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or mixtures thereof.

Nasal and pulmonary spray solutions of the present disclosure typically comprise the drug or drug to be delivered, optionally formulated with a surface active agent, such as a nonionic surfactant (e.g., polysorbate-80), and one or more buffers. In some embodiments of the present disclosure, the nasal spray solution further comprises a propellant. The pH of the nasal spray solution may be from pH 6.8 to 7.2. The pharmaceutical solvents employed can also be a slightly acidic aqueous buffer of pH 4-6. Other components may be added to enhance or maintain chemical stability, including preservatives, surfactants, dispersants, or gases.

In some embodiments, a pharmaceutical product which includes a solution containing a composition of this disclosure and an actuator for a pulmonary, mucosal, or intranasal spray or aerosol is provided.

A dosage form of the composition of this disclosure can be liquid, in the form of droplets or an emulsion, or in the form of an aerosol.

A dosage form of the composition of this disclosure can be solid, which can be reconstituted in a liquid prior to administration. The solid can be administered as a powder. The solid can be in the form of a capsule, tablet, or gel.

To formulate compositions for pulmonary delivery within the present disclosure, the biologically active agent can be combined with various pharmaceutically acceptable additives, as well as a base or carrier for dispersion of the active agent(s). Examples of additives include pH control agents such as arginine, sodium hydroxide, glycine, hydrochloric acid, citric acid, and mixtures thereof. Other additives include local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione). When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the mucosa at the site of administration. Generally, the tonicity of the solution is adjusted to a value of ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g., maleic anhydride) with other monomers (e.g., methyl(meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly (hydroxybutyric acid-glycolic acid) copolymer, and mixtures thereof. Alternatively, synthetic fatty acid esters such as polyglycerin fatty acid esters, sucrose fatty acid esters, etc., can be employed as carriers. Hydrophilic polymers and other carriers can be used alone or in combination and enhanced structural integrity can be imparted to the carrier by partial crystallization, ionic bonding, crosslinking, and the like. The carrier can be provided in a variety of forms, including fluid or viscous solutions, gels, pastes, powders, microspheres, and films for direct application to the nasal mucosa. The use of a selected carrier in this context may result in promotion of absorption of the biologically active agent.

Formulations for mucosal, nasal, or pulmonary delivery may contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10,000 and preferably not more than 3,000. Examples of hydrophilic low molecular weight compounds include polyol compounds, such as oligo-, di- and monosaccharides including sucrose, mannitol, lactose, L-arabinose, D-erythrose, D-ribose, D-xylose, D-mannose, D-galactose, lactulose, cellobiose, gentibiose, glycerin, polyethylene glycol, and mixtures thereof. Further examples of hydrophilic low molecular weight compounds include N-methylpyrrolidone, alcohols (e.g., oligovinyl alcohol, ethanol, ethylene glycol, propylene glycol, etc.), and mixtures thereof.

The compositions of this disclosure may alternatively contain as pharmaceutically acceptable carrier substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the biologically active agent may be administered in a time release formulation, for example in a composition which includes a slow release polymer. The active agent can be prepared with carriers that will protect against rapid release, for example a controlled release vehicle such as a polymer, microencapsulated delivery system, or bioadhesive gel. Prolonged delivery of the active agent, in various compositions of the disclosure can be brought about by including in the composition agents that delay absorption, for example, aluminum monosterate hydrogels and gelatin.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications, and equivalents. In particular, this disclosure includes any combination of the features, terms, or elements of the various illustrative components and examples.

EXAMPLES

The present disclosure is further described in the following examples, which do not limit the scope of the disclosure herein.

Example 1

Synthesis of Conjugate 1

Exemplary oligonucleotide Conjugate 1 was synthesized using Compound 7 as shown below, which was prepared as shown below with Scheme 1.

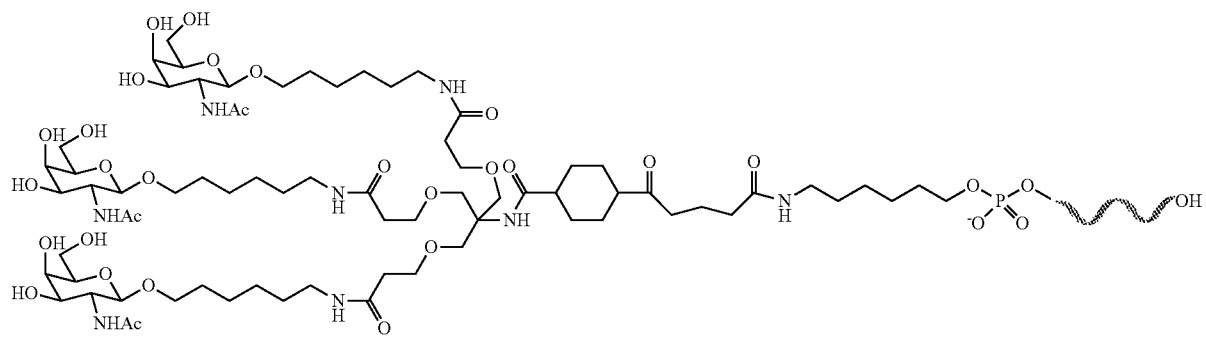

1 wherein for the purposes of Example 1, the substituent

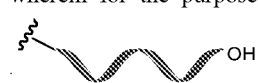

represents the mFVII ASO (Mouse Factor VII Antisense Oligonucleotide) connected through a hexylamino linker to the 5' end of the mFVII ASO.

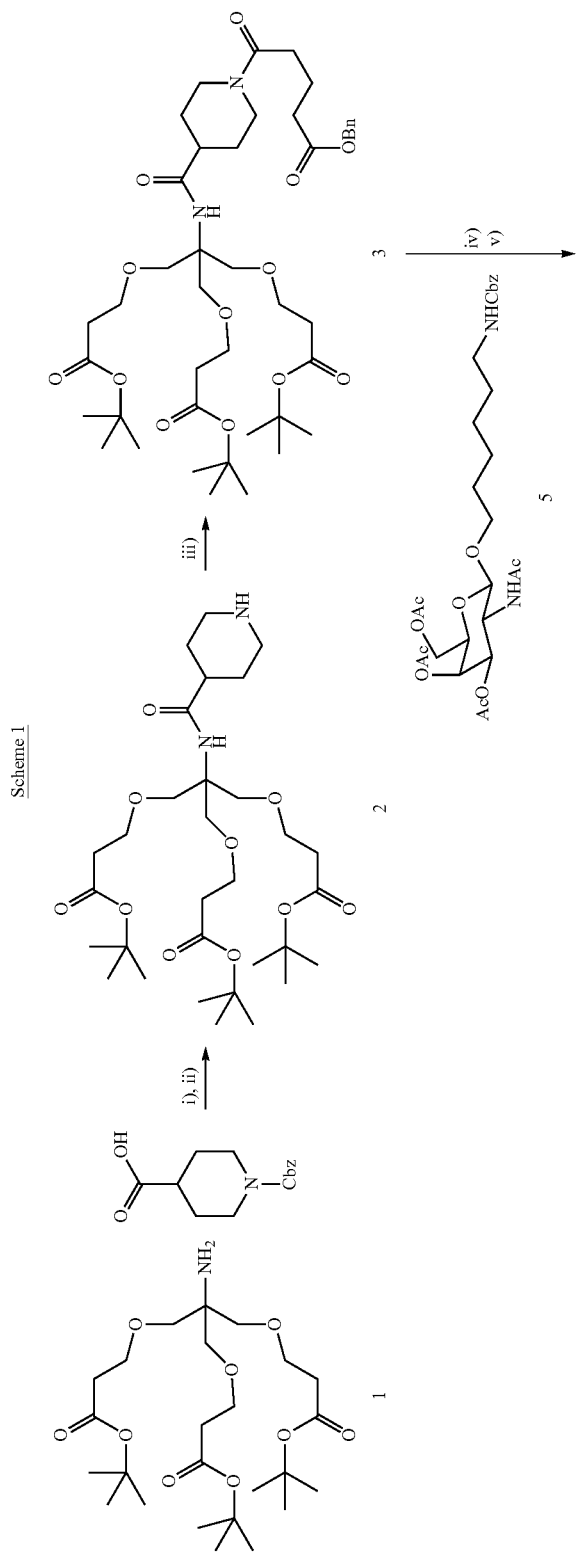

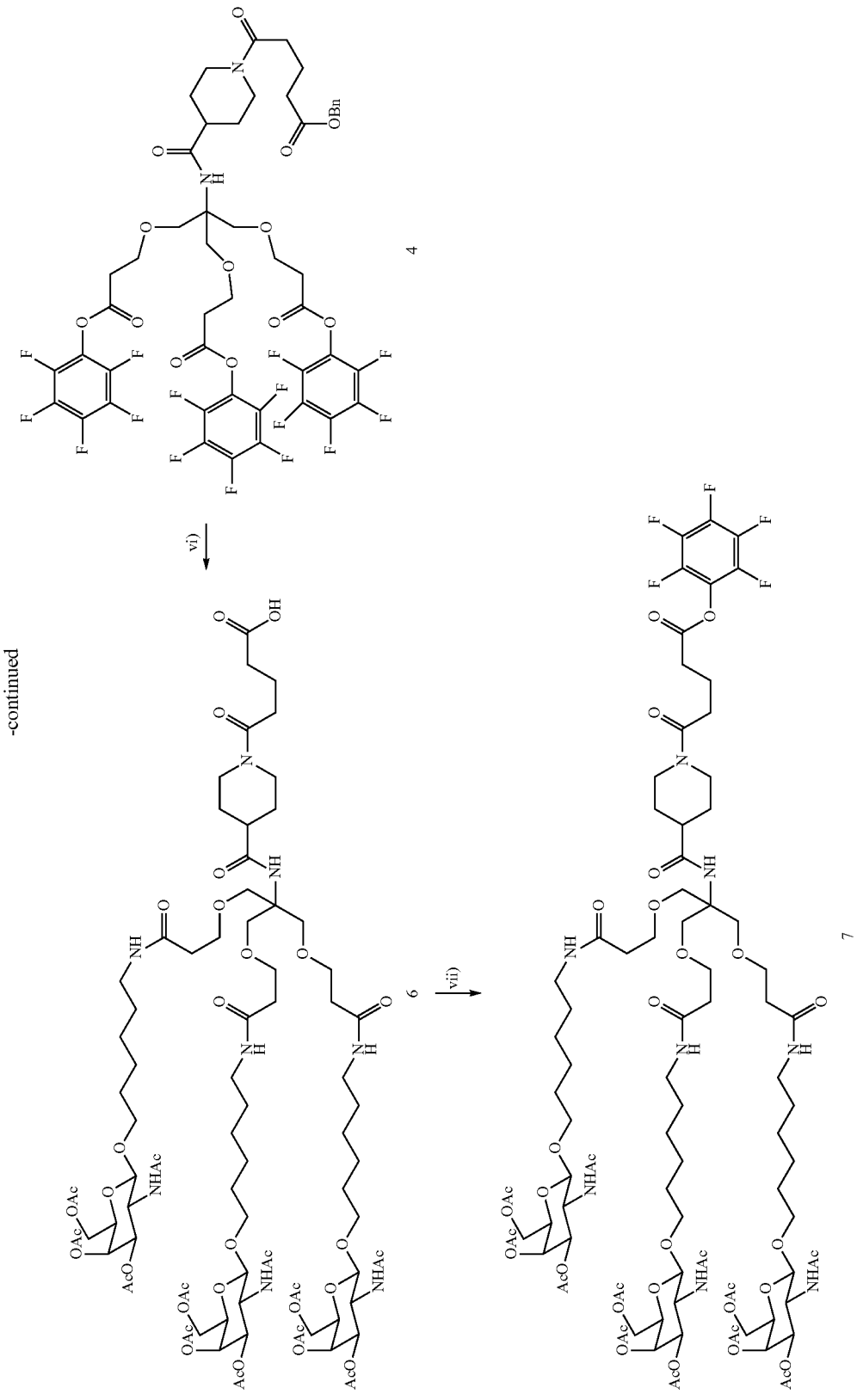

Conjugate 1: Steps 1 and 2

To an equimolar mixture of 5.05 g (10 mmol) of 1 (di-tert-butyl 3,3'-((2-amino-2-((3-(tert-butoxy)-3-oxo-propoxy)methyl)propane-1,3-diyl)bis(oxy))dipropionate (prepared according to *J. Org. Chem.* 2002, 67, 1411-1413) and 2.63 g (10 mmol) of 1-((benzyloxy)carbonyl)piperidine-4-carboxylic acid, 3.80 g of HATU (1-[Bis(dimethylamino)methylene]-1H-1,2,3-triazolo[4,5-b]pyridinium 3-oxid hexafluorophosphate) and 3.72 g (5 mL, 30 mmol) of DIEA (Diisopropylethyl Amine) were stirred in 50 mL anhydrous DMF (N,N-Dimethylformamide) at room temperature for between 12-16 hrs. The mixture was diluted with ethyl acetate (200 mL) and washed with water (300 mL), washed with brine (200 mL), dried over $Na_2SO_4$, and the solvent was evaporated under reduced pressure. The residue was purified on a silica gel column (80 g, Teledyne ISCO) on a Combiflash® system with an ethyl acetate:hexane gradient (0-100% over 30 minutes). The product eluted in fractions with 30-35% ethyl acetate:hexane. The fractions containing the product were pooled and the solvent was evaporated at reduced pressure to afford 6 g (80%) of the product as a colorless syrup. Mass: 750.43 (Calcd.), 773.60 (M+Na, observed). Then, to a solution of 5.6 g of the product from Step 1 in methanol (60 mL) was added 560 mg, 10% wt/wt of Pd-C (10%, wet Degusa type). The mixture was hydrogenated under a hydrogen filled balloon for 18 hrs. The mixture was filtered through a pad of Celite® and the Celite® pad was washed with 30 mL of methanol. The filtered methanol solution was evaporated to afford 4.5 g of 2 as a colorless solid. Mass: 616.8 (Calcd.), 617.8 (M+H, Observed).

2

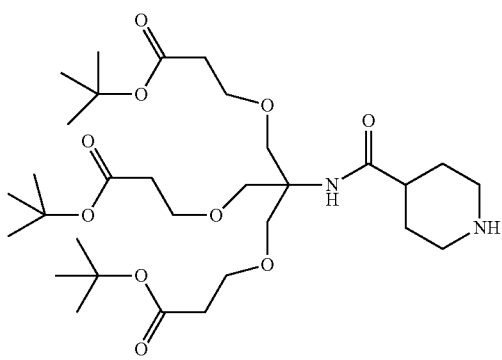

Conjugate 1: Step 3

To a solution of 4.5 g (7.3 mmol) of 2 in 50 mL anhydrous DMF was added monobenzyl pentanedioic acid (1.62 g, 7.3 mmol) followed by the addition of DIEA (2.4 g, 19.2 mmol) and HATU (2.8 g, 7.3 mmol). The mixture was stirred at room temperature overnight. Then, the mixture was diluted with ethyl acetate (120 mL), washed with water (2×150 mL), washed with brine (1×150 mL), dried over $Na_2SO_4$, and the solvent was evaporated under reduced pressure. The residue was purified on a Teledyne ISCO silica gel column (80 g) using a methanol:dichloromethane gradient. The fractions containing the product were eluted with 12-15% methanol:dichloromethane and combined. Then, the solvent was evaporated under reduced pressure to afford 4.75 g of 3. Mass: 821.02 (Calcd.), 843.4 (M+Na, Observed).

3

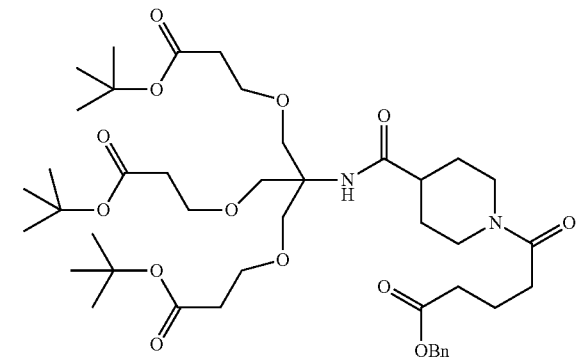

Conjugate 1: Steps 4 and 5

To a solution of 4.7 g of 3 in 45 mL dichloromethane added 45 mL TFA (Trifluoroacetic Acid) and the mixture was stirred at room temperature for 16 hrs. The solvent was evaporated under reduced pressure and placed under high vacuum for 24 hrs to afford a quantitative amount of product (3.7 g). Then, to a solution of 3.1 g (4.7 mmol) of the product isolated from Step 4 in 40 mL anhydrous DMF was added DIEA (4.7 g, 38 mmol), followed by slow addition of pentafluorophenyl trifluoroacetate (5.3 g, 18.8 mmol). The mixture was stirred at room temperature for 16 hrs. The mixture was diluted with 250 mL of ethyl acetate and washed with 250 mL of saturated aqueous sodium bicarbonate. The aqueous layer was washed with 100 mL ethyl acetate. The combined organic solution was washed with water (200 mL), washed with brine (200 mL), dried over $Na_2SO_4$, filtered and the solvent was evaporated. The residue was purified on an 80 g Teledyne ISCO silica gel column using an ethyl acetate:hexane gradient. The product was eluted in fractions with 60-70% ethyl acetate:hexane and monitored by TLC (Thin Layer Chromatography). The pure fractions were combined, and the solvent was evaporated under reduced pressure to afford 1.9 g of 4. Mass: 1150.84 (Calcd.), 1173.2 (M−H+Na, Observed).

4

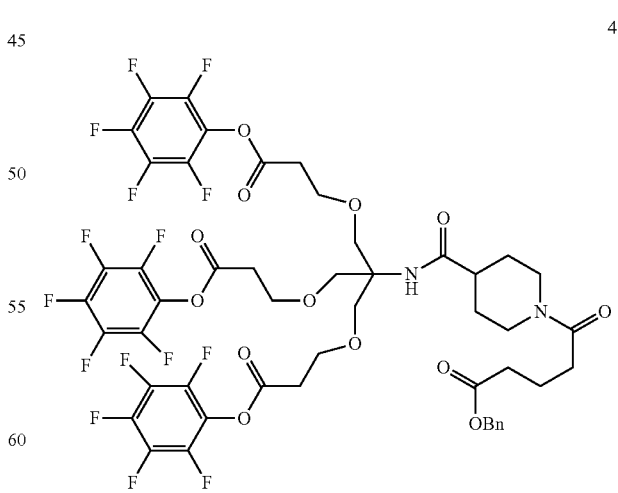

Conjugate 1: Step 6

To a solution of 3.1 g (2.69 mmol) of 4 and 4.9 g (8.44 mmol, 3.1 eq.) of 5 (see literature procedures as presented with *International Journal of Peptide & Protein Research*, Volume 43 Issue 5 Pages 477-85, 1994; *Bioorganic & Medicinal Chemistry*, 13(10), 3553-3564; 2005; US 20140031533 A1; and WO 2015/168514 A1) in 1:1 v/v ethyl acetate:acetonitrile (60 mL) added palladium hydroxide on charcoal (10-20% loading, 1 g), and the mixture was hydrogenated under a hydrogen filled balloon for 18 hrs. The mixture was filtered through a pad of Celite® and the Celite® pad was washed with 40 mL of acetonitrile. Then, the solvent was evaporated, and the residue was purified on a Teledyne ISCO silica gel column (80 g) using a methanol/dichloromethane gradient. A major product eluted with 20-25% methanol/dichloromethane. Then, the fractions containing pure product were combined and the solvent was evaporated under reduced pressure to afford 1.4 g of pure 6. Mass: 1848.02 (Calcd.), 1870.1 (M−H+Na, Observed).

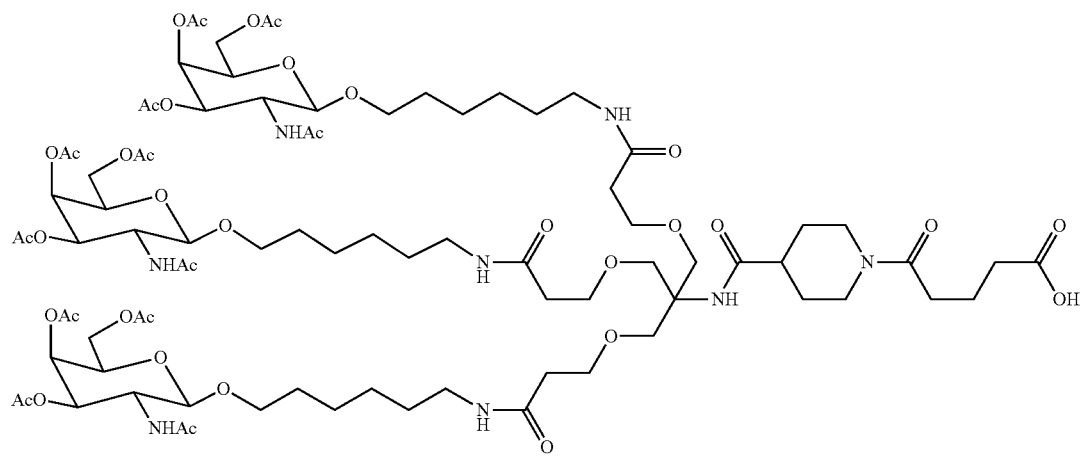

Conjugate 1: Step 8

To a solution of 6 (360 mg, 0.19 mmol) in anhydrous N,N-dimethylformamide (4 mL) in a 50 mL round-bottom flask under an argon atmosphere added triethylamine (57 mg, 0.57 mmol) followed by the addition of pentafluorophenyl trifluoroacetate (106 mg, 0.38 mmol), and the reaction mixture was stirred at room temperature for 2.5 hrs. The solution was cooled in an ice-bath and quenched with a saturated aqueous sodium bicarbonate solution (1.5 mL). The resulting solution was diluted with water (2 mL) and extracted with ethyl acetate (2×3 mL). The combined organic solution was washed with 1N aqueous sodium bisulfate, dried (anhydrous sodium sulfate), filtered and concentrated under reduced pressure. The residue was purified on a Teledyne ISCO gold silica gel column (12 g) using a methanol:dichloromethane gradient. A major product eluted with 12-14% methanol: dichloromethane. The fractions containing the major product were combined and the solvent was evaporated. The residue was dried under vacuum in the presence of phosphorus pentoxide to afford 300 mg of pure 7. Mass: 2012.87 (Calcd.), 2035.7 (M+Na, Observed).

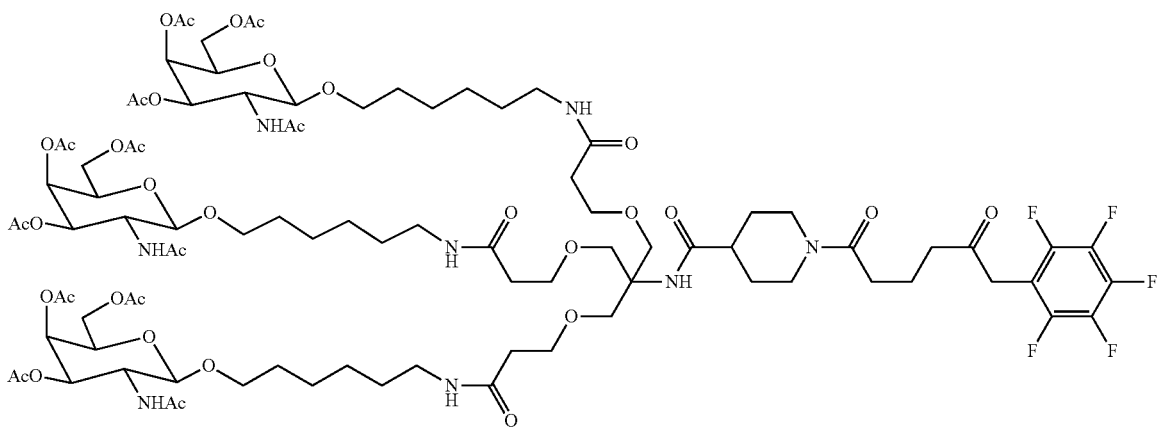

Conjugate 1: Step 8

Compound 7 was then used in the post-synthesis conjugation to the 5'-end of mouse Factor VII antisense oligonucleotide through a hexylamino linker using established protocols of oligonucleotide synthesis to afford Conjugate 1. As such, the oligonucleotide was prepared with an amino group at the 5'-end using standard phosphoramidite chemistry. After purification with IE-HPLC (Ion Exchange-High Performance Liquid Chromatography), the oligonucleotide was suspended in a phosphate buffer (pH 7.4) and a solution of ARCT-GalNAc PFP ester (Third Party Reagent) in DMSO (Dimethyl Sulfoxide) was added to the suspension. The reaction was monitored by MALDI-TOF MS (Matrix-Assisted Laser Desorption/Ionization-Time of Flight Mass Spectrometry). After 2 hrs, the reaction was complete, and the reaction mixture was lyophilized. Then, the residue was resuspended in concentrated ammonium hydroxide for 2 hrs and lyophilized. The residue was purified by RP-HPLC (Reverse Phase-High Performance Liquid Chromatography) to afford Conjugate 1.

Example 2

Synthesis of Conjugate 2

Conjugate 2 as shown below was synthesized using 13 prepared as shown below with Scheme 2 in similar fashion as Scheme 1 and Step 7 of Conjugate 1.

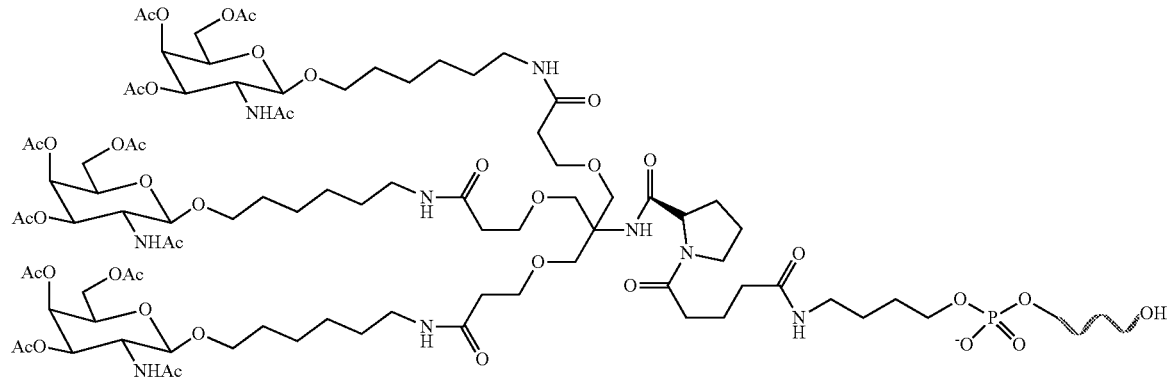

wherein for the purposes of Example 2, the substituent

 represents the mFVII ASO (Mouse Factor VII Antisense Oligonucleotide) connected through a hexylamino linker to the 5' end of the mFVII ASO.

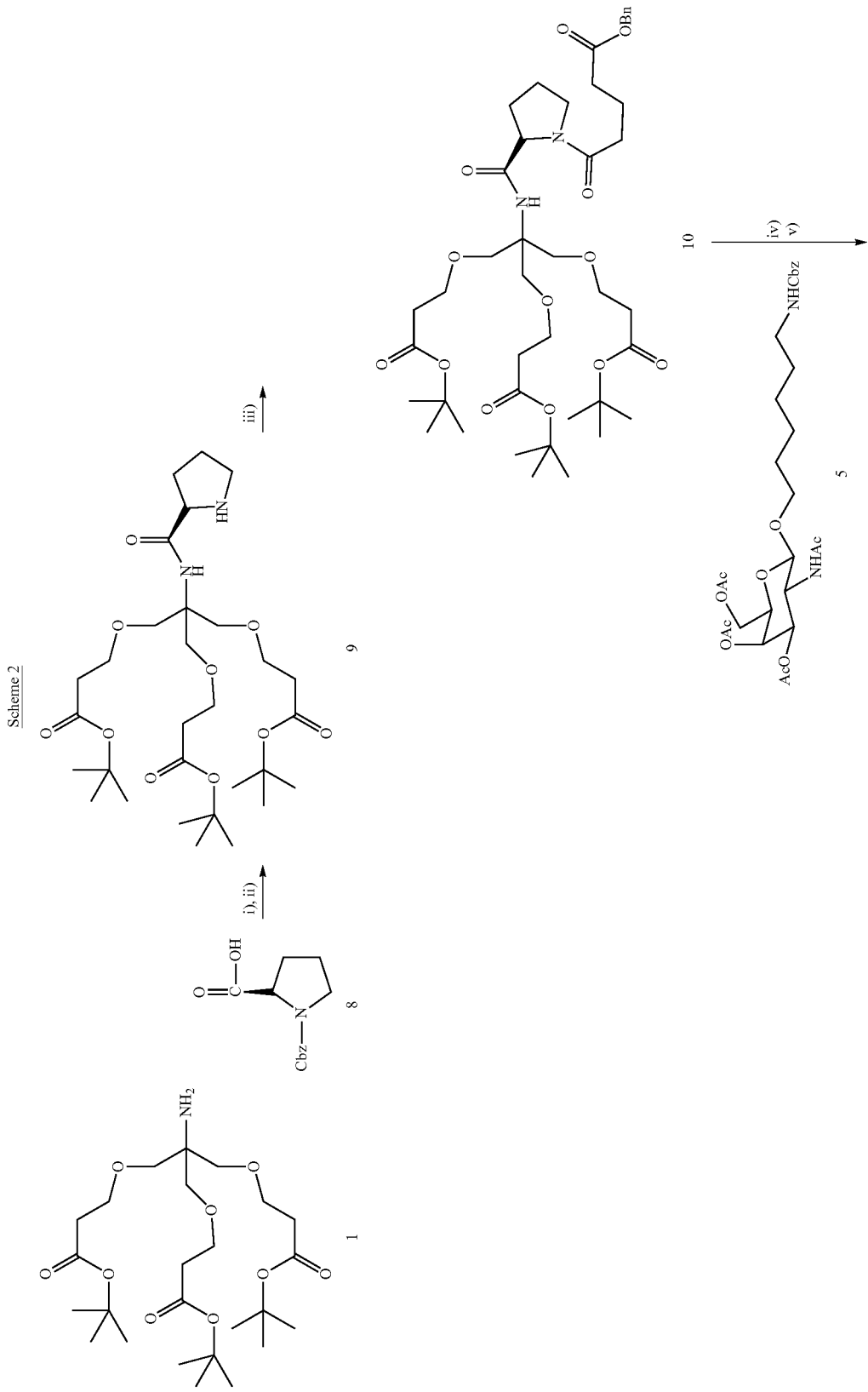

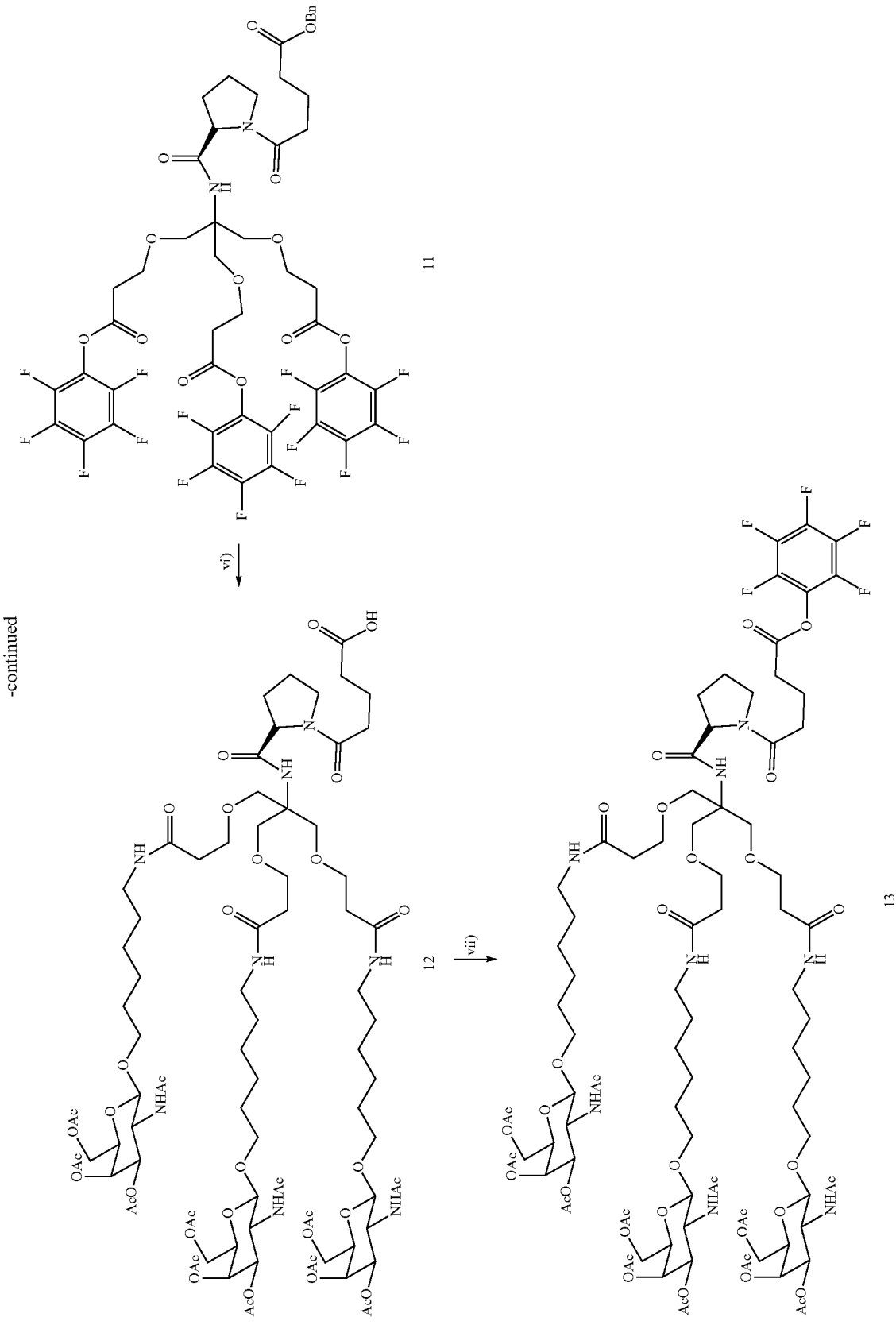

Scheme 2: Reagents and conditions: i) HATU, DIEA, DMF, room temperature, overnight; ii) Pd-C(10%), 10% wt/wt, H₂ (Balloon), MeOH, room temperature overnight; iii) dipentanoic acid mono-benzyl ester, HATU, DIEA, DMF, room temperature, overnight; iv) TFA:DCM (Dichloromethane) (1:1 v/v), room temperature 16 hrs; v) Pentafluorophenyl trifluoroacetate, DIEA, room temperature, overnight; vi) 5, Pd(OH)₂-C(20%), 20% (wt/wt), H₂ (balloon), Ethyl acetate:Acetonitrile (1:1 v/v), overnight; vii) Pentafluorophenyl trifluoroacetate, DIEA, room temperature, overnight.

Example 3

Synthesis of Conjugate 3

Conjugate 3 as shown below was synthesized using Compound 19 prepared as shown below with Scheme 3 in similar fashion as Scheme 1 of Conjugate 1.

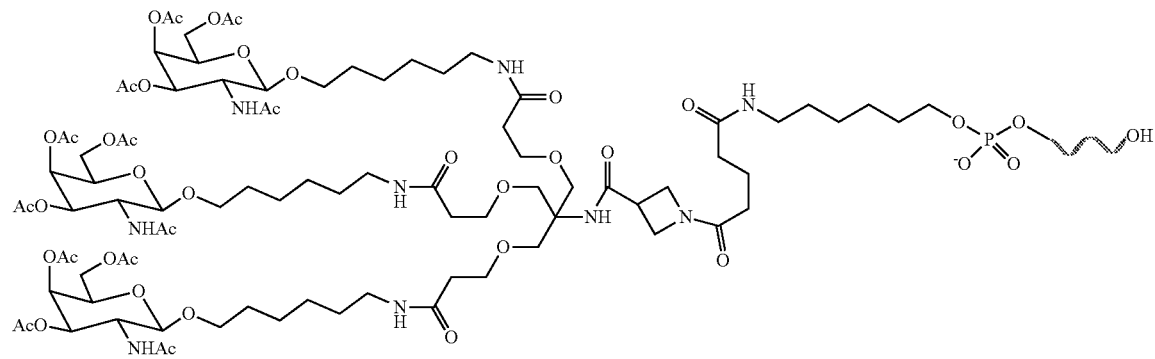

Conjugate 3 wherein for the purposes of Example 3, the substituent

 represents the mouse Factor VII antisense oligonucleotide (mFVII ASO) connected through a hexylamino linker to the 5' end of mFVII ASO.

Scheme 3
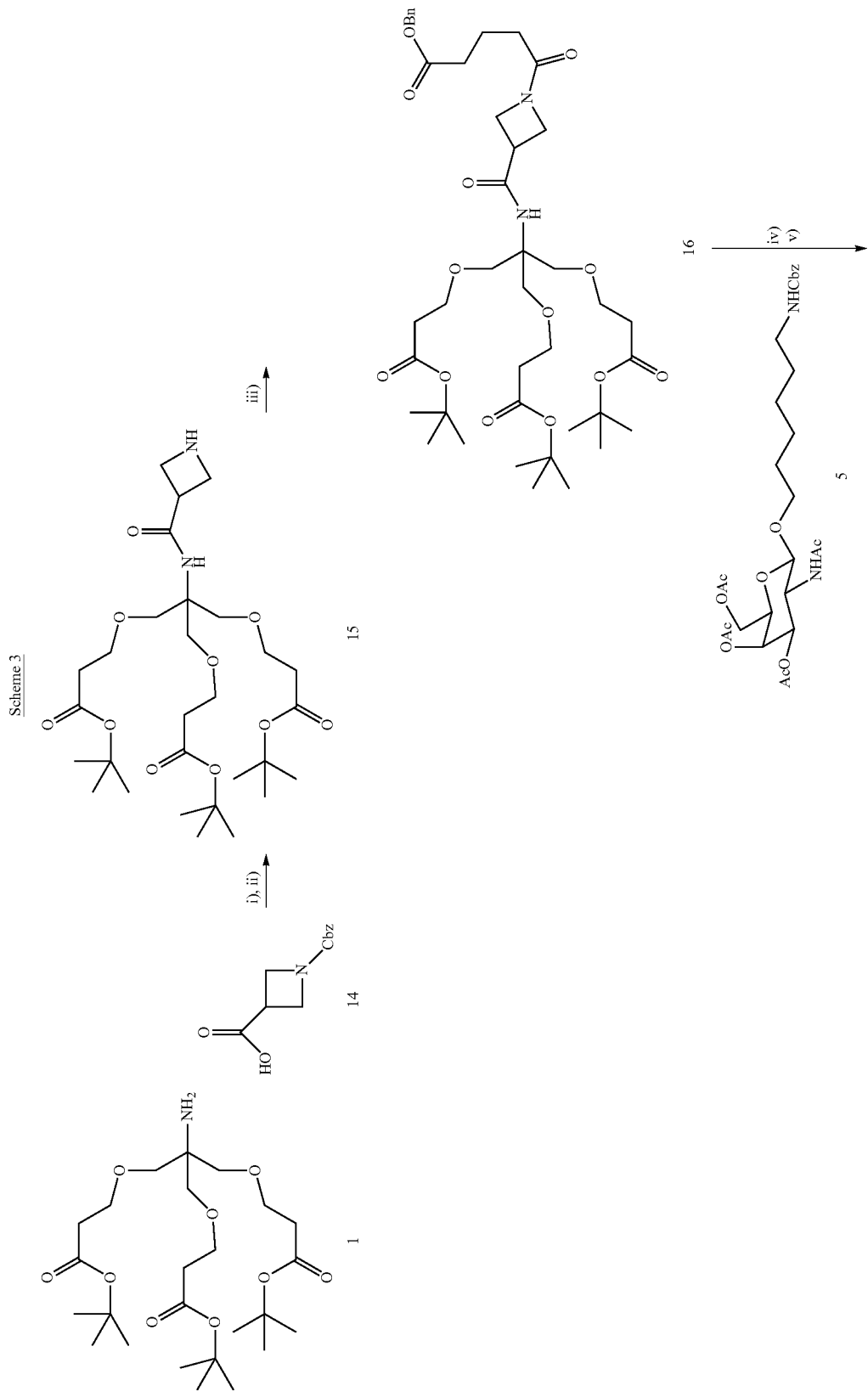

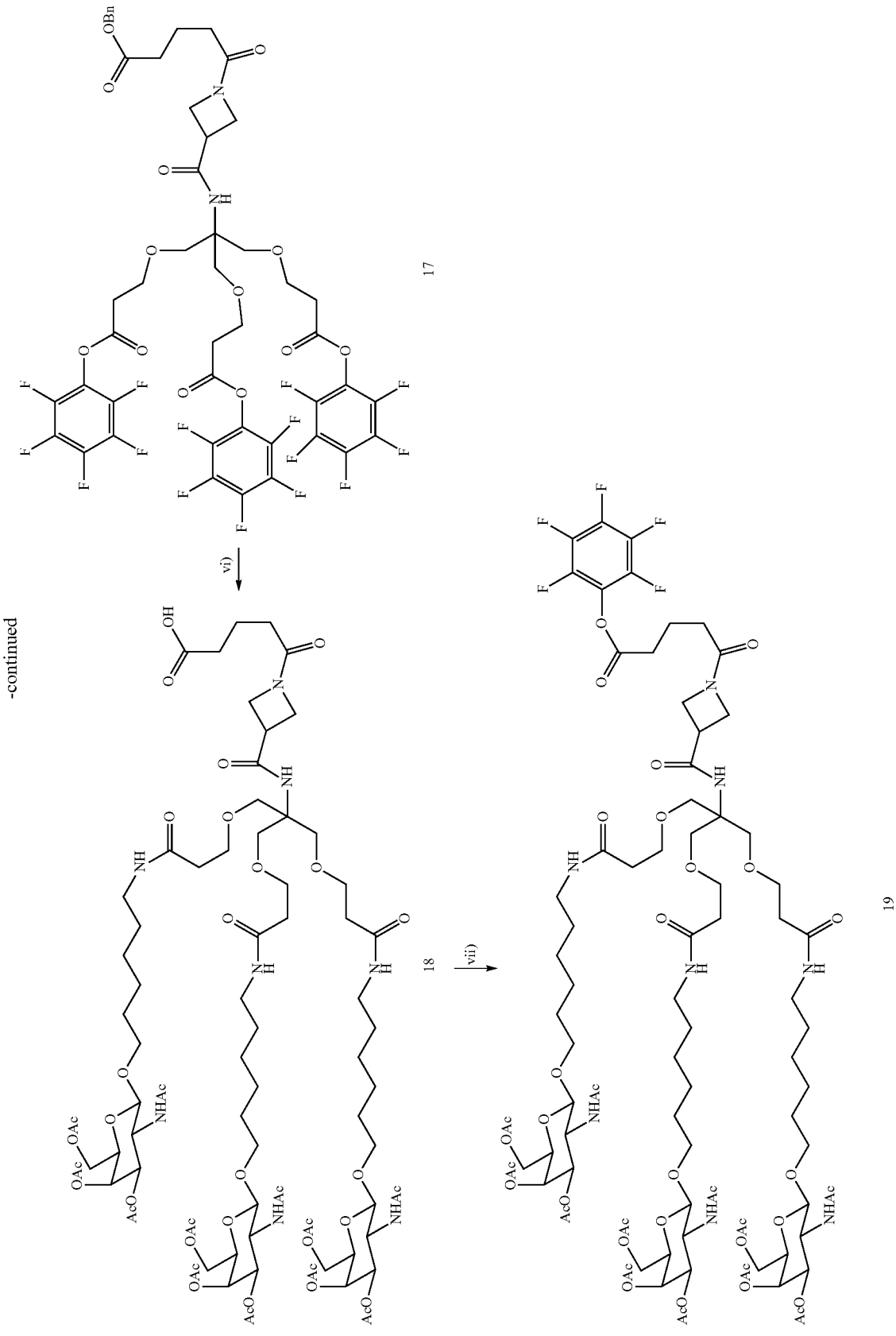

Scheme 3: Reagents and conditions: i) HATU, DIEA, DMF, room temperature, overnight; ii) Pd-C(10%), 10% wt/wt, H2 (Balloon), MeOH, room temperature overnight; iii) dipentanoic acid mono-benzyl ester, HATU, DIEA, DMF, room temperature, overnight; iv) TFA:DCM (1:1 v/v), room temperature, 16 hrs; v) Pentafluorophenyl trifluoroacetate, DIEA, room temperature, overnight; vi) 5, Pd(OH)2-C(20%), 20% (wt/wt), $H_2$ (balloon), Ethyl acetate:Acetonitrile (1:1 v/v), overnight; vii) Pentafluorophenyl trifluoroacetate, DIEA, room temperature, overnight.

Example 4

Synthesis of Conjugate 22

Prepare a 200 mM THPTA (Tris-Hydroxypropyltriazolylmethylamine) aqueous solution and a 100 mM $CuSO_4$ aqueous solution. Incubate a 1:2 mixture of the 100 mM $CuSO_4$ solution and the 200 mM THPTA ligand solution for several minutes. Then, to an aqueous solution of 21 add a 10 mM DMSO/tBuOH solution of the azide 20 (4-50 eq), add 100 mM sodium ascorbate solution in water (10-15 eq) followed by 25 equivalents of the incubated THPTA/$CuSO_4$ mixture. Then, incubate the mixture at room temperature for 30-60 minutes. The Conjugate 22 as shown below can be purified via an ethanol precipitation and/or column chromatography.

Scheme 4
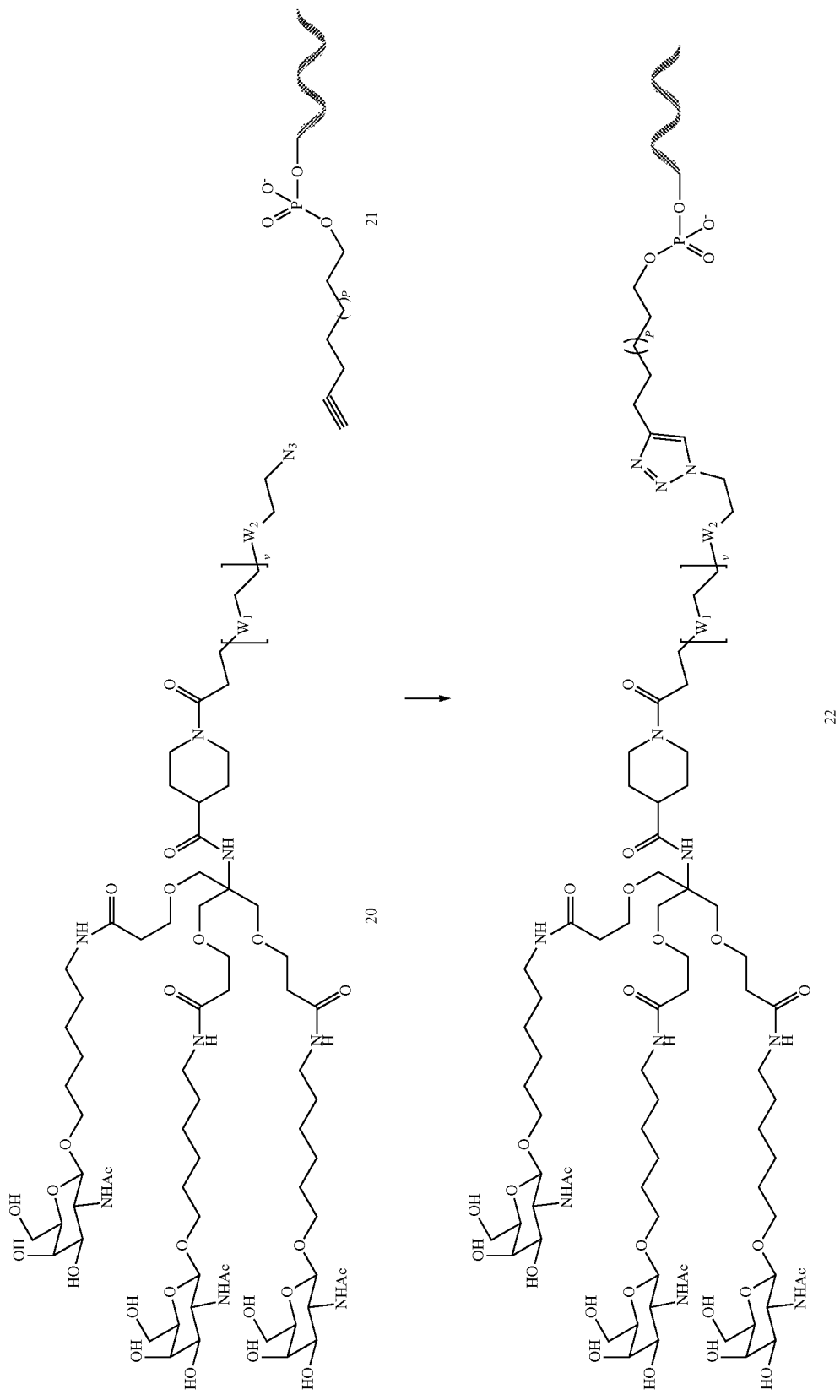

wherein $W^1$ and $W^2$ are O or —$CH_2$—; v is 1-6; and P is $C_1$-$C_{10}$ alkyl or $C_2$-$C_{10}$ alkenyl.

Examples 5, 6 and 7

Synthesis of Conjugates 23, 24 and 25

The preparation of Conjugates 23, 24 and 25 can be performed in similar fashion as Conjugate 22 via Schemes 5, 6 and 7, respectively.

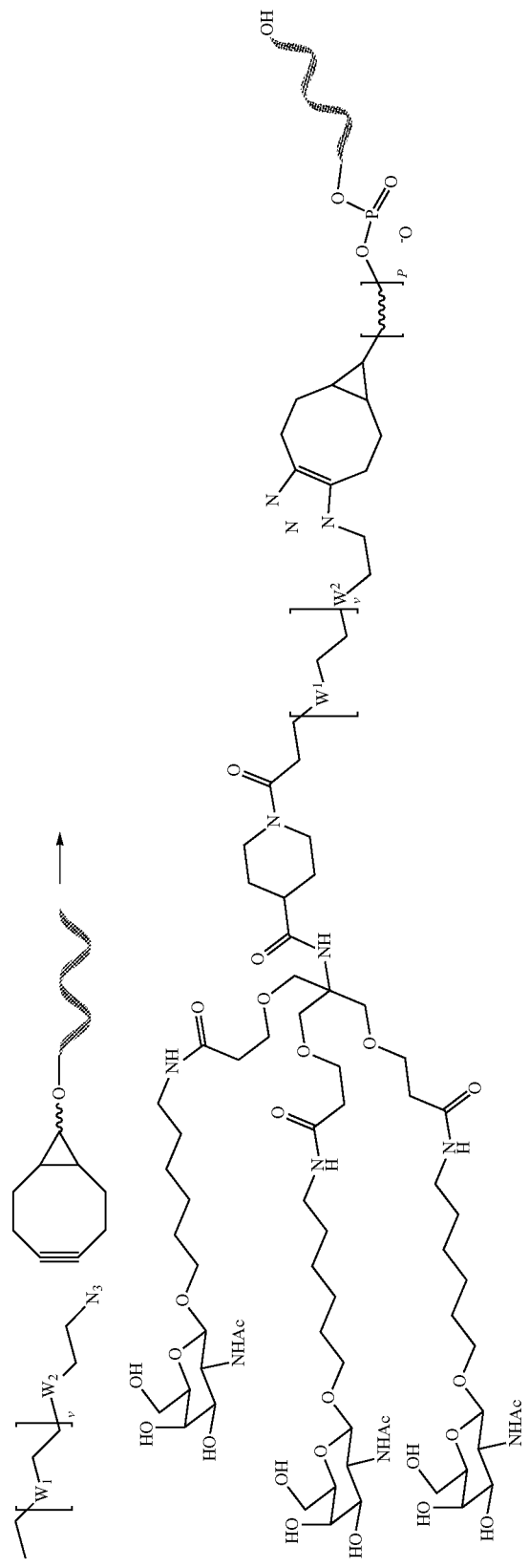

-continued
Scheme 6
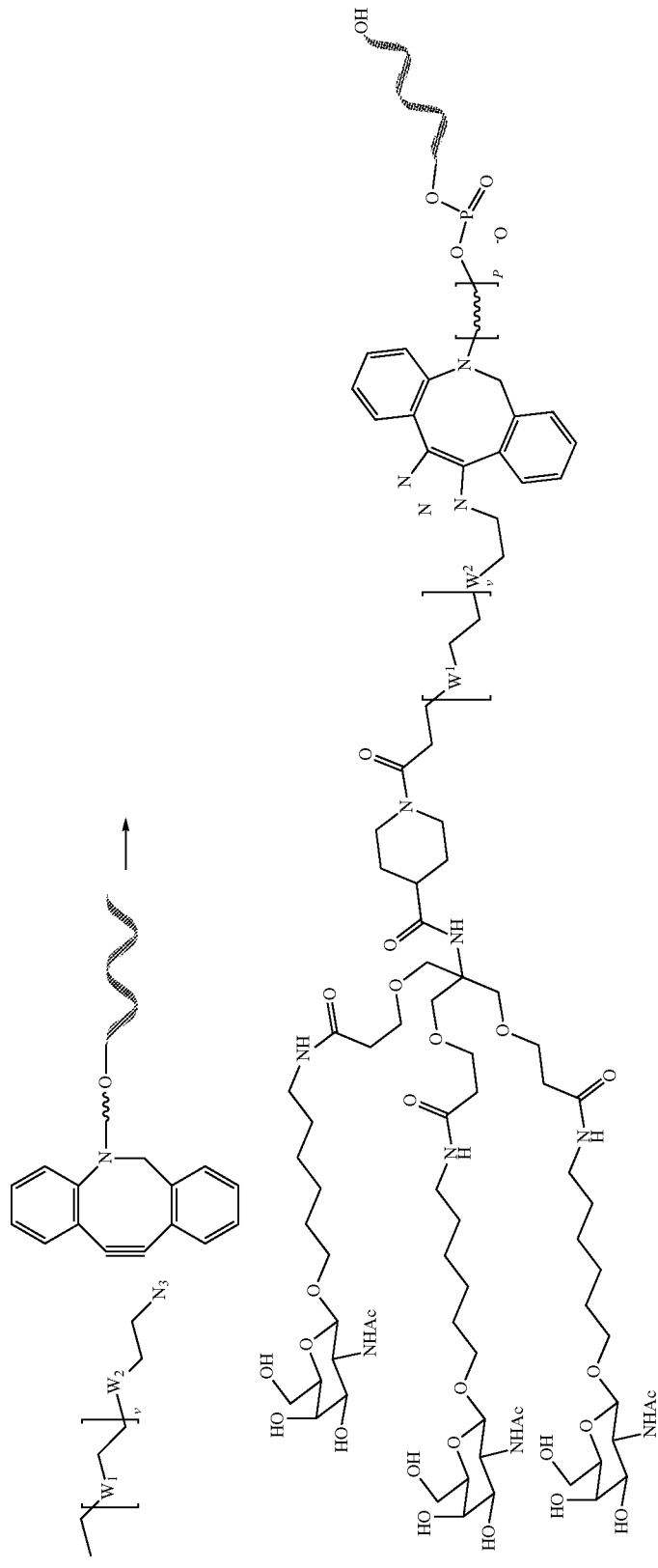

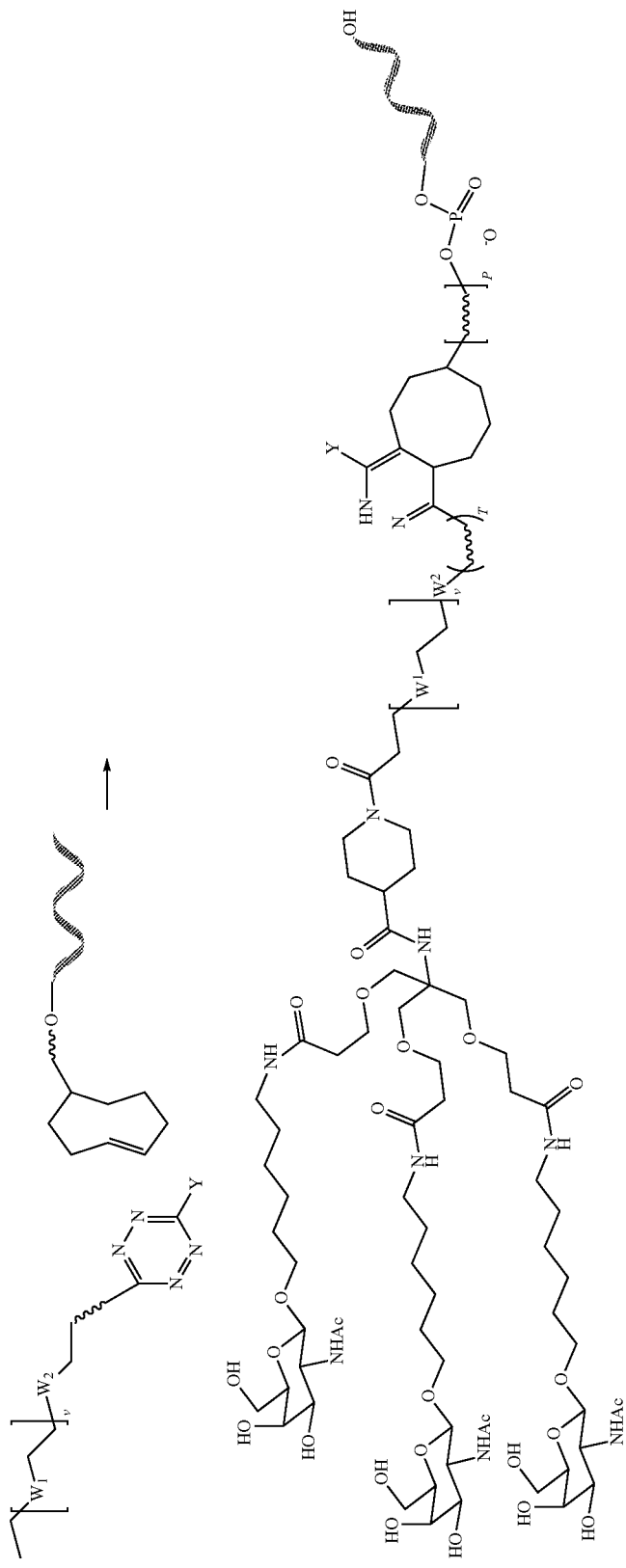

wherein $W^1$ and $W^2$ are O or —$CH_2$—; v is 1-6; Y is hydrogen or methyl; T is $C_1$-$C_{10}$ alkyl or $C_1$-$C_{10}$ alkenyl; and P is $C_1$-$C_{10}$ alkyl or $C_2$-$C_{10}$ alkenyl.

Example 8

Synthesis of Conjugate 27

Conjugate 27 as shown below was synthesized using Compound 26 prepared as shown below with Scheme 8 in similar fashion as Scheme 1 of Conjugate 1. Preparation of 26 was accomplished with similar synthetic methods as the examples presented with U.S. Pat. No. 9,962,449 B2.

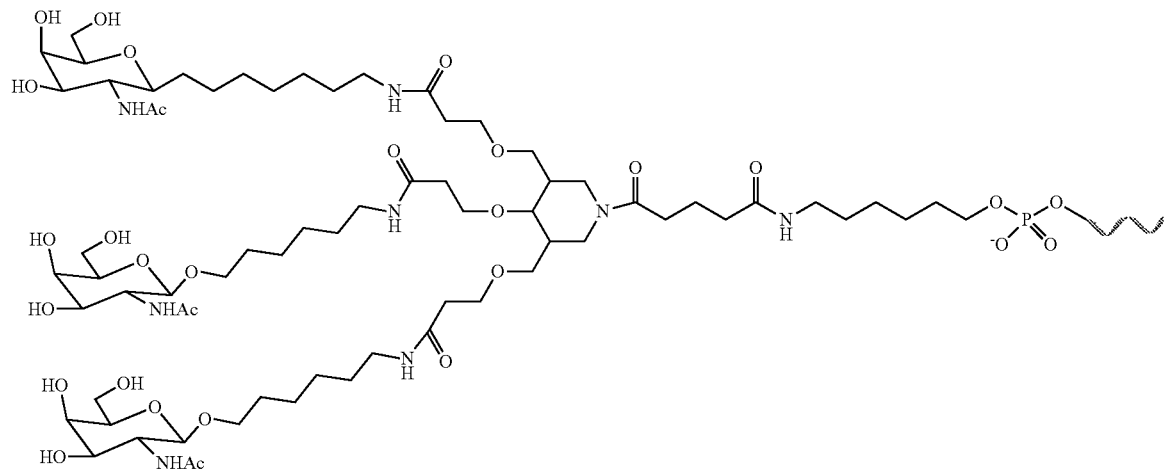

Conjugate 27 wherein for the purposes of Example 8, the substituent represents the mouse Factor VII antisense oligonucleotide (mFVII ASO) connected through a hexylamino linker to the 5' end of mFVII ASO.

Scheme 8

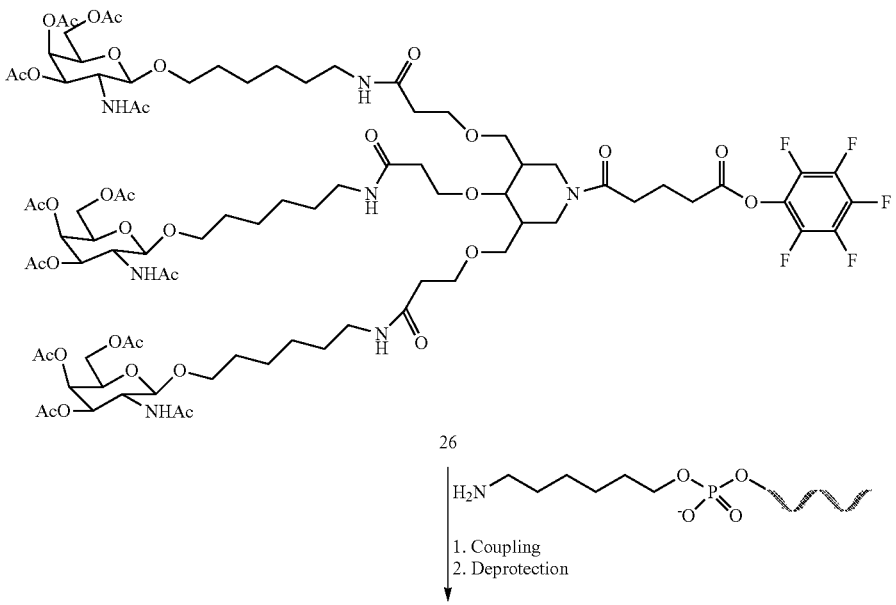

26

1. Coupling
2. Deprotection

-continued

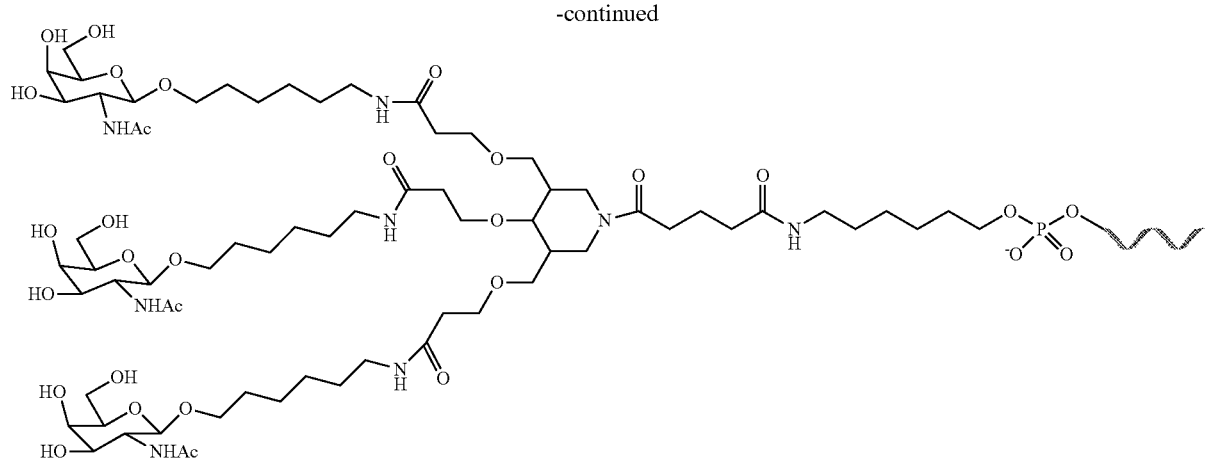

Example 9

In Vivo Mouse Factor VII Silencing

Using a liver-directed in vivo screen of the liposome libraries, a series of compounds were tested that facilitate high levels of siRNA mediated gene silencing in hepatocytes, the cells comprising the liver parenchyma. Factor VII, a blood clotting factor, is a suitable target gene for assaying functional siRNA delivery to liver. Because this factor is produced specifically in hepatocytes, gene silencing indicates successful delivery to parenchyma, as opposed to delivery to the cells of the reticulo-endothelial system (e.g., Kupffer cells). Furthermore, Factor VII is a secreted protein that can be readily measured in serum, obviating the need to euthanize animals. Silencing at the mRNA level can be readily determined by measuring levels of protein. This is because the protein's short half-life (2-5 hour). Compositions with siRNA directed to Factor VII of Conjugate 1 (F7 ASO-L-GalNAc) and Conjugate 27 (F7 ASO-L2-GalNAc) were formulated, as well as a comparators F7 ASO (Antisense Oligonucleotide; naked control) and negative control phosphate-buffered saline (PBS). Female C57BL/6 mice (6-8 week old) were used for the FVII siRNA knockdown (KD) experiments.

All formulations were administered subcutaneously at a dose of 0.1, 0.3, 1, 3 and 6 mg/kg. Terminal blood collection was performed via cardiac puncture under 2% isoflurane at 48 hours after formulation injections. Blood was collected into 0.109 M citrate buffer tubes and processed by centrifugation at 1200 G for 10 min. Plasma was collected after centrifugation and Factor VII protein levels were analyzed by chromogenic assay (Biophen FVII, Aniara Corporation). A standard curve was constructed using samples from PBS-injected mice and relative Factor VII expression was determined by comparing treated groups to untreated PBS control. The results showed that Conjugate 1 (F7 ASO-L-GalNAc) and Conjugate 27 (F7 ASO-L2-GalNAc) were significantly effective at 1, 3, and 6 mg/kg (FIG. 1) while the naked F7 ASO was less effective at all tested concentrations.

Figure 2:
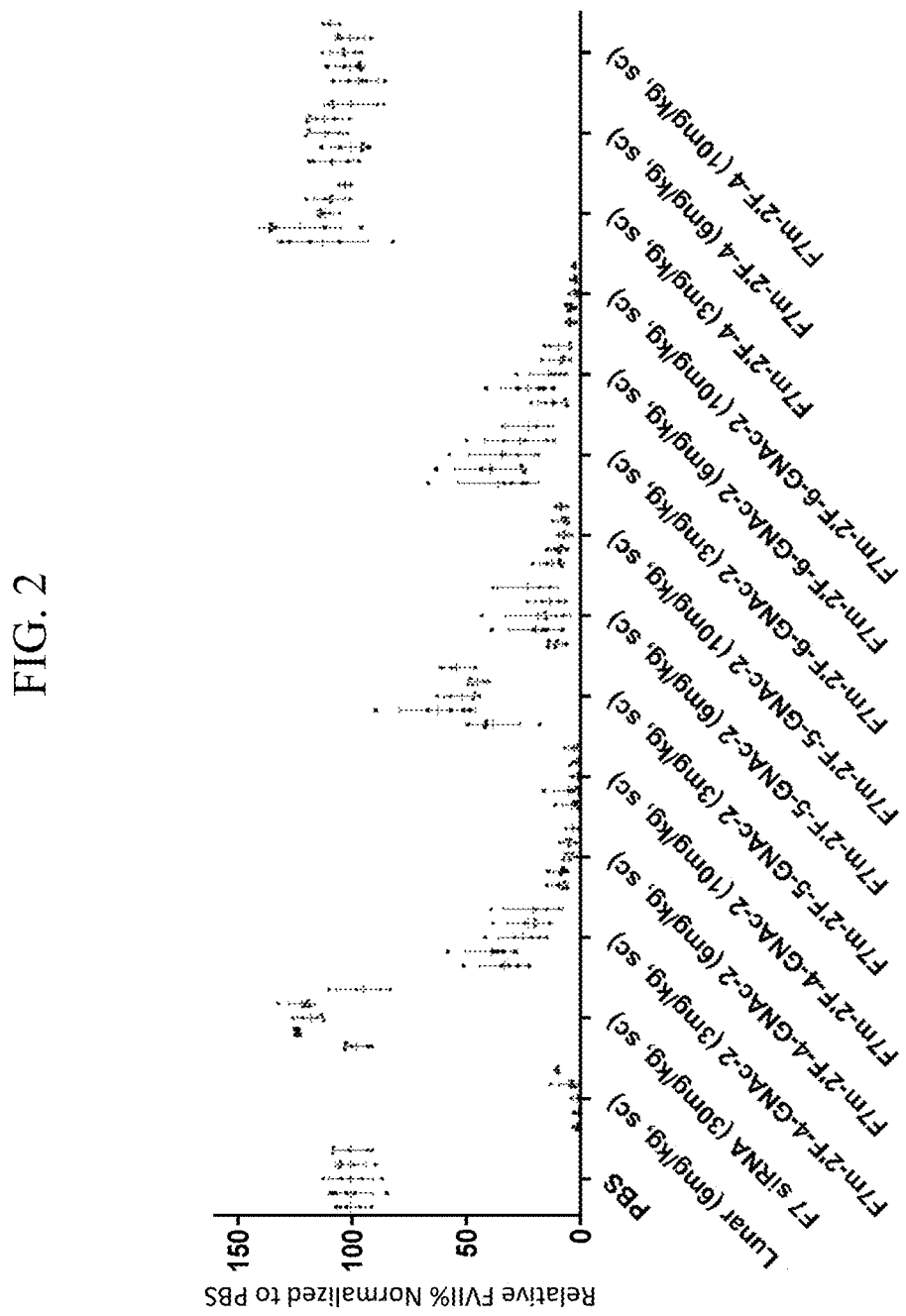
FIG. 2 shows the duration for FVII knockdown for FVII siRNA conjugated to Conjugate 27 (GNAc-2) as compared to naked formulations and a lipid nanoparticle-encapsulated formulation.

Further experiments were performed to assess the duration of knockdown activity for FVII constructs conjugated to conjugate 27 (compositions designated with -GNAc-2 at the end) in comparison with naked siRNAs (F7 siRNA and F7m-2'F-4), siRNA encapsulated in a lipid nanoparticle (F7 siRNA +Lunar), and the negative control of PBS. The results are provided in FIG. 2, which shows the progression of relative FVII percentage normalized to PBS at timepoints starting from left to right for each tested concentration at Day 2, Day 3, Day 4, Day 7, and Day 10. The siRNA encapsulated in the lipid nanoparticle showed complete knockdown for most of the time period with just a small amount of expression beginning to shown at Days 7 and 10 at the tested dose of 6 mg/kg. The naked F7 siRNA and F7m-2'F-4 did not showing appreciable knockdown over the same time period. In contrast, the conjugated samples showed comparable knockdown to the lipid nanoparticle encapsulated siRNA at comparable dose levels of 6 mg/kg. Thus, the constructs of the present disclosure show great activity in delivering siRNA in vivo.

Finally, three conjugates were tested for knockdown activity using an siRNA specially designed to knockdown a protein, which is expressed in many tissues and cell types, designated herein as siRNA2. The siRNA2 was conjugated to each of the three conjugates using methods described herein, with the first conjugate being Conjugate 27 of Example 8 (siRNA2-GNAc-2), the second being Conjugate 2 of Example 2 (siRNA2-GNAc-3), and finally the third conjugate being Conjugate 3 of Example 3 (siRNA2-GNAc-4).

The conjugates were administered subcutaneously at doses of 6 and 10 mg/kg as well as the controls of PBS (negative control) and naked siRNA2 (30 mg/kg). Terminal blood collection was performed via cardiac puncture under 2% isoflurane at 48 hours after formulation injections over a time course at Days 2, 3, 7, 14, 21, 28, 35, and 42. Blood was collected into 0.109 M citrate buffer tubes and processed by centrifugation at 1200 G for 10 min. Plasma was collected after centrifugation and the applicable protein levels were analyzed by chromogenic assay (Biophen FVII, Aniara Corporation). A standard curve was constructed using samples from PBS-injected mice and relative protein expression was determined by comparing treated groups to untreated PBS control.

The results are provided in Table 1 below, which shows the relative protein expression levels (%KD) at each dose level over the indicated time course. Each of the conjugates showed effective knockdown over the naked siRNA2 at both the 6 mg/kg and 10 mg/kg doses. This knockdown had a lasting effect with expression levels still below 30% for the 10 mg/kg doses after 28 days for each of the conjugates. An appreciable knockdown was also observed for all doses and cojugates even at 42 days. Thus, the constructs of the present disclosure are able to effectively deliver nucleic acids with a lasting activity.

TABLE 1

Duration of Relative Protein Expression Levels After Treatment with siRNA-2 Conjugates

| Sample | % KD Day 2 | % KD Day 3 | % KD Day 7 | % KD Day 14 | % KD Day 21 | % KD Day 28 | % KD Day 35 | % KD Day 42 |
|---|---|---|---|---|---|---|---|---|
| PBS | 100.0 | 100.0 | 100.0 | 100.0 | 100.0 | 100.0 | 100.0 | 100.0 |
| siRNA2 (30 mg/kg) | 112.0 | 103.9 | 92.7 | 68.2 | 70.6 | 71.5 | 81.4 | 53.9 |
| siRNA2-GNac-2 (6 mg/kg) | 24.1 | 14.6 | 6.2 | 11.3 | 12.8 | 14.2 | 36.7 | 65.6 |
| SiRNA2-GNac-2 (10 mg/kg) | 15.6 | 7.3 | 3.1 | 5.8 | 10.1 | 11.0 | 49.5 | 76.2 |
| SiRNA2-GNac-3 (6 mg/kg) | 33.3 | 15.6 | 8.7 | 11.8 | 15.3 | 25.3 | 54.7 | 55.7 |
| SiRNA2-GNac-3 (10 mg/kg) | 26.4 | 19.0 | 6.3 | 13.0 | 7.0 | 11.3 | 36.9 | 57.8 |
| SiRNA2-GNac-4 (6 mg/kg) | 25.7 | 11.4 | 5.6 | 10.9 | 16.2 | 32.5 | 67.6 | 73.3 |
| SiRNA2-GNac-4 (10 mg/kg) | 31.1 | 15.2 | 5.2 | 8.1 | 7.7 | 17.0 | 54.5 | 60.9 |

What is claimed is:

1. A compound of Formula IA

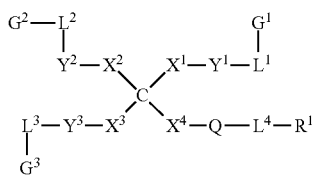

or a pharmaceutically acceptable salt or solvate thereof, wherein $X^1$, $X^2$ and $X^3$ are each independently selected from the group consisting of $C_1$-$C_{10}$ alkyl, —$(CH_2)_m$—O—$(CH_2)_n$— and —$(CH_2)_m$—N—$(CH_2)_n$—, wherein n is 1-36 and m is 1-30;

$Y^1$, $Y^2$ and $Y^3$ are each independently selected from the group consisting of —NHC(O)—, —C(O)NH—, —OC(O)—, —C(O)O—, —SC(O)—, —C(O)S— and P(Z)(OH)$O_2$, wherein Z is O or S;

$L^1$, $L^2$ and $L^3$ are each independently selected from the group consisting of a $C_1$-$C_{10}$ alkyl, —$(CH_2)_e$—O—$(CH_2)_f$—, —$(CH_2)_e$—S—$(CH_2)_f$—, —$(CH_2)_e$—S(O)$_2$—$(CH_2)_f$—, —$(CH_2)_e$—N—$(CH_2)_f$ and —$(CH_2$—$CH_2$—O)$_k$$(CH_2)_2$—, wherein e is 1-10, f is 1-16 and k is 1-20;

$G^1$, $G^2$ and $G^3$ are each independently selected from the group consisting of a monosaccharide, a monosaccharide derivative, a vitamin, a polyol, a polysialic acid and a polysialic acid derivative;

$X^4$ is selected from the group consisting of

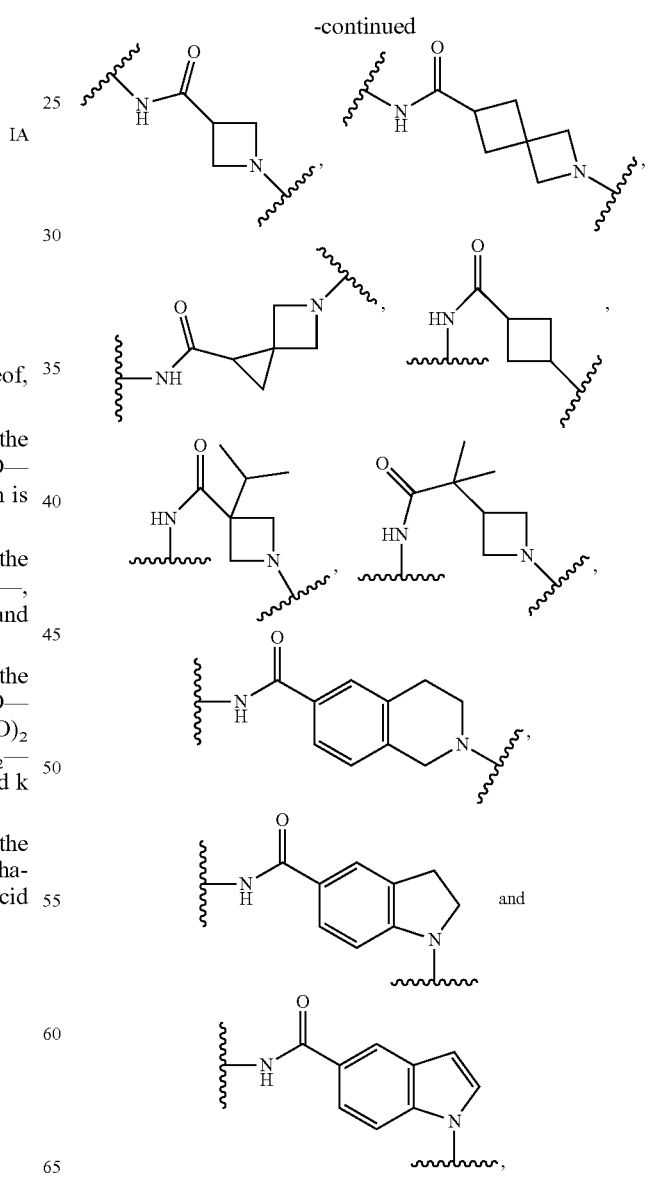

wherein $X^4$ is optionally substituted;

$R^N$ is H, methyl, or mono-, di-, or trifluoromethyl;

Q is akyalkylamino, —C(O)—(CH$_2$)$_i$—, —(CH$_2$)$_i$—O—(CH$_2$)$_j$—, —(CH$_2$)$_i$—NR$^3$—(CH$_2$)$_j$—, —(CH$_2$)$_i$—S—S—(CH$_2$)$_j$—, —(CH$_2$)$_i$—S—(CH$_2$)$_j$—, —(CH$_2$)$_i$—S(O)$_2$—(CH$_2$)$_j$—, —(CH$_2$)$_i$—NHC(O)—(CH$_2$)$_j$—, —(CH$_2$)$_i$—C(O)NH—(CH$_2$)$_j$—, —(CH$_2$)$_i$—SC(O)—(CH$_2$)$_j$—, or —(CH$_2$)$_i$—C(O)S—(CH$_2$)$_j$—, wherein i is 1-10; j is 1-10; and R$^3$ is hydrogen or an alkyl;

L$^4$ is absent, —C(O)O—, —C(O)NH—, —O—P(O)$_2$—O—, C$_1$-C$_{10}$ alkyl-O—P(O)$_2$—O—, C$_3$-C$_{10}$ alkenyl-O—P(O)$_2$—O—, —O—P(O)(S)—O—, C$_1$-C$_{10}$ alkyl-O—P(O)(S)—O—, C$_3$-C$_{10}$ alkenyl-O—P(O)(S)—O—, —O—P(O)(BH$_3$)—O—, a C$_1$-C$_{10}$ alkyl-O—P(O)(BH$_3$)—O—, a C$_3$-C$_{10}$ alkenyl-O—P(O)(BH$_3$)—O—, —C(O)NH—C$_1$-C$_{10}$alkyl-O—P(O)$_2$—O—, —C(O)NH—C$_3$-C$_{10}$alkenyl-O—P(O)$_2$—O—, —C(O)O—C$_1$-C$_{10}$alkyl-O—P(O)$_2$—O—, —C(O)O—C$_3$-C$_{10}$alkenyl-O—P(O)$_2$—O—, —C(O)NH—C$_1$-C$_{10}$alkyl-O—P(O)(S)—O—, —C(O)NH—C$_3$-C$_{10}$alkenyl-O—P(O)(S)—O—, —C(O)O—C$_1$-C$_{10}$alkyl-O—P(O)(S)—O—, —C(O)O—C$_3$-C$_{10}$alkenyl-O—P(O)(S)—O—, —C(O)—NH—C$_1$-C$_{10}$alkyl-O—P(O)(BH$_3$)—O—, —C(O)—NH—C$_3$-C$_{10}$alkyl-O—P(O)(BH$_3$)—O—, —C(O)O—C$_1$-C$_{10}$alkyl-O—P(O)(BH$_3$)—O— or —C(O)O—C$_3$-C$_{10}$alkenyl-O—P(O)(BH$_3$)—O—; and R$^1$ is a biologically active molecule.

2. The compound of claim 1, wherein X$^1$, X$^2$ and X$^3$ are each independently (—CH$_2$)$_m$—O—CH$_2$—, wherein m is 1-4.

3. The compound of claim 1, wherein Y$^1$, Y$^2$ and Y$^3$ are each independently —NHC(O)— or —C(O)NH—.

4. The compound of claim 1, wherein L$^1$, L$^2$ and L$^3$ are each independently C$_3$-C$_8$ alkyl or —(CH$_2$—CH$_2$—O)$_k$(CH$_2$)$_2$—, wherein k is 1-10.

5. The compound of claim 1, wherein L$^1$, L$^2$ and L$^3$ are each independently —(CH$_2$—CH$_2$—O)$_k$(CH$_2$)$_2$—, wherein k is 2-4.

6. The compound of claim 1, wherein L$^1$, L$^2$ and L$^3$ are each independently C$_1$-C$_{10}$ alkyl.

7. The compound of claim 1, wherein G$^1$, G$^2$ and G$^3$ are each independently selected from the group consisting of folic acid, ribose, retinol, niacin, riboflavin, biotin, glucose, mannose, fucose, sucrose, lactose, mannose-6-phosphate, N-acetyl galactosamine, N-acetylglucosamine, a sialic acid, a sialic acid derivative, allose, altrose, arabinose, cladinose, erythrose, erythrulose, fructose, fucitol, fucosamine, fucose, fuculose, galactosamine, galactosaminitol, galactose, glucosamine, glucosaminitol, glucose-6 phosphate, gulose glyceraldehyde, glycero-mannosheptose, glycerol, glycerone, gulose, idose, lyxose, mannosamine, psicose, quinovose, quinovosamine, rhamnitol, rhamnosamine, rhamnose, ribulose, sedoheptulose, sorbose, tagatose, talose, threose, xylose and xylulose.

8. The compound of claim 1, wherein G$^1$, G$^2$ and G$^3$ are each N-acetylgalactosamine.

9. The compound of claim 1, wherein X$^4$ is

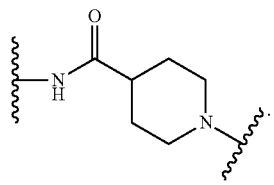

10. The compound of claim 1, wherein Q is —C(O)—(CH$_2$)$_{1-10}$— and L$^4$ is a —C(O)NH—(CH$_2$)$_{1-10}$—O—P(O)$_2$—O—.

11. The compound of claim 1, wherein Q is —C(O)—(CH$_2$)$_3$— and L$^4$ is a —C(O)NH—(CH$_2$)$_6$—O—P(O)$_2$—O—.

12. The compound of claim 1, wherein L$^4$ is —C(O)O—.

13. The compound of claim 1, wherein L$^4$ is a —C(O)NH—(CH$_2$)$_{1-10}$—O—P(O)$_2$—O—.

14. The compound of claim 1, wherein R$^1$ is selected from the group consisting of pentafluorophenyl, tetrafluorophenyl, succinimide, maleimide, azide, pyridyldithiol, methyl phosphonate, a helper lipid, and a nucleic acid.

15. The compound of claim 1, wherein R$^1$ is an ASO (Antisense Oligonucleotide), a siRNA (Small Interfering RNA), a miRNA (MicroRNA), a microRNA mimic, an AMO (Anti-miRNA Oligonucleotide), a long non-coding RNA, a PNA (Peptide Nucleic Acid), a helper lipid, or a PMO (Phosphorodiamidate Morpholino Oligomer), wherein the nucleic acid is optionally modified.

16. The compound of claim 1, wherein R$^1$ is an ASO (Antisense Oligonucleotide).

17. The compound of claim 1, having the formula:

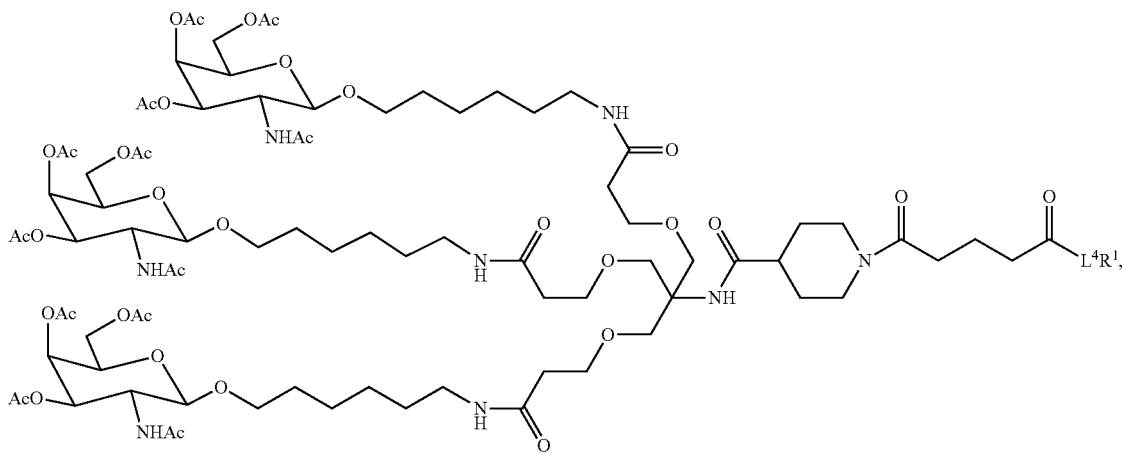

181
wherein R[1] is an ASO (Antisense Oligonucleotide), a siRNA (Small Interfering RNA), a miRNA (MicroRNA), a microRNA mimic, an AMO (Anti-miRNA Oligonucleotide), a long non-coding RNA, a PNA
182
(Peptide Nucleic Acid), a helper lipid, or a PMO (Phosphorodiamidate Morpholino Oligomer).
18. A compound selected from the group consisting of
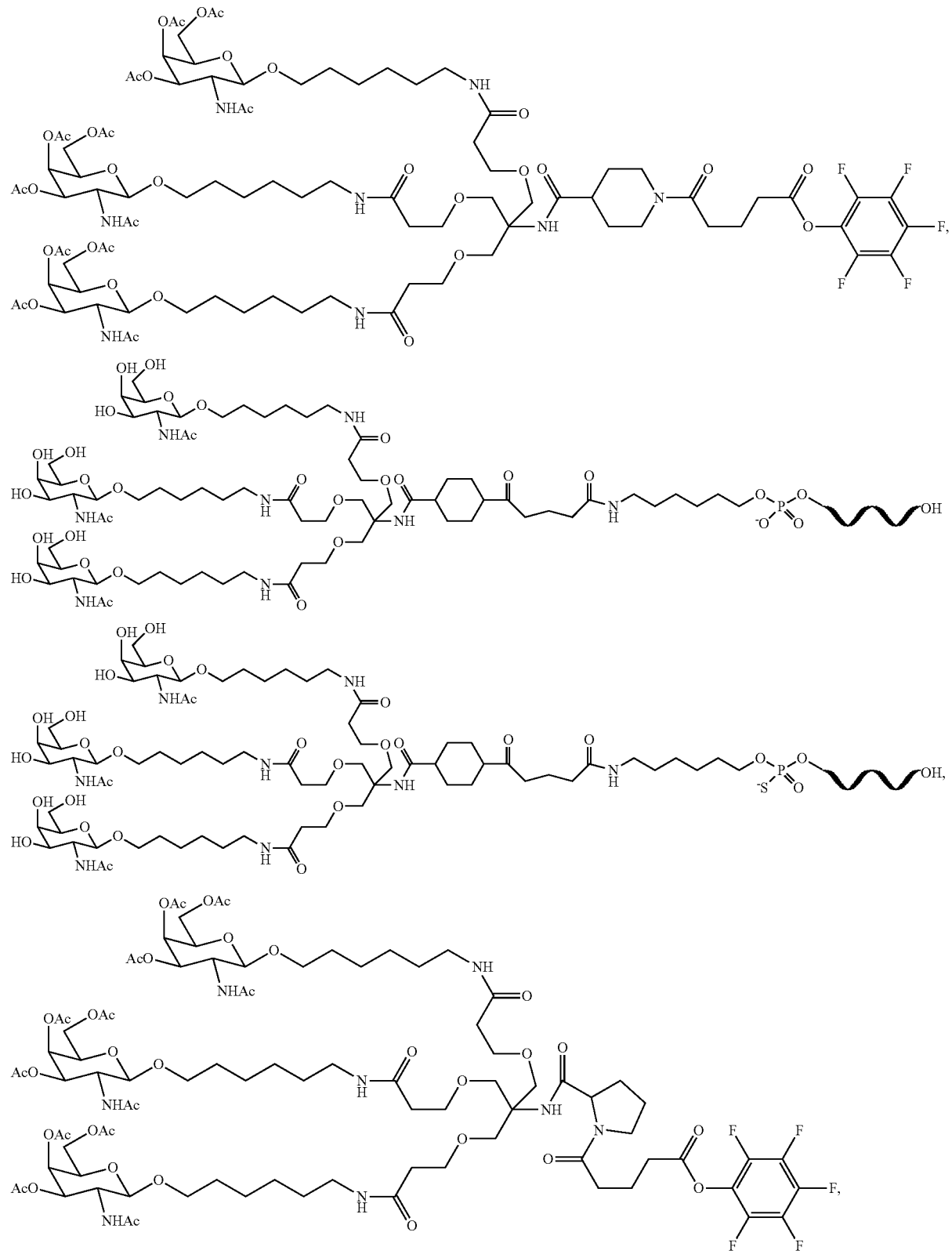

183
-continued
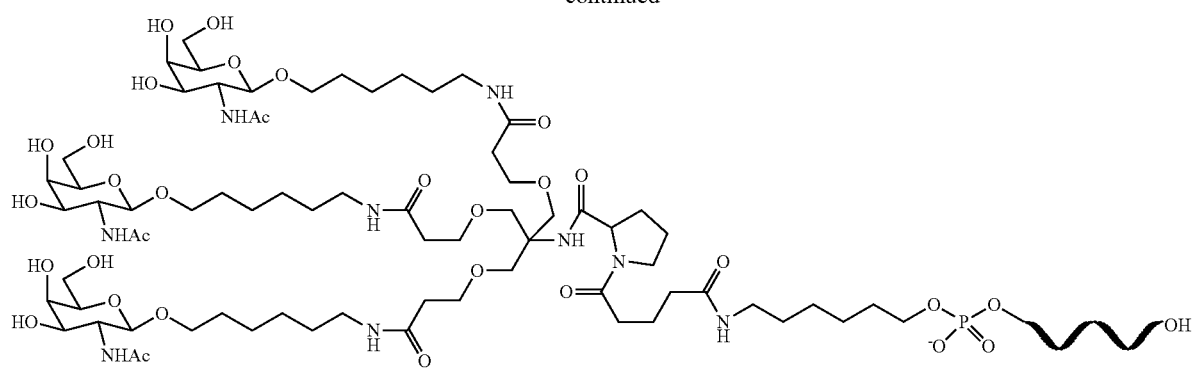
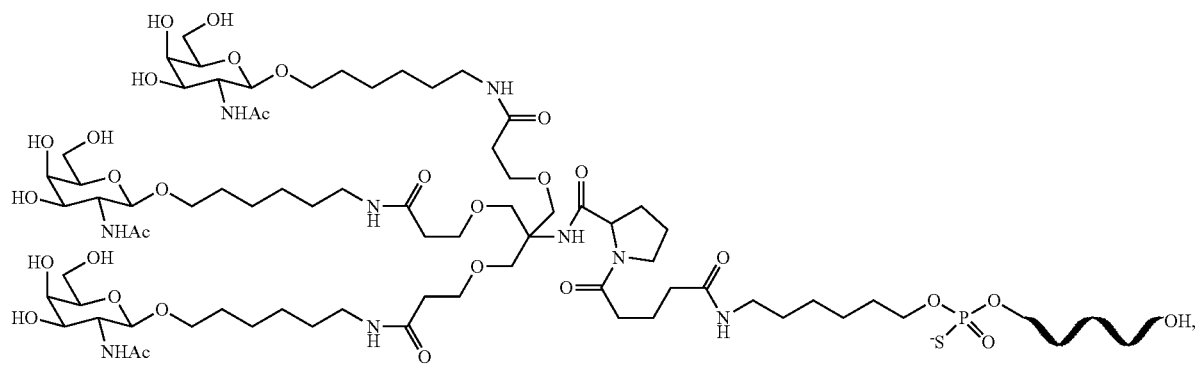
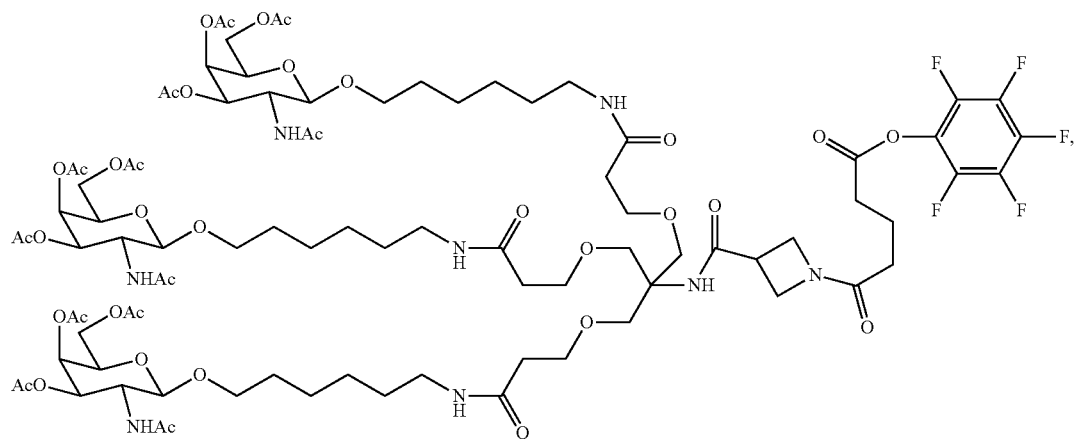
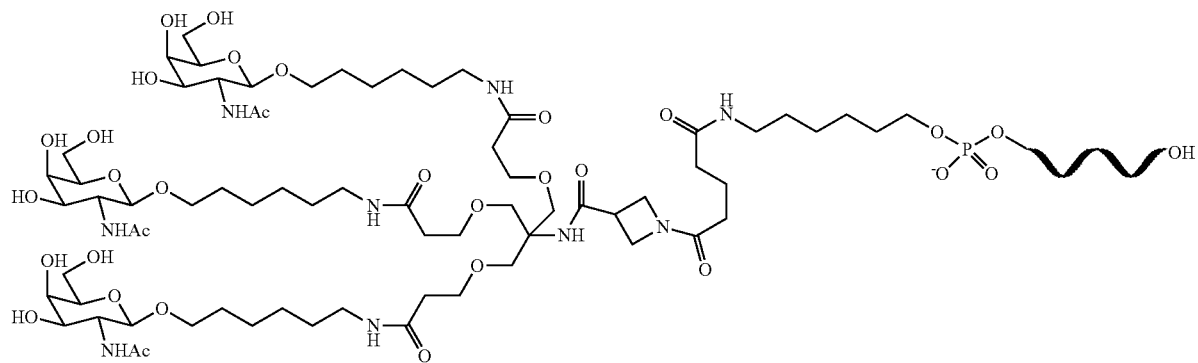

185
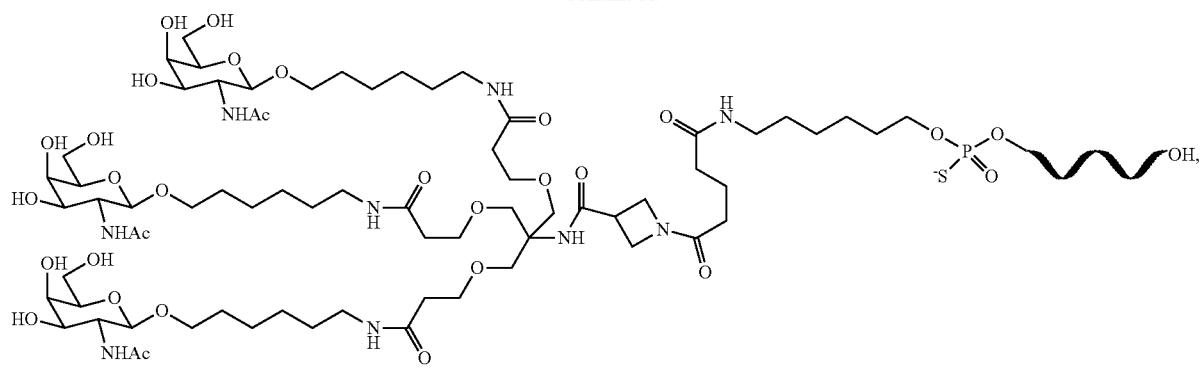
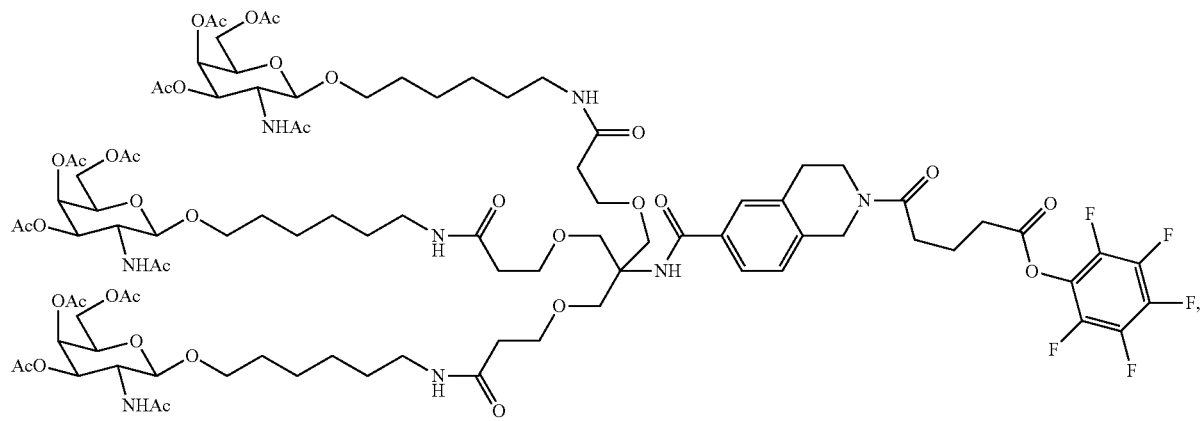
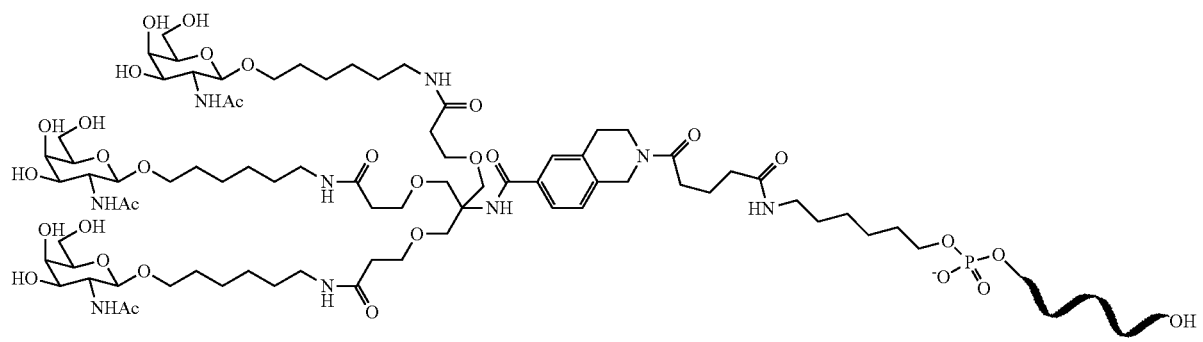
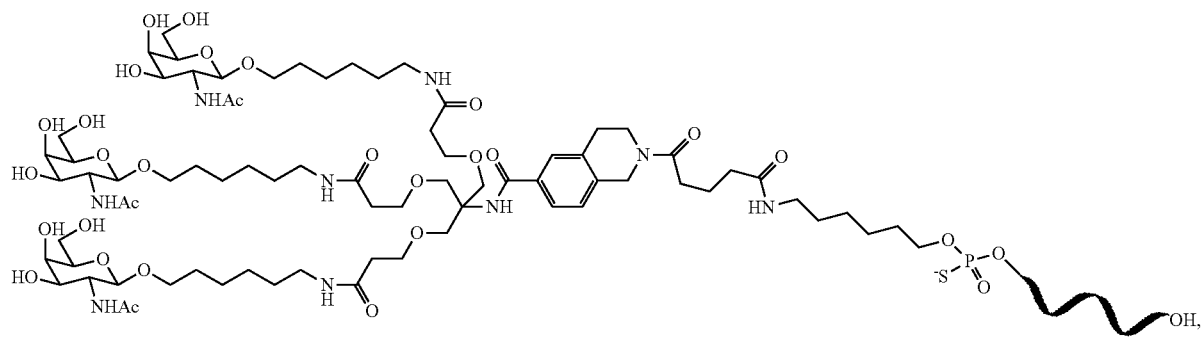

187
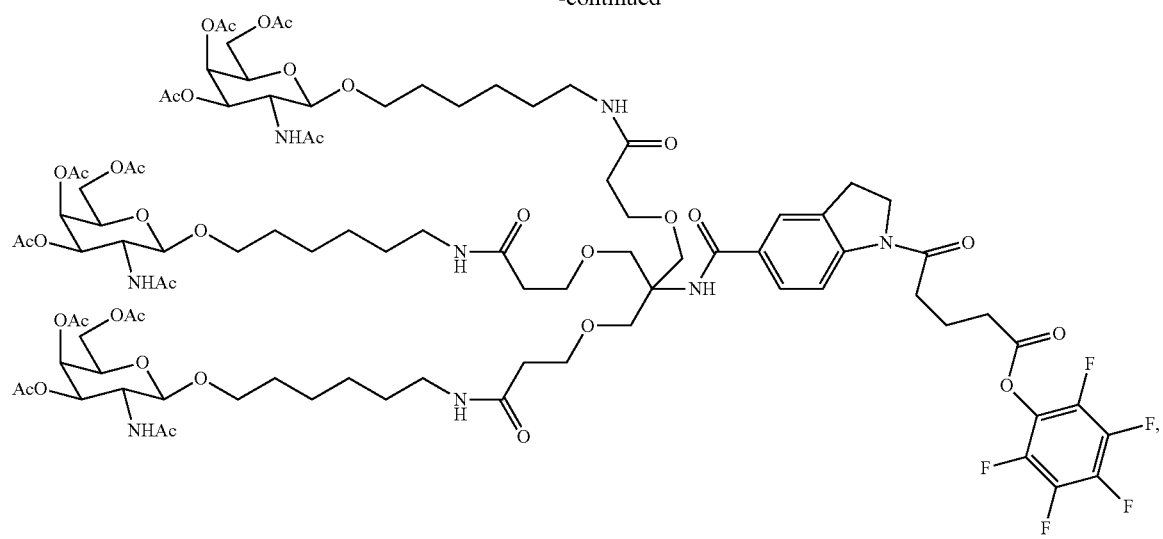
188
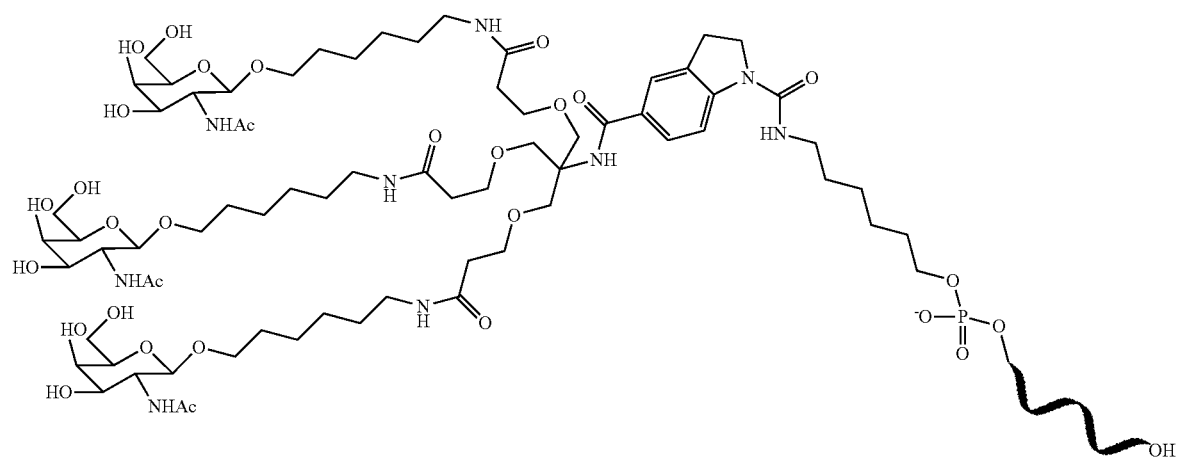
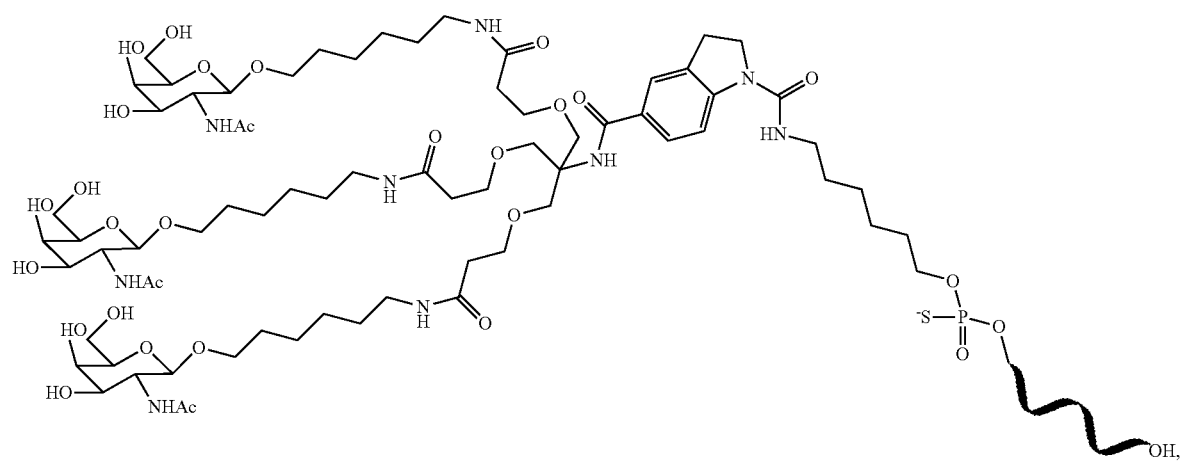

-continued
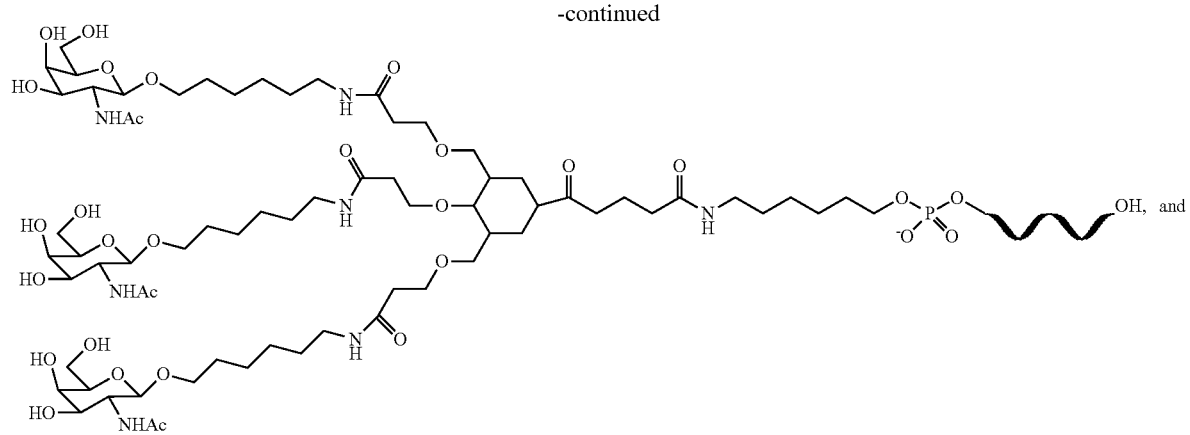
, and
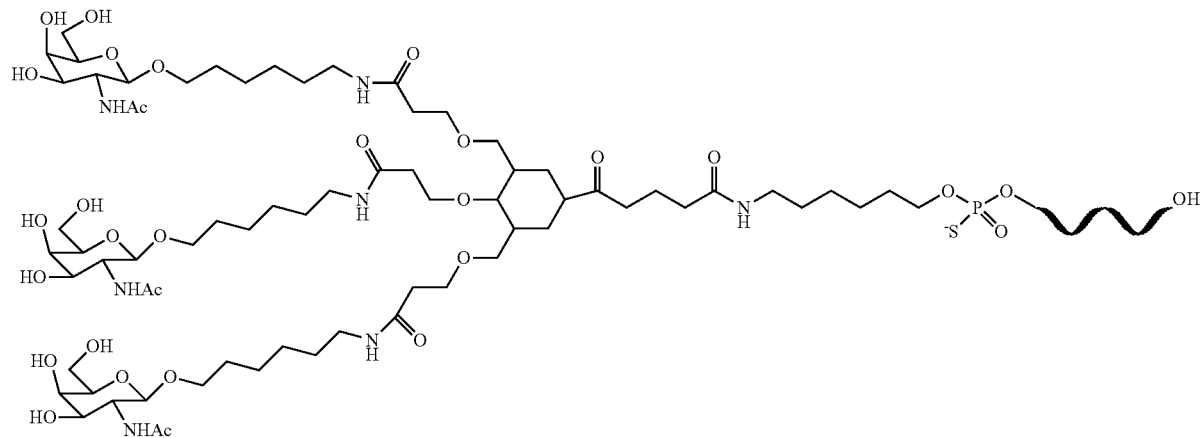
wherein ~~~OH is an oligonucleotide.
19. A compound selected from the group consisting of
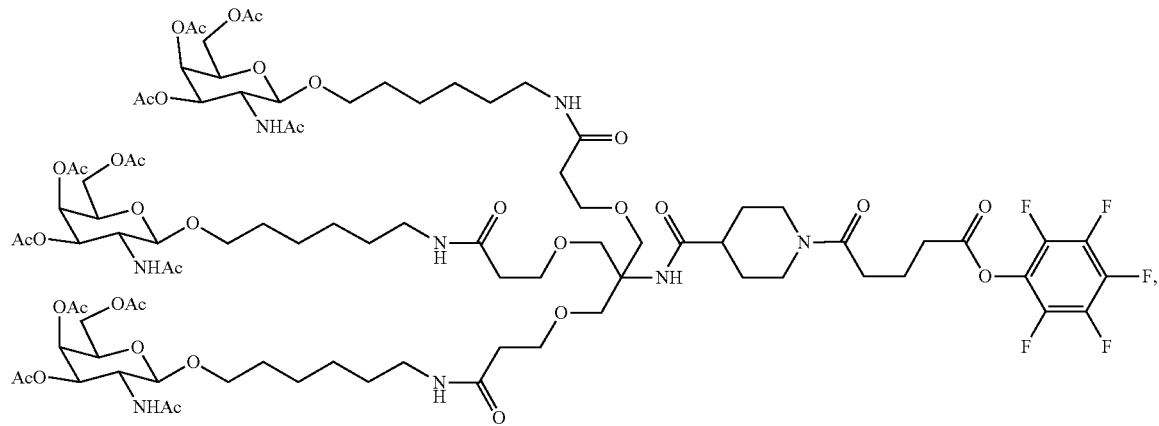
,

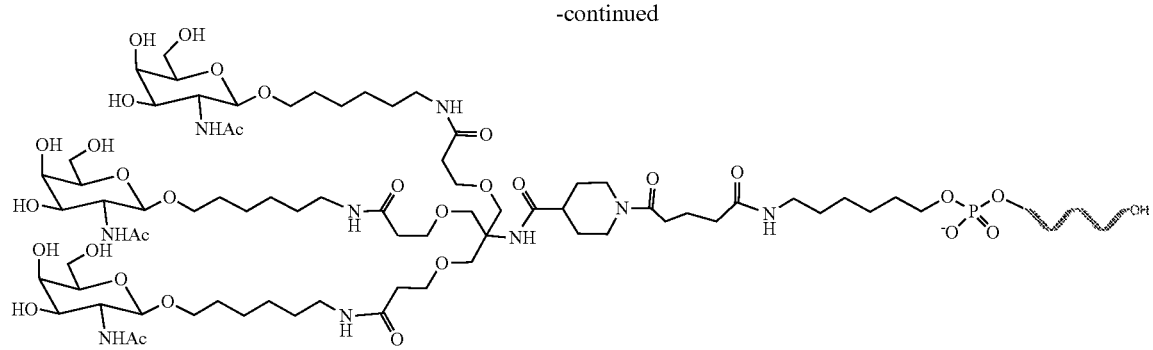
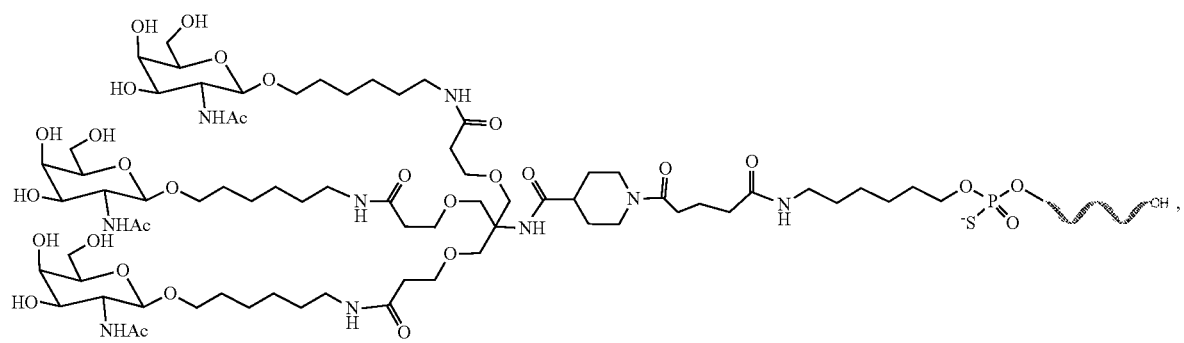
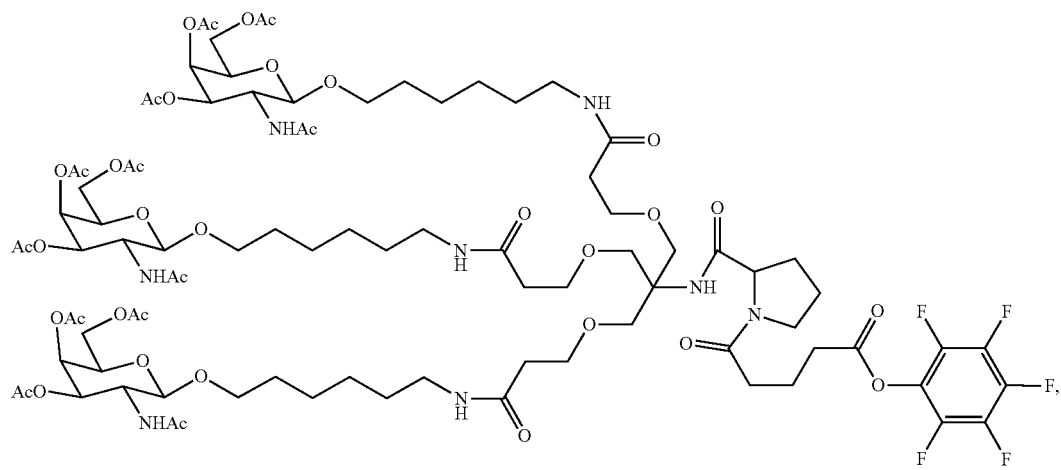
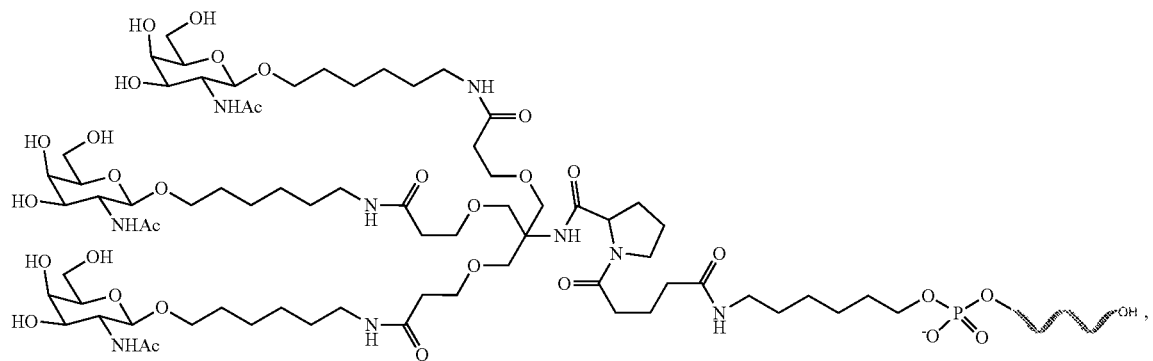

193
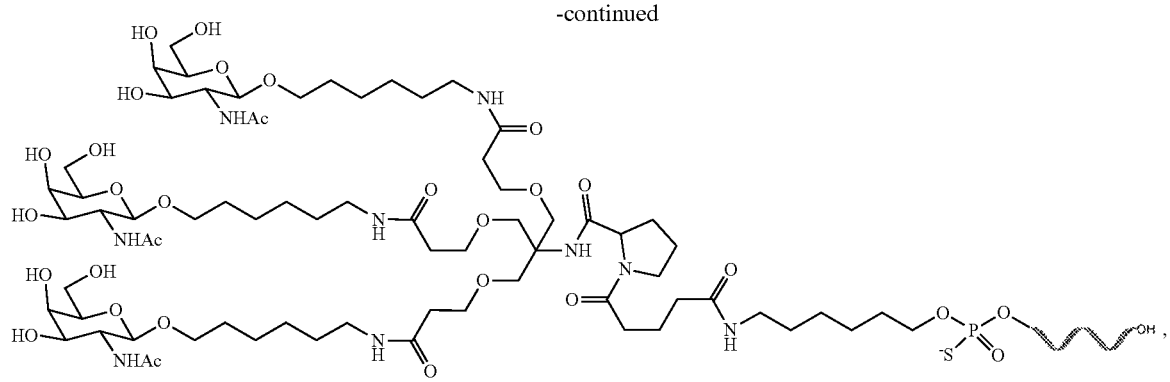
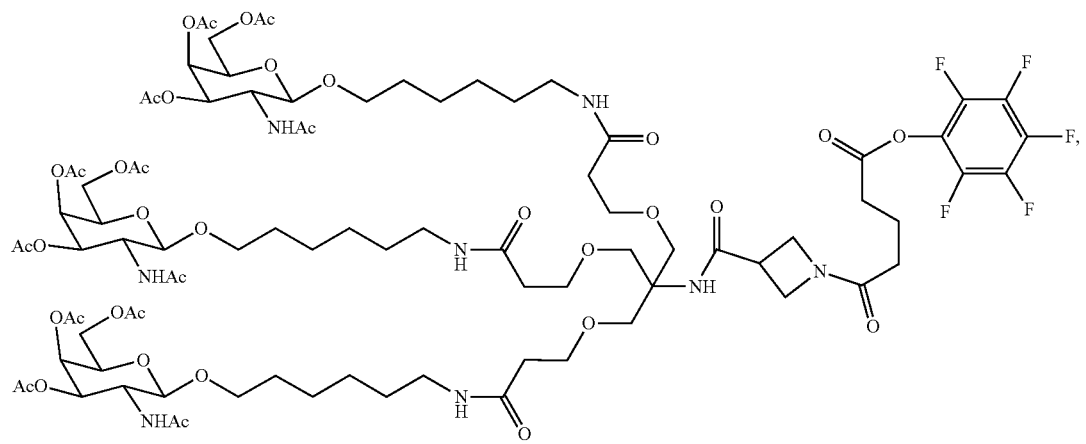
194
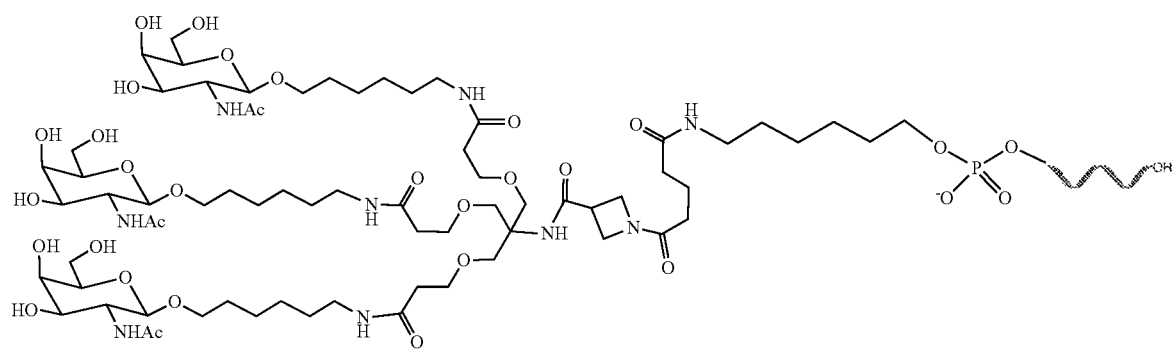
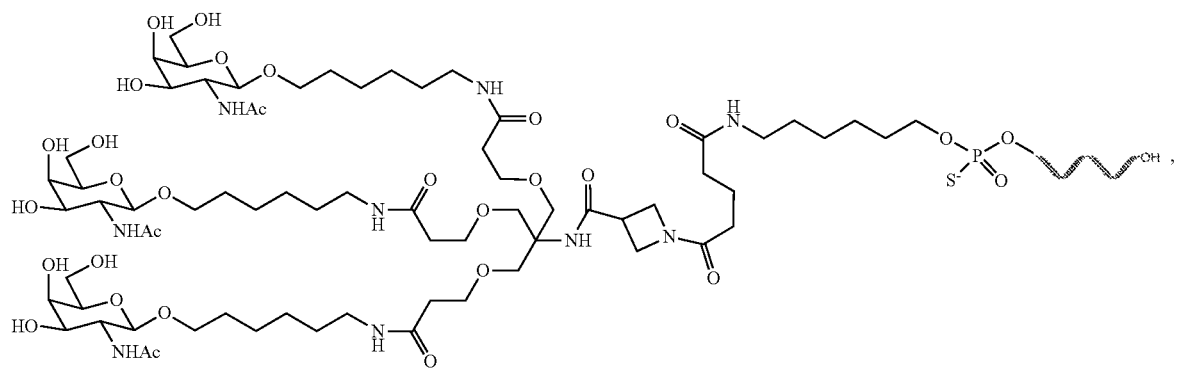

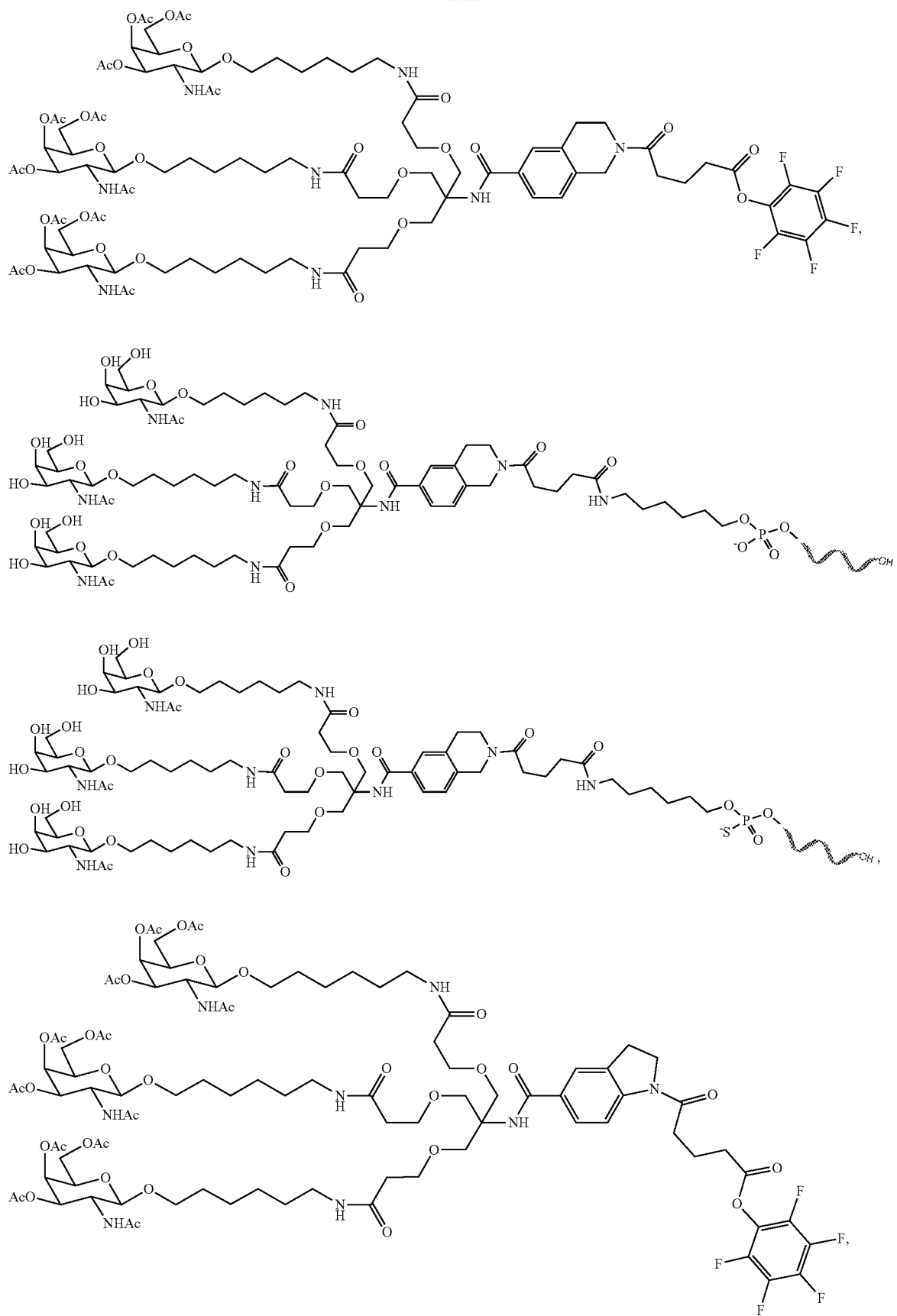

-continued
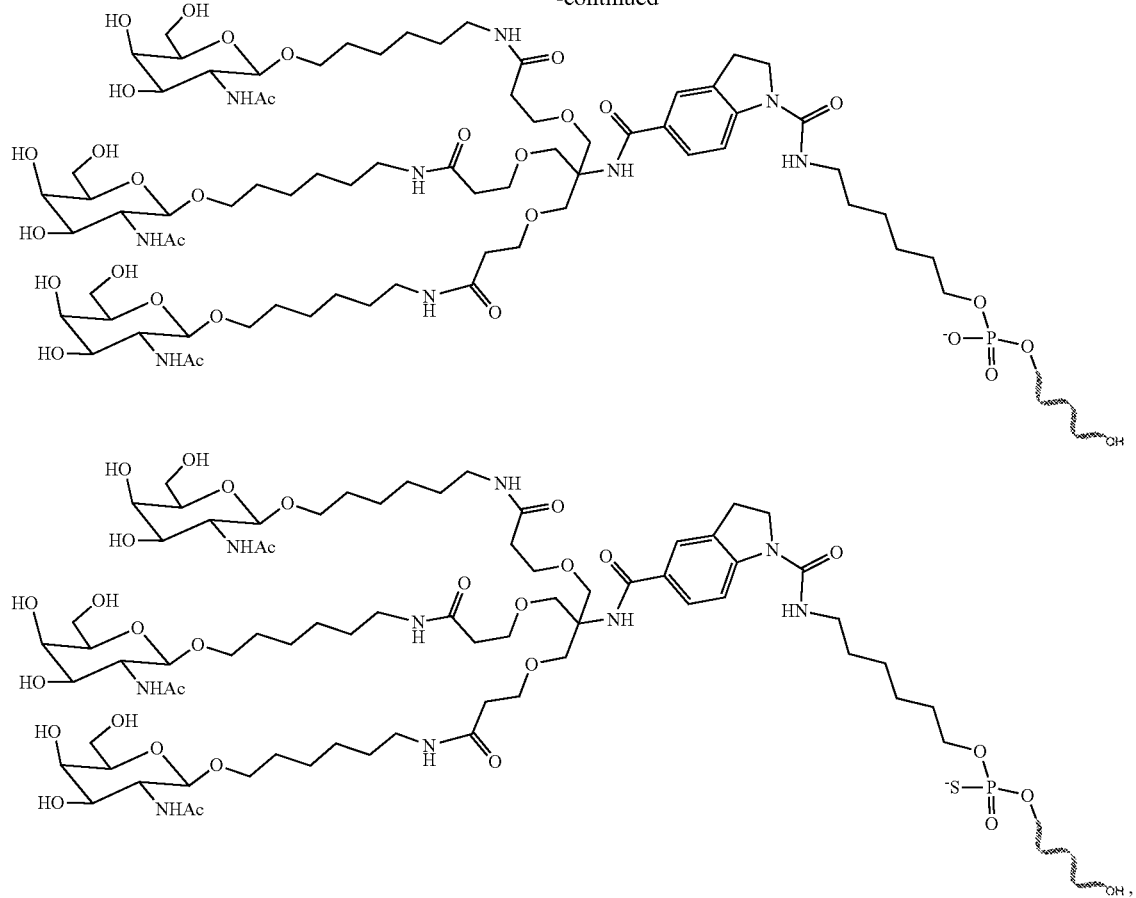
wherein ⁓⁓⁓OH is an oligonucleotide.
* * * * *